US012583888B2

(12) United States Patent
Teesalu et al.

(10) Patent No.: US 12,583,888 B2
(45) Date of Patent: Mar. 24, 2026

(54) BI-SPECIFIC EXTRACELLULAR MATRIX BINDING PEPTIDES AND METHODS OF USE THEREOF

(71) Applicant: University of Tartu, Tartu (EE)

(72) Inventors: Tambet Teesalu, Tartu (EE); Prakash Lingasamy, Tartu (EE)

(73) Assignee: University of Tartu, Tartu (EE)

( * ) Notice: Subject to any disclaimer, the term of this patent is extended or adjusted under 35 U.S.C. 154(b) by 948 days.

(21) Appl. No.: 17/428,484

(22) PCT Filed: Feb. 3, 2020

(86) PCT No.: PCT/IB2020/050847
§ 371 (c)(1),
(2) Date: Aug. 4, 2021

(87) PCT Pub. No.: WO2020/161602
PCT Pub. Date: Aug. 13, 2020

(65) Prior Publication Data
US 2022/0119450 A1      Apr. 21, 2022

Related U.S. Application Data

(60) Provisional application No. 62/800,879, filed on Feb. 4, 2019.

(51) Int. Cl.
| | |
|---|---|
| *C07K 7/08* | (2006.01) |
| *A61K 38/00* | (2006.01) |
| *A61P 35/00* | (2006.01) |
| *C07K 7/06* | (2006.01) |
| *C07K 14/00* | (2006.01) |

(52) U.S. Cl.
CPC ............... *C07K 7/08* (2013.01); *A61P 35/00* (2018.01); *C07K 7/06* (2013.01); *C07K 14/00* (2013.01); *A61K 38/00* (2013.01)

(58) Field of Classification Search
CPC . C07K 7/08; C07K 7/06; C07K 14/00; A61K 38/00; A61P 35/00
See application file for complete search history.

(56) References Cited

U.S. PATENT DOCUMENTS

| | | | |
|---|---|---|---|
| 4,016,100 | A | 4/1977 | Suzuki |
| 4,089,801 | A | 5/1978 | Schneider |
| 4,235,871 | A | 11/1980 | Papahadjopoulos |
| 4,485,054 | A | 11/1984 | Mezei |
| 4,853,228 | A | 8/1989 | Wallach |
| 5,628,936 | A | 5/1997 | Wallach |
| 5,653,996 | A | 8/1997 | Hsu |
| 5,885,613 | A | 3/1999 | Holland |
| 5,925,720 | A | 7/1999 | Kataoka |
| 5,929,177 | A | 7/1999 | Kataoka |
| 6,320,017 | B1 | 11/2001 | Ansell |
| 6,506,405 | B1 | 1/2003 | Desai |
| 6,530,944 | B2 | 3/2003 | West |
| 6,537,579 | B1 | 3/2003 | Desai |
| 6,759,199 | B2 | 7/2004 | Mirkin |
| 2003/0194696 | A1* | 10/2003 | Zauderer ............ C12N 15/1079 435/7.1 |
| 2005/0004002 | A1 | 1/2005 | Desai |
| 2006/0242725 | A1 | 10/2006 | Strong |
| 2008/0234183 | A1* | 9/2008 | Hallbrink .................. A61P 3/10 435/320.1 |
| 2009/0031733 | A1 | 2/2009 | Weaver, Jr. |
| 2009/0317802 | A1 | 12/2009 | Bhatia |
| 2009/0325866 | A1 | 12/2009 | Kim |
| 2010/0022750 | A1 | 1/2010 | Bishop |
| 2010/0061932 | A1 | 3/2010 | Brock |
| 2010/0061942 | A1 | 3/2010 | Ma |
| 2010/0099627 | A1 | 4/2010 | Seger |
| 2010/0322862 | A1 | 12/2010 | Ruoslahti |
| 2014/0010832 | A1 | 1/2014 | Hubbell |
| 2017/0224848 | A1 | 8/2017 | Lu |

FOREIGN PATENT DOCUMENTS

| | | |
|---|---|---|
| WO | 1996032434 | 10/1996 |
| WO | 1997000623 | 1/1997 |
| WO | 2002044184 | 6/2002 |
| WO | 2009028838 | 3/2009 |
| WO | 2016172515 | 10/2016 |
| WO | 2018085846 | 5/2018 |
| WO | 2020161602 | 8/2020 |

OTHER PUBLICATIONS

Transcription factor E3 isoform a [Mus musculus], from https://www.ncbi.nlm.nih.gov/protein/NP_766060.2, 2024, pp. 1-4.*

Drumm et al, Genetic Variation and Clinical Heterogeneity in Cystic Fibrosis, Annu. Rev. Pathol. Mech. Dis., 2012, 7, pp. 267-282.*

Yampolsky et al., The Exchangeability of Amino Acids in Proteins, Genetics, 2005, 170, pp. 1459-1472.*

Peptidyl-prolyl isomerase cwc27 [Dispira simplex], from https://www.ncbi.nlm.nih.gov/protein/KAJ1648049.1?report=genbank&log$=protalign&blast_rank=6&RID=YV2456AH013, 2022, pp. 1-2.*

Agemy, et al., "Targeted nanoparticle enhanced proapoptotic peptide as potential therapy for glioblastoma", PNAS, 108(42):17450-17455 (2011).

Akabani, et al., "Dosimetry and Radiographic Analysis of 131I-Labeled AntiTenascin 81C6 Murine Monoclonal Antibody in Newly Diagnosed Patients with Malignant Gliomas: A Phase II Study", J. Nucl. Med., 46:1042-1051 (2005).

Bougnaud, et al., "Molecular crosstalk between tumour and brain parenchyma instructs histopathological features in glioblastoma", Oncotarget, 7(22):31955-71 (2016).

(Continued)

*Primary Examiner* — Li N Komatsu
(74) *Attorney, Agent, or Firm* — Pabst Patent Group LLP

(57) ABSTRACT

Disclosed are compositions, compounds, and methods relating to peptides that can target and home to cancer, tumors, and extracellular matrix. This is based on the discovery of peptides that can specifically bind to fibronectin extra domain B (FN-EDB), tenascin-C C domain (TNC-C), or both.

24 Claims, 7 Drawing Sheets

Specification includes a Sequence Listing.

(56) References Cited

OTHER PUBLICATIONS

Braun, et al., "Etchable plasmonic nanoparticle probes to image and quantify cellular internalization", Nat. Mater., 13(9):904-11 (2014).

Brewis, et al., "Particle assembly incorporating a VP22-BH3 fusion protein, facilitating intracellular delivery, regulated release, and apoptosis", Molecular Therapy, 7(2):262-270 (2003).

Candolfi, et al., "Intracranial glioblastoma models in preclinical neuro-oncology: neuropathological characterization and tumor progression", J. Neurooncol., 85(2):133-148 (2007).

Carnemolla, et al., "Identification of a Glioblastoma-Associated Tenascin-C Isoform by a High Affinity Recombinant Antibody", Am. J. Pathol., 154(5):1345-52 (1999).

Carter, et al., "Next generation antibody drugs: pursuit of the 'high-hanging fruit'", Nat. Rev. Drug Discov., 17(3):197-223 (2018).

Casi, et al., "Noninternalizing Targeted Cytotoxics for Cancer Therapy", Mol. Pharm., 12:1880-1884 (2015).

Christian, et al., "Nucleolin expressed at the cell surface is a marker of endothelial cells in angiogenic blood vessels", J. Cell Biol., 163(4):871-878 (2003).

Dal Corso, et al., "A non-internalizing antibody-drug conjugate based on an anthracycline payload displays potent therapeutic activity in vivo", J. Control. Release, 264:211-218 (2017).

Daniels, et al., "A tenascin-C aptamer identified by tumor cell SELEX: systematic evolution of ligands by exponential enrichment", PNAS, 100(26):15416-15421 (2003).

Dervan, et al., "Sequence-specific DNA recognition by polyamide", Curr. Opin. Chem. Biol., 3(6):688-93 (1999).

Ellerby, et al., "Anti-cancer activity of targeted pro-apoptotic peptides", Nat. Med., 5(9):1032-1038 (1999).

Faul, et al., "G*Power 3: a flexible statistical power analysis program for the social, behavioral, and biomedical sciences", Behavior Research Methods, 39(2):175-191 (2007).

Forster, et al., "A review of the development of tumor vasculature and its effects on the tumor microenvironment", Hypoxia (Auckl)., 5:21-32 (2017).

GenBank Accession: ECO393808.1, "hypothetical protein GOS_3486438, partial [marine metagenome]", retrieved from the internet, <https://www.ncbi.nlm.nih.gov/protein/eco93808 >, retrieved Jan. 23, 2023.

Giblin, et al., "Tenascin-C: Form versus function", Cell Adh. Migr., 9(1-2):48-82 (2015).

Groziak, "Boron therapeutics on the horizon", Am. J. Ther., 8(5):321-8 (2001).

Hussain, et al., "Quantity and accessibility for specific targeting of receptors in tumours", Sci. Rep., 4:5232 (2014).

Järveläinen, et al., "Extracellular matrix molecules: potential targets in pharmacotherapy", Pharmacol Rev., 61(2):198-223 (2009).

Kang, et al., "Synergistic targeting tenascin C and neuropilin-1 for specific penetration of nanoparticles for anti-glioblastoma treatment", Biomaterials, 101: 60-75 (2016).

Kennedy, et al., "Editorial: which iron preparation for patients with IBD?", Pharmacol. Ther., 46(2):194-195 (2017).

Khan, et al., "EDB fibronectin and angiogenesis—a novel mechanistic pathway", Angiogenesis, 8(3):183-96 (2005).

Kim, et al., "Selection and characterization of tenascin C targeting peptide", Mol. Cells., 33(1):71-77 (2012).

Kirsch, et al., "Anti-angiogenic treatment strategies for malignant brain tumors", J Neurooncol., 50(1-2):149-63 (2000).

Kohori, et al., "Control of adriamycin cytotoxic activity using thermally responsive polymeric micelles composed of poly(Nisopropylacrylamide-co-N,N-dimethylacrylamide)-b-poly(D,L-lacide).-", Colloids Surfaces B: Biointerfaces, 16(1-4):195-205 (1999).

Kohori, et al., "Preparation and characterization of thermally Responsive block copolymer micelles comprising poly(N-isopropylacrylamide-b-D,L-lactide)", J. Control. Rel., 55(1):87-98 (1998).

Kreitman, "Recombinant toxins containing human granulocyte-macrophage colony-stimulating factor and either pseudomonas exotoxin or diphtheria toxin kill gastrointestinal cancer and leukemia cells", Blood, 90(1):252-9 (1997).

Kumra, et al., "Fibronectin-targeted drug delivery in cancer", Adv. Drug Deliv. Rev., 97:101-110 (2016).

Lambert, et al., "Antibody-Drug Conjugates (ADCs) for Personalized Treatment of Solid Tumors: A Review", Adv. In Ther., 34:1015-1035 (2017).

Liggins, et al., "Polyetherpolyester diblock copolymers for the preparation of paclitaxel loaded polymeric micelle formulations", Adv. Drug Del. Rev., 54(2):191-202 (2002).

Lin, et al., "Photonic pseudo-gap-based modification of photoluminescence from CdS nanocrystal satellites around polymer microspheres in a photonic crystal", Appl. Phys Lett., 81:3134 (2002).

Lingasamy, et al., "Bi-specific tenascin-C and fibronectin targeted peptide for solid tumor Delivery", Biomaterials, 219(119373):1-11 (2019).

Matejuk, et al., "Vaccines targeting the neovasculature of tumors", Vasc. Cell., 3(1):7 (2011).

Meade, et al., "Exogenous siRNA delivery using peptide transduction domains/cell penetrating peptides", Adv. Drug. Deliv. Rev., 59(2-3):134-40 (2007).

Mitra, et al., "Structure-activity relationship analysis of peptides targeting the EphA2 receptor", Biochemistry, 49(31):6687-6695 (2010).

Nagy, et al., "Chapter 3. The adenoviral vector angiogenesis/lymphangiogenesis assay", Methods Enzymol., 444:43-64 (2008).

Nilsson, et al., "Targeted delivery of tissue factor to the ED-B domain of fibronectin, a marker of angiogenesis, mediates the infarction of solid tumors in mice", Cancer Res., 61(2):711-716 (2001).

Paasonen, et al., "New p32/gC1qR Ligands for Targeted Tumor Drug Delivery", ChemBioChem., 17(7):570-575 (2016).

Park, et al., "Magnetic Iron Oxide Nanoworms for Tumor Targeting and Imaging", Adv. Mater., 20(9):1630-1635 (2008).

Park, et al., "Fibronectin extra domain B-specific aptide conjugated nanoparticles for targeted cancer imaging", J. Control. Release, 163:111-118 (2012).

Pedretti, et al., "Combination of temozolomide with immunocytokine F16-IL2 for the treatment of glioblastoma", Br. J. Cancer., 103(6):827-836 (2010).

Raavé, et al., "Chemotherapeutic drug delivery by tumoral extracellular matrix targeting", J. Control. Release, 274:1-8 (2018).

Rizo, et al., "Constrained peptides: models of bioactive peptides and protein substructures", Ann. Rev. Biochem., 61:387-418 (1992).

Ruoslahti, "Tumor penetrating peptides for improved drug delivery", Adv. Drug Deliv. Rev., 110-111:3-12 (2016).

Rupp, et al., "Tenascin-C Orchestrates Glioblastoma Angiogenesis by Modulation of Pro- and Anti-angiogenic Signaling", Cell Reports, 17(10):2607-2619 (2016).

Schliemann, et al., "Antibody-based targeting of the tumor vasculature", Biochim Biophys Acta., 1776(2):175-92 (2007).

Silacci, et al., "Human monoclonal antibodies to domain C of tenascin-C selectively target solid tumors in vivo", Protein Eng. Des. Sel., 19(10):471-478 (2006).

Simberg, et al., "Biomimetic amplification of nanoparticle homing to tumors", PNAS, 104(3):932-6 (2007).

Spenlé, et al., "Tenascin-C: Exploitation and collateral damage in cancer management", Cell Adh. Migr., 9(1-2):141-53 (2015).

Sugahara, et al., "Tissue-penetrating delivery of compounds and nanoparticles into tumors", Cancer Cell., 16(6):510-520 (2009).

Teesalu, et al., "Mapping of vascular ZIP codes by phage display", Methods Enzymol., 503:35-56 (2012).

Teesalu, et al., "C-end rule peptides mediate neuropilin-1-dependent cell, vascular, and tissue penetration", PNAS, 106(38):16157-62 (2009).

Tkachenko, et al., "Multifunctional gold nanoparticle-peptide complexes for nuclear targeting", J. Am. Chem. Soc., 125(16):4700-4701 (2003).

Trachsel, et al., "A Human mAb Specific to Oncofetal Fibronectin Selectively Targets Chronic Skin Inflammation In Vivo", J. Invest. Dermatol., 127(4):881-886 (2007).

Wang, et al., "Selectivity of Ligand-Receptor Interactions between Nanoparticle and Cell Surfaces", Phys. Rev. Lett., 109:238102 (2012).

(56)        References Cited

OTHER PUBLICATIONS

Wang, et al., "New Directions in Anti-Angiogenic Therapy for Glioblastoma", Neurotherapeutics, 14:321-332 (2017).

Wilhelm, et al., "Poly(styrene-ethylene oxide) block copolymer micelle formation in water: a fluorescence probe study", Macromolecules, 24(5):1033-1040 (1991).

Willmore, et al., "Targeted silver nanoparticles for ratiometric cell phenotyping", Nanoscale, 8(17):9096-9101 (2016).

Xing, et al., "Identification of a peptide for folate receptor alpha by phage display and its tumor targeting activity in ovary cancer xenograft", Sci. Rep., 8(1):8426 (2018).

Zorko, et al., "Cell-penetrating peptides: mechanism and kinetics of cargo delivery", Adv. Drug Deliv. Rev., 57(4):529-45 (2005).

International Search report for corresponding application PCT/IB2020/050847 dated Jun. 24, 2020.

Nham et al., "Macromolecular Conjugate and Biological Carrier Approaches for the Targeted Delivery of Antibotics" Antibiotics vol. 6 No. 3 (2017).

Hussain et al., "Antibiotic-loaded nanoparticles targeted to the site of infection enhance antibacterial efficacy", Nature Biomedical Engineering, Nature Publishing Group UK, London vol. 2 No. 2 p. 95-103 (2018).

Lehar et al., "Novel antibody-antibiotic conjugate eliminates intracellular *S. aureus*" Nature, vol. 527 No. 7578 p. 323-238 (2015).

David, et al., "Antibiotics-Peptide Conjugates Against Multidrug-resistant Bacterial Pathogens", Current Topics in Medicinal Chemistry, vol. 18, No. 22, 2019, pp. 1926-1936.

* cited by examiner

BI-SPECIFIC EXTRACELLULAR MATRIX BINDING PEPTIDES AND METHODS OF USE THEREOF

CROSS-REFERENCE TO RELATED APPLICATIONS

This application is a National Phase application under 35 U.S.C. 371 of PCT/IB2020/050847, filed Feb. 3, 2020, which claims the benefit of and priority to U.S. Provisional Application No. 62/800,879 filed Feb. 4, 2019, which is hereby incorporated by reference in its entirety.

REFERENCE TO SEQUENCE LISTING

The Sequence Listing submitted Feb. 4, 2020, as a text file named "TARTU_100_PCT_ST25.txt," created on Jan. 6, 2020, and having a size of 19,915 bytes is hereby incorporated by reference pursuant to 37 C.F.R. § 1.52(e)(5).

FIELD OF THE INVENTION

The present invention relates generally to the field of molecular medicine, cancer treatment, and, more specifically, to cell and tissue-targeting peptides.

BACKGROUND OF THE INVENTION

Targeting of anticancer drugs with affinity ligands, such as antibodies and homing peptides, is widely used to achieve a balance between increased drug concentration at the tumor site and reduced systemic exposure (Kennedy et al., Pharmacol. Ther. (2017), doi:10.1016/j.pharmthera.2017.03.004; Ruoslahti, Adv. Drug Deliv. Rev. (2016), doi:10.1016/j.addr.2016.03.008). In particular, antibody drug conjugates (ADCs) have seen clinical successes, with four ADCs clinically approved and >100 in different stages of clinical testing (Lambert and Morris, Adv. Ther., 1-21 (2017)). However, antibodies are expensive to manufacture and show poor tissue penetration due to a combination of large size and high affinity (Carter and Lazar, Nat. Rev. Drug Discov. 17:197-223 (2018)). In vivo peptide phage display, an agnostic explorative technique, has been used to probe vascular heterogeneity of live animals and to identify tumor homing peptides (Teesalu et al., Methods Enzymol. 503:35-56 (2012)). As phage used for in vivo display is a nanoparticle itself, the peptides are particularly well-suited for delivery of nanoparticle payloads (Ruoslahti, Adv. Drug Deliv. Rev. (2016), doi:10.1016/j.addr.2016.03.008). Homing peptide target molecules (receptors) include different cell surface molecules: e.g., av-integrins, NRP-1, folate receptor alpha, EphA2, and molecules aberrantly expressed on the surface of tumor and stromal cells such as p32, nucleolin, and calreticulin; components of blood clots and the tumor extracellular matrix (Willmore et al., Nanoscale. 8:9096-9101 (2016); Sugahara et al., Cancer Cell. 16:510-520 (2009); Paasonen et al., ChemBioChem. 17, 570-575 (2016); Christian et al., J. Cell Biol. 163:871-878 (2003); Xing et al., Sci. Rep. 8:8426 (2018); Simberg et al., Proc. Natl. Acad. Sci. U.S.A 104:932-6 (2007); Mitra et al., Biochemistry. 49:6687-6695 (2010)).

Some ECM proteins (e.g., periostin, hyaluronan, certain collagens, laminins, perlecan, fibronectin, and tenascins), over-represented in the tumor microenvironment, can provide a more robust target for affinity delivery than antigens expressed on the cell surface (Jarvelainen, Pharmacol Rev. 61:198-223 (2009)). Alternatively spliced fibronectin Extra Domain-B (FN-EDB) and Tenascin-C (TNC) are overexpressed in many solid tumors (Silacci et al., Protein Eng. Des. Sel. 19:471-478 (2006); Carnemolla et al., Am. J. Pathol. 154:1345-52 (1999); Park et al., J. Control. Release. 163:111-118 (2012)). TNC isoform C (TNC-C) shows particularly low baseline expression in non-malignant tissues and a robust upregulation in solid tumors such as malignant brain tumors and lung carcinoma (Silacci et al., Protein Eng. Des. Sel. 19:471-478 (2006); Carnemolla et al., Am. J. Pathol. 154:1345-52 (1999)). FN-EDB and TNC antibodies (e.g., FN-EDB ScFV L19, TNC-C ScFV GI1, F16, and 81C6) can be used as guiding modules for cytokines (e.g., IL2, TNF) and radionuclides (Kumra and Reinhardt, Adv. Drug Deliv. Rev. 97:101-110 (2016); Spenlé et al., Cell Adh. Migr. 9:141-53 (2015)). In addition, these antibodies have been evaluated as diagnostic imaging agents for immuno-PET, SPECT/CT and radioimmunotherapy (RIT) in malignant primary and metastatic brain tumors, and in head-and-neck squamous cell carcinoma (Kumra and Reinhardt, Adv. Drug Deliv. Rev. 97:101-110 (2016); Spenlé et al., Cell Adh. Migr. 9:141-53 (2015); Akabani et al., J. Nucl. Med. 46:1042-1051 (2005)).

Importantly, recent studies demonstrate that ECM-directed non-internalizing antibodies can be used to potentiate the cytotoxic activity of intracellularly acting cytotoxic drugs (Dal Corso et al., J. Control. Release. 264:211-218 (2017)).

However, targeting FN-EDB and TNC-C has proven difficult. Thus, there is a need for compositions and therapeutics for targeting FN-EDB, TNC-C, or both FN-EDB and TNC-C.

It is an object of the present invention to provide compositions and methods for targeting FN-EDB, TNC-C, or both FN-EDB and TNC-C.

BRIEF SUMMARY OF THE INVENTION

Disclosed are compositions, compounds, and methods relating to peptides that can target and home to cancer, tumors, and extracellular matrix. This is based on the discovery of peptides that can specifically bind to fibronectin extra domain B (FN-EDB), tenascin-C C domain (TNC-C), or both. In particular, disclosed are peptides comprising an amino acid sequence comprising (a) the sequence PPRRGLIKLKTS (SEQ ID NO:1) or a variant of the sequence PPRRGLIKLKTS (SEQ ID NO:1) with one, two, three, four, five, six, seven, eight, nine, or ten amino acid substitutions, wherein position 6 remains leucine and position 11 remains threonine, (b) the sequence TSKQNSR (SEQ ID NO:3) or a variant of the sequence TSKQNSR (SEQ ID NO:3) with one, two, three, four, five, or six amino acid substitutions, wherein position 7 remains arginine and/or position 6 remains serine, (c) the sequence AGRGRLVR (SEQ ID NO:4) or a variant of the sequence AGRGRLVR (SEQ ID NO:4) with one, two, three, four, five, six, or seven amino acid substitutions, wherein position 3 remains arginine, or (d) combinations thereof.

In some forms, the amino acid sequence can comprise the sequence PPRRGLIKLKTS (SEQ ID NO:1) or a variant of the sequence PPRRGLIKLKTS (SEQ ID NO:1) with one, two, three, four, five, six, seven, or eight amino acid substitutions. In some forms, the amino acid sequence can comprise the sequence PPRRGLIKLKTS (SEQ ID NO:1) or a variant of the sequence PPRRGLIKLKTS (SEQ ID NO:1) with one, two, three, four, five, or six amino acid substitutions. In some forms, the amino acid sequence can comprise the sequence PPRRGLIKLKTS (SEQ ID NO:1) or a variant of the sequence PPRRGLIKLKTS (SEQ ID NO:1) with one, two, three, or four amino acid substitutions. In some forms, the amino acid sequence can comprise the sequence PPRR-GLIKLKTS (SEQ ID NO:1) or a variant of the sequence PPRRGLIKLKTS (SEQ ID NO:1) having at least 50% sequence identity with the sequence PPRRGLIKLKTS (SEQ ID NO:1). In some forms, the amino acid sequence can comprise the sequence PPRRGLIKLKTS (SEQ ID NO:1) or a variant of the sequence PPRRGLIKLKTS (SEQ ID NO:1) having at least 58% sequence identity with the sequence PPRRGLIKLKTS (SEQ ID NO:1). In some forms, the amino acid sequence can comprise the sequence PPRR-GLIKLKTS (SEQ ID NO:1) or a variant of the sequence PPRRGLIKLKTS (SEQ ID NO:1) having at least 66% sequence identity with the sequence PPRRGLIKLKTS (SEQ ID NO:1). In some forms, the amino acid sequence can comprise the sequence PPRRGLIKLKTS (SEQ ID NO:1) or a variant of the sequence PPRRGLIKLKTS (SEQ ID NO:1) having at least 75% sequence identity with the sequence PPRRGLIKLKTS (SEQ ID NO:1). In some forms, the amino acid sequence can comprise the sequence PPRR-GLIKLKTS (SEQ ID NO:1) or a variant of the sequence PPRRGLIKLKTS (SEQ ID NO:1) having at least 83% sequence identity with the sequence PPRRGLIKLKTS (SEQ ID NO:1). In some forms, the amino acid sequence can comprise the sequence PPRRGLIKLKTS (SEQ ID NO:1) or a variant of the sequence PPRRGLIKLKTS (SEQ ID NO:1) having at least 91% sequence identity with the sequence PPRRGLIKLKTS (SEQ ID NO:1).

In some forms, the amino acid sequence can comprise the sequence TSKQNSR (SEQ ID NO:3) or a variant of the sequence TSKQNSR (SEQ ID NO:3) with one, two, three, four, or five amino acid substitutions. In some forms, the amino acid sequence can comprise the sequence TSKQNSR (SEQ ID NO:3) or a variant of the sequence TSKQNSR (SEQ ID NO:3) with one, two, three, or four amino acid substitutions. In some forms, the amino acid sequence can comprise the sequence TSKQNSR (SEQ ID NO:3) or a variant of the sequence TSKQNSR (SEQ ID NO:3) with one, two, or three amino acid substitutions.

In some forms, the amino acid sequence can comprise the sequence TSKQNSR (SEQ ID NO:3) or a variant of the sequence TSKQNSR (SEQ ID NO:3) with one or two amino acid substitutions. In some forms, the amino acid sequence can comprise the sequence TSKQNSR (SEQ ID NO:3) or a variant of the sequence TSKQNSR (SEQ ID NO:3) having at least 14% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 28% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 42% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 57% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 71% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 85% sequence identity with the sequence TSKQNSR (SEQ ID NO:3).

In some forms, the amino acid sequence can comprise the sequence AGRGRLVR (SEQ ID NO:4) or a variant of the sequence AGRGRLVR (SEQ ID NO:4) with one, two, three, four, five, or six amino acid substitutions, wherein position 6 remains leucine and/or position eight remains arginine. In some forms, the amino acid sequence can comprise the sequence AGRGRLVR (SEQ ID NO:4) or a variant of the sequence AGRGRLVR (SEQ ID NO:4) with one, two, three, four, or five amino acid substitutions, wherein position 6 remains leucine, position eight remains arginine, and position 5 remains arginine. In some forms, the amino acid sequence can comprise the sequence AGRGRLVR (SEQ ID NO:4) or a variant of the sequence AGRGRLVR (SEQ ID NO:4) with one, two, three, or four amino acid substitutions. In some forms, the amino acid sequence can comprise the sequence AGRGRLVR (SEQ ID NO:4) or a variant of the sequence AGRGRLVR (SEQ ID NO:4) with one, two, or three amino acid substitutions. In some forms, the amino acid sequence can comprise the sequence AGRGRLVR (SEQ ID NO:4) or a variant of the sequence AGRGRLVR (SEQ ID NO:4) with one or two amino acid substitutions. In some forms, the amino acid sequence can comprise the sequence AGRGRLVR (SEQ ID NO:4) or a variant of the sequence AGRGRLVR (SEQ ID NO:4) having at least 25% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 37% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 50% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 62% sequence identity with the sequence AGRGRLVR (SEQ ID NO:4). In some forms, the amino acid sequence can comprise the sequence AGR-GRLVR (SEQ ID NO:4) or a variant of the sequence AGRGRLVR (SEQ ID NO:4) having at least 75% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 87% sequence identity with the sequence AGRGRLVR (SEQ ID NO:4).

In some forms, (a) the amino acid sequence can comprise the formula $X_1$-$X_2$-$X_3$-$X_4$-$X_5$-$X_6$-$X_7$-$X_8$-$X_9$-$X_{10}$-$X_{11}$-$X_{12}$, (b) the amino acid sequence can comprise the formula $X_{13}$-$X_{14}$-$X_{15}$-$X_{16}$-$X_{17}$-$X_{18}$-$X_{19}$, (c) the amino acid sequence comprises the formula $X_{20}$-$X_{21}$-$X_{22}$-$X_{23}$-$X_{24}$-$X_{25}$-$X_{26}$-$X_{27}$, or (d) combinations thereof, wherein $X_6$ is leucine, wherein $X_7$ is isoleucine, leucine, or valine, wherein $X_9$ is leucine, isoleucine, or valine, wherein $X_{11}$ is threonine, wherein $X_{19}$ is arginine, lysine, histidine, glutamate, glutamine, aspartate, asparagine, or alanine, wherein $X_{18}$ is serine, alanine, glycine, asparagine, or threonine, wherein $X_{22}$ is arginine, lysine, or histidine, wherein $X_{25}$ is leucine, isoleucine, valine, or alanine, wherein $X_{27}$ is arginine, lysine, histidine, glutamate, glutamine, aspartate, asparagine, or alanine, and wherein $X_1$, $X_2$, $X_3$, $X_4$, $X_5$, $X_8$, $X_{10}$, $X_{12}$, $X_{13}$, $X_{14}$, $X_{15}$, $X_{16}$, $X_{17}$, $X_{20}$, $X_{21}$, $X_{23}$, $X_{24}$, and $X_{26}$ are each, independently, any amino acid.

In some forms, the amino acid sequence can comprise the formula $X_1$-$X_2$-$X_3$-$X_4$-$X_5$-$X_6$-$X_7$-$X_8$-$X_9$-$X_{10}$-$X_{11}$-$X_{12}$, wherein $X_8$ is leucine, wherein $X_7$ is isoleucine, leucine, or valine, wherein $X_9$ is leucine, isoleucine, or valine, wherein $X_{11}$ is threonine, and wherein $X_1$, $X_2$, $X_3$, $X_4$, $X_5$, $X_8$, $X_{10}$, and $X_{12}$ are each, independently, any amino acid. In some forms, $X_1$ can be proline, glycine, alanine, serine, or asparagine, wherein $X_2$ can be proline, glycine, alanine, serine, or asparagine, and wherein $X_5$ can be glycine, alanine, valine, leucine, or isoleucine. In some forms, $X_7$ can be isoleucine and wherein $X_9$ can be leucine.

In some forms, $X_2$ can be proline. In some forms, $X_3$ can be arginine, lysine, histidine, glutamate, glutamine, aspartate, asparagine, or alanine, wherein $X_4$ can be arginine, lysine, histidine, glutamate, glutamine, aspartate, asparagine, or alanine, wherein $X_8$ can be alanine, lysine, histidine, arginine, glutamate, glutamine, tyrosine, or tryptophan, wherein $X_{10}$ can be alanine, lysine, histidine, arginine, glutamate, glutamine, tyrosine, or tryptophan, and wherein $X_{12}$ can be serine, alanine, glycine, asparagine, threonine, glutamine, aspartate, or proline. In some forms, $X_1$ can be proline, glycine, or alanine, wherein $X_3$ can be arginine, lysine, or histidine, wherein $X_4$ can be arginine, lysine, or histidine, wherein $X_5$ can be glycine, alanine, or valine, wherein $X_8$ can be alanine, lysine, histidine, or arginine, wherein $X_{10}$ can be alanine, lysine, histidine, or arginine, and wherein $X_{12}$ can be serine, alanine, glycine, asparagine, or threonine. In some forms, any amino acid substitution at $X_7$ and $X_9$ are conservative amino acid substitutions. In some forms, any amino acid substitutions are conservative amino acid substitutions. In some forms, the amino acid sequence can comprise the sequence PPRRGLIKLKTS (SEQ ID NO:1).

In some forms, the amino acid sequence can comprise the formula $X_{13}$-$X_{14}$-$X_{15}$-$X_{16}$-$X_{17}$-$X_{18}$-$X_{19}$, wherein $X_{19}$ is arginine, lysine, histidine, glutamate, glutamine, aspartate, asparagine, or alanine, wherein $X_{18}$ is serine, alanine, glycine, asparagine, or threonine, and wherein $X_{13}$, $X_{14}$, $X_{15}$, $X_{16}$, and $X_{17}$ are each, independently, any amino acid. In some forms, $X_{16}$ can be glutamine, asparagine, glutamate, serine, threonine, aspartate, arginine, lysine, histidine, alanine, or glycine, wherein $X_{14}$ can be serine, asparagine, alanine, glycine, glutamine, threonine, aspartate, glutamate, arginine, lysine, or histidine, and wherein $X_{15}$ can be lysine, arginine, histidine, glutamate, glutamine, aspartate, asparagine, or alanine. In some forms, $X_{17}$ can be asparagine, serine, threonine, glutamine, aspartate, alanine, glycine, arginine, valine, glutamate, tyrosine, tryptophan, or lysine, and wherein $X_{13}$ can be threonine, asparagine, serine, valine, alanine, glycine, tyrosine, tryptophan, glutamine, isoleucine, leucine, phenylalanine, lysine, or aspartate. In some forms, $X_{19}$ can be arginine, lysine, or histidine, wherein $X_{18}$ can be serine or asparagine. In some forms, $X_{16}$ can be glutamine, asparagine, glutamate, serine, threonine, aspartate, or arginine, wherein $X_{14}$ can be serine, asparagine, alanine, glycine, glutamine, threonine, or aspartate, and wherein $X_{15}$ can be lysine, arginine, histidine, glutamate, glutamine, aspartate, asparagine, or alanine. In some forms, $X_{19}$ can be arginine, wherein $X_{18}$ can be serine. In some forms, $X_{16}$ can be glutamine or asparagine, wherein $X_{14}$ can be serine or asparagine, and wherein $X_{15}$ can be lysine, arginine, or histidine. In some forms, any amino acid substitution at $X_{19}$ and $X_{18}$ are conservative amino acid substitutions. In some forms, any amino acid substitutions are conservative amino acid substitutions. In some forms, the amino acid sequence can comprise the sequence TSKQNSR (SEQ ID NO:3).

In some forms, the amino acid sequence comprises the formula $X_{20}$-$X_{21}$-$X_{22}$-$X_{23}$-$X_{24}$-$X_{25}$-$X_{26}$-$X_{27}$, wherein $X_{22}$ is arginine, lysine, or histidine, wherein $X_{25}$ is leucine, isoleucine, valine, or alanine, wherein $X_{27}$ is arginine, lysine, histidine, glutamate, glutamine, aspartate, asparagine, or alanine, and wherein $X_{20}$, $X_{21}$, $X_{23}$, $X_{24}$, and $X_{26}$ are each, independently, any amino acid. In some forms, $X_{24}$ can be arginine, lysine, histidine, glutamate, glutamine, aspartate, asparagine, or alanine. In some forms, $X_{21}$ can be glycine, alanine, valine, leucine, or isoleucine, $X_{23}$ can be glycine, alanine, valine, leucine, or isoleucine and wherein $X_{26}$ can be valine, leucine, isoleucine, glycine, or alanine. In some forms, $X_{20}$ can be alanine, glycine, valine, leucine, or isoleucine. In some forms, $X_{22}$ can be arginine or lysine, wherein $X_{25}$ can be leucine, isoleucine, or valine, wherein $X_{27}$ can be arginine, lysine, or histidine. In some forms, $X_{24}$ can be arginine, lysine, or histidine. In some forms, $X_{24}$ can be arginine or lysine. In some forms, $X_{22}$ can be arginine, wherein $X_{25}$ can be leucine, wherein $X_{27}$ can be arginine. In some forms, $X_{24}$ can be arginine. In some forms, any amino acid substitution at $X_{22}$, $X_{25}$, and $X_{27}$ are conservative amino acid substitutions. In some forms, any amino acid substitutions are conservative amino acid substitutions. In some forms, the amino acid sequence can comprise the sequence AGRGRLVR (SEQ ID NO:4). In some forms, the amino acid sequence can comprise the sequence AGRGRLVRAKLAAALE (SEQ ID NO:14).

Also disclosed are peptides comprising a first amino acid sequence comprising the sequence TSKQNSR (SEQ ID NO:3) or a variant of the sequence TSKQNSR (SEQ ID NO:3) with one, two, three, four, five, or six amino acid substitutions, wherein position 7 remains arginine and/or position 6 remains serine, and a second amino acid sequence comprising the sequence AGRGRLVR (SEQ ID NO:4) or a variant of the sequence AGRGRLVR (SEQ ID NO:4) with one, two, three, four, five, six, or seven amino acid substitutions, wherein position 3 remains arginine. In some forms, the peptide can selectively bind to fibronectin extra domain B (FN-EDB) via the amino acid sequence. In some forms, the peptide can comprise an amino acid sequence having the sequence TSKQNSR (SEQ ID NO:3). In some forms, the peptide can selectively bind to tenascin-C C domain (TNC-C) via the amino acid sequence. In some forms, the peptide can comprise an amino acid sequence having the sequence AGRGRLVR (SEQ ID NO:4). In some forms, the peptide can selectively bind to both fibronectin extra domain B (FN-EDB) and tenascin-C C domain (TNC-C) via the amino acid sequence.

In some forms, the peptide can be less than 20 amino acids in length. In some forms, the peptide can be less than 15 amino acids in length. In some forms, the peptide can be 12 amino acids in length. In some forms, the peptide can comprise the sequence PPRRGLIKLKTSSNTKENS-VVASLRP (SEQ ID NO:2). In some forms, the peptide is linear. In some forms, the peptide is cyclic. In some forms, the peptide is a modified peptide. In some forms, the peptide is a methylated peptide. In some forms, the methylated peptide can comprise a methylated amino acid segment. In some forms, the peptide is N- or C-methylated in at least one position.

Also disclosed are compositions comprising any one or more of the disclosed peptides. In some forms, the composition further comprises a cargo composition, wherein the peptide and the cargo composition are covalently coupled or non-covalently associated with each other. In some forms, the peptide can selectively home to tumors expressing FN-EDB, TNC-C, or both FN-EDB and TNC-C. In some forms, the composition can selectively home to extracellular matrix having FN-EDB, TNC-C, or both FN-EDB and TNC-C. In some forms, the peptide can selectively home to tumors expressing NRP-1 (e.g., the NRP-1 b1b2 domain). In some forms, the composition can selectively home to extracellular matrix having NRP-1 (e.g., the NRP-1 b1b2 domain).

In some forms, the cargo composition can comprise a therapeutic agent, a detectable agent, a carrier, vehicle, surface molecule, or combinations thereof.

In some forms, the cargo composition can comprise a therapeutic agent. In some forms, the therapeutic agent is an anti-angiogenic agent, an anti-bacterial agent, an anti-cancer agent, an anti-inflammatory agent, a chemotherapeutic agent (such as a cancer chemotherapeutic agent), a cytotoxic agent, an immunostimulating agent, an immunosuppressing agent, a nucleic acid molecule, a polypeptide, a pro-angiogenic agent, a pro-apoptotic agent, a pro-inflammatory agent, a small molecule, or a toxin. In some forms, the therapeutic agent is $_D$(KLAKLAK)$_2$ (klaklakklaklak).

In some forms, the cargo composition can comprise a detectable agent. In some forms, the detectable agent is a label, a labeling agent, a contrast agent, an imaging agent, a microbubble (such as a fluorocarbon microbubble), a fluorophore (such as FAM, fluorescein, or rhodamine), or a radionuclide (such as carbon-11, carbon-13, indium-111, or technetium-99). In some forms, the detectable agent is FAM.

In some forms, the cargo composition can comprise a carrier, a vehicle, a surface molecule, or combinations thereof. In some forms, the carrier, vehicle and/or surface molecule independently comprise a bead, a liposome, a micelle, a microparticle, a nanoparticle (such as an albumin nanoparticle, an iron oxide nanoparticle, or a silver nanoparticle), a nanoworm (such as an iron oxide nanoworm), a phospholipid, a polymer, a phage, a phage capsid, a phage particle, a viral capsid, a viral particle, a virus, a virus-like particle, or a microbubble (such as a fluorocarbon microbubble).

In some forms, the composition can comprise a plurality of cargo compositions. In some forms, the cargo composition can comprise a surface molecule. In some forms, the peptide is conjugated with the surface molecule. In some forms, one or more of the conjugated peptides is indirectly conjugated to the surface molecule via a linker. In some forms, the composition can further comprise a plurality of linkers. In some forms, at least one of the linkers can comprise polyethylene glycol.

In some forms, the surface molecule can comprise a nanoparticle, a nanoworm, an iron oxide nanoworm, an iron oxide nanoparticle, an albumin nanoparticle, a silver nanoparticle, a liposome, a micelle, a phospholipid, a polymer, a microparticle, or a fluorocarbon microbubble. In some forms, the surface molecule can comprise a liposome. In some forms, the surface molecule can comprise an iron oxide nanoworm.

In some forms, the composition binds tumors expressing FN-EDB, TNC-C, or both FN-EDB and TNC-C. In some forms, the composition binds extracellular matrix having FN-EDB, TNC-C, or both FN-EDB and TNC-C. In some forms, the composition binds tumors expressing NRP-1 (e.g., the NRP-1 b1b2 domain). In some forms, the composition binds extracellular matrix having NRP-1 (e.g., the NRP-1 b1b2 domain). In some forms, the composition can be internalized in cells. In some forms, the composition can reduce tumor growth. In some forms, the composition further comprises one or more copies of the peptide. In some forms, the composition can comprise at least 100 copies of the peptide. In some forms, the composition can comprise at least 1000 copies of the peptide.

Also disclosed are methods comprising exposing a tumor to any one or more of the disclosed compositions. In some forms, the composition selectively binds to the tumor. In some forms, the tumor is in a subject. In some forms, the tumor is exposed to the composition by administering the composition to the subject. In some forms, the tumor expresses FN-EDB, TNC-C, or both FN-EDB and TNC-C. In some forms, the composition selectively binds to the tumor expressing FN-EDB, TNC-C, or both FN-EDB and TNC-C. In some forms, the tumor expresses NRP-1 (e.g., the NRP-1 b1b2 domain). In some forms, the composition selectively binds to the tumor expressing NRP-1 (e.g., the NRP-1 b1b2 domain).

Also disclosed are methods comprising exposing extracellular matrix to any one or more of the disclosed compositions. In some forms, the composition selectively binds to the extracellular matrix. In some forms, the extracellular matrix is in a subject. In some forms, the extracellular matrix is exposed to the composition by administering the composition to the subject. In some forms, the extracellular matrix has FN-EDB, TNC-C, or both FN-EDB and TNC-C. In some forms, the composition selectively binds to the extracellular matrix having FN-EDB, TNC-C, or both FN-EDB and TNC-C. In some forms, the extracellular matrix has NRP-1 (e.g., the NRP-1 b1b2 domain). In some forms, the composition selectively binds to the extracellular matrix having NRP-1 (e.g., the NRP-1 b1b2 domain).

In some forms, the composition has a therapeutic effect. In some forms, the therapeutic effect can comprise increase in apoptosis. In some forms, the subject has a disease or condition. In some forms, the disease is cancer. In some forms, the composition selectively homes to tumors expressing FN-EDB, TNC-C, or both FN-EDB and TNC-C. In some forms, the composition selectively homes to extracellular matrix having FN-EDB, TNC-C, or both FN-EDB and TNC-C. In some forms, the composition selectively homes to tumors expressing NRP-1 (e.g., the NRP-1 b1b2 domain). In some forms, the composition selectively homes to extracellular matrix having NRP-1 (e.g., the NRP-1 b1b2 domain).

Also disclosed are any of the disclosed compositions for use as a medicament. Also disclosed are any of the disclosed compositions for use in the treatment of cancer in a subject. Also disclosed are any of the disclosed compositions for use in the detection of cancer in a subject. Also disclosed are any of the disclosed compositions for use in the visualization of cancer in a subject. Also disclosed are any of the disclosed compositions for use in the localization of cancer in a subject.

Also disclosed is use of any of the disclosed compositions for the manufacture of a medicament for cancer treatment. Also disclosed is use of any of the disclosed compositions for the manufacture of a medicament for cancer detection.

Also disclosed are cancer diagnosis methods comprising administering an effective amount of any one or more of the disclosed compositions to a subject in need thereof.

In some forms of the disclosed methods, the disclosed compositions, or the disclosed uses, the cancer can be a cancer listed in Table 10.

In some forms of the disclosed methods, the disclosed compositions, or the disclosed uses, the cancer can be a solid tumor cancer such as cancers listed in Table 11.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A is a schematic representation of TNC-C and FN-EDB expression cassettes cloned in pET28a+ plasmid.

FIG. 1B is a diagram of expression and purification workflow for FN-EDB, TNC-C, ScFV-L19-FN-EDB and ScFV-G11-TNC-C.

FIG. 4C shows binding of peptides generated by alanine scanning of the PL2 peptide. Amino acid sequences in FIG. 4A, from left to right, are SEQ ID NOs:3, 21, 22, 69, 23, and 43. Amino acid sequences in FIG. 4B, from left to right, are SEQ ID NOs:3 and 43. Amino acid sequences in FIG. 4C, from the second sequence from the top to the bottom, are SEQ ID NOs:70-76 and 3.

DETAILED DESCRIPTION OF THE INVENTION

Figure 1A:
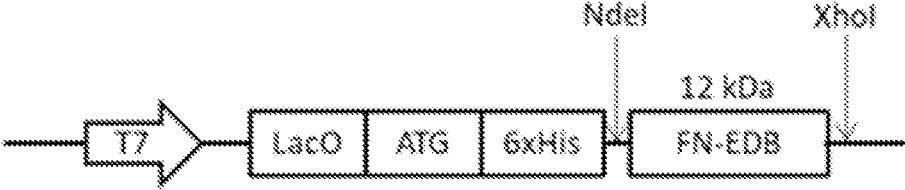
FIGS. 1A and 1B are diagrams depicting expression and purification of FN-EDB, TNC-C, single chain antibodies to FN-EDB and TNC-C.

The disclosed method and compositions can be understood more readily by reference to the following detailed description of particular embodiments and the Examples included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

As used herein, the terms "including", "includes", "having", "has", "with", or variants thereof, are intended to be inclusive similar to the term "comprising."

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

As used herein, "amino acid segment" refers to a particular portion of a larger or reference amino acid sequence (including up to the entire reference amino acid sequence). Thus, the term "amino acid segment" is generally used to make convenient reference to a specified portion of a larger or reference amino acid sequence. For example, reference to an amino acid segment can be used to refer to a defined amino acid sequence or to a portion of a reference amino acid sequence that has particular properties, functions, effects, etc. For example, a methylated amino acid segment can be used to refer to a portion of a reference amino acid sequence where the segment is methylated.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

B. General

Oncofetal fibronectin containing the extra domain B (FN-EDB) and tenascin-C C domain (TNC-C), are nearly absent in extracellular matrix of normal adult tissues, but are expressed during embryonic development and upregulated in tumors. Simultaneous affinity targeting of multiple molecules in the tumor-associated ECM can be advantageous over targeting one receptor at the time. First, expression of the tumor ECM is heterogeneous and multitargeting can result in a more uniform biodistribution of payloads in the malignant tissue. Secondly, dual targeting can alleviate issues related to limited number of available receptors for affinity ligands—a major bottleneck in affinity targeting (Hussain et al., Sci. Rep. 4:5232 (2014)).

A new bispecific peptide (PL1; amino acid sequence: PPRRGLIKLKTS; SEQ ID NO:1) has been discovered that recognizes both FN-EDB and TNC-C. It was also discovered that this dual-targeted peptide can be used for robust and specific delivery of imaging agents and therapeutic payloads to solid tumors. The PL1 peptide was derived from a 26 amino acid peptide discovered using peptide phage biopanning. It is significant to note that this result was more difficult to achieve than is typical for phage display screens. It took ten attempts (with each attempt taking about two to three weeks of work) to identify the bispecific discovery peptide. Usually, only three cycles of selection are needed to obtain a specific peptide. Here, five cycles were needed. Indeed, after three cycles, the phage binding was only a bit over 10 fold greater than background, which is still quite flat. After five cycles (about three weeks of work, versus two weeks for three cycles), a 1000 fold increase in phage binding was achieved. Before this result was obtained, it was possible that no bispecific peptide could be identified by phage display screening. The result here was the first demonstration that this was possible. Finally, the discovery was also based on an unexpected and unplanned mutation in one of the phages. A library of random peptides of 7 amino acids was used. With such a library, it was expected and almost universal that hit peptides would have 7 amino acids (the same as the length of the library peptides). Surprisingly, the discovery peptide had 26 amino acids, which occurred due to a random frameshift mutation in the phage sequence.

Systemic PL1-functionalized iron oxide nanoworms (NWs) and metallic silver nanoparticles homed to glioblastoma (GBM) and prostate carcinoma xenografts, and to intradermal angiogenic neovessels induced by VEGF-driving adenovirus, suggesting a diagnostic utility of PL1-functionalized contrast agents. GBM bearing mice treated with NWs coated with PL1 peptide in tandem with proapoptotic peptide showed a reduction of tumor volume with an increased survival, whereas treatment with untargeted particles had no effect. These discoveries show that the PL1 peptide has applications as a affinity ligand for targeted delivery of diagnostic and therapeutic compounds to cancer and tumors, especially solid tumors.

Disclosed are compositions, compounds, and methods relating to peptides that can target and home to cancer, tumors, and extracellular matrix. This is based on the discovery of peptides that can specifically bind to fibronectin extra domain B (FN-EDB), tenascin-C C domain (TNC-C), or both. In particular, disclosed are peptides comprising an amino acid sequence comprising (a) the sequence PPRRG-LIKLKTS (SEQ ID NO:1) or a variant of the sequence PPRRGLIKLKTS (SEQ ID NO:1) with one, two, three, four, five, six, seven, eight, nine, or ten amino acid substitutions, wherein position 6 remains leucine and position 11 remains threonine, (b) the sequence TSKQNSR (SEQ ID NO:3) or a variant of the sequence TSKQNSR (SEQ ID NO:3) with one, two, three, four, five, or six amino acid substitutions, wherein position 7 remains arginine and/or position 6 remains serine, (c) the sequence AGRGRLVR (SEQ ID NO:4) or a variant of the sequence AGRGRLVR (SEQ ID NO:4) with one, two, three, four, five, six, or seven amino acid substitutions, wherein position 3 remains arginine, or (d) combinations thereof. Thus, in some forms, the peptides can target cells and tissues having FN-EDB, TNC-C, or both. The disclosed peptides can also mediate targeting and delivery of compounds and compositions coupled to, associated with, conjugated to, or even co-administered with the peptide.

C. Peptides

Peptides have been discovered with useful binding properties. As described herein, these peptides and variants of these peptides can be combined with other useful materials and compositions and can be used in various methods.

Figure 2:
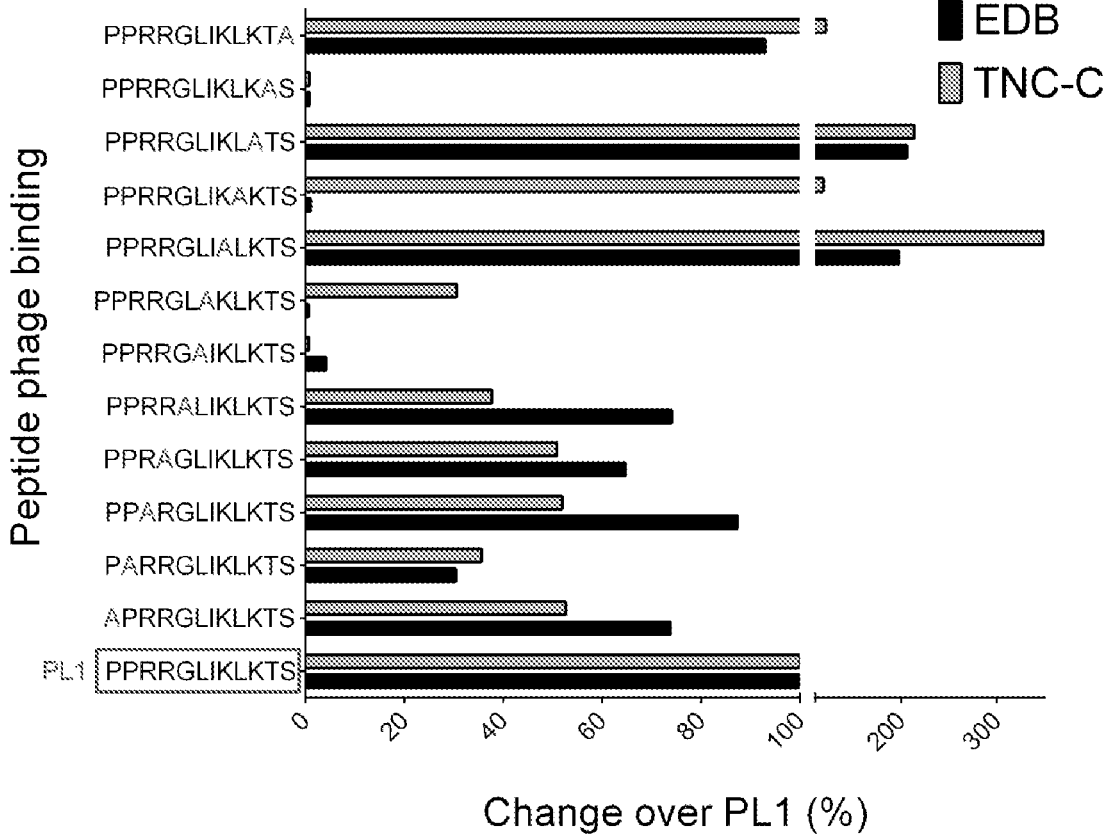
FIG. 2 is a graph showing alanine scanning mutagenesis of PL1 peptide displayed on T7 phage. The amino acids in the PL1 sequence (last sequence in the box at the bottom of the y-axis) were one-by-one substituted with an alanine residue and the phage binding to immobilized FN-EDB and TNC-C was studied. The phage binding is expressed as percent binding over parental PL1 peptide. The amino acid sequences, from top to bottom, are SEQ ID NOs:54-65 and 1.
Figure 3:
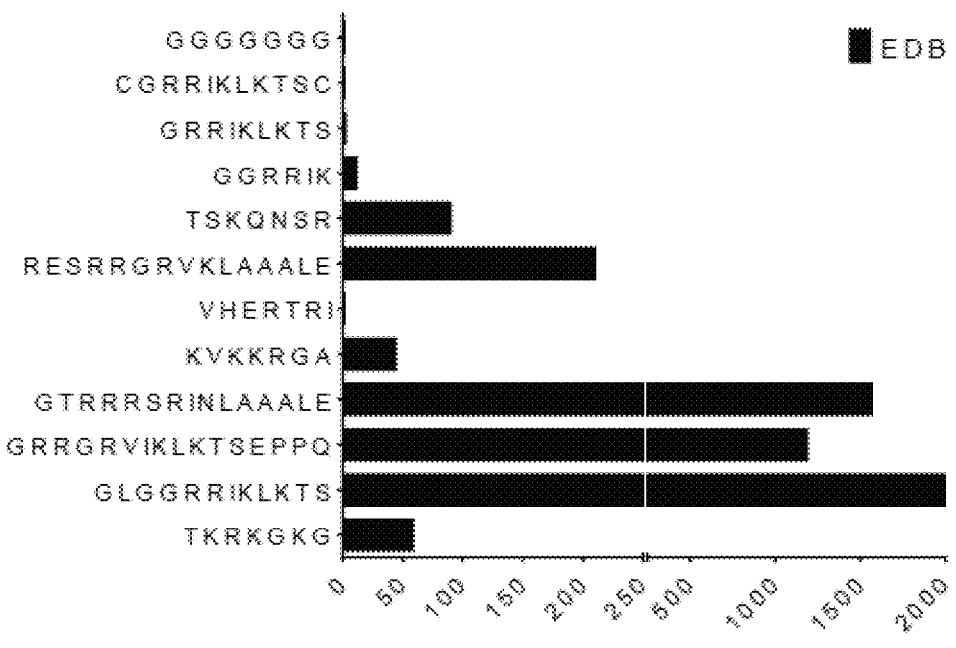
FIG. 3 is a graph showing binding of various hit peptide displaying phages to Fn-EDB (shown as fold over control phage). Amino acid sequences, from top to bottom, are SEQ ID NOs:20, 66, 67, 68, 3, 27, 26, 25, 24, 23, 22, and 21.

One type of disclosed peptide is based on the discovery sequence PPRRGLIKLKTS (SEQ ID NO:1), which is derived from an original hit sequence PPRRG-LIKLKTSSNTKENSVVASLRP (SEQ ID NO:2). Peptides related to PPRRGLIKLKTS (SEQ ID NO:1) can be referred to as LI peptides. Analysis revealed that many of the amino acids can be substituted with the peptide retaining useful binding ability. Amino acid positions 6 and 9 appear to be more important, with position 7 being important for FN-EDB binding but less important for TNC-C binding (FIG. 2). Thus, some forms of LI peptides can comprise an amino acid sequence comprising the sequence PPRRGLIKLKTS (SEQ ID NO:1) or a variant of the sequence PPRRGLIKLKTS (SEQ ID NO:1) with one, two, three, four, five, six, seven, eight, nine, or ten amino acid substitutions, wherein position 6 remains leucine and position 11 remains threonine. In some forms, the amino acid sequence can comprise the sequence PPRRGLIKLKTS (SEQ ID NO:1) or a variant of the sequence PPRRGLIKLKTS (SEQ ID NO:1) with one, two, three, four, five, six, seven, or eight amino acid substitutions. In some forms, the amino acid sequence can comprise the sequence PPRRGLIKLKTS (SEQ ID NO:1) or a variant of the sequence PPRRGLIKLKTS (SEQ ID NO:1) with one, two, three, four, five, or six amino acid substitutions. In some forms, the amino acid sequence can comprise the sequence PPRRGLIKLKTS (SEQ ID NO:1) or a variant of the sequence PPRRGLIKLKTS (SEQ ID NO:1) with one, two, three, or four amino acid substitutions. In some forms, the amino acid sequence can comprise the sequence PPRR-GLIKLKTS (SEQ ID NO:1) or a variant of the sequence PPRRGLIKLKTS (SEQ ID NO:1) having at least 50% sequence identity with the sequence PPRRGLIKLKTS (SEQ ID NO:1). In some forms, the amino acid sequence can comprise the sequence PPRRGLIKLKTS (SEQ ID NO:1) or a variant of the sequence PPRRGLIKLKTS (SEQ ID NO:1) having at least 58% sequence identity with the sequence PPRRGLIKLKTS (SEQ ID NO:1). In some forms, the amino acid sequence can comprise the sequence PPRR-GLIKLKTS (SEQ ID NO:1) or a variant of the sequence PPRRGLIKLKTS (SEQ ID NO:1) having at least 66% sequence identity with the sequence PPRRGLIKLKTS (SEQ ID NO:1). In some forms, the amino acid sequence can comprise the sequence PPRRGLIKLKTS (SEQ ID NO:1) or a variant of the sequence PPRRGLIKLKTS (SEQ ID NO:1) having at least 75% sequence identity with the sequence PPRRGLIKLKTS (SEQ ID NO:1). In some forms, the amino acid sequence can comprise the sequence PPRR-GLIKLKTS (SEQ ID NO:1) or a variant of the sequence PPRRGLIKLKTS (SEQ ID NO:1) having at least 83% sequence identity with the sequence PPRRGLIKLKTS (SEQ ID NO:1). In some forms, the amino acid sequence can comprise the sequence PPRRGLIKLKTS (SEQ ID NO:1) or a variant of the sequence PPRRGLIKLKTS (SEQ ID NO:1) having at least 91% sequence identity with the sequence PPRRGLIKLKTS (SEQ ID NO:1). Peptides related to PPRRGLIKLKTS (SEQ ID NO:1) can be referred to as LI peptides.

Figure 4A:
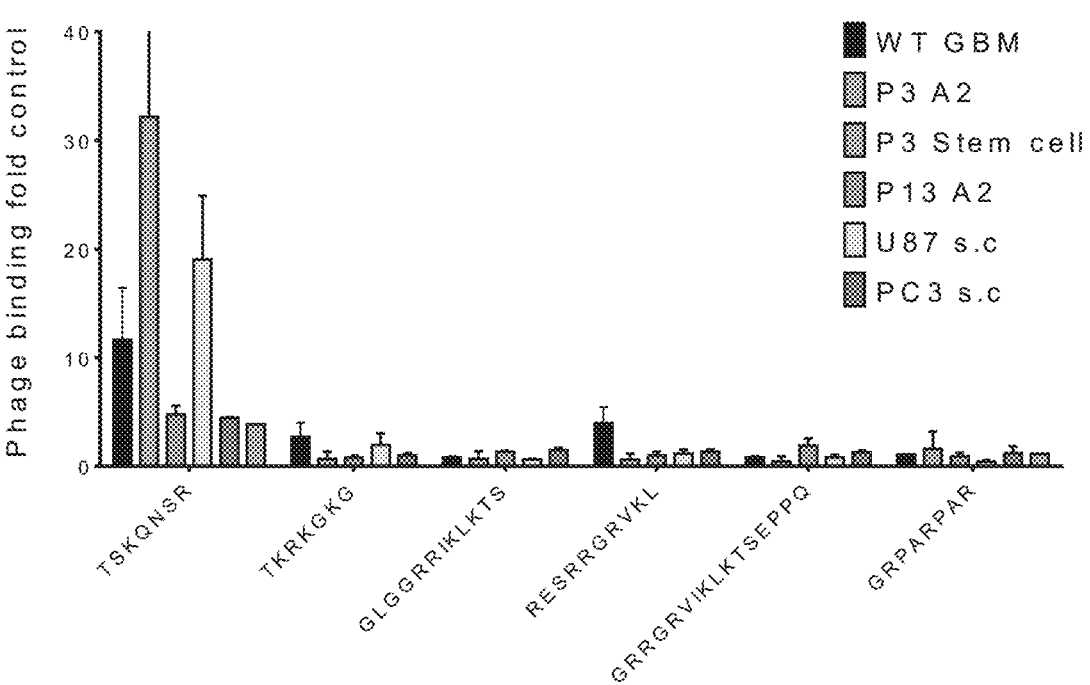
FIGS. 4A-4C are graphs showing binding of various peptides.
Figure 4B:
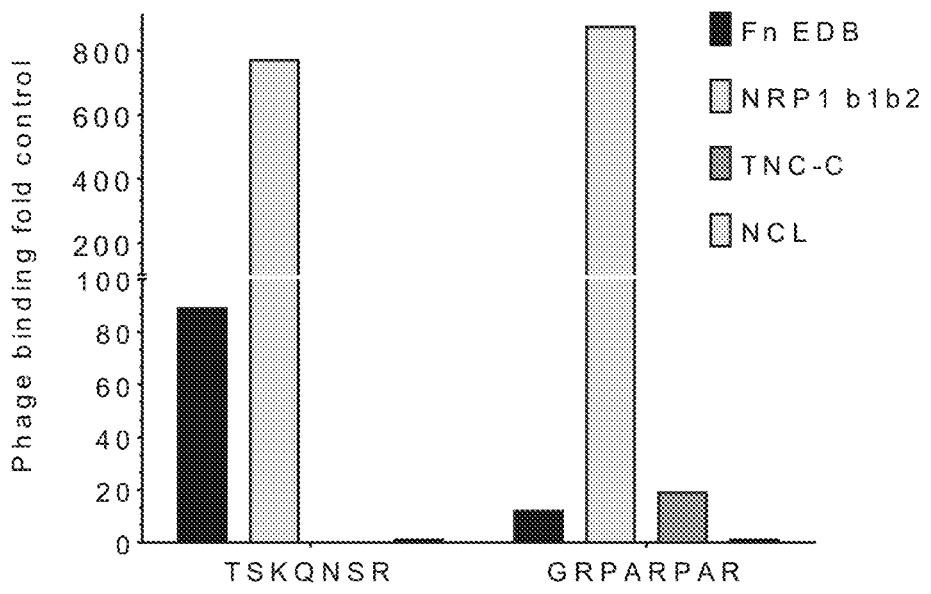
Figure 4C:
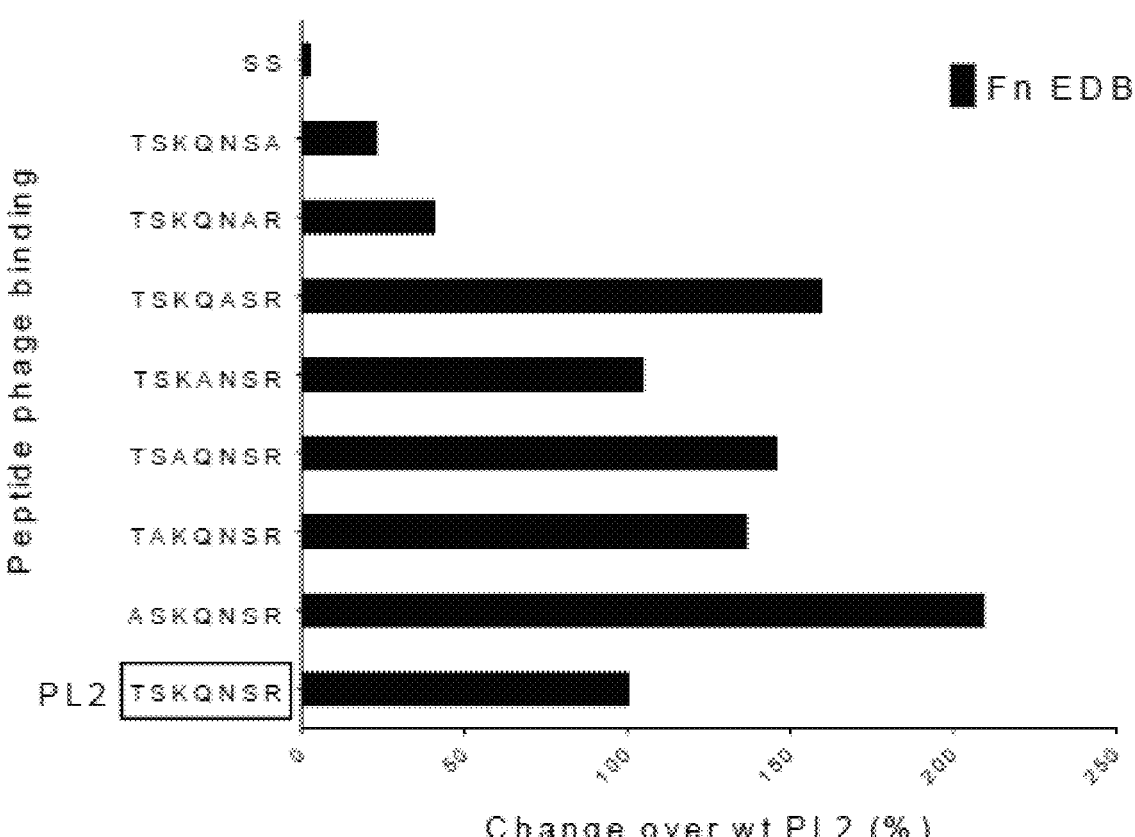
Figure 5:
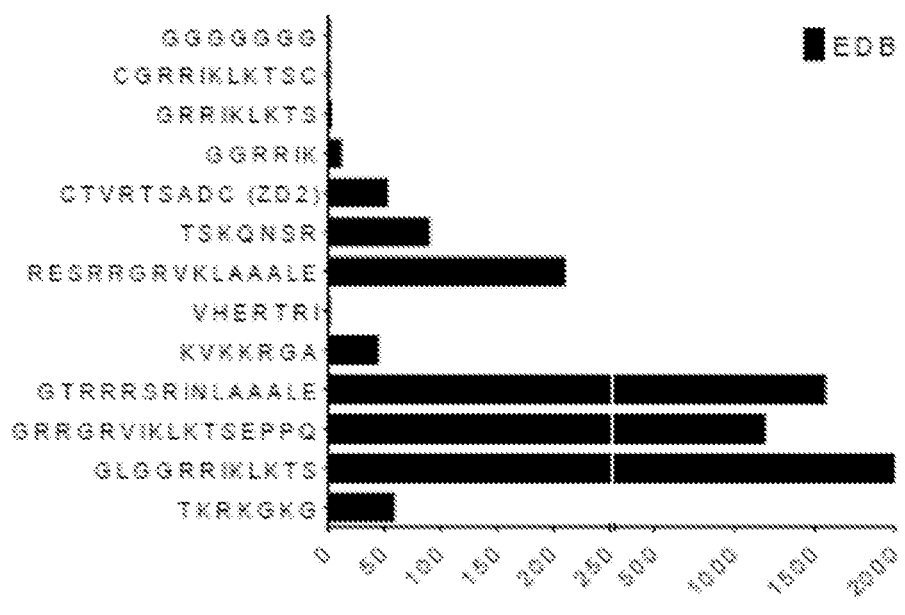
FIG. 5 is a graph showing binding of various peptides, including PL2, to Fn-EDB. Amino acid sequences in FIG. 5, from top to bottom, are SEQ ID NOs:20, 66, 67, 68, 77, 3, 27, 26, 25, 24, 23, 22, and 21.

Another type of disclosed peptide is based on the discovery sequence TSKQNSR (SEQ ID NO:3). Peptides related to TSKQNSR (SEQ ID NO:3) can be referred to as SR peptides. Analysis revealed that many of the amino acids can be substituted with the peptide retaining useful binding ability. Amino acid positions 6 and 7 appear to be more important (FIG. 4C). Thus, some forms of SR peptides can comprise an amino acid sequence comprising the sequence TSKQNSR (SEQ ID NO:3) or a variant of the sequence TSKQNSR (SEQ ID NO:3) with one, two, three, four, five, or six amino acid substitutions, wherein position 7 remains arginine and/or position 6 remains serine. In some forms, the amino acid sequence can comprise the sequence TSKQNSR (SEQ ID NO:3) or a variant of the sequence TSKQNSR (SEQ ID NO:3) with one, two, three, four, or five amino acid substitutions. In some forms, the amino acid sequence can comprise the sequence TSKQNSR (SEQ ID NO:3) or a variant of the sequence TSKQNSR (SEQ ID NO:3) with one, two, three, or four amino acid substitutions. In some forms, the amino acid sequence can comprise the sequence TSKQNSR (SEQ ID NO:3) or a variant of the sequence TSKQNSR (SEQ ID NO:3) with one, two, or three amino acid substitutions. In some forms, the amino acid sequence can comprise the sequence TSKQNSR (SEQ ID NO:3) or a variant of the sequence TSKQNSR (SEQ ID NO:3) with one or two amino acid substitutions. In some forms, the amino acid sequence can comprise the sequence TSKQNSR (SEQ ID NO:3) or a variant of the sequence TSKQNSR (SEQ ID NO:3) having at least 14% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 28% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 42% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 57% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 71% sequence identity with the sequence TSKQNSR (SEQ ID NO:3). In some forms, the amino acid sequence can comprise the sequence TSKQNSR (SEQ ID NO:3) or a variant of the sequence TSKQNSR (SEQ ID NO:3) having at least 85% sequence identity with the sequence TSKQNSR (SEQ ID NO:3). Peptides related to TSKQNSR (SEQ ID NO:3) can be referred to as SR peptides.

Figure 6:
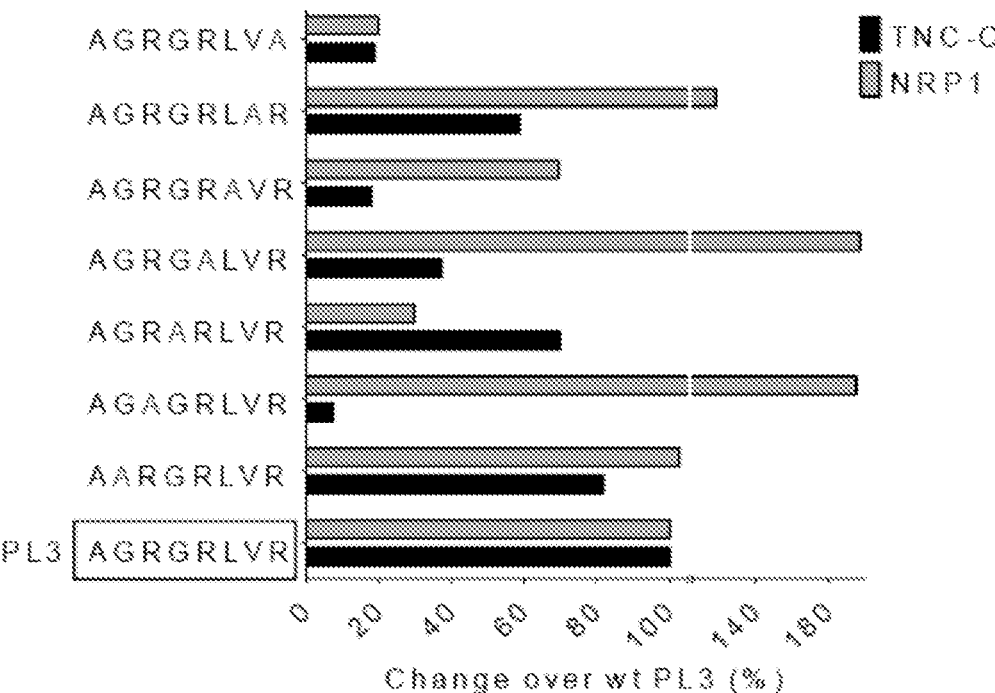
FIG. 6 is a graph showing binding of peptides generated by alanine scanning of the PL3 peptide. Amino acid sequences in FIG. 6, from top to bottom, are SEQ ID NOs:78-84 and 4.

Another type of disclosed peptide is based on the discovery sequence AGRGRLVR (SEQ ID NO:4). Peptides related to AGRGRLVR (SEQ ID NO:4) can be referred to as RLR peptides. Analysis revealed that many of the amino acids can be substituted with the peptide retaining useful binding ability. Amino acid positions 3, 5, 6, and 8 appear to be more important for TNC-C binding (FIG. 6). Thus, some forms of RLR peptides can comprise an amino acid sequence comprising the sequence AGRGRLVR (SEQ ID NO:4) or a variant of the sequence AGRGRLVR (SEQ ID NO:4) with one, two, three, four, five, six, or seven amino acid substitutions, wherein position 3 remains arginine. In some forms, the amino acid sequence can comprise the sequence AGR-GRLVR (SEQ ID NO:4) or a variant of the sequence AGRGRLVR (SEQ ID NO:4) with one, two, three, four, five, or six amino acid substitutions, wherein position 6 remains leucine and/or position eight remains arginine. In some forms, the amino acid sequence can comprise the sequence AGRGRLVR (SEQ ID NO:4) or a variant of the sequence AGRGRLVR (SEQ ID NO:4) with one, two, three, four, or five amino acid substitutions, wherein position 6 remains leucine, position eight remains arginine, and position 5 remains arginine. In some forms, the amino acid sequence can comprise the sequence AGRGRLVR (SEQ ID NO:4) or a variant of the sequence AGRGRLVR (SEQ ID NO:4) with one, two, three, or four amino acid substitutions. In some forms, the amino acid sequence can comprise the sequence AGRGRLVR (SEQ ID NO:4) or a variant of the sequence AGRGRLVR (SEQ ID NO:4) with one, two, or three amino acid substitutions. In some forms, the amino acid sequence can comprise the sequence AGRGRLVR (SEQ ID NO:4) or a variant of the sequence AGRGRLVR (SEQ ID NO:4) with one or two amino acid substitutions. In some forms, the amino acid sequence can comprise the sequence AGRGRLVR (SEQ ID NO:4) or a variant of the sequence AGRGRLVR (SEQ ID NO:4) having at least 25% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 37% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 50% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 62% sequence identity with the sequence AGRGRLVR (SEQ ID NO:4). In some forms, the amino acid sequence can comprise the sequence AGR-GRLVR (SEQ ID NO:4) or a variant of the sequence AGRGRLVR (SEQ ID NO:4) having at least 75% sequence identity with the sequence AGRGRLVR (SEQ ID NO:4). In some forms, the amino acid sequence can comprise the sequence AGRGRLVR (SEQ ID NO:4) or a variant of the sequence AGRGRLVR (SEQ ID NO:4) having at least 87% sequence identity with the sequence AGRGRLVR (SEQ ID NO:4). Peptides related to AGRGRLVR (SEQ ID NO:4) can be referred to as RLR peptides.

In some forms, the (a) the amino acid sequence can comprise the formula $X_1$-$X_2$-$X_3$-$X_4$-$X_5$-$X_6$-$X_7$-$X_8$-$X_9$-$X_{10}$-$X_{11}$-$X_{12}$, (b) the amino acid sequence can comprise the formula $X_{13}$-$X_{14}$-$X_{15}$-$X_{16}$-$X_{17}$-$X_{18}$-$X_{19}$, (c) the amino acid sequence comprises the formula $X_{20}$-$X_{21}$-$X_{22}$-$X_{23}$-$X_{24}$-$X_{25}$-$X_{26}$-$X_{27}$, or (d) combinations thereof, wherein $X_6$ is leucine, wherein $X_7$ is isoleucine, leucine, or valine, wherein $X_9$ is leucine, isoleucine, or valine, wherein $X_{11}$ is threonine, wherein $X_{19}$ is arginine, lysine, histidine, glutamate, gluta-mine, aspartate, asparagine, or alanine, wherein $X_{18}$ is ser-ine, alanine, glycine, asparagine, or threonine, wherein $X_{22}$ is arginine, lysine, or histidine, wherein $X_{25}$ is leucine, isoleucine, valine, or alanine, wherein $X_{27}$ is arginine, lysine, histidine, glutamate, glutamine, aspartate, aspara-gine, or alanine, and wherein $X_1$, $X_2$, $X_3$, $X_4$, $X_5$, $X_8$, $X_{10}$, $X_{12}$, $X_{13}$, $X_{14}$, $X_{15}$, $X_{16}$, $X_{17}$, $X_{20}$, $X_{21}$, $X_{23}$, $X_{24}$, and $X_{26}$ are each, independently, any amino acid. Peptides of the formula $X_1$-$X_2$-$X_3$-$X_4$-$X_5$-$X_6$-$X_7$-$X_8$-$X_9$-$X_{10}$-$X_{11}$-$X_{12}$ are LI peptides. Peptides of the formula $X_{13}$-$X_{14}$-$X_{15}$-$X_{16}$-$X_{17}$-$X_{18}$-$X_{19}$ are SR peptides. Peptides of the formula $X_{20}$-$X_{21}$-$X_{22}$-$X_{23}$-$X_{24}$-$X_{25}$-$X_{26}$-$X_{27}$ are RLR peptides.

LI peptides can also be described in terms of an amino acid sequence comprising the formula $X_1$-$X_2$-$X_3$-$X_4$-$X_5$-$X_6$-$X_7$-$X_8$-$X_9$-$X_{10}$-$X_{11}$-$X_{12}$, wherein $X_6$ is leucine, wherein $X_7$ is isoleucine, leucine, or valine, wherein $X_9$ is leucine, isoleucine, or valine, wherein $X_{11}$ is threonine, and wherein $X_1$, $X_2$, $X_3$, $X_4$, $X_5$, $X_8$, $X_{10}$, and $X_{12}$, are each, indepen-dently, any amino acid. In some forms, the amino acid sequence can comprise the formula $X_1$-$X_2$-$X_3$-$X_4$-$X_5$-$X_6$-$X_7$-$X_8$-$X_9$-$X_{10}$-$X_{11}$-$X_{12}$, wherein $X_6$ is leucine, wherein $X_7$ is isoleucine, leucine, or valine, wherein $X_9$ is leucine, isoleucine, or valine, wherein $X_{11}$ is threonine, and wherein $X_1$, $X_2$, $X_3$, $X_4$, $X_5$, $X_8$, $X_{10}$, and $X_{12}$ are each, indepen-dently, any amino acid. In some forms, $X_1$ can be proline, glycine, alanine, serine, or asparagine, wherein $X_2$ can be proline, glycine, alanine, serine, or asparagine, and wherein $X_5$ can be glycine, alanine, valine, leucine, or isoleucine. In some forms, $X_7$ can be isoleucine and wherein $X_9$ can be leucine. In some forms, $X_2$ can be proline. In some forms, $X_3$ can be arginine, lysine, histidine, glutamate, glutamine, aspartate, asparagine, or alanine, wherein $X_4$ can be argi-nine, lysine, histidine, glutamate, glutamine, aspartate, asparagine, or alanine, wherein $X_8$ can be alanine, lysine, histidine, arginine, glutamate, glutamine, tyrosine, or tryp-tophan, wherein $X_{10}$ can be alanine, lysine, histidine, argi-nine, glutamate, glutamine, tyrosine, or tryptophan, and wherein $X_{12}$ can be serine, alanine, glycine, asparagine, threonine, glutamine, aspartate, or proline. In some forms, $X_1$ can be proline, glycine, or alanine, wherein $X_3$ can be arginine, lysine, or histidine, wherein $X_4$ can be arginine, lysine, or histidine, wherein $X_5$ can be glycine, alanine, or valine, wherein $X_8$ can be alanine, lysine, histidine, or arginine, wherein $X_{10}$ can be alanine, lysine, histidine, or arginine, and wherein $X_{12}$ can be serine, alanine, glycine, asparagine, or threonine. In some forms, any amino acid substitution at $X_7$ and $X_9$ are conservative amino acid substitutions. In some forms, any amino acid substitutions are conservative amino acid substitutions. In some forms, the amino acid sequence can comprise the sequence PPRR-GLIKLKTS (SEQ ID NO:1).

SR peptides can also be described in terms of an amino acid sequence comprising the formula $X_{13}$-$X_{14}$-$X_{15}$-$X_{16}$-$X_{17}$-$X_{18}$-$X_{19}$, wherein $X_{19}$ is arginine, lysine, histidine, glutamate, glutamine, aspartate, asparagine, or alanine, wherein $X_{18}$ is serine, alanine, glycine, asparagine, or threo-nine, and wherein $X_{13}$, $X_{14}$, $X_{15}$, $X_{16}$, and $X_{17}$, are each, independently, any amino acid. In some forms, the amino acid sequence can comprise the formula $X_{13}$-$X_{14}$-$X_{15}$-$X_{16}$-$X_{17}$-$X_{18}$-$X_{19}$, wherein $X_{19}$ is arginine, lysine, histidine, glutamate, glutamine, aspartate, asparagine, or alanine, wherein $X_{18}$ is serine, alanine, glycine, asparagine, or threo-nine, and wherein $X_{13}$, $X_{14}$, $X_{15}$, $X_{16}$, and $X_{17}$ are each, independently, any amino acid. In some forms, $X_{16}$ can be glutamine, asparagine, glutamate, serine, threonine, aspar-tate, arginine, lysine, histidine, alanine, or glycine, wherein $X_{14}$ can be serine, asparagine, alanine, glycine, glutamine, threonine, aspartate, glutamate, arginine, lysine, or histidine, and wherein $X_{15}$ can be lysine, arginine, histidine, gluta-mate, glutamine, aspartate, asparagine, or alanine. In some forms, $X_{17}$ can be asparagine, serine, threonine, glutamine, aspartate, alanine, glycine, arginine, valine, glutamate, tyro-sine, tryptophan, or lysine, and wherein $X_{13}$ can be threo-nine, asparagine, serine, valine, alanine, glycine, tyrosine, tryptophan, glutamine, isoleucine, leucine, phenylalanine, lysine, or aspartate. In some forms, $X_{19}$ can be arginine, lysine, or histidine, wherein $X_{18}$ can be serine or asparagine. In some forms, $X_{16}$ can be glutamine, asparagine, glutamate, serine, threonine, aspartate, or arginine, wherein $X_{14}$ can be serine, asparagine, alanine, glycine, glutamine, threonine, or aspartate, and wherein $X_{15}$ can be lysine, arginine, histidine, glutamate, glutamine, aspartate, asparagine, or alanine. In some forms, $X_{19}$ can be arginine, wherein $X_{18}$ can be serine. In some forms, $X_{16}$ can be glutamine or asparagine, wherein $X_{14}$ can be serine or asparagine, and wherein $X_{15}$ can be lysine, arginine, or histidine. In some forms, any amino acid substitution at $X_{19}$ and $X_{18}$ are conservative amino acid substitutions. In some forms, any amino acid substitutions are conservative amino acid substitutions. In some forms, the amino acid sequence can comprise the sequence TSKQNSR (SEQ ID NO:3).

RLR peptides can also be described in terms of an amino acid sequence comprising the formula $X_{20}$-$X_{21}$-$X_{22}$-$X_{23}$-$X_{24}$-$X_{25}$-$X_{26}$-$X_{27}$, wherein $X_{22}$ is arginine, lysine, or histidine, wherein $X_{25}$ is leucine, isoleucine, valine, or alanine, wherein $X_{27}$ is arginine, lysine, histidine, glutamate, glutamine, aspartate, asparagine, or alanine, and wherein $X_{20}$, $X_{21}$, $X_{23}$, $X_{24}$, and $X_{26}$ are each, independently, any amino acid. In some forms, the amino acid sequence comprises the formula $X_{20}$-$X_{21}$-$X_{22}$-$X_{23}$-$X_{24}$-$X_{25}$-$X_{26}$-$X_{27}$, wherein $X_{22}$ is arginine, lysine, or histidine, wherein $X_{25}$ is leucine, isoleucine, valine, or alanine, wherein $X_{27}$ is arginine, lysine, histidine, glutamate, glutamine, aspartate, asparagine, or alanine, and wherein $X_{20}$, $X_{21}$, $X_{23}$, $X_{24}$, and $X_{26}$ are each, independently, any amino acid. In some forms, $X_{24}$ can be arginine, lysine, histidine, glutamate, glutamine, aspartate, asparagine, or alanine. In some forms, $X_{21}$ can be glycine, alanine, valine, leucine, or isoleucine, $X_{23}$ can be glycine, alanine, valine, leucine, or isoleucine and wherein $X_{26}$ can be valine, leucine, isoleucine, glycine, or alanine. In some forms, $X_{20}$ can be alanine, glycine, valine, leucine, or isoleucine. In some forms, $X_{22}$ can be arginine or lysine, wherein $X_{25}$ can be leucine, isoleucine, or valine, wherein $X_{27}$ can be arginine, lysine, or histidine. In some forms, $X_{24}$ can be arginine, lysine, or histidine. In some forms, $X_{24}$ can be arginine or lysine. In some forms, $X_{22}$ can be arginine, wherein $X_{25}$ can be leucine, wherein $X_{27}$ can be arginine. In some forms, $X_{24}$ can be arginine. In some forms, any amino acid substitution at $X_{22}$, $X_{25}$, and $X_{27}$ are conservative amino acid substitutions. In some forms, any amino acid substitutions are conservative amino acid substitutions. In some forms, the amino acid sequence can comprise the sequence AGRGRLVR (SEQ ID NO:4). In some forms, the amino acid sequence can comprise the sequence AGRGRLVRAKLAAALE (SEQ ID NO:14).

Also disclosed are peptides comprising a first amino acid sequence comprising the sequence TSKQNSR (SEQ ID NO:3) or a variant of the sequence TSKQNSR (SEQ ID NO:3) with one, two, three, four, five, or six amino acid substitutions, wherein position 7 remains arginine and/or position 6 remains serine, and a second amino acid sequence comprising the sequence AGRGRLVR (SEQ ID NO:4) or a variant of the sequence AGRGRLVR (SEQ ID NO:4) with one, two, three, four, five, six, or seven amino acid substitutions, wherein position 3 remains arginine. In some forms, the peptide can selectively bind to fibronectin extra domain B (FN-EDB) via the amino acid sequence. In some forms, the peptide can comprise an amino acid sequence having the sequence TSKQNSR (SEQ ID NO:3). In some forms, the peptide can selectively bind to tenascin-C C domain (TNC-C) via the amino acid sequence. In some forms, the peptide can comprise an amino acid sequence having the sequence AGRGRLVR (SEQ ID NO:4). In some forms, the peptide can selectively bind to both fibronectin extra domain B (FN-EDB) and tenascin-C C domain (TNC-C) via the amino acid sequence.

In some forms, the peptide can be less than 20 amino acids in length. In some forms, the peptide can be less than 15 amino acids in length. In some forms, the peptide can be 12 amino acids in length. In some forms, the peptide can comprise the sequence PPRRGLIKLKTSSNTKENS-VVASLRP (SEQ ID NO:2). In some forms, the peptide is linear. In some forms, the peptide is cyclic. In some forms, the peptide is a modified peptide. In some forms, the peptide is a methylated peptide. In some forms, the methylated peptide can comprise a methylated amino acid segment. In some forms, the peptide is N- or C-methylated in at least one position.

The disclosed peptides preferably include the sequences of (1) one or more LI peptides, (2) one or more SR peptides, (3) one or more RLR peptides, (4) one or more LI peptides and one or more SR peptides, (5) one or more LI peptides and one or more RLR peptides, (6) one or more SR peptides and one or more RLR peptides, or (7) one or more LI peptides, one or more SR peptides, and one or more RLR peptides. Such peptides (i.e., peptides having any of these combinations) can be referred to as LSR peptides. The disclosed compositions preferably include (1) one or more LI peptides, (2) one or more SR peptides, (3) one or more RLR peptides, (4) one or more LI peptides and one or more SR peptides, (5) one or more LI peptides and one or more RLR peptides, (6) one or more SR peptides and one or more RLR peptides, or (7) one or more LI peptides, one or more SR peptides, and one or more RLR peptides. Such compositions can be referred to as LSR compositions.

Peptides including the sequences of one or more LI peptides and one or more SR peptides can be referred to as LS peptides. Peptides including the sequences of one or more LI peptides and one or more RLR peptides can be referred to as LR peptides. Peptides including the sequences of one or more SR peptides and one or more RLR peptides can be referred to as RS peptides. Peptides including the sequences of one or more LI peptides, one or more SR peptides, and one or more RLR peptides can be referred to as LSR peptides.

Peptides including the sequences of one or more LI peptides, one or more SR peptides, or both, can be referred to as L/S peptides. Peptides including the sequences of one or more LI peptides, one or more RLR peptides, or both, can be referred to as L/R peptides. Peptides including the sequences of one or more SR peptides, one or more RLR peptides, or both can be referred to as S/R peptides. Peptides including the sequences of one or more LI peptides, one or more SR peptides, one or more RLR peptides, or combinations thereof, can be referred to as L/S/R peptides.

Peptides that can bind FN-EDB can be referred to as FN-EDB peptides. Peptides that can bind TNC-C can be referred to as TNC-C peptides. Peptides that can bind both FN-EDB and TNC-C can be referred to as FN-EDB/TNC-C peptides. Note that an FN-EDB/TNC-C peptide also constitutes an FN-EDB peptide and a TNC-C peptide. Peptides that bind FN-EDB or TNC-C or both FN-EDB and TNC-C can be referred to as F/T/F&T peptides. Note that F/T/F&T peptides include FN-EDB peptide, TNC-C peptides, and FN-EDB/TNC-C peptides.

In the case of the disclosed F/T/F&T peptides, the peptides can provide both homing to cells and tissue that has FN-EDB, TNC-C, or both FN-EDB and TNC-C. For example, some cancer and extracellular matrix has FN-EDB. In some forms, the peptides can selectively home to or bind cells expressing FN-EDB, TNC-C, or both FN-EDB and TNC-C. In some forms, the peptides can selectively home to or bind cells expressing NRP-1 (e.g., b1b2 domain), TNC-C, or both NRP-1 (e.g., b1b2 domain) and TNC-C.

Any of the disclosed peptides (such as F/T/F&T peptides) can be composed of, for example, amino acids, amino acid analogs, peptide analogs, amino acid mimetics, peptide mimetics, etc. Although structures, design, etc. of the disclosed peptides is described herein in terms of amino acids and peptides composed of amino acids for convenience, it is understood that analogous analogs, mimetics, modified forms, etc. of amino acids and peptides can also be used as the disclosed peptides and designed using similar principles.

Any component, such as the components disclosed herein, can overlap, be adjacent to, and/or be upstream, downstream, or both of a peptide, such as an F/T/F&T peptide. Examples of such components include accessory molecules, homing molecules, protease cleavage sites, etc. It is useful to have some components coupled to or associated with a peptide, such as an F/T/F&T peptide to be downstream (C-terminal) of the peptide. For example, activatable peptide having an accessory protein or a homing peptide downstream of the peptide (and thus downstream from the cleavage site for activation) will be separated from the peptide when it is activated. As another example, activatable peptides having an accessory molecule or a homing molecule downstream of the peptide (and thus downstream from the cleavage site for activation) will be separated from the peptide when it is activated. This can have some advantages such as making the peptide function more efficient or reducing the chance for extraneous effects of the eliminated component.

As used herein, the term "variant" refers to a peptide, polypeptide, oligonucleotide, or polynucleotide that differs from a reference peptide, polypeptide, oligonucleotide, or polynucleotide, but retains essential properties. A typical variant of a peptide differs in amino acid sequence from another, reference peptide. Generally, differences are limited so that the sequences of the reference peptide and the variant are closely similar overall and, in many regions, identical. A variant and reference peptide may differ in amino acid sequence by one or more modifications (e.g., substitutions, additions, and/or deletions). A substituted or inserted amino acid residue may or may not be one encoded by the genetic code. A variant of a peptide, polypeptide, oligonucleotide, or polynucleotide may be naturally occurring such as an allelic variant, or it may be a variant that is not known to occur naturally.

Modifications and changes can be made in the structure of the peptides and polypeptides and still obtain a molecule having similar characteristics as the peptide or polypeptide (e.g., a conservative amino acid substitution). For example, certain amino acids can be substituted for other amino acids in a sequence without appreciable loss of activity. Because it is the interactive capacity and nature of a peptide or polypeptide that defines that peptide's or polypeptide's biological or chemical functional activity, certain amino acid sequence substitutions can be made in a peptide or polypeptide sequence and nevertheless obtain a peptide or polypeptide with like properties.

In making some such changes, various factors and modes can be considered. For example, in some forms, the hydropathic index of amino acids can be considered. The importance of the hydropathic amino acid index in conferring interactive biologic function on a peptide or polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred. Substitutions based on similarity in hydropathic index can be referred to as hydropathic index substitutions.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred. Substitutions based on similarity in hydrophilicity values can be referred to as hydrophilicity values substitutions.

As outlined above, amino acid substitutions can generally be based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). As used herein, a conservative amino acid substitution is such a substitution.

Amino acid substitutions can also be based on other categorizations of amino acids an amino acid substitutions. For example, amino acid substitutions can be based on Taylor classification (Taylor, *J. Theor. Biol.* 119:205-218 (1986)). Taylor classification is based multiple amino acid characteristics, principally size of the side chain and hydrophobicity.

Figure 10:
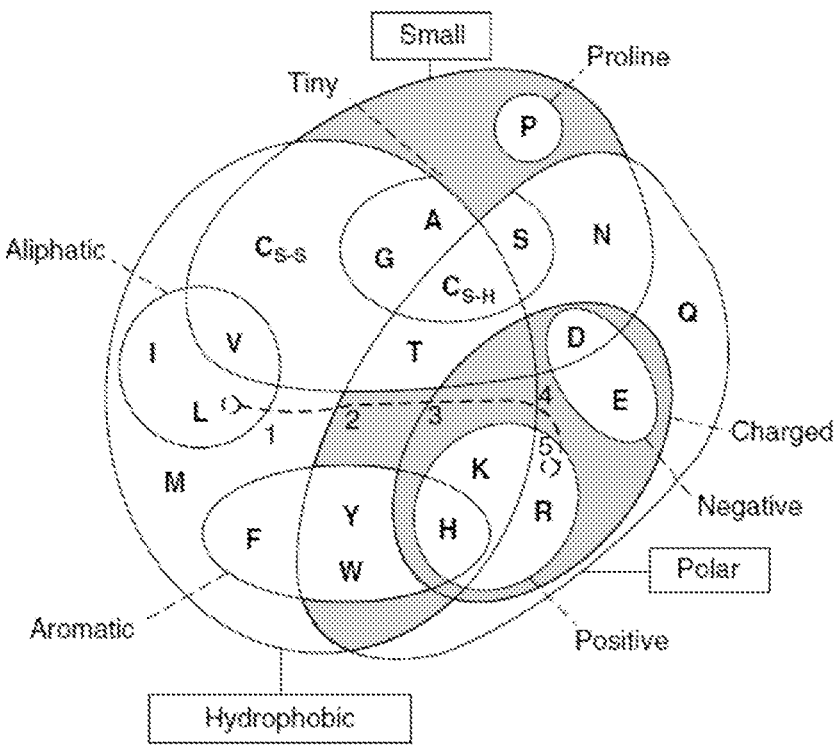
FIG. 10 is a Venn diagram showing Taylor classification of amino acids.

The Taylor classification is normally displayed as a Venn diagram (FIG. 10). Taylor classification can be used by specifying amino acid substitutions in terms of how many boundaries are crossed to trace a path form the original or current amino acid to the substituting amino acid. This is illustrated in FIG. 10 by showing that five boundaries are crossed in moving from leucine (L) to arginine (R). Thus, Taylor amino acid substitutions can be specified as up to one boundary crossing, two boundary crossings, three boundary crossings, four boundary crossings, five boundary crossings, six boundary crossings, or seven boundary crossings. Preferred amino acids substitutions are those with up to three boundary crossings. More preferred are amino acids substitutions with up to two boundary crossings. Most preferred are amino acids substitutions are those with up to one boundary crossing.

Functional or biological equivalents of a peptide are contemplated as set forth above. In particular, embodiments of the peptides or polypeptides can include variants having about 50%, 60%, 70%, 80%, 90%, 95%, 96%, 97%, 98%, 99%, or more sequence identity to the peptide of interest.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have a length of up to 10, 20, 30, 40, 50, 100, 150, 200, 250, 300, 400, 500, 1000 or 2000 residues. In particular embodiments, the disclosed peptides can have a length of at least 7, 8, 9, 10, 15, 20, 25, 30, 40, 50, 60, 70, 80, 90, 100 or 200 residues. In further embodiments, the disclosed peptides can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

A protein or peptide containing an L/S/R or F/T/F&T peptide can have a length of up to 50, 100, 150, 200, 250, 300, 400, 500, 1000 or 2000 residues. In particular embodiments, the protein or peptide portion of an L/S/R or F/T/F&T composition can have a length of at least 10, 20, 30, 40, 50, 60, 70, 80, 90, 100 or 200 residues. In further embodiments, the protein or peptide containing an L/S/R or F/T/F&T peptide can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The disclosed conjugates can have a length of up to 50, 100, 150, 200, 250, 300, 400, 500, 1000 or 2000 residues. In particular embodiments, the disclosed conjugates can have a length of at least 10, 20, 30, 40, 50, 60, 70, 80, 90, 100 or 200 residues. In further embodiments, the disclosed conjugates can have a length of 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The protein or peptide portion of an L/S/R or F/T/F&T composition can have a length of up to 50, 100, 150, 200, 250, 300, 400, 500, 1000 or 2000 residues. In particular embodiments, the protein or peptide portion of an L/S/R or F/T/F&T composition can have a length of at least 10, 20, 30, 40, 50, 60, 70, 80, 90, 100 or 200 residues. In further embodiments, the protein or peptide portion of an L/S/R or F/T/F&T composition can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The disclosed compositions can have a length of up to 50, 100, 150, 200, 250, 300, 400, 500, 1000 or 2000 residues. In particular embodiments, the disclosed compositions can have a length of at least 10, 20, 30, 40, 50, 60, 70, 80, 90, 100 or 200 residues. In further embodiments, the disclosed compositions can have a length of 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

F/T/F&T and other disclosed peptides can be stabilized against proteolysis. For example, the stability and activity of peptides can be increased by protecting some of the peptide bonds with N-methylation or C-methylation. Accessory peptides and homing peptides can also or similarly be stabilized against proteolysis.

The disclosed peptides can be made in the form of stabilized peptides and/or formulated as long-circulating forms. For example, a polyethylene glycol conjugate can be used. The disclosed peptides and/or cargos can also be administered over a period of time. For example, disclosed peptides and/or cargos can be delivered with an osmotic pump. This can extend the permeability of the target cells and tissues. Modified forms of the disclosed peptides can be used. For example, disclosed peptides can be methylated (which can stabilize the peptides against proteolysis). Stability against cleavage is desirable, except for bonds to be cleaved to activate a peptide. Modifications to the disclosed peptides generally should leave them functional. A peptide with a structural difference from naturally occurring forms of peptides can be considered a modified peptide.

It is understood that there are numerous amino acid and peptide analogs which can be incorporated into the disclosed compositions, conjugates, molecules, proteins, peptides, and elements. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10): 400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH) $CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH) $CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides as long as activity is preserved. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

The disclosed peptides can be validated by, for example, testing in vitro binding to FN-EDB, TNC-C, or both, and in vivo homing to cells and tissues having FN-EDB, TNC-C, or both. A peptide can be screened or tested for the binding and homing ability of the disclosed peptides by, for example, testing in vitro binding to FN-EDB, TNC-C, or both, and in vivo homing to cells and tissues having FN-EDB, TNC-C, or both. For example, specific binding to cells and tissues having FN-EDB, TNC-C, or both can be tested by assessing binding of the peptide to cells and tissues having FN-EDB, TNC-C, or both or an appropriate test cell or cell line. For example, specific binding to cells and tissues having FN-EDB, TNC-C, or both can be tested or assessed using cells of the cell lines J774A.1 and RAW264.7. Specificity of binding to the cell or tissue having FN-EDB, TNC-C, or both or appropriate test cell can be tested or assessed by comparing the binding observed in a control cell, such as a cell that is not a cell or tissue having FN-EDB, TNC-C, or both or not an appropriate test cell. Preferably, such a control cell is a cell or tissue not having FN-EDB, TNC-C, or either. Testing peptides for a lack of homing to cells and tissues having FN-EDB, TNC-C, or both in a non-human animal can also be sued as a control.

A peptide can be screened or tested for the by assessing homing to the target and effectively delivery of the cargo molecules in a non-human animal. Generally, the peptide can be tested as part of an L/S/R or F/T/F&T composition or L/S/R or F/T/F&T conjugate but with the test peptide used in place of the L/S/R or F/T/F&T peptide. A peptide useful as an L/S/R or F/T/F&T peptide can be identified, for example, when, in such a screen or test, the test composition homes to the target and effectively delivers the cargo molecules.

Synthetic peptides can be used to show that the activities associated with the selected phage are reproduced by the peptide the phage displays. Techniques for this are well known (e.g. Zhang et al., 2005; Simberg et al., 2007; Karmali et al., 2008). The peptides generally can be labeled with a fluorophore to allow detection in tissues, and both the free peptide and a multimeric conjugate on nanoparticles (which more closely resembles the multivalent presentation on phage) can be tested.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

A variety of peptides can be used in the disclosed compositions, conjugates and methods. Such peptides include, without limitation, F/T/F&T and L/S/R peptides as disclosed herein. The disclosed compounds, compositions, conjugates and methods can include or use the disclosed peptides in various forms, including L/S/R and F/T/F&T peptides and peptidomimetics as disclosed. For convenience of expression, in many places herein the use or inclusion of peptides will be recited. It is understood that, in such cases, it is considered that peptides in various forms can also be used or included in the same or similar ways as is described in terms of L/S/R and F/T/F&T peptides, and such use and inclusion is specifically contemplated and disclosed thereby.

D. Compositions

The disclosed peptides can be used in and with various other components and in various modes and configurations. Such compositions and other forms can be used to accomplish a variety of purposes and effects as described herein. Thus, disclosed are compositions comprising any one or more of the disclosed peptides. In some forms, the composition further comprises a cargo composition, wherein the peptide and the cargo composition are covalently coupled or non-covalently associated with each other. In some forms, the composition can selectively home to tumors expressing FN-EDB, TNC-C, or both FN-EDB and TNC-C. In some forms, the composition can selectively home to extracellular matrix having FN-EDB, TNC-C, or both FN-EDB and TNC-C. In some forms, the composition can selectively home to cells expressing FN-EDB, TNC-C, or both FN-EDB and TNC-C. In some forms, the composition can selectively home to tumors expressing NRP-1 (e.g., b1b2 domain), TNC-C, or both NRP-1 (e.g., b1b2 domain) and TNC-C. In some forms, the composition can selectively home to extracellular matrix expressing NRP-1 (e.g., b1b2 domain), TNC-C, or both NRP-1 (e.g., b1b2 domain) and TNC-C. In some forms, the composition can selectively home to cells expressing NRP-1 (e.g., b1b2 domain), TNC-C, or both NRP-1 (e.g., b1b2 domain) and TNC-C.

In some forms, the cargo composition can comprise a therapeutic agent, a detectable agent, a carrier, vehicle, surface molecule, or combinations thereof.

In some forms, the cargo composition can comprise a therapeutic agent. In some forms, the therapeutic agent is an anti-angiogenic agent, an anti-bacterial agent, an anti-cancer agent, an anti-inflammatory agent, a chemotherapeutic agent (such as a cancer chemotherapeutic agent), a cytotoxic agent, an immunostimulating agent, an immunosuppressing agent, a nucleic acid molecule, a polypeptide, a pro-angiogenic agent, a pro-apoptotic agent, a pro-inflammatory agent, a small molecule, or a toxin. In some forms, the therapeutic agent is $_D$(KLAKLAK)$_2$ (klaklakklaklak).

In some forms, the cargo composition can comprise a detectable agent. In some forms, the detectable agent is a label, a labeling agent, a contrast agent, an imaging agent, a microbubble (such as a fluorocarbon microbubble), a fluorophore (such as FAM, fluorescein, or rhodamine), or a radionuclide (such as carbon-11, carbon-13, indium-111, or technetium-99). In some forms, the detectable agent is FAM.

In some forms, the cargo composition can comprise a carrier, a vehicle, a surface molecule, or combinations thereof. In some forms, the carrier, vehicle and/or surface molecule independently comprise a bead, a liposome, a micelle, a microparticle, a nanoparticle (such as an albumin nanoparticle, an iron oxide nanoparticle, or a silver nanoparticle), a nanoworm (such as an iron oxide nanoworm), a phospholipid, a polymer, a phage, a phage capsid, a phage particle, a viral capsid, a viral particle, a virus, a virus-like particle, or a microbubble (such as a fluorocarbon microbubble).

In some forms, the composition can comprise a plurality of cargo compositions. In some forms, the cargo composition can comprise a surface molecule. In some forms, the peptide is conjugated with the surface molecule. In some forms, one or more of the conjugated peptides is indirectly conjugated to the surface molecule via a linker. In some forms, the composition can further comprise a plurality of linkers. In some forms, at least one of the linkers can comprise polyethylene glycol.

In some forms, the surface molecule can comprise a nanoparticle, a nanoworm, an iron oxide nanoworm, an iron oxide nanoparticle, an albumin nanoparticle, a silver nanoparticle, a liposome, a micelle, a phospholipid, a polymer, a microparticle, or a fluorocarbon microbubble. In some forms, the surface molecule can comprise a liposome. In some forms, the surface molecule can comprise an iron oxide nanoworm.

In some forms, the composition binds tumors expressing FN-EDB, TNC-C, or both FN-EDB and TNC-C. In some forms, the composition binds extracellular matrix having FN-EDB, TNC-C, or both FN-EDB and TNC-C. In some forms, the composition can be internalized in cells. In some forms, the composition can reduce tumor growth. In some forms, the composition further comprises one or more copies of the peptide. In some forms, the composition can comprise at least 100 copies of the peptide. In some forms, the composition can comprise at least 1000 copies of the peptide.

Compositions including one or more LI peptides and one or more SR peptides can be referred to as LS compositions. Compositions including one or more LI peptides and one or more RLR peptides can be referred to as LR compositions.

Compositions including one or more SR peptides and one or more RLR peptides can be referred to as RS compositions. Compositions including one or more LI peptides, one or more SR peptides, and one or more RLR peptides can be referred to as LSR compositions.

Compositions including one or more LI peptides, one or more SR peptides, or both, can be referred to as L/S compositions. Compositions including one or more LI peptides, one or more RLR peptides, or both, can be referred to as L/R compositions. Compositions including one or more SR peptides, one or more RLR peptides, or both can be referred to as S/R compositions. Compositions including one or more LI peptides, one or more SR peptides, one or more RLR peptides, or combinations thereof, can be referred to as L/S/R compositions.

Disclosed are LI compositions, LI conjugates, LI molecules, LI proteins, and LI peptides. LI peptides are the basic feature of LI compositions, LI conjugates, LI molecules, LI proteins, and the like. LI compositions are any composition, conglomeration, conjugate, molecule, protein, peptide, etc. that comprises an LI peptide. LI conjugates are associations, whether covalent or non-covalent, of an LI peptide and one or more other elements, peptides, proteins, compounds, molecules, agents, compounds, etc. For example, an LI conjugate can comprise an LI peptide, LI protein, LI compound, LI molecule, etc. LI molecules are molecules that comprise an LI peptide. For example, an LI molecule can comprise an LI protein, LI peptide, etc. In general, LI peptides, LI proteins, LI molecules, and LI conjugates are all forms of LI compositions. LI compounds, LI peptides and LI proteins can be forms of LI molecules. Unless the context indicates otherwise, reference to an LI composition is intended to refer to LI compositions, LI molecules, LI proteins, LI peptides, and the like. An LI component is any molecule, peptide, protein, compound, conjugate, composition, etc. that comprises an LI peptide. Examples of LI components include, for example, LI compositions, LI molecules, LI proteins, and LI peptides. LI components can comprise one or more LI peptides.

Disclosed are SR compositions, SR conjugates, SR molecules, SR proteins, and SR peptides. SR peptides are the basic feature of SR compositions, SR conjugates, SR molecules, SR proteins, and the like. SR compositions are any composition, conglomeration, conjugate, molecule, protein, peptide, etc. that comprises an SR peptide. SR conjugates are associations, whether covalent or non-covalent, of an SR peptide and one or more other elements, peptides, proteins, compounds, molecules, agents, compounds, etc. For example, an SR conjugate can comprise an SR peptide, SR protein, SR compound, SR molecule, etc. SR molecules are molecules that comprise an SR peptide. For example, an SR molecule can comprise an SR protein, SR peptide, etc. In general, SR peptides, SR proteins, SR molecules, and SR conjugates are all forms of SR compositions. SR compounds, SR peptides and SR proteins can be forms of SR molecules. Unless the context indicates otherwise, reference to an SR composition is intended to refer to SR compositions, SR molecules, SR proteins, SR peptides, and the like. An SR component is any molecule, peptide, protein, compound, conjugate, composition, etc. that comprises an SR peptide. Examples of SR components include, for example, SR compositions, SR molecules, SR proteins, and SR peptides. SR components can comprise one or more SR peptides.

Compositions, conjugates, molecules, proteins, and peptides of a given designation (such as LI, SR, RLR, LS, LR, RS, LSR, L/S, L/R, S/R, or L/S/R) refer to such compositions, conjugates, molecules, proteins, and peptides that include the peptides or sequences of the peptides that are characteristic of the given designation.

By way of example, proteins including the sequences of one or more LI peptides and one or more SR peptides can be referred to as LS proteins. Proteins including the sequences of one or more LI peptides and one or more RLR peptides can be referred to as LR proteins. Proteins including the sequences of one or more SR peptides and one or more RLR peptides can be referred to as RS proteins. Proteins including the sequences of one or more LI peptides, one or more SR peptides, and one or more RLR peptides can be referred to as LSR proteins.

Proteins including the sequences of one or more LI peptides, one or more SR peptides, or both, can be referred to as L/S proteins. Proteins including the sequences of one or more LI peptides, one or more RLR peptides, or both, can be referred to as L/R proteins. Proteins including the sequences of one or more SR peptides, one or more RLR peptides, or both can be referred to as S/R proteins. Proteins including the sequences of one or more LI peptides, one or more SR peptides, one or more RLR peptides, or combinations thereof, can be referred to as L/S/R proteins.

Disclosed are RLR compositions, RLR conjugates, RLR molecules, RLR proteins, and RLR peptides. RLR peptides are the basic feature of RLR compositions, RLR conjugates, RLR molecules, RLR proteins, and the like. RLR compositions are any composition, conglomeration, conjugate, molecule, protein, peptide, etc. that comprises an RLR peptide. RLR conjugates are associations, whether covalent or non-covalent, of an RLR peptide and one or more other elements, peptides, proteins, compounds, molecules, agents, compounds, etc. For example, an RLR conjugate can comprise an RLR peptide, RLR protein, RLR compound, RLR molecule, etc. RLR molecules are molecules that comprise an RLR peptide. For example, an RLR molecule can comprise an RLR protein, RLR peptide, etc. In general, RLR peptides, RLR proteins, RLR molecules, and RLR conjugates are all forms of RLR compositions. RLR compounds, RLR peptides and RLR proteins can be forms of RLR molecules. Unless the context indicates otherwise, reference to an RLR composition is intended to refer to RLR compositions, RLR molecules, RLR proteins, RLR peptides, and the like. An RLR component is any molecule, peptide, protein, compound, conjugate, composition, etc. that comprises an RLR peptide. Examples of RLR components include, for example, RLR compositions, RLR molecules, RLR proteins, and RLR peptides. RLR components can comprise one or more RLR peptides.

Disclosed are LS compositions, LS conjugates, LS molecules, LS proteins, and LS peptides. LS peptides are the basic feature of LS compositions, LS conjugates, LS molecules, LS proteins, and the like. LS compositions are any composition, conglomeration, conjugate, molecule, protein, peptide, etc. that comprises an LS peptide. LS conjugates are associations, whether covalent or non-covalent, of an LS peptide and one or more other elements, peptides, proteins, compounds, molecules, agents, compounds, etc. For example, an LS conjugate can comprise an LS peptide, LS protein, LS compound, LS molecule, etc. LS molecules are molecules that comprise an LS peptide. For example, an LS molecule can comprise an LS protein, LS peptide, etc. In general, LS peptides, LS proteins, LS molecules, and LS conjugates are all forms of LS compositions. LS compounds, LS peptides and LS proteins can be forms of LS molecules. Unless the context indicates otherwise, reference to an LS composition is intended to refer to LS compositions, LS molecules, LS proteins, LS peptides, and the like. An LS component is any molecule, peptide, protein, compound, conjugate, composition, etc. that comprises an LS peptide. Examples of LS components include, for example, LS compositions, LS molecules, LS proteins, and LS peptides. LS components can comprise one or more LS peptides.

Disclosed are LR compositions, LR conjugates, LR molecules, LR proteins, and LR peptides. LR peptides are the basic feature of LR compositions, LR conjugates, LR molecules, LR proteins, and the like. LR compositions are any composition, conglomeration, conjugate, molecule, protein, peptide, etc. that comprises an LR peptide. LR conjugates are associations, whether covalent or non-covalent, of an LR peptide and one or more other elements, peptides, proteins, compounds, molecules, agents, compounds, etc. For example, an LR conjugate can comprise an LR peptide, LR protein, LR compound, LR molecule, etc. LR molecules are molecules that comprise an LR peptide. For example, an LR molecule can comprise an LR protein, LR peptide, etc. In general, LR peptides, LR proteins, LR molecules, and LR conjugates are all forms of LR compositions. LR compounds, LR peptides and LR proteins can be forms of LR molecules. Unless the context indicates otherwise, reference to an LR composition is intended to refer to LR compositions, LR molecules, LR proteins, LR peptides, and the like. An LR component is any molecule, peptide, protein, compound, conjugate, composition, etc. that comprises an LR peptide. Examples of LR components include, for example, LR compositions, LR molecules, LR proteins, and LR peptides. LR components can comprise one or more LR peptides.

Disclosed are RS compositions, RS conjugates, RS molecules, RS proteins, and RS peptides. RS peptides are the basic feature of RS compositions, RS conjugates, RS molecules, RS proteins, and the like. RS compositions are any composition, conglomeration, conjugate, molecule, protein, peptide, etc. that comprises an RS peptide. RS conjugates are associations, whether covalent or non-covalent, of an RS peptide and one or more other elements, peptides, proteins, compounds, molecules, agents, compounds, etc. For example, an RS conjugate can comprise an RS peptide, RS protein, RS compound, RS molecule, etc. RS molecules are molecules that comprise an RS peptide. For example, an RS molecule can comprise an RS protein, RS peptide, etc. In general, RS peptides, RS proteins, RS molecules, and RS conjugates are all forms of RS compositions. RS compounds, RS peptides and RS proteins can be forms of RS molecules. Unless the context indicates otherwise, reference to an RS composition is intended to refer to RS compositions, RS molecules, RS proteins, RS peptides, and the like. An RS component is any molecule, peptide, protein, compound, conjugate, composition, etc. that comprises an RS peptide. Examples of RS components include, for example, RS compositions, RS molecules, RS proteins, and RS peptides. RS components can comprise one or more RS peptides.

Disclosed are LSR compositions, LSR conjugates, LSR molecules, LSR proteins, and LSR peptides. LSR peptides are the basic feature of LSR compositions, LSR conjugates, LSR molecules, LSR proteins, and the like. LSR compositions are any composition, conglomeration, conjugate, molecule, protein, peptide, etc. that comprises an LSR peptide. LSR conjugates are associations, whether covalent or non-covalent, of an LSR peptide and one or more other elements, peptides, proteins, compounds, molecules, agents, compounds, etc. For example, an LSR conjugate can comprise an LSR peptide, LSR protein, LSR compound, LSR molecule, etc. LSR molecules are molecules that comprise an LSR peptide. For example, an LSR molecule can comprise an LSR protein, LSR peptide, etc. In general, LSR peptides, LSR proteins, LSR molecules, and LSR conjugates are all forms of LSR compositions. LSR compounds, LSR peptides and LSR proteins can be forms of LSR molecules. Unless the context indicates otherwise, reference to an LSR composition is intended to refer to LSR compositions, LSR molecules, LSR proteins, LSR peptides, and the like. An LSR component is any molecule, peptide, protein, compound, conjugate, composition, etc. that comprises an LSR peptide. Examples of LSR components include, for example, LSR compositions, LSR molecules, LSR proteins, and LSR peptides. LSR components can comprise one or more LSR peptides.

Disclosed are L/S compositions, L/S conjugates, L/S molecules, L/S proteins, and L/S peptides. L/S peptides are the basic feature of L/S compositions, L/S conjugates, L/S molecules, L/S proteins, and the like. L/S compositions are any composition, conglomeration, conjugate, molecule, protein, peptide, etc. that comprises an L/S peptide. L/S conjugates are associations, whether covalent or non-covalent, of an L/S peptide and one or more other elements, peptides, proteins, compounds, molecules, agents, compounds, etc. For example, an L/S conjugate can comprise an L/S peptide, L/S protein, L/S compound, L/S molecule, etc. L/S molecules are molecules that comprise an L/S peptide. For example, an L/S molecule can comprise an L/S protein, L/S peptide, etc. In general, L/S peptides, L/S proteins, L/S molecules, and L/S conjugates are all forms of L/S compositions. L/S compounds, L/S peptides and L/S proteins can be forms of L/S molecules. Unless the context indicates otherwise, reference to an L/S composition is intended to refer to L/S compositions, L/S molecules, L/S proteins, L/S peptides, and the like. An L/S component is any molecule, peptide, protein, compound, conjugate, composition, etc. that comprises an L/S peptide. Examples of L/S components include, for example, L/S compositions, L/S molecules, L/S proteins, and L/S peptides. L/S components can comprise one or more L/S peptides.

Disclosed are L/R compositions, L/R conjugates, L/R molecules, L/R proteins, and L/R peptides. L/R peptides are the basic feature of L/R compositions, L/R conjugates, L/R molecules, L/R proteins, and the like. L/R compositions are any composition, conglomeration, conjugate, molecule, protein, peptide, etc. that comprises an L/R peptide. L/R conjugates are associations, whether covalent or non-covalent, of an L/R peptide and one or more other elements, peptides, proteins, compounds, molecules, agents, compounds, etc. For example, an L/R conjugate can comprise an L/R peptide, L/R protein, L/R compound, L/R molecule, etc. L/R molecules are molecules that comprise an L/R peptide. For example, an L/R molecule can comprise an L/R protein, L/R peptide, etc. In general, L/R peptides, L/R proteins, L/R molecules, and L/R conjugates are all forms of L/R compositions. L/R compounds, L/R peptides and L/R proteins can be forms of L/R molecules. Unless the context indicates otherwise, reference to an L/R composition is intended to refer to L/R compositions, L/R molecules, L/R proteins, L/R peptides, and the like. An L/R component is any molecule, peptide, protein, compound, conjugate, composition, etc. that comprises an L/R peptide. Examples of L/R components include, for example, L/R compositions, L/R molecules, L/R proteins, and L/R peptides. L/R components can comprise one or more L/R peptides.

Disclosed are S/R compositions, S/R conjugates, S/R molecules, S/R proteins, and S/R peptides. S/R peptides are the basic feature of S/R compositions, S/R conjugates, S/R molecules, S/R proteins, and the like. S/R compositions are any composition, conglomeration, conjugate, molecule, protein, peptide, etc. that comprises an S/R peptide. S/R conjugates are associations, whether covalent or non-covalent, of an S/R peptide and one or more other elements, peptides, proteins, compounds, molecules, agents, compounds, etc. For example, an S/R conjugate can comprise an S/R peptide, S/R protein, S/R compound, S/R molecule, etc. S/R molecules are molecules that comprise an S/R peptide. For example, an S/R molecule can comprise an S/R protein, S/R peptide, etc. In general, S/R peptides, S/R proteins, S/R molecules, and S/R conjugates are all forms of S/R compositions. S/R compounds, S/R peptides and S/R proteins can be forms of S/R molecules. Unless the context indicates otherwise, reference to an S/R composition is intended to refer to S/R compositions, S/R molecules, S/R proteins, S/R peptides, and the like. An S/R component is any molecule, peptide, protein, compound, conjugate, composition, etc. that comprises an S/R peptide. Examples of S/R components include, for example, S/R compositions, S/R molecules, S/R proteins, and S/R peptides. S/R components can comprise one or more S/R peptides.

Disclosed are L/S/R compositions, L/S/R conjugates, L/S/R molecules, L/S/R proteins, and L/S/R peptides. L/S/R peptides are the basic feature of L/S/R compositions, L/S/R conjugates, L/S/R molecules, L/S/R proteins, and the like. L/S/R compositions are any composition, conglomeration, conjugate, molecule, protein, peptide, etc. that comprises an L/S/R peptide. L/S/R conjugates are associations, whether covalent or non-covalent, of an L/S/R peptide and one or more other elements, peptides, proteins, compounds, molecules, agents, compounds, etc. For example, an L/S/R conjugate can comprise an L/S/R peptide, L/S/R protein, L/S/R compound, L/S/R molecule, etc. L/S/R molecules are molecules that comprise an L/S/R peptide. For example, an L/S/R molecule can comprise an L/S/R protein, L/S/R peptide, etc. In general, L/S/R peptides, L/S/R proteins, L/S/R molecules, and L/S/R conjugates are all forms of L/S/R compositions. L/S/R compounds, L/S/R peptides and L/S/R proteins can be forms of L/S/R molecules. Unless the context indicates otherwise, reference to an L/S/R composition is intended to refer to L/S/R compositions, L/S/R molecules, L/S/R proteins, L/S/R peptides, and the like. An L/S/R component is any molecule, peptide, protein, compound, conjugate, composition, etc. that comprises an L/S/R peptide. Examples of L/S/R components include, for example, L/S/R compositions, L/S/R molecules, L/S/R proteins, and L/S/R peptides. L/S/R components can comprise one or more L/S/R peptides.

Disclosed are F/T/F&T compositions, F/T/F&T conjugates, F/T/F&T molecules, F/T/F&T proteins, and F/T/F&T peptides. F/T/F&T peptides are the basic feature of F/T/F&T compositions, F/T/F&T conjugates, F/T/F&T molecules, F/T/F&T proteins, and the like. F/T/F&T compositions are any composition, conglomeration, conjugate, molecule, protein, peptide, etc. that comprises an F/T/F&T peptide. F/T/F&T conjugates are associations, whether covalent or non-covalent, of an F/T/F&T peptide and one or more other elements, peptides, proteins, compounds, molecules, agents, compounds, etc. For example, an F/T/F&T conjugate can comprise an F/T/F&T peptide, F/T/F&T protein, F/T/F&T compound, F/T/F&T molecule, etc. F/T/F&T molecules are molecules that comprise an F/T/F&T peptide. For example, an F/T/F&T molecule can comprise an F/T/F&T protein, F/T/F&T peptide, etc. In general, F/T/F&T peptides, F/T/F&T proteins, F/T/F&T molecules, and F/T/F&T conjugates are all forms of F/T/F&T compositions. F/T/F&T compounds, F/T/F&T peptides and F/T/F&T proteins can be forms of F/T/F&T molecules. Unless the context indicates otherwise, reference to an F/T/F&T composition is intended to refer to F/T/F&T compositions, F/T/F&T molecules, F/T/F&T proteins, F/T/F&T peptides, and the like. An F/T/F&T component is any molecule, peptide, protein, compound, conjugate, composition, etc. that comprises an F/T/F&T peptide. Examples of F/T/F&T components include, for example, F/T/F&T compositions, F/T/F&T molecules, F/T/F&T proteins, and F/T/F&T peptides. F/T/F&T components can comprise one or more F/T/F&T peptides.

In the case of the disclosed FN-EDB peptides, the peptides can provide both homing to cells and tissue that has FN-EDB. For example, some cancer and extracellular matrix has FN-EDB.

Disclosed are FN-EDB compositions, FN-EDB conjugates, FN-EDB molecules, FN-EDB proteins, and FN-EDB peptides. FN-EDB peptides are the basic feature of FN-EDB compositions, FN-EDB conjugates, FN-EDB molecules, FN-EDB proteins, and the like. FN-EDB compositions are any composition, conglomeration, conjugate, molecule, protein, peptide, etc. that comprises an FN-EDB peptide. FN-EDB conjugates are associations, whether covalent or non-covalent, of an FN-EDB peptide and one or more other elements, peptides, proteins, compounds, molecules, agents, compounds, etc. For example, an FN-EDB conjugate can comprise an FN-EDB peptide, FN-EDB protein, FN-EDB compound, FN-EDB molecule, etc. FN-EDB molecules are molecules that comprise an FN-EDB peptide. For example, an FN-EDB molecule can comprise an FN-EDB protein, FN-EDB peptide, etc. In general, FN-EDB peptides, FN-EDB proteins, FN-EDB molecules, and FN-EDB conjugates are all forms of FN-EDB compositions. FN-EDB compounds, FN-EDB peptides and FN-EDB proteins can be forms of FN-EDB molecules. Unless the context indicates otherwise, reference to an FN-EDB composition is intended to refer to FN-EDB compositions, FN-EDB molecules, FN-EDB proteins, FN-EDB peptides, and the like. An FN-EDB component is any molecule, peptide, protein, compound, conjugate, composition, etc. that comprises an FN-EDB peptide. Examples of FN-EDB components include, for example, FN-EDB compositions, FN-EDB molecules, FN-EDB proteins, and FN-EDB peptides. FN-EDB components can comprise one or more FN-EDB peptides.

In the case of the disclosed TNC-C peptides, the peptides can provide both homing to cells and tissue that has TNC-C. For example, some cancer and extracellular matrix has TNC-C.

Disclosed are TNC-C compositions, TNC-C conjugates, TNC-C molecules, TNC-C proteins, and TNC-C peptides. TNC-C peptides are the basic feature of TNC-C compositions, TNC-C conjugates, TNC-C molecules, TNC-C proteins, and the like. TNC-C compositions are any composition, conglomeration, conjugate, molecule, protein, peptide, etc. that comprises a TNC-C peptide. TNC-C conjugates are associations, whether covalent or non-covalent, of a TNC-C peptide and one or more other elements, peptides, proteins, compounds, molecules, agents, compounds, etc. For example, a TNC-C conjugate can comprise a TNC-C peptide, TNC-C protein, TNC-C compound, TNC-C molecule, etc. TNC-C molecules are molecules that comprise a TNC-C peptide. For example, a TNC-C molecule can comprise a TNC-C protein, TNC-C peptide, etc. In general, TNC-C peptides, TNC-C proteins, TNC-C molecules, and TNC-C conjugates are all forms of TNC-C compositions. TNC-C compounds, TNC-C peptides and TNC-C proteins can be forms of TNC-C molecules. Unless the context indicates otherwise, reference to a TNC-C composition is intended to refer to TNC-C compositions, TNC-C molecules, TNC-C proteins, TNC-C peptides, and the like. A TNC-C component is any molecule, peptide, protein, compound, conjugate, composition, etc. that comprises a TNC-C peptide. Examples of TNC-C components include, for example, TNC-C compositions, TNC-C molecules, TNC-C proteins, and TNC-C peptides. TNC-C components can comprise one or more TNC-C peptides.

Disclosed are FN-EDB/TNC-C compositions, FN-EDB/TNC-C conjugates, FN-EDB/TNC-C molecules, FN-EDB/TNC-C proteins, and FN-EDB/TNC-C peptides. FN-EDB/TNC-C peptides are the basic feature of FN-EDB/TNC-C compositions, FN-EDB/TNC-C conjugates, FN-EDB/TNC-C molecules, FN-EDB/TNC-C proteins, and the like. FN-EDB/TNC-C compositions are any composition, conglomeration, conjugate, molecule, protein, peptide, etc. that comprises a FN-EDB/TNC-C peptide. FN-EDB/TNC-C conjugates are associations, whether covalent or non-covalent, of a FN-EDB/TNC-C peptide and one or more other elements, peptides, proteins, compounds, molecules, agents, compounds, etc. For example, a FN-EDB/TNC-C conjugate can comprise a FN-EDB/TNC-C peptide, FN-EDB/TNC-C protein, FN-EDB/TNC-C compound, FN-EDB/TNC-C molecule, etc. FN-EDB/TNC-C molecules are molecules that comprise a FN-EDB/TNC-C peptide. For example, a FN-EDB/TNC-C molecule can comprise a FN-EDB/TNC-C protein, FN-EDB/TNC-C peptide, etc. In general, FN-EDB/TNC-C peptides, FN-EDB/TNC-C proteins, FN-EDB/TNC-C molecules, and FN-EDB/TNC-C conjugates are all forms of FN-EDB/TNC-C compositions. FN-EDB/TNC-C compounds, FN-EDB/TNC-C peptides and FN-EDB/TNC-C proteins can be forms of FN-EDB/TNC-C molecules. Unless the context indicates otherwise, reference to a FN-EDB/TNC-C composition is intended to refer to FN-EDB/TNC-C compositions, FN-EDB/TNC-C molecules, FN-EDB/TNC-C proteins, FN-EDB/TNC-C peptides, and the like. A FN-EDB/TNC-C component is any molecule, peptide, protein, compound, conjugate, composition, etc. that comprises a FN-EDB/TNC-C peptide. Examples of FN-EDB/TNC-C components include, for example, FN-EDB/TNC-C compositions, FN-EDB/TNC-C molecules, FN-EDB/TNC-C proteins, and FN-EDB/TNC-C peptides. FN-EDB/TNC-C components can comprise one or more FN-EDB/TNC-C peptides.

In some forms, the F/T/F&T composition and the cargo are not bound to each other. In some forms, the F/T/F&T composition, cargo, and/or cargo composition can comprise a therapeutic agent. In some forms, the F/T/F&T composition, cargo, and/or cargo composition can comprise a detectable agent. In some forms, the F/T/F&T composition, cargo, and/or cargo composition can comprise a carrier, vehicle, or both. In some forms, the F/T/F&T composition, cargo, and/or cargo composition can comprise a therapeutic protein, a therapeutic compound, a therapeutic composition, a pro-apoptotic agent, a pro-inflammatory agent, an immuno-stimulating agent, an anti-inflammatory agent, an immuno-suppressing agent, an anti-angiogenic agent, a pro-angiogenic agent, a cancer chemotherapeutic agent, a toxin, an anti-bacterial agent, a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

In some forms, the L/S/R composition and the cargo are not bound to each other. In some forms, the L/S/R composition, cargo, and/or cargo composition can comprise a therapeutic agent. In some forms, the L/S/R composition, cargo, and/or cargo composition can comprise a detectable agent. In some forms, the L/S/R composition, cargo, and/or cargo composition can comprise a carrier, vehicle, or both. In some forms, the L/S/R composition, cargo, and/or cargo composition can comprise a therapeutic protein, a therapeutic compound, a therapeutic composition, a pro-apoptotic agent, a pro-inflammatory agent, an immunostimulating agent, an anti-inflammatory agent, an immunosuppressing agent, an anti-angiogenic agent, a pro-angiogenic agent, a cancer chemotherapeutic agent, a toxin, an anti-bacterial agent, a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

In some forms, the F/T/F&T composition can comprise one or more accessory molecules. In some forms, the L/S/R composition can comprise one or more accessory molecules.

Multiple different F/T/F&T peptides, F/T/F&T compounds, F/T/F&T conjugates, F/T/F&T compositions, or a combination can be used together. Similarly, multiple different cargos, multiple different cargo compositions, or a combination can be used together. Where such multiple different F/T/F&T peptides, F/T/F&T compounds, F/T/F&T conjugates, F/T/F&T compositions, or a combination are used together, they can be used with a single type of cargo, a single type of cargo composition, multiple different cargos, multiple different cargo compositions, or a combination. Similarly, when multiple different cargos, multiple different cargo compositions, or a combination can be used together, they can be used with a single type of F/T/F&T peptide, F/T/F&T compound, F/T/F&T conjugate, F/T/F&T composition, or with multiple different F/T/F&T peptides, F/T/F&T compounds, F/T/F&T conjugates, F/T/F&T compositions, or a combination.

For example, an PPRRGLIKLKTS (SEQ ID NO:1) can be used together with one or multiple different F/T/F&T peptides, F/T/F&T compounds, F/T/F&T conjugates, F/T/F&T compositions, or a combination, one or multiple different cargos, multiple different cargo compositions, or a combination, or any combination of these. In such combinations, the PPRRGLIKLKTS (SEQ ID NO:1) itself can be combined in the same conjugate or composition with one or more cargo compositions, one or more accessory molecules, etc.

Multiple different L/S/R peptides, L/S/R compounds, L/S/R conjugates, L/S/R compositions, or a combination can be used together. Similarly, multiple different cargos, multiple different cargo compositions, or a combination can be used together. Where such multiple different L/S/R peptides, L/S/R compounds, L/S/R conjugates, L/S/R compositions, or a combination are used together, they can be used with a single type of cargo, a single type of cargo composition, multiple different cargos, multiple different cargo compositions, or a combination. Similarly, when multiple different cargos, multiple different cargo compositions, or a combination can be used together, they can be used with a single type of L/S/R peptide, L/S/R compound, L/S/R conjugate, L/S/R composition, or with multiple different L/S/R peptides, L/S/R compounds, L/S/R conjugates, L/S/R compositions, or a combination.

For example, an PPRRGLIKLKTS (SEQ ID NO:1) can be used together with one or multiple different L/S/R peptides, L/S/R compounds, L/S/R conjugates, L/S/R compositions, or a combination, one or multiple different cargos, multiple different cargo compositions, or a combination, or any combination of these. In such combinations, the PPRR-GLIKLKTS (SEQ ID NO:1) itself can be combined in the same conjugate or composition with one or more cargo compositions, one or more accessory molecules, etc.

The F/T/F&T peptide or the L/S/R peptide can be comprised in an amino acid sequence in a protein or peptide. In some forms, the protein or peptide can be targeted, delivered, or both to cells and tissues having FN-EDB, TNC-C, or both when the amino acid sequence is present in the protein or peptide but not when the amino acid sequence is not present in the protein or peptide. In some forms, the protein or peptide can be targeted, delivered, or both to cells and tissues having FN-EDB, TNC-C, or both when the amino acid sequence is present in the protein or peptide but not when the amino acid sequence is not present in the protein or peptide. In some forms, the amino acid sequence is the only functional homing molecule in the protein or peptide.

The F/T/F&T peptide can be associated with one or more accessory molecules. For example, an accessory molecule can be a part of an amino acid sequence, a protein, or a peptide that comprises the F/T/F&T peptide. As another example, the accessory molecule can be covalently coupled or non-covalently associated with the F/T/F&T peptide or an amino acid sequence, a protein, or a peptide that comprises the F/T/F&T peptide. The accessory molecule can be separate from or overlapping with the F/T/F&T peptide. For example, some accessory molecules are amino acid sequences. This can allow the amino acid sequence consisting of the F/T/F&T peptide to overlap the amino acid sequence that consists of the accessory amino acid sequence. Alternatively the accessory peptide can be a separate entity that does not overlap with the F/T/F&T peptide. In some forms, the accessory molecule can comprise a sequence in, for example, an F/T/F&T peptide that binds to a specific receptor distinct from the receptor for the F/T/F&T peptide.

The L/S/R peptide can be associated with one or more accessory molecules. For example, an accessory molecule can be a part of an amino acid sequence, a protein, or a peptide that comprises the L/S/R peptide. As another example, the accessory molecule can be covalently coupled or non-covalently associated with the L/S/R peptide or an amino acid sequence, a protein, or a peptide that comprises the L/S/R peptide. The accessory molecule can be separate from or overlapping with the L/S/R peptide. For example, some accessory molecules are amino acid sequences. This can allow the amino acid sequence consisting of the L/S/R peptide to overlap the amino acid sequence that consists of the accessory amino acid sequence. Alternatively the accessory peptide can be a separate entity that does not overlap with the L/S/R peptide. In some forms, the accessory molecule can comprise a sequence in, for example, an L/S/R peptide that binds to a specific receptor distinct from the receptor for the L/S/R peptide.

The amino acid sequence can comprise one or more accessory peptides. The protein or peptide can comprise one or more accessory peptides. In some forms, the cargo does not comprise an accessory molecule. The cargo can comprise one or more accessory molecules. In some forms, the cargo does not comprise an accessory peptide. The cargo can comprise one or more accessory peptides. The cargo can selectively home to cells and tissues having FN-EDB, TNC-C, or both. In some forms, the cargo does not selectively home to cells and tissues having FN-EDB, TNC-C, or both. The cargo can selectively home to cells and tissues having FN-EDB, TNC-C, or both. In some forms, the cargo composition does not comprise an accessory molecule. The cargo composition can comprise one or more accessory molecules. In some forms, the cargo composition does not comprise an accessory peptide. The cargo composition can comprise one or more accessory peptides. The cargo composition can selectively home to cells and tissues having FN-EDB, TNC-C, or both. In some forms, the cargo composition does not selectively home to cells and tissues having FN-EDB, TNC-C, or both. The cargo composition can selectively home to cells and tissues having FN-EDB, TNC-C, or both.

The peptide can be associated with one or more therapeutic agents. For example, a therapeutic agent can be a part of an amino acid sequence, a protein, or a peptide that comprises the peptide. As another example, the therapeutic agent can be covalently coupled or non-covalently associated with the peptide or an amino acid sequence, a protein, or a peptide that comprises the peptide. The therapeutic agent can be separate from or overlapping with the peptide. For example, some therapeutic agents are amino acid sequences. This can allow the amino acid sequence consisting of the peptide to overlap the amino acid sequence that consists of the therapeutic amino acid sequence. Alternatively the therapeutic agent can be a separate entity that does not overlap with the peptide. In some forms, the therapeutic agent can comprise a sequence in, for example, a peptide that binds to a specific receptor distinct from the target for the peptide.

The disclosed peptides home to specific cells (cells and tissues having FN-EDB, TNC-C, or both) and many homing molecules home to the vasculature of the target tissue. However, for the sake of convenience homing is referred to in some places herein as homing to the tissue associated with FN-EDB, TNC-C, or both, or with the vasculature, to which the peptide or homing peptide may actually home. Thus, for example, a homing peptide that homes to cells and tissues having FN-EDB, TNC-C, or both can be referred to herein as homing to tumor tissue or to tumor cells. By including or associating a peptide or homing peptide with, for example, a protein, peptide, amino acid sequence, cargo, or cargo composition, the protein, peptide, amino acid sequence, cargo, or cargo composition can be targeted or can home to the target of the peptide or homing peptide. In this way, the protein, peptide, amino acid sequence, cargo, or cargo composition, or can be said to home to the target of the peptide or homing peptide. For convenience and unless otherwise indicated, reference to homing of a protein, peptide, amino acid sequence, cargo, cargo composition, etc. is intended to indicate that the protein, peptide, amino acid sequence, cargo, cargo composition, etc. includes or is associated with an appropriate peptide or homing peptide.

In some forms, the peptide and the cargo are not covalently coupled or directly non-covalently associated with each other. In some forms, the cargo does not comprise a peptide. The cargo can comprise one or more peptides. In some forms, the cargo does not comprise an LI peptide, an SR peptide, an RLR peptide, or a homing peptide. The cargo can comprise one or more LI peptides, SR peptides, RLR peptides, or homing peptides. The cargo can selectively home to cells and tissues having FN-EDB, TNC-C, or both. In some forms, the cargo does not selectively home to cells and tissues having FN-EDB, TNC-C, or both.

In some forms, the peptide and the cargo composition are not covalently coupled or directly non-covalently associated with each other. In some forms, the cargo composition does not comprise a peptide. The cargo composition can comprise one or more peptides. In some forms, the cargo composition does not comprise an LI peptide, an SR peptide, an RLR peptide, or a homing peptide. The cargo composition can comprise one or more LI peptides, SR peptides, RLR peptides, or homing peptides. The cargo composition can selectively home to cells and tissues having FN-EDB, TNC-C, or both. In some forms, the cargo composition does not selectively home to cells and tissues having FN-EDB, TNC-C, or both.

As used herein, reference to components (such as an F/T/F&T peptide and a cargo) as being "not covalently coupled" means that the components are not connected via covalent bonds (for example, that the F/T/F&T peptide and the cargo are not connected via covalent bonds). That is, there is no continuous chain of covalent bonds between, for example, the F/T/F&T peptide and the cargo. Conversely, reference to components (such as an F/T/F&T peptide and a cargo composition) as being "covalently coupled" means that the components are connected via covalent bonds (for example, that the F/T/F&T peptide and the cargo composition are connected via covalent bonds). That is, there is a continuous chain of covalent bonds between, for example, the F/T/F&T peptide and the cargo composition. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as an F/T/F&T peptide and a cargo) as not being "non-covalently associated" means that there is no direct or indirect non-covalent association between the components. That is, for example, no atom covalently coupled to an F/T/F&T peptide is involved in a non-covalent bond with an atom covalently coupled to a cargo. Within this meaning, an F/T/F&T peptide and a cargo can be together in a composition where they are indirectly associated via multiple intervening non-covalent bonds while not being non-covalently associated as that term is defined herein. For example, an F/T/F&T peptide and a cargo can be mixed together in a carrier where they are not directly non-covalently associated. An F/T/F&T peptide and a cargo that are referred to as not indirectly non-covalently associated cannot be mixed together in a continuous composition. Reference to components (such as an F/T/F&T peptide and a cargo) as not being "directly non-covalently associated" means that there is no direct non-covalent association between the components (an indirect non-covalent association may be present). Reference to components (such as an F/T/F&T peptide and a cargo) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

In some forms, the cargo does not comprise a peptide. The cargo can comprise a peptide. In some forms, the cargo does not comprise a homing peptide. The cargo can comprise a homing peptide. The cargo can selectively home to cells and tissues having FN-EDB, TNC-C, or both. In some forms, the cargo does not selectively home to cells and tissues having FN-EDB, TNC-C, or both. The cargo can selectively home to cells and tissues having FN-EDB, TNC-C, or both. In some forms, the cargo does not comprise an accessory molecule. The cargo can comprise an accessory molecule. In some forms, the cargo does not comprise an accessory peptide. The cargo can comprise an accessory peptide. The cargo can selectively home to cells and tissues having FN-EDB, TNC-C, or both.

The F/T/F&T peptide can be associated with one or more accessory molecules. For example, an accessory molecule can be a part of an amino acid sequence, protein, peptide, conjugate, or composition that comprises the F/T/F&T peptide. As another example, the accessory molecule can be covalently coupled or non-covalently associated with the F/T/F&T peptide or an amino acid sequence, protein, peptide, conjugate, or composition that comprises the F/T/F&T peptide. Accessory molecules can be any molecule, compound, component, etc. that has a useful function and that can be used in combination with an F/T/F&T composition, F/T/F&T conjugate, F/T/F&T molecule, F/T/F&T protein, and/or F/T/F&T peptide. Examples of useful accessory molecules include peptides, targeting molecules, affinity ligands, cell penetrating molecules, endosomal escape molecules, subcellular targeting molecules, nuclear targeting molecules. Different accessory molecules can have similar or different functions from each other. Accessory molecules having similar functions, different functions, or both, can be associated an F/T/F&T composition, F/T/F&T conjugate, F/T/F&T molecule, F/T/F&T protein, and/or F/T/F&T peptide.

The L/S/R peptide can be associated with one or more accessory molecules. For example, an accessory molecule can be a part of an amino acid sequence, protein, peptide, conjugate, or composition that comprises the L/S/R peptide. As another example, the accessory molecule can be covalently coupled or non-covalently associated with the L/S/R peptide or an amino acid sequence, protein, peptide, conjugate, or composition that comprises the L/S/R peptide.

Accessory molecules can be any molecule, compound, component, etc. that has a useful function and that can be used in combination with an L/S/R composition, L/S/R conjugate, L/S/R molecule, L/S/R protein, and/or L/S/R peptide. Examples of useful accessory molecules include peptides, targeting molecules, affinity ligands, cell penetrating molecules, endosomal escape molecules, subcellular targeting molecules, nuclear targeting molecules. Different accessory molecules can have similar or different functions from each other. Accessory molecules having similar functions, different functions, or both, can be associated an L/S/R composition, L/S/R conjugate, L/S/R molecule, L/S/R protein, and/or L/S/R peptide.

The accessory molecule can be separate from or overlapping with the F/T/F&T peptide. For example, some accessory molecules are amino acid sequences. This can allow the amino acid sequence consisting of the F/T/F&T peptide to overlap the amino acid sequence that consists of the accessory amino acid sequence. Alternatively the accessory molecule can be a separate entity that does not overlap with the F/T/F&T peptide. In some forms, the accessory molecule can comprise a sequence in, for example, a peptide that binds to a specific receptor distinct from the receptor for the F/T/F&T peptide.

The accessory molecule can be separate from or overlapping with the L/S/R peptide. For example, some accessory molecules are amino acid sequences. This can allow the amino acid sequence consisting of the L/S/R peptide to overlap the amino acid sequence that consists of the accessory amino acid sequence. Alternatively the accessory molecule can be a separate entity that does not overlap with the L/S/R peptide. In some forms, the accessory molecule can comprise a sequence in, for example, a peptide that binds to a specific receptor distinct from the receptor for the L/S/R peptide.

The F/T/F&T peptide can be associated with one or more accessory molecules. For example, an accessory molecule can be a part of an amino acid sequence, protein, peptide, conjugate, or composition that comprises the F/T/F&T peptide. As another example, the accessory molecule can be covalently coupled or non-covalently associated with the F/T/F&T peptide or an amino acid sequence, protein, peptide, conjugate, or composition that comprises the F/T/F&T peptide. The F/T/F&T conjugate can be associated with one or more accessory molecules. For example, an accessory molecule can be a part of a conjugate or composition that comprises the F/T/F&T conjugate. As another example, the accessory molecule can be covalently coupled or non-covalently associated with the F/T/F&T conjugate or a conjugate or composition that comprises the F/T/F&T conjugate. The F/T/F&T composition can be associated with one or more accessory molecules. For example, an accessory molecule can be a part of a composition that comprises the F/T/F&T composition. As another example, the accessory molecule can be covalently coupled or non-covalently associated with the F/T/F&T composition or a composition that comprises the F/T/F&T composition.

The L/S/R peptide can be associated with one or more accessory molecules. For example, an accessory molecule can be a part of an amino acid sequence, protein, peptide, conjugate, or composition that comprises the L/S/R peptide. As another example, the accessory molecule can be covalently coupled or non-covalently associated with the L/S/R peptide or an amino acid sequence, protein, peptide, conjugate, or composition that comprises the L/S/R peptide. The L/S/R conjugate can be associated with one or more accessory molecules. For example, an accessory molecule can be a part of a conjugate or composition that comprises the L/S/R conjugate. As another example, the accessory molecule can be covalently coupled or non-covalently associated with the L/S/R conjugate or a conjugate or composition that comprises the L/S/R conjugate. The L/S/R composition can be associated with one or more accessory molecules. For example, an accessory molecule can be a part of a composition that comprises the L/S/R composition. As another example, the accessory molecule can be covalently coupled or non-covalently associated with the L/S/R composition or a composition that comprises the L/S/R composition.

The amino acid sequence can be associated with one or more accessory molecules. For example, an accessory molecule can be a part of an amino acid sequence, protein, peptide, conjugate, or composition that comprises the amino acid sequence. As another example, the accessory molecule can be covalently coupled or non-covalently associated with the amino acid sequence or an amino acid sequence, protein, peptide, conjugate, or composition that comprises the amino acid sequence. The protein or peptide can be associated with one or more accessory molecules. For example, an accessory molecule can be a part of a protein, peptide, conjugate, or composition that comprises the peptide. As another example, the accessory molecule can be covalently coupled or non-covalently associated with the peptide or a protein, peptide, conjugate, or composition that comprises the peptide. For example, an accessory molecule can be a part of a protein, conjugate, or composition that comprises the protein. As another example, the accessory molecule can be covalently coupled or non-covalently associated with the protein or a protein, conjugate, or composition that comprises the protein. The conjugate can be associated with one or more accessory molecules. For example, an accessory molecule can be a part of a conjugate or composition that comprises the conjugate. As another example, the accessory molecule can be covalently coupled or non-covalently associated with the conjugate or a conjugate or composition that comprises the conjugate. The composition can be associated with one or more accessory molecules. For example, an accessory molecule can be a part of a composition that comprises the composition. As another example, the accessory molecule can be covalently coupled or non-covalently associated with the composition or a composition that comprises the composition.

The F/T/F&T peptide can be associated with one or more peptides. For example, a peptide can be a part of an amino acid sequence, protein, peptide, conjugate, or composition that comprises the F/T/F&T peptide. As another example, the peptide can be covalently coupled or non-covalently associated with the F/T/F&T peptide or an amino acid sequence, protein, peptide, conjugate, or composition that comprises the F/T/F&T peptide. The peptide can be separate from or overlapping with the F/T/F&T peptide. For example, some peptides are amino acid sequences. This can allow the amino acid sequence consisting of the F/T/F&T peptide to overlap the amino acid sequence that consists of the homing amino acid sequence. Alternatively the peptide can be a separate entity that does not overlap with the F/T/F&T peptide. In some forms, the peptide can comprise a sequence in, for example, an F/T/F&T peptide that binds to a specific receptor distinct from the receptor for the F/T/F&T peptide.

The F/T/F&T conjugate can be associated with one or more peptides. For example, a peptide can be a part of a conjugate or composition that comprises the F/T/F&T conjugate. As another example, the peptide can be covalently coupled or non-covalently associated with the F/T/F&T conjugate or a conjugate or composition that comprises the F/T/F&T conjugate. The F/T/F&T composition can be associated with one or more peptides. For example, a peptide can be a part of a composition that comprises the F/T/F&T composition. As another example, the peptide can be covalently coupled or non-covalently associated with the F/T/F&T composition or a composition that comprises the F/T/F&T composition.

The L/S/R peptide can be associated with one or more peptides. For example, a peptide can be a part of an amino acid sequence, protein, peptide, conjugate, or composition that comprises the L/S/R peptide. As another example, the peptide can be covalently coupled or non-covalently associated with the L/S/R peptide or an amino acid sequence, protein, peptide, conjugate, or composition that comprises the L/S/R peptide. The peptide can be separate from or overlapping with the L/S/R peptide. For example, some peptides are amino acid sequences. This can allow the amino acid sequence consisting of the L/S/R peptide to overlap the amino acid sequence that consists of the homing amino acid sequence. Alternatively the peptide can be a separate entity that does not overlap with the L/S/R peptide. In some forms, the peptide can comprise a sequence in, for example, an L/S/R peptide that binds to a specific receptor distinct from the receptor for the L/S/R peptide.

The L/S/R conjugate can be associated with one or more peptides. For example, a peptide can be a part of a conjugate or composition that comprises the L/S/R conjugate. As another example, the peptide can be covalently coupled or non-covalently associated with the L/S/R conjugate or a conjugate or composition that comprises the L/S/R conjugate. The L/S/R composition can be associated with one or more peptides. For example, a peptide can be a part of a composition that comprises the L/S/R composition. As another example, the peptide can be covalently coupled or non-covalently associated with the L/S/R composition or a composition that comprises the L/S/R composition.

The amino acid sequence can be associated with one or more peptides. For example, a peptide can be a part of an amino acid sequence, protein, peptide, conjugate, or composition that comprises the amino acid sequence. As another example, the peptide can be covalently coupled or non-covalently associated with the amino acid sequence or an amino acid sequence, protein, peptide, conjugate, or composition that comprises the amino acid sequence. The protein or peptide can be associated with one or more peptides. For example, a peptide can be a part of a protein, peptide, conjugate, or composition that comprises the peptide. As another example, the peptide can be covalently coupled or non-covalently associated with the peptide or a protein, peptide, conjugate, or composition that comprises the peptide. For example, a peptide can be a part of a protein, conjugate, or composition that comprises the protein. As another example, the peptide can be covalently coupled or non-covalently associated with the protein or a protein, conjugate, or composition that comprises the protein. The conjugate can be associated with one or more peptides. For example, a peptide can be a part of a conjugate or composition that comprises the conjugate. As another example, the peptide can be covalently coupled or non-covalently associated with the conjugate or a conjugate or composition that comprises the conjugate. The composition can be associated with one or more peptides. For example, a peptide can be a part of a composition that comprises the composition. As another example, the peptide can be covalently coupled or non-covalently associated with the composition or a composition that comprises the composition.

The amino acid sequence can be selected for homing to cells and tissues having FN-EDB, TNC-C, or both. The protein or peptide can be selected for homing to cells and tissues having FN-EDB, TNC-C, or both. The conjugate can be selected for homing to cells and tissues having FN-EDB, TNC-C, or both. The composition can be selected for homing to cells and tissues having FN-EDB, TNC-C, or both.

The F/T/F&T peptide, F/T/F&T conjugate, F/T/F&T composition, amino acid sequence, protein or peptide, conjugate, composition, cargo, cargo composition, or a combination can selectively home to cells and tissues having FN-EDB, TNC-C, or both. The F/T/F&T peptide, F/T/F&T conjugate, F/T/F&T composition, amino acid sequence, protein or peptide, conjugate, composition, cargo, cargo composition, or a combination can selectively home to cells and tissues having FN-EDB, TNC-C, or both. The F/T/F&T peptide, F/T/F&T conjugate, F/T/F&T composition, amino acid sequence, protein or peptide, conjugate, composition, cargo, cargo composition, or a combination can selectively home to one or more particular types of tumor. The F/T/F&T peptide, F/T/F&T conjugate, F/T/F&T composition, amino acid sequence, protein or peptide, conjugate, composition, cargo, cargo composition, or a combination can selectively home to the vasculature of one or more particular types of tumor. The F/T/F&T peptide, F/T/F&T conjugate, F/T/F&T composition, amino acid sequence, protein or peptide, conjugate, composition, cargo, cargo composition, or a combination can selectively home to one or more particular stages of a tumor or cancer. The F/T/F&T peptide, F/T/F&T conjugate, F/T/F&T composition, amino acid sequence, protein or peptide, conjugate, composition, cargo, cargo composition, or a combination can selectively home to the vasculature of one or more particular stages of a tumor or cancer. The F/T/F&T peptide, F/T/F&T conjugate, F/T/F&T composition, amino acid sequence, protein or peptide, conjugate, composition, cargo, cargo composition, or a combination can selectively home to one or more particular stages of one or more particular types of tumor. The F/T/F&T peptide, F/T/F&T conjugate, F/T/F&T composition, amino acid sequence, protein or peptide, conjugate, composition, cargo, cargo composition, or a combination can selectively home to the vasculature of one or more different stages of one or more particular types of tumor.

The L/S/R peptide, L/S/R conjugate, L/S/R composition, amino acid sequence, protein or peptide, conjugate, composition, cargo, cargo composition, or a combination can selectively home to cells and tissues having FN-EDB, TNC-C, or both. The L/S/R peptide, L/S/R conjugate, L/S/R composition, amino acid sequence, protein or peptide, conjugate, composition, cargo, cargo composition, or a combination can selectively home to cells and tissues having FN-EDB, TNC-C, or both. The L/S/R peptide, L/S/R conjugate, L/S/R composition, amino acid sequence, protein or peptide, conjugate, composition, cargo, cargo composition, or a combination can selectively home to one or more particular types of tumor. The L/S/R peptide, L/S/R conjugate, L/S/R composition, amino acid sequence, protein or peptide, conjugate, composition, cargo, cargo composition, or a combination can selectively home to the vasculature of one or more particular types of tumor. The L/S/R peptide, L/S/R conjugate, L/S/R composition, amino acid sequence, protein or peptide, conjugate, composition, cargo, cargo composition, or a combination can selectively home to one or more particular stages of a tumor or cancer. The L/S/R peptide, L/S/R conjugate, L/S/R composition, amino acid sequence, protein or peptide, conjugate, composition, cargo, cargo composition, or a combination can selectively home to the vasculature of one or more particular stages of a tumor or cancer. The L/S/R peptide, L/S/R conjugate, L/S/R composition, amino acid sequence, protein or peptide, conjugate, composition, cargo, cargo composition, or a combination can selectively home to one or more particular stages of one or more particular types of tumor. The L/S/R peptide, L/S/R conjugate, L/S/R composition, amino acid sequence, protein or peptide, conjugate, composition, cargo, cargo composition, or a combination can selectively home to the vasculature of one or more different stages of one or more particular types of tumor.

F/T/F&T compositions, F/T/F&T conjugates, F/T/F&T molecules, F/T/F&T proteins, and F/T/F&T peptides can be designed and produced in any suitable manner. For example, the F/T/F&T peptide in the disclosed F/T/F&T compositions, F/T/F&T conjugates, F/T/F&T molecules, and F/T/F&T proteins can be designed or produced by selecting an amino acid sequence for homing to cells and tissues having FN-EDB, TNC-C, or both.

L/S/R compositions, L/S/R conjugates, L/S/R molecules, L/S/R proteins, and L/S/R peptides can be designed and produced in any suitable manner. For example, the L/S/R peptide in the disclosed L/S/R compositions, L/S/R conjugates, L/S/R molecules, and L/S/R proteins can be designed or produced by selecting an amino acid sequence for homing to cells and tissues having FN-EDB, TNC-C, or both.

The F/T/F&T peptide can be comprised in an amino acid sequence. The amino acid sequence can be comprised in a protein or peptide. The F/T/F&T peptide can be comprised in a protein or peptide. In some forms, the protein or peptide can be homing to cells and tissues having FN-EDB, TNC-C, or both when the amino acid sequence is present in the protein or peptide but not when the amino acid sequence is not present in the protein or peptide. In some forms, the protein or peptide can be homing to cells and tissues having FN-EDB, TNC-C, or both when the amino acid sequence is present in the protein or peptide but not when the amino acid sequence is not present in the protein or peptide. In some forms, the protein or peptide can be internalized into a cell and penetrate tissue when the F/T/F&T amino acid sequence is present in the protein or peptide but not when the F/T/F&T amino acid sequence is not present in the protein or peptide.

The L/S/R peptide can be comprised in an amino acid sequence. The amino acid sequence can be comprised in a protein or peptide. The L/S/R peptide can be comprised in a protein or peptide. In some forms, the protein or peptide can be homing to cells and tissues having FN-EDB, TNC-C, or both when the amino acid sequence is present in the protein or peptide but not when the amino acid sequence is not present in the protein or peptide. In some forms, the protein or peptide can be homing to cells and tissues having FN-EDB, TNC-C, or both when the amino acid sequence is present in the protein or peptide but not when the amino acid sequence is not present in the protein or peptide. In some forms, the protein or peptide can be internalized into a cell and penetrate tissue when the L/S/R amino acid sequence is present in the protein or peptide but not when the L/S/R amino acid sequence is not present in the protein or peptide.

The amino acid sequence can be associated with one or more accessory molecules. The protein or peptide can be associated with one or more accessory molecules. One or more of the accessory molecules can be independently a peptide, a targeting molecule, an affinity ligand, a cell penetrating peptide, an endosomal escape molecule, a subcellular targeting molecule, a nuclear targeting molecule, or a combination. One or more of the accessory molecules can be peptides.

The amino acid sequence can be selected for homing to cells and tissues having FN-EDB, TNC-C, or both.

The F/T/F&T peptide can be comprised in an F/T/F&T composition. The F/T/F&T composition can comprise one or more accessory molecules. The F/T/F&T composition can comprise one or more cargo compositions. The F/T/F&T composition can comprise one or more peptides. The F/T/F&T peptide can be comprised in an F/T/F&T conjugate. The F/T/F&T conjugate can comprise one or more accessory molecules. The F/T/F&T conjugate can comprise one or more cargo compositions. The F/T/F&T conjugate can comprise one or more peptides.

The L/S/R peptide can be comprised in an L/S/R composition. The L/S/R composition can comprise one or more accessory molecules. The L/S/R composition can comprise one or more cargo compositions. The L/S/R composition can comprise one or more peptides. The L/S/R peptide can be comprised in an L/S/R conjugate. The L/S/R conjugate can comprise one or more accessory molecules. The L/S/R conjugate can comprise one or more cargo compositions. The L/S/R conjugate can comprise one or more peptides.

As used herein, "selecting an amino acid sequence for homing to cells and tissues having FN-EDB, TNC-C, or both "refers to selecting, identifying designing or otherwise categorizing an amino acid sequence with the specific intention of targeting to cells and tissues having FN-EDB, TNC-C, or both of a protein or peptide that is comprised of the amino acid sequence. Thus, for example, selecting an amino acid sequence for some purpose or capability other than homing to cells and tissues having FN-EDB, TNC-C, or both of a protein or peptide that is comprised of the amino acid sequence and in the absence of an intention of homing to cells and tissues having FN-EDB, TNC-C, or both of a protein or peptide that is comprised of the amino acid sequence does not constitute "selecting an amino acid sequence for homing to cells and tissues having FN-EDB, TNC-C, or both." Selecting an amino acid sequence for some purpose or capability as well as for homing to cells and tissues having FN-EDB, TNC-C, or both of a protein or peptide that is comprised of the amino acid sequence does constitute "selecting an amino acid sequence for homing to cells and tissues having FN-EDB, TNC-C, or both." Thus, the presence of additional goals or purposes does not alter that selection of an amino acid sequence at least with the specific intention of homing to cells and tissues having FN-EDB, TNC-C, or both of a protein or peptide that is comprised of the amino acid sequence constitutes "selecting an amino acid sequence for homing to cells and tissues having FN-EDB, TNC-C, or both."

As used herein, unless the context indicates otherwise, "selecting a cargo for homing to cells and tissues having FN-EDB, TNC-C, or both" refers to selecting, identifying designing or otherwise categorizing a cargo and an F/T/F&T composition, F/T/F&T conjugate, F/T/F&T molecule, F/T/F&T protein, or F/T/F&T peptide with the specific intention of homing to cells and tissues having FN-EDB, TNC-C, or both of both the cargo and the F/T/F&T composition, F/T/F&T conjugate, F/T/F&T molecule, F/T/F&T protein, or F/T/F&T peptide. Thus, for example, selecting a cargo for some purpose or capability other than homing to cells and tissues having FN-EDB, TNC-C, or both in combination with entry of a selected F/T/F&T composition, F/T/F&T conjugate, F/T/F&T molecule, F/T/F&T protein, or F/T/F&T peptide and in the absence of an intention of homing to cells and tissues having FN-EDB, TNC-C, or both of both the cargo and the F/T/F&T composition, F/T/F&T conjugate, F/T/F&T molecule, F/T/F&T protein, or F/T/F&T peptide does not constitute "selecting cargo for homing to cells and tissues having FN-EDB, TNC-C, or both." Selecting a cargo for some purpose or capability as well as for homing to cells and tissues having FN-EDB, TNC-C, or both of the cargo does constitute "selecting cargo for homing to cells and tissues having FN-EDB, TNC-C, or both." Thus, the presence of additional goals or purposes does not alter that selection of a cargo at least with the specific intention of homing to cells and tissues having FN-EDB, TNC-C, or both of a cargo constitutes "selecting a cargo for homing to cells and tissues having FN-EDB, TNC-C, or both."

As used herein, unless the context indicates otherwise, "selecting a cargo composition for homing to cells and tissues having FN-EDB, TNC-C, or both" refers to selecting, identifying designing or otherwise categorizing a cargo composition and an F/T/F&T composition, F/T/F&T conjugate, F/T/F&T molecule, F/T/F&T protein, or F/T/F&T peptide with the specific intention of homing to cells and tissues having FN-EDB, TNC-C, or both of both the cargo composition and the F/T/F&T composition, F/T/F&T conjugate, F/T/F&T molecule, F/T/F&T protein, or F/T/F&T peptide. Thus, for example, selecting a cargo composition for some purpose or capability other than homing to cells and tissues having FN-EDB, TNC-C, or both in combination with entry of a selected F/T/F&T composition, F/T/F&T conjugate, F/T/F&T molecule, F/T/F&T protein, or F/T/F&T peptide and in the absence of an intention of homing to cells and tissues having FN-EDB, TNC-C, or both of both the cargo composition and the F/T/F&T composition, F/T/F&T conjugate, F/T/F&T molecule, F/T/F&T protein, or F/T/F&T peptide does not constitute "selecting cargo composition for homing to cells and tissues having FN-EDB, TNC-C, or both." Selecting a cargo composition for some purpose or capability as well as for homing to cells and tissues having FN-EDB, TNC-C, or both of the cargo composition does constitute "selecting cargo composition for homing to cells and tissues having FN-EDB, TNC-C, or both." Thus, the presence of additional goals or purposes does not alter that selection of a cargo composition at least with the specific intention of homing to cells and tissues having FN-EDB, TNC-C, or both of a cargo composition constitutes "selecting a cargo composition for homing to cells and tissues having FN-EDB, TNC-C, or both."

As used herein, "causing a compound or composition to be covalently coupled or directly non-covalently associated" with something else refers to any action that results in a compound or composition that is not covalently coupled or directly non-covalently associated with the something else becoming or coming into the state of being covalently coupled or directly non-covalently associated with the something else. As an example, covalently coupling an accessory molecule to an F/T/F&T peptide constitutes "causing an accessory molecule to be covalently coupled or directly non-covalently associated" with the F/T/F&T peptide. As another example, an F/T/F&T peptide that starts as a nonexistent concept and then is synthesized as part of a composition that includes the thing to which the F/T/F&T peptide is to be coupled or associated constitutes "causing an F/T/F&T peptide to be covalently coupled or directly non-covalently associated" with the thing. For example, synthesis of a peptide that includes both an amino acid sequence of interest and an amino acid sequence comprising a C-terminal element constitutes causing the amino acid sequence of interest to be covalently coupled or directly non-covalently associated with the amino acid sequence comprising a C-terminal element. However, and in general, synthesis of a protein or peptide that naturally includes both the amino acid sequence of interest and an amino acid sequence comprising a C-terminal element can be excluded as a process of "causing the amino acid sequence of interest to be covalently coupled or directly non-covalently associated" with the amino acid sequence comprising a C-terminal element.

As used herein, "causing a cargo to be covalently coupled or directly non-covalently associated" with something else refers to any action that results in a cargo that is not covalently coupled or directly non-covalently associated with the something else becoming or coming into the state of being covalently coupled or directly non-covalently associated with the something else. More clearly, "causing a cargo to be covalently coupled or directly non-covalently associated" with something else refers to any action that results in a cargo and the something else becoming or coming into the state of being covalently coupled or directly non-covalently associated. As an example, covalently coupling a cargo to another cargo constitutes "causing a cargo to be covalently coupled or directly non-covalently associated" with the other cargo. As another example, a cargo that starts as a nonexistent concept and then is synthesized as part of a composition that includes the thing to which the cargo is to be coupled or directly associated constitutes "causing a cargo to be covalently coupled or directly non-covalently associated" with the thing.

As used herein, "causing a cargo composition to be covalently coupled or directly non-covalently associated" with something else refers to any action that results in a cargo composition that is not covalently coupled or directly non-covalently associated with the something else becoming or coming into the state of being covalently coupled or non-covalently associated with the something else. More clearly, "causing a cargo composition to be covalently coupled or directly non-covalently associated" with something else refers to any action that results in a cargo composition and the something else becoming or coming into the state of being covalently coupled or directly non-covalently associated. As an example, covalently coupling a cargo composition to another cargo composition constitutes "causing a cargo composition to be covalently coupled or directly non-covalently associated" with the other cargo composition. As another example, a cargo composition that starts as a nonexistent concept and then is synthesized as part of a composition that includes the thing to which the cargo composition is to be coupled or directly associated constitutes "causing a cargo composition to be covalently coupled or directly non-covalently associated" with the thing.

The cargo can be, for example, a nanoparticle, or a molecule, or complex of molecules with therapeutic or diagnostic applications. Therapeutic cargos that can be targeted with the disclosed peptides include but are not limited to a nanoparticle, a molecule, a complex of molecules, a pro-apoptotic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a pro-cell survival agent, a cell differentiating agent, a neuroprotective agent, an anti-arthritic agent, an anti-viral agent, or a combination of these. Therapeutic cargos that can be targeted with the disclosed peptides include but are not limited to a therapeutic protein, a therapeutic compound, a therapeutic composition, a pro-apoptotic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, a toxin, an anti-bacterial agent, a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic cargos that can be targeted with the disclosed peptides include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

The cargo composition can be, for example, a nanoparticle, or a molecule, or complex of molecules with therapeutic or diagnostic applications. Therapeutic cargo compositions that can be targeted with the disclosed peptides include but are not limited to a nanoparticle, a molecule, a complex of molecules, a pro-apoptotic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, an anti-bacterial agent, a cytotoxic agent, a pro-cell survival agent, a cell differentiating agent, a neuroprotective agent, an anti-arthritic agent, an anti-viral agent, or a combination of these. Therapeutic cargo compositions that can be targeted with the disclosed peptides include but are not limited to a therapeutic protein, a therapeutic compound, a therapeutic composition, a pro-apoptotic agent, an immunomodulatory agent, a pro-inflammatory agent, an immunostimulating agent, an anti-inflammatory agent, an immunosuppressing agent, an anti-angiogenic agent, a pro-angiogenic agent, a cancer chemotherapeutic agent, a toxin, an anti-bacterial agent, a cytotoxic agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic cargo compositions that can be targeted with the disclosed peptides include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

Disclosed are polyfunctional compositions which, in addition to the L/S/R or F/T/F&T peptide, contain, for example, an accessory peptide, an accessory peptide fused to the L/S/R or F/T/F&T peptide, an accessory molecule covalently coupled to or non-covalently associated with the L/S/R or F/T/F&T peptide, a cargo composition fused to the L/S/R or F/T/F&T peptide, and/or a cargo composition covalently coupled to or non-covalently associated with the L/S/R or F/T/F&T peptide. Additional compounds having separate functions can be added to the composition. Such polyfunctional conjugates have at least two functions conferred by different portions of the composition and can, for example, display anti-inflammatory activity or pro-apoptotic activity in addition to selective homing activity.

By "selectively binds," in the context of a molecule that binds to a target molecule or component, is meant that the molecule binds preferentially to the target as compared to non-target. For example, the molecule can bind preferentially to a target receptor, as compared to other receptors and proteins. Selective binding to, for example, cells and tissues having FN-EDB, TNC-C, or both generally is characterized by at least a two-fold greater binding to cells and tissues having FN-EDB, TNC-C, or both, as compared to several tissue types of non-cells and tissues having FN-EDB, TNC-C, or both and other cells and tissues. A molecule can be characterized by, for example, 5-fold, 10-fold, 20-fold or more preferential binding to the target as compared to one or more non-targets. For example, a molecule can be characterized by, for example, 5-fold, 10-fold, 20-fold or more preferential binding to cells and tissues having FN-EDB, TNC-C, or both as compared to several or many other non-cells and tissues having FN-EDB, TNC-C, or both, or as compared to all non-tumoral tissue. As another example, a molecule can be characterized by, for example, 5-fold, 10-fold, 20-fold or more preferential binding to cells and tissues having FN-EDB, TNC-C, or both as compared to non-cells and tissues having FN-EDB, TNC-C, or both, or as compared to-most or all other cells and tissues. Thus, it is understood that, in some cases, a molecule binds, in part, to one or more non-targets in addition to binding to the target.

Binding of a molecule to a target via a component generally means that the component is bound to or a part of the target, that the molecule binds to the components, and that, thereby, the molecule is indirectly bound to or associated with the target.

The term "homing molecule" as used herein, means any molecule that selectively homes in vivo to specific cells or specific tissue in preference to normal tissue. Similarly, the term "homing peptide" or "homing peptidomimetic" means a peptide that selectively homes in vivo to specific cells or specific tissue in preference to normal tissue. It is understood that a homing molecule that selectively homes in vivo to specific cells or specific tissue or can exhibit preferential homing to specific cells or specific tissue. The disclosed F/T/F&T and L/S/R peptides are examples of homing molecules that home to cells and tissues having FN-EDB, TNC-C, or both.

By "selectively homes" is meant that, in vivo, the homing molecule binds preferentially to the target as compared to non-target. For example, the homing molecule can bind preferentially to cells and tissues having FN-EDB, TNC-C, or both, as compared to non-cells and tissues having FN-EDB, TNC-C, or both. Selective homing to, for example, cells and tissues having FN-EDB, TNC-C, or both generally is characterized by at least a two-fold greater localization around cells and tissues having FN-EDB, TNC-C, or both, as compared to several tissue types of non-cells and tissues having FN-EDB, TNC-C, or both and other cells and tissues. A homing molecule can be characterized by, for example, 5-fold, 10-fold, 20-fold or more preferential localization to the target as compared to one or more non-targets. For example, a homing molecule can be characterized by, for example, 5-fold, 10-fold, 20-fold or more preferential localization to cells and tissues having FN-EDB, TNC-C, or both as compared to several or many other non-cells and tissues having FN-EDB, TNC-C, or both, or as compared to all non-tumoral tissue. As another example, a homing molecule can be characterized by, for example, 5-fold, 10-fold, 20-fold or more preferential localization to cells and tissues having FN-EDB, TNC-C, or both as compared to non-cells and tissues having FN-EDB, TNC-C, or both, or as compared to-most or all other cells and tissues. Thus, it is understood that, in some cases, a homing molecule homes, in part, to one or more normal organs in addition to homing to the target tissue. Selective homing can also be referred to as targeting. The molecules, proteins, cells, tissues, etc. that are targeted by homing molecules can be referred to as targeted molecules, proteins, cells, tissues, etc.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces.

Surface molecules can be associated with and arranged in the compositions in a variety of configurations. In some forms, surface molecules can be associated with, conjugated to, and/or covalently coupled to a plurality of peptides, a plurality of cargo molecules, or both. In some forms, surface molecules can be associated with, conjugated to, and/or covalently coupled to a plurality of peptides, wherein the peptides can be associated with, conjugated to, and/or covalently coupled to a plurality of cargo molecules. In some forms, surface molecules can be associated with, conjugated to, and/or covalently coupled to a plurality of cargo molecules, wherein the cargo molecules can be associated with, conjugated to, and/or covalently coupled to a plurality of peptides. Combinations of these combinations can also be used.

The surface molecules, alternatively referred to as a surface particles, disclosed herein can be conjugated with peptides and cargo molecules in such a way that the composition is delivered to a target. The surface molecule can be any substance that can be used with the peptides and cargo molecules, and is not restricted by size or substance. Examples include, but are not limited to, nanoparticles (such as iron oxide nanoparticles or albumin nanoparticles), liposomes, small organic molecules, microparticles, or microbubbles, such as fluorocarbon microbubbles. The term surface molecule is used to identify a component of the disclosed composition but is not intended to be limiting. In particular, the disclosed surface molecules are not limited to substances, compounds, compositions, particles or other materials composed of a single molecule. Rather, the disclosed surface molecules are any substance(s), compound(s), composition(s), particle(s) and/or other material(s) that can be conjugated with a plurality of peptides and cargo molecules such that at least some of the peptides and/or cargo molecules are presented and/or accessible on the surface of the surface molecule. A variety of examples of suitable surface molecules are described and disclosed herein.

The surface molecule can be detectable, or can be a therapeutic agent such as an agent that affects or regulates macrophages. In some forms, the therapeutic agent inhibits expression of the phosphotidylinositide 3-kinase (PI3K) gamma gene. In some forms, the therapeutic agent inhibits PI3K gamma. In some forms, the therapeutic agent can be a PI3K gamma inhibitor (such as TG100-115), and TNF-alpha. The section herein which discusses cargo molecules and moieties that can be detectable or therapeutic also applies to the surface molecule.

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohoms, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

The nanoparticles can be comprised of cargo molecules and a carrier protein (such as albumin). Such nanoparticles are useful, for example, to deliver hydrophobic or poorly soluble compounds. Nanoparticles of poorly water soluble drugs (such as taxane) have been disclosed in, for example, U.S. Pat. Nos. 5,916,596; 6,506,405; and 6,537,579 and also in U.S. Pat. Pub. No. 2005/0004002A1.

In forms, the nanoparticles can have an average or mean diameter of no greater than about 1000 nanometers (nm), such as no greater than about any of 900, 800, 700, 600, 500, 400, 300, 200, and 100 nm. In some forms, the average or mean diameters of the nanoparticles can be no greater than about 200 nm. In some forms, the average or mean diameters of the nanoparticles can be no greater than about 150 nm. In some forms, the average or mean diameters of the nanoparticles can be no greater than about 100 nm. In some forms, the average or mean diameter of the nanoparticles can be about 20 to about 400 nm. In some forms, the average or mean diameter of the nanoparticles can be about 40 to about 200 nm. In some embodiments, the nanoparticles are sterile-filterable.

The nanoparticles can be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferrin, fibronectin, factor VII, factor VIII, factor IX, factor X, and the like. In some embodiments, the carrier protein is non-blood protein, such as casein, alpha-lactalbumin, and beta-lactoglobulin. The carrier proteins may either be natural in origin or synthetically prepared. In some embodiments, the pharmaceutically acceptable carrier comprises albumin, such as human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, JAMA 237:355-360, 460-463 (1977)) and Houser et al., Surgery, Gynecology and Obstetrics, 150:811-816 (1980)) and in conjunction with exchange transfusion in the treatment of neonatal hyperbilirubinemia (see, e.g., Finlayson, Seminars in Thrombosis and Hemostasis, 6:85-120 (1980)). Other albumins are contemplated, such as bovine serum albumin. Use of such non-human albumins could be appropriate, for example, in the context of use of these compositions in non-human mammals, such as the veterinary (including domestic pets and agricultural context).

Carrier proteins (such as albumin) in the composition generally serve as a carrier for the hydrophobic cargo molecules, i.e., the carrier protein in the composition makes the cargo molecules more readily suspendable in an aqueous medium or helps maintain the suspension as compared to compositions not comprising a carrier protein. This can avoid the use of toxic solvents (or surfactants) for solubilizing the cargo molecules, and thereby can reduce one or more side effects of administration of the cargo molecules into an individual (such as a human). Thus, in some embodiments, the composition described herein can be substantially free (such as free) of surfactants, such as Cremophor (including Cremophor EL® (BASF)). In some embodiments, the composition can be substantially free (such as free) of surfactants. A composition is "substantially free of Cremophor" or "substantially free of surfactant" if the amount of Cremophor or surfactant in the composition is not sufficient to cause one or more side effect(s) in an individual when the composition is administered to the individual.

The amount of carrier protein in the composition described herein will vary depending on other components in the composition. In some embodiments, the composition, cargo, cargo composition, and/or L/S/R or F/T/F&T composition can comprise a carrier protein in an amount that is sufficient to stabilize the cargo molecules in an aqueous suspension, for example, in the form of a stable colloidal suspension (such as a stable suspension of nanoparticles). In some embodiments, the carrier protein is in an amount that reduces the sedimentation rate of the cargo molecules in an aqueous medium. For particle-containing compositions, the amount of the carrier protein also depends on the size and density of nanoparticles of the cargo molecules.

Methods of making nanoparticle compositions are known in the art. For example, nanoparticles containing cargo molecules and carrier protein (such as albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1.

Briefly, the hydrophobic carrier molecules can be dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Targeting molecules can be attached to the disclosed compositions and/or carriers. For example, the targeting molecules can be antibodies or fragments thereof, ligands for specific receptors, or other proteins specifically binding to the surface of the cells to be targeted.

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. These MLVs were first described by Bangham, et al., J Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 m. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 μm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

"Micelle" as used herein refers to a structure comprising an outer lipid monolayer. Micelles can be formed in an aqueous medium when the Critical Micelle Concentration (CMC) is exceeded. Small micelles in dilute solution at approximately the critical micelle concentration (CMC) are generally believed to be spherical. However, under other conditions, they may be in the shape of distorted spheres, disks, rods, lamellae, and the like. Micelles formed from relatively low molecular weight amphiphile molecules can have a high CMC so that the formed micelles dissociate rather rapidly upon dilution. If this is undesired, amphiphile molecules with large hydrophobic regions can be used. For example, lipids with a long fatty acid chain or two fatty acid chains, such as phospholipids and sphingolipids, or polymers, specifically block copolymers, can be used.

Polymeric micelles have been prepared that exhibit CMCs as low as $10^{-6}$ M (molar). Thus, they tend to be very stable while at the same time showing the same beneficial characteristics as amphiphile micelles. Any micelle-forming polymer presently known in the art or as such may become known in the future may be used in the disclosed compositions and methods. Examples of micelle-forming polymers include, without limitation, methoxy poly(ethylene glycol)-b-poly(ε-caprolactone), conjugates of poly(ethylene glycol) with phosphatidyl-ethanolamine, poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates).

Micelles can be produced by processes conventional in the art. Examples of such are described in, for example, Liggins (Liggins, R. T. and Burt, H. M., "Polyether-polyester diblock copolymers for the preparation of paclitaxel loaded polymeric micelle formulations." Adv. Drug Del. Rev. 54: 191-202, (2002)); Zhang, et al. (Zhang, X. et al., "Development of amphiphilic diblock copolymers as micellar carriers of taxol." Int. J. Pharm. 132: 195-206, (1996)); and Churchill (Churchill, J. R., and Hutchinson, F. G., "Biodegradable amphipathic copolymers." U.S. Pat. No. 4,745,160, (1988)). In one such method, polyether-polyester block copolymers, which are amphipathic polymers having hydrophilic (polyether) and hydrophobic (polyester) segments, are used as micelle forming carriers.

Another type of micelle can be formed using, for example, AB-type block copolymers having both hydrophilic and hydrophobic segments, as described in, for example, Tuzar (Tuzar, Z. and Kratochvil, P., "Block and graft copolymer micelles in solution.", Adv. Colloid Interface Sci. 6:201-232, (1976)); and Wilhelm, et al. (Wilhelm, M. et al., "Poly(styrene-ethylene oxide) block copolymer micelle formation in water: a fluorescence probe study.", Macromolecules 24: 1033-1040 (1991)). These polymeric micelles are able to maintain satisfactory aqueous stability. These micelles, in the range of approximately <200 nm in size, are effective in reducing non-selective RES scavenging and show enhanced permeability and retention.

Further, U.S. Pat. No. 5,929,177 to Kataoka, et al. describes a polymeric molecule which is usable as, inter alia, a drug delivery carrier. The micelle is formed from a block copolymer having functional groups on both of its ends and which comprises hydrophilic/hydrophobic segments. The polymer functional groups on the ends of the block copolymer include amino, carboxyl and mercapto groups on the alpha-terminal and hydroxyl, carboxyl group, aldehyde group and vinyl group on the omega-terminal. The hydrophilic segment comprises polyethylene oxide, while the hydrophobic segment is derived from lactide, lactone or (meth)acrylic acid ester.

Further, for example, poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hr, or a temperature as high as 190° C. can be used if the reaction is carried out for only about 2 hr.

As another example, N-isopropylacrylamide ("IPAAm") (Kohjin, Tokyo, Japan) and dimethylacrylamide ("DMAAm") (Wako Pure Chemicals, Tokyo, Japan) can be used to make hydroxyl-terminated poly(IPAAm-co-DMAAm) in a radical polymerization process, using the method of Kohori, F. et al. (1998). (Kohori, F. et al., "Preparation and characterization of thermally Responsive block copolymer micelles comprising poly(N-isopropylacrylamide-b-D,L-lactide)." J. Control. Rel. 55: 87-98, (1998)). The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori, F. et al. (1999). (Kohori, F. et al., "Control of adriamycin cytotoxic activity using thermally responsive polymeric micelles composed of poly(N-isopropylacrylamide-co-N,N-dimethylacrylamide)-b-poly(D,L-lacide).", Colloids Surfaces B: Biointerfaces 16: 195-205, (1999)).

Examples of block copolymers from which micelles can be prepared which can be used to coat a support surface are found in U.S. Pat. No. 5,925,720, to Kataoka, et al., U.S. Pat. No. 5,412,072 to Sakarai, et al., U.S. Pat. No. 5,410,016 to Kataoka, et al., U.S. Pat. No. 5,929,177 to Kataoka, et al., U.S. Pat. No. 5,693,751 to Sakurai, et al., U.S. Pat. No. 5,449,513 to Yokoyama, et al., WO 96/32434, WO 96/33233 and WO 97/0623, the contents of all of which are incorporated by reference. Modifications thereof which are prepared by introducing thereon a suitable functional group (including an ethyleneically unsaturated polymerizable group) are also examples of block copolymers from which micelles of the present invention are preferably prepared. Preferable block copolymers are those disclosed in the above-mentioned patents and or international patent publications. If the block copolymer has a sugar residue on one end of the hydrophilic polymer segment, as in the block copolymer of WO 96/32434, the sugar residue should preferably be subjected to Malaprade oxidation so that a corresponding aldehyde group may be formed.

Lipids are synthetically or naturally-occurring molecules which includes fats, waxes, sterols, prenol lipids, fat-soluble vitamins (such as vitamins A, D, E and K), glycerolipids, monoglycerides, diglycerides, triglycerides, glycerophospholipids, sphingolipids, phospholipids, fatty acids monoglycerides, saccharolipids and others. Lipids can be hydrophobic or amphiphilic small molecules; the amphiphilic nature of some lipids allows them to form structures such as monolayers, vesicles, micelles, liposomes, bi-layers or membranes in an appropriate environment i.e. aqueous environment. Any of a number of lipids can be used as amphiphile molecules, including amphipathic, neutral, cationic, and anionic lipids. Such lipids can be used alone or in combination, and can also include bilayer stabilizing components such as polyamide oligomers (see, e.g., U.S. Pat. No. 6,320,017, "Polyamide Oligomers", by Ansell), peptides, proteins, detergents, lipid-derivatives, such as PEG coupled to phosphatidylethanolamine and PEG conjugated to ceramides (see, U.S. Pat. No. 5,885,613). In a preferred embodiment, cloaking agents, which reduce elimination of liposomes by the host immune system, can also be included, such as polyamide-oligomer conjugates, e.g., ATTA-lipids, (see, U.S. patent application Ser. No. 08/996,783, filed Feb. 2, 1998) and PEG-lipid conjugates (see, U.S. Pat. Nos. 5,820,873, 5,534,499 and 5,885,613).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

Cationic lipids, carry a net positive charge at physiological pH, can readily be used as amphiphile molecules. Such lipids include, but are not limited to, N,N-dioleyl-N,N-dimethylammonium chloride ("DODAC"); N-(2,3-dioleyloxy) propyl-N,N-N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3.beta.-(N-(N',N'-dimethylaminoethane)-carbamoyl)cholesterol ("DC-Chol"), N-(1-(2,3-dioleyloxy)propyl)-N-2-(sperminecarboxamido) ethyl)-N,N-dimethyl-ammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids can be used as amphiphile molecules and include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidyletha-nolamine, lysylphosphatidylglycerol, and other anionic modifying groups joined to neutral lipids.

Amphipathic lipids can also be suitable amphiphile molecules. "Amphipathic lipids" refer to any suitable material, wherein the hydrophobic portion of the lipid material orients into a hydrophobic phase, while the hydrophilic portion orients toward the aqueous phase. Such compounds include, but are not limited to, fatty acids, phospholipids, aminolip-ids, and sphingolipids. Representative phospholipids include sphingomyelin, phosphatidylcholine, phosphatidyletha-nolamine, phosphatidylserine, phosphatidylinositol, phos-phatidic acid, palmitoyloleoyl phosphatdylcholine, lyso-phosphatidylcholine, lysophosphatidylethanolamine, dipalmitoylphosphatidylcholine, dioleoylphosphatidylcho-line, distearoylphosphatidylcholine, or dilinoleoylphospha-tidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols. Zwitterionic lipids are a form of amphiphatic lipid.

Sphingolipids are fatty acids conjugated to the aliphatic amino alcohol sphingosine. The fatty acid can be covalently bond to sphingosine via an amide bond. Any amino acid as described above can be covalently bond to sphingosine to form a sphingolipid. A sphingolipid can be further modified by covalent bonding through the α-hydroxyl group. The modification can include alkyl groups, alkenyl groups, alky-nyl groups, aromatic groups, heteroaromatic groups, cyclyl groups, heterocyclyl groups, phosphonic acid groups. Non-limiting examples of shingolipids are N-acylsphingosine, N-Acylsphingomyelin, Forssman antigen.

Saccharolipids are compounds that contain both fatty acids and sugars. The fatty acids are covalently bonded to a sugar backbone. The sugar backbone can contain one or more sugars. The fatty acids can bond to the sugars via either amide or ester bonds. The sugar can be any sugar base. The fatty acid can be any fatty acid as described elsewhere herein. The provided compositions can comprise either natural or synthetic saccharolipids. Non-limiting saccharo-lipids are UDP-3-O-(p-hydroxymyristoyl)-GlcNAc, lipid IV A, Kdo2-lipid A.

The disclosed compositions, cargos, cargo compositions, and L/S/R or F/T/F&T compositions can include one or more cargo molecules. Generally, the disclosed composi-tions can include a plurality of cargo molecules. The dis-closed compositions can include a single type of cargo molecule or a plurality of different types of cargo molecules. Thus, for example, the disclosed compositions can include a plurality of different types of cargo molecules where a plurality of one or more of the different types of cargo molecules can be present.

Cargo molecules can be any compound, molecule, con-jugate, composition, etc. that is desired to be delivered using the disclosed compositions. For example, the cargo mol-ecules can be therapeutic agents, detectable agents, or a combination. For example, the cargo molecules can be pro-apoptotic molecules, immunomodulatory molecules, pro-inflammatory molecules, immunostimulating mol-ecules, anti-inflammatory molecules, immunosuppressing molecules, pro-apoptotic molecules, pore-generating mol-ecules, antimicrobial molecules, mitochondria-affecting molecules, mitochondria-targeted molecules, or a combina-tion. Examples of some useful cargo molecules are described below and elsewhere herein. In some forms, the therapeutic agent inhibits expression of the phosphotidylinositide 3-kinase (PI3K) gamma gene. In some forms, the therapeutic agent inhibits PI3K gamma. In some forms, the therapeutic agent can be a PI3K gamma inhibitor (such as TG100-115), and TNF-alpha.

Cargo molecules can be associated with and arranged in the compositions in a variety of configurations. In some forms, cargo molecules can be associated with, conjugated to, and/or covalently coupled to a plurality of surface molecules. In some forms, cargo molecules can be associ-ated with, conjugated to, and/or covalently coupled to a plurality of peptides. In some forms, cargo molecules can be associated with, conjugated to, and/or covalently coupled to a plurality of peptides, wherein the peptides can be associ-ated with, conjugated to, and/or covalently coupled to a plurality of surface molecules. Combinations of these com-binations can also be used.

Membrane perturbing molecules include molecules that can disrupt membranes, that can form pores in membranes, that can make membranes leaky, that can be targeted to or affect intracellular membranes or organelles, such mitochon-dria or lysosomes. Some forms of membrane perturbing molecules can be pro-apoptotic while others can be non-apoptotic. Some forms of membrane perturbing molecules can be pro-apoptotic for only some types of cells.

In some forms, the composition can further comprise a surface molecule and a plurality of membrane perturbing molecules. In some forms, one or more of the membrane perturbing molecules can comprise the amino acid sequence $_D$(KLAKLAK)$_2$ or a conservative variant thereof, (KLAKLAK)$_2$ (SEQ ID NO:6) or a conservative variant thereof, (KLAKKLA)$_2$ (SEQ ID NO:17) or a conservative variant thereof, (KAAKKAA)$_2$ (SEQ ID NO:18) or a con-servative variant thereof, or (KLGKKLG)$_3$ (SEQ ID NO:19) or a conservative variant thereof, or a combination. In some forms, one or more of the membrane perturbing molecules can comprise the amino acid sequence $_D$(KLAKLAK)$_2$, (KLAKLAK)$_2$ (SEQ ID NO:6), (KLAKKLA)$_2$ (SEQ ID NO:17), (KAAKKAA)$_2$ (SEQ ID NO:18), or (KLGKKLG)$_3$ (SEQ ID NO:19), or a combination. In some forms, one or more of the membrane perturbing molecules can comprise the amino acid sequence $_D$(KLAKLAK)$_2$ or a conservative variant thereof. In some forms, one or more of the membrane perturbing molecules can comprise the amino acid sequence $_D$(KLAKLAK)$_2$.

A plurality of modified and/or unmodified membrane perturbing molecules can each be independently selected from, for example, an amino acid segment comprising a modified or unmodified form of the amino acid sequence of a homing peptide, an amino acid segment comprising a modified or unmodified form of the amino acid sequence $_D$(KLAKLAK)$_2$, (KLAKLAK)$_2$ (SEQ ID NO:6), (KLAKKLA)$_2$ (SEQ ID NO:17), (KAAKKAA)$_2$ (SEQ ID NO:18), (KLGKKLG)$_3$ (SEQ ID NO:19), or a combination. A plurality of the membrane perturbing molecules can each independently comprise an amino acid segment comprising a modified or unmodified form of the amino acid sequence of a homing peptide.

The composition, cargo, cargo composition, and/or L/S/R or F/T/F&T composition can comprise a sufficient number and composition of membrane perturbing molecules (modi-fied or not) such that the composition has a membrane perturbing effect on the target. In one example, sufficiency of the number and composition of modified and/or unmodified membrane perturbing molecules can be determined by assessing membrane disruption, apoptosis, and/or therapeu-tic effect on the target.

The composition, cargo, cargo composition, and/or L/S/R or F/T/F&T composition can comprise any number of modified and/or unmodified membrane perturbing molecules. By way of example, the composition, cargo, cargo composition, and/or L/S/R or F/T/F&T composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more modified and/or unmodified membrane perturbing molecules. The composition can also comprise any number in between those numbers listed above.

Membrane perturbing molecules can be associated with and arranged in the compositions in a variety of configurations. In some forms, membrane perturbing molecules can be associated with, conjugated to, and/or covalently coupled to a plurality of surface molecules. In some forms, membrane perturbing molecules can be associated with, conjugated to, and/or covalently coupled to a plurality of homing molecules. In some forms, membrane perturbing molecules can be associated with, conjugated to, and/or covalently coupled to a plurality of homing molecules, wherein the homing molecules can be associated with, conjugated to, and/or covalently coupled to a plurality of surface molecules. Combinations of these combinations can also be used.

The disclosed membrane perturbing molecules can include modified forms of membrane perturbing molecules. The membrane perturbing molecules can have any useful modification. For example, some modifications can stabilize the membrane perturbing molecule. For example, the disclosed membrane perturbing molecules include methylated membrane perturbing molecules. Methylated membrane perturbing molecules are particularly useful when the membrane perturbing molecule includes a protein, peptide or amino acid segment. For example, a membrane perturbing molecule can be a modified membrane perturbing molecule, where, for example, the modified membrane perturbing molecule includes a modified amino acid segment or amino acid sequence. For example, a modified membrane perturbing molecule can be a methylated membrane perturbing molecule, where, for example, the methylated membrane perturbing molecule includes a methylated amino acid segment or amino acid sequence. Other modifications can be used, either alone or in combination. Where the membrane perturbing molecule is, or includes, a protein, peptide, amino acid segment and/or amino acid sequences, the modification can be to the protein, peptide, amino acid segment, amino acid sequences and/or any amino acids in the protein, peptide, amino acid segment and/or amino acid sequences. Amino acid and peptide modifications are known to those of skill in the art, some of which are described below and elsewhere herein. Methylation is a particularly useful modification for the disclosed membrane perturbing molecules. Using modified forms of membrane perturbing molecules can increase their effectiveness.

The disclosed compositions, surface molecules, cargo molecules, peptides, proteins, amino acid sequences, etc. can comprise one or more internalization elements, tissue penetration elements, or both. Internalization elements and tissue penetration elements can be incorporated into or fused with other peptide components of the composition, such as peptide homing molecules and peptide cargo molecules. Internalization elements are molecules, often peptides or amino acid sequences, that allow the internalization element and components with which it is associated, to pass through biological membranes. Tissue penetration elements are molecules, often peptides or amino acid sequences, that allow the tissue penetration element and components with which it is associated to passage into and through tissue.

Internalization elements include, for example, cell-penetrating peptides (CPPs) and CendR elements. Peptides that are internalized into cells are commonly referred to as cell-penetrating peptides. There are two main classes of such peptides: hydrophobic and cationic (Zorko and Langel, 2005). The cationic peptides, which are commonly used to introduce nucleic acids, proteins into cells, include the prototypic cell-penetrating peptides (CPP), Tat, and penetratin (Derossi et al., 1998; Meade and Dowdy, 2007). A herpes virus protein, VP22, is capable of both entering and exiting cells and carrying a payload with it (Elliott and O'Hare, 1997; Brewis et al., 2003).

Various compositions can be internalized through the CendR mechanism (U.S. Application Publication No. 2010/0322862). The CendR pathway can also be used for exit of compositions of interest from the vasculature and their spread into tissue. The C-terminal element can cause spread of compositions from the vasculature (and thus can be spread into tumor tissue from an intravenous injection, for example). CendR elements can also be used to mediate passage of compositions of interest through other CendR-capable membranes, such as mucous membranes and the blood-brain barrier. As used herein, "tissue penetration" and "penetration of tissue" refer to passage to a tissue beyond or through the outer or a first layer of cells or through a tissue membrane. Such passage or penetration through tissue (which can also be referred to as extravasation and tissue penetration) can be a function of, for example, cell internalization and passage between cells in the tissue. Throughout this application, when the term "tissue penetration" is used, it is understood that such penetration can also extend to other barriers and CendR-capable membranes found throughout the body, such as the blood brain barrier. A peptide can be an activatable peptide. The activatable peptide can be a protease-activatable peptide.

Association of the components of the disclosed compositions can be aided or accomplished via molecules, conjugates and/or compositions. Where such molecules, conjugates and/or compositions are other than L/S/R or F/T/F&T peptides, surface molecules, homing molecules, accessory molecules, cargos, cargo compositions, or cargo molecules (such as membrane perturbing molecules, internalization elements, tissue penetration elements, and moieties), they can be referred to herein as linkers. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components (such as peptides and accessory molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Sufficiency of the number and composition of peptides in the composition can be determined by assessing homing to the target and effectively delivery of the cargo molecules in a non-human animal. The composition, cargo, cargo composition, and/or L/S/R or F/T/F&T composition can comprise a sufficient number and composition of peptides (modified or not) such that the composition homes to the target and effectively delivers the cargo molecules. In one example, sufficiency of the number and composition of modified and/or unmodified peptides can be determined by assessing cargo delivery and/or therapeutic effect on the target.

The composition, cargo, cargo composition, and/or L/S/R or F/T/F&T composition can comprise a sufficient density and composition of peptides such that the composition homes to the target and effectively delivers the cargo molecules. Sufficiency of the density and composition of peptides can be determined by assessing cargo delivery and/or therapeutic effect on the target in a non-human animal.

The density of peptides on a surface molecule can be described in any suitable manner. For example, the density can be expressed as the number of peptides per, for example, a given area, surface area, volume, unit, subunit, arm, etc. of the surface molecule. The density can also be relative to, for example, the area, surface area, volume, unit, subunit, arm, etc. of the entire surface molecule or to the area, surface area, volume, unit, subunit, arm, etc. of a portion of the surface molecule. For example, a sufficient density of peptide can be present in a portion of the surface molecule. Thus, a composition having a sufficient density of peptides can have a threshold density (or above) for the entire surface molecule or for just one or more portions of the surface molecule. Unless otherwise stated, densities refer to average density over the designated portion of the surface molecule. For example, a density of 1 peptide per square nM of the surface molecule refers to an average density of the peptides over the entire surface molecule. As another example, a density of 1 peptide per square nM of a portion of the surface molecule refers to an average density of the peptides over just that portion of the surface molecule.

The density can be measured or calculated in any suitable manner. For example, the number or amount of peptides present on a surface molecule or group of surface molecules can be measured by, for example, detecting the level or intensity of signal produced by labeled peptides and calculating the density based on the structural characteristics of the surface molecule.

The density or threshold density of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per square nM of the entire or a portion of the surface molecule. The composition can also comprise any density in between those densities listed above.

The density or threshold density of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per square μM of the entire or a portion of the surface molecule. The composition can also comprise any density in between those densities listed above.

The density or threshold density of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per cubic nM of the entire or a portion of the surface molecule. The composition can also comprise any density in between those densities listed above.

The density or threshold density of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per cubic μM of the entire or a portion of the surface molecule. The composition can also comprise any density in between those densities listed above.

Such density measures and considerations can be applied as well to any of the components of the disclosed compositions other than the peptides.

The number of peptides on a surface molecule can be described in any suitable manner. For example, the number can be expressed as the number of peptides per, for example, a given area, surface area, volume, unit, subunit, arm, etc. of the surface molecule. The number can also be relative to, for example, the area, surface area, volume, unit, subunit, arm, etc. of the entire surface molecule or to the area, surface area, volume, unit, subunit, arm, etc. of a portion of the surface molecule. For example, a sufficient number of peptide can be present in a portion of the surface molecule. Thus, a composition having a sufficient number of peptides can have a threshold number (or above) for the entire surface molecule or for just one or more portions of the surface molecule.

The number can be measured or calculated in any suitable manner. For example, the number or amount of peptides present on a surface molecule or group of surface molecules can be measured by, for example, detecting the level or intensity of signal produced by labeled peptides and calculating the number based on the structural characteristics of the surface molecule.

The number or threshold number of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides on the surface molecule. The composition can also comprise any number in between those numbers listed above.

The number or threshold number of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per square nM of the entire or a portion of the surface molecule. The composition can also comprise any number in between those numbers listed above.

The number or threshold number of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per square μM of the entire or a portion of the surface molecule. The composition can also comprise any number in between those numbers listed above.

The number or threshold number of peptides can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 peptides per cubic nM of the entire or a portion of the surface molecule. The composition can also comprise any number in between those numbers listed above.

The number or threshold number of peptides can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 peptides per cubic μM of the entire or a portion of the surface molecule. The composition can also comprise any number in between those numbers listed above.

Such numbers can be applied as well to any of the components of the disclosed compositions other than the peptides.

Disclosed are linkers for associating components of the disclosed compositions. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components (such as peptides and accessory molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Linkers of different lengths can be used to bind the disclosed components to surface molecules and to each other. A flexible linker can function well even if relatively short, while a stiffer linker can be longer to allow effective exposure and density. The length of a linker can refer to the number of atoms in a continuous covalent chain between the attachment points on the components being linked or to the length (in nanometers, for example) of a continuous covalent chain between the attachment points on the components being linked. Unless the context clearly indicates otherwise, the length refers to the shortest continuous covalent chain between the attachment points on the components being linked not accounting for side chains, branches, or loops. Due to flexibility of the linker, all of the linkers may not have same distance from the surface molecule. Thus linkers with different chain lengths can make the resulting composition more effective (by increasing density, for example). Branched linkers bearing multiple components also allow attachment of more than one component at a given site of the surface molecule. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 atoms. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 nanometers. Any range of these lengths and all lengths between the listed lengths are specifically contemplated.

Hydrophilic or water-solubility linkers can increase the mobility of the attached components. Examples of water-soluble, biocompatible polymers which can serve as linkers include, but are not limited to polymers such polyethylene glycol (PEG), polyethylene oxide (PEO), polyvinyl alcohol, polyhydroxyethyl methacrylate, polyacrylamide, and natural polymers such as hyaluronic acid, chondroitin sulfate, carboxymethylcellulose, and starch. Useful forms of branched tethers include star PEO and comb PEO. Star PEO can be formed of many PEO "arms" emanating from a common core.

Polyethylene glycols (PEGs) are simple, neutral polyethers which have been given much attention in biotechnical and biomedical applications (Milton Harris, J. (ed) "Poly(ethylene glycol) chemistry, biotechnical and biomedical applications" Plenum Press, New York, 1992). PEGs are soluble in most solvents, including water, and are highly hydrated in aqueous environments, with two or three water molecules bound to each ethylene glycol segment; this hydration phenomenon has the effect of preventing adsorption either of other polymers or of proteins onto PEG-modified surfaces. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes. Appropriate molecular weights for PEG linkers used in the disclosed compositions can be from about 120 daltons to about 20 kilodaltons. For example, PEGs can be at least, up to, about, exactly, or between 100, 150, 200, 250, 300, 350, 400, 450, 500, 600, 700, 800, 900, 1000, 1200, 1400, 1500, 1600, 1800, 2000, 2500, 3000, 3500, 4000, 4500, 5000, 5500, 6000, 6500, 7000, 7500, 8000, 8500, 9000, 9500, 10,000, 20,000, 30,000, 40,000, and 50,000 daltons. Any range of these masses and all masses between the listed masses are specifically contemplated. PEGs are usually available as mixtures of somewhat heterogeneous masses with a stated average mass (PEG-5000, for example).

The disclosed compositions can be produced using any suitable techniques. Many techniques, reactive groups, chemistries, etc. for linking components of the types disclosed herein are known and can be used with the disclosed components and compositions.

Protein crosslinkers that can be used to crosslink other molecules, elements, moieties, etc. to the disclosed compositions, surface molecules, peptides, internalization elements, tissue penetration elements, cargo compositions, L/S/R peptides, F/T/F&T peptides, compositions, peptides, amino acid sequences, etc. are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-β-hydroxybenzimidate hydrochloride, 98%), DMA (Dimethyladipimidate hydrochloride).

Components of the disclosed compositions, such as surface molecules, peptides, internalization elements, tissue penetration elements, etc., can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide](Avanti Polar Lipids) by making use of a free cysteine sulfhydryl group on the component. The reaction can be performed, for example, in aqueous solution at room temperature for 4 hours. This coupling chemistry can be used to couple components of cargos and cargo compositions.

Components of the disclosed compositions, such as surface molecules, peptides, internalization elements, tissue penetration elements, etc., can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., Pharm. Rev. 53, 283-318 (2001)). The particles can have surface modifications, for example, for reticuloendothelial system avoidance (PEG) and homing peptides, endosome escape (pH-sensitive peptide; for example, Pirollo et al., Cancer Res.67, 2938-43 (2007)), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery.

The provided peptides and polypeptides can have additional N-terminal, C-terminal, or intermediate amino acid sequences, e.g., amino acid linkers or tags. The term "amino acid linker" refers to an amino acid sequences or insertions that can be used to connect or separate two distinct peptides, polypeptides, or polypeptide fragments, where the linker does not otherwise contribute to the essential function of the composition. The term "amino acid tag" refers to a distinct amino acid sequence that can be used to detect or purify the provided polypeptide, wherein the tag does not otherwise contribute to the essential function of the composition. The provided peptides and polypeptides can further have deleted N-terminal, C-terminal or intermediate amino acids that do not contribute to the essential activity of the peptides and polypeptides.

Components can be directly or indirectly covalently bound to surface molecules or each other by any functional group (e.g., amine, carbonyl, carboxyl, aldehyde, alcohol). For example, one or more amine, alcohol or thiol groups on the components can be reacted directly with isothiocyanate, acyl azide, N-hydroxysuccinimide ester, aldehyde, epoxide, anhydride, lactone, or other functional groups incorporated onto the surface molecules or other components. Schiff bases formed between the amine groups on the components and aldehyde groups on the surface molecule or other components can be reduced with agents such as sodium cyanoborohydride to form hydrolytically stable amine links (Ferreira et al., J. Molecular Catalysis B: Enzymatic 2003, 21, 189-199). Components can be coupled to surface molecules and other components by, for example, the use of a heterobifunctional silane linker reagent, or by other reactions that activate functional groups on either the surface molecule or the components.

Useful modes for linking components to surface molecules and to other components include heterobifunctional linkers or spacers. Such linkers can have both terminal amine and thiol reactive functional groups for reacting amines on components with sulfhydryl groups, thereby coupling the components in an oriented way. These linkers can contain a variable number of atoms. Examples of such linkers include, but are not limited to, N-Succinimidyl 3-(2-pyridyldithio)propionate (SPDP, 3- and 7-atom spacer), long-chain-SPDP (12-atom spacer), (Succinimidyloxycarbonyl-a-methyl-2-(2-pyridyldithio) toluene) (SMPT, 8-atom spacer), Succinimidyl-4-(N-maleimidomethyl)cyclohexane-1-carboxylate) (SMCC, 11-atom spacer) and Sulfosuccinimidyl-4-(N-maleimidomethyl)cyclohexane-1-carboxylate, (sulfo-SMCC, 11-atom spacer), m-Maleimidobenzoyl-N hydroxysuccinimide ester (MBS, 9-atom spacer), N-(g-maleimidobutyryloxy)succinimide ester (GMBS, 8-atom spacer), N-(g-maleimidobutyryloxy) sulfosuccinimide ester (sulfo-GMBS, 8-atom spacer), Succinimidyl 6-((iodoacetyl) amino) hexanoate (SIAX, 9-atom spacer), Succinimidyl 6-(6-(((4-iodoacetyl)amino)hexanoyl)amino)hexanoate (SI-AXX, 16-atom spacer), and β-nitrophenyl iodoacetate (NPIA, 2-atom spacer). One ordinarily skilled in the art also will recognize that a number of other coupling agents or links, with different number of atoms, may be used.

Hydrophilic spacer atoms can be incorporated into linkers to increase the distance between the reactive functional groups. For example, polyethylene glycol (PEG) can be incorporated into sulfo-GMBS. Hydrophilic molecules such as PEG have also been shown to decrease non-specific binding (NSB) and increase hydrophilicity of surfaces when covalently coupled. PEG can also be used as the primary linker material.

Free amine groups of components can also be attached to surface molecules or other components containing reactive amine groups via homobifunctional linkers. Linkers such as dithiobis(succinimidylpropionate) (DSP, 8-atom spacer), disuccinimidyl suberate (DSS, 8-atom spacer), glutaraldehyde (4-atom spacer), Bis[2-(succinimidyloxycarbonyloxy) ethyl]sulfone (BSOCOES, 9-atom spacer), all requiring high pH, can be used for this purpose. Examples of homobifunctional sulfhydryl-reactive linkers include, but are not limited to, 1,4-Di-[3'-2'-pyridyldithio)propion-amido]butane (DPDPB, 16-atom spacer) and Bismaleimidohexane (BMH, 14-atom spacer). For example, these homobifunctional linkers are first reacted with a thiolated surface in aqueous solution (for example PBS, pH 7.4), and then in a second step, the thiolated antibody or protein is joined by the link. Homo- and heteromultifunctional linkers can also be used.

Direct binding of components to thiol, amine, or carboxylic acid functional groups on surface molecules and other components be used to produce compositions which exhibit viral binding (due to increased density of components, for example), resulting in enhanced sensitivity.

As an example, when necessary to achieve high peptide coupling density, additional amino groups can be added to the surface molecules (such as commercially obtained SPIO) as follows: First, to crosslink the particles before the amination step, 3 ml of the colloid (~1 0mgFe/ml in double-distilled water) was added to 5 ml of 5M NaOH and 2 ml of epichlorohydrin (Sigma, St. Louis, MO). The mixture was agitated for 24 hours at room temperature to promote interaction between the organic phase (epichlorohydrin) and aqueous phase (dextran-coated particle colloid). In order to remove excess epichlorohydrin, the reacted mixture was dialyzed against double-distilled water for 24 hours using a dialysis cassette (10,000 Da cutoff, Pierce, Rockford IL). Amino groups were added to the surface of the particles as follows: 0.02 ml of concentrated ammonium hydroxide (30%) was added to 1 ml of colloid (~10 mg Fe/ml). The mixture was agitated at room temperature for 24 hours. The reacted mixture was dialyzed against double-distilled water for 24 hours. To further rinse the particles, the colloid was trapped on a MACS® Midi magnetic separation column (Miltenyi Biotec, Auburn CA), rinsed with PBS three times, and eluted from the column with 1 ml PBS.

To conjugate peptides to SPIO, the particles were re-suspended at a concentration of 1 mg Fe/ml, and heterobifunctional linker N-[a-maleimidoacetoxy]succinimide ester (AMAS; Pierce) was added (2.5 mg linker per 2 mg Fe) under vortexing. After incubation at room temperature for 40 min, the particles were washed 3 times with 10 ml PBS on a MACS column. The peptide with free terminal cysteine was then added (100 μg peptide per 2 mg Fe). After incubation overnight at 4° C. the particles were washed again and re-suspended in PBS at a concentration of 0.35 mg/ml of Fe). To quantify the number of peptide molecules conjugated to the particles, a known amount of stock or AMAS-activated particles was incubated with varying amounts of the peptide. After completion of the incubation the particles were pelleted at 100.000G using Beckman TLA 100.3 ultracentrifuge rotor (30 min) and the amount of the unbound peptide was quantified by fluorescence. To cleave the conjugated peptide from the particles, the particles were incubated at 37° C. overnight at pH 10. The concentration of free peptide in the supernatant was determined by reading fluorescence and by using the calibration curve obtained for the same peptide. The fluorescence intensity of known amounts of particles was plotted as a function of peptide conjugation density, and the slope equation was used to determine conjugation density in different batches.

Accessory molecules can be any molecule, compound, component, etc. that has a useful function and that can be used in combination with an F/T/F&T composition, F/T/F&T conjugate, F/T/F&T molecule, F/T/F&T protein, F/T/F&T peptide, an L/S/R composition, L/S/R conjugate, L/S/R molecule, L/S/R protein, L/S/R peptide, composition, cargo, and/or cargo composition. Examples of useful accessory molecules include homing molecules, targeting molecules, affinity ligands, cell penetrating molecules, endosomal escape molecules, subcellular targeting molecules, nuclear targeting molecules. Different accessory molecules can have similar or different functions from each other.

Molecules that target, home, or have affinity for certain molecules, structures, cells, tissues, etc. are particularly useful as accessory molecules. In addition to the homing molecules described elsewhere herein, there are numerous molecules and compounds known that have affinity for particular target molecules, structures, cells, tissues, etc. and can aid in accumulating and/or directing the disclosed components and compositions to desired targets. For convenience, such affinity effects can be referred to as homing. Descriptions of homing and homing effects elsewhere herein can be applied to these molecules.

An affinity ligand is a molecule that interacts specifically with a particular molecule, moiety, cell tissue, etc. The molecule, moiety, cell tissue, etc. that interacts specifically with an affinity ligand is referred to herein as a target or target molecule, moiety, cell tissue, etc. It is to be understood that the term target molecule refers to both separate molecules and to portions of such molecules, such as an epitope of a protein, that interacts specifically with an affinity ligand. Antibodies, either member of a receptor/ligand pair, synthetic polyamides (Dervan and Burli, *Sequence-specific DNA recognition by polyamides.* Curr Opin Chem Biol, 3(6):688-93 (1999); Wemmer and Dervan, *Targeting the minor groove of DNA.* Curr Opin Struct Biol, 7(3):355-61 (1997)), and other molecules with specific binding affinities are examples of affinity ligands.

An affinity ligand that interacts specifically with a particular target molecule is said to be specific for that target molecule. For example, where the affinity ligand is an antibody that binds to a particular antigen, the affinity ligand is said to be specific for that antigen. The antigen is the target molecule. The affinity ligand can also be referred to as being specific for a particular target molecule. Examples of useful affinity ligands are antibodies, ligands, binding proteins, receptor proteins, haptens, aptamers, carbohydrates, lectins, folic acid, synthetic polyamides, and oligonucleotides. Useful binding proteins include DNA binding proteins. Useful DNA binding proteins include zinc finger motifs, leucine zipper motifs, and helix-turn-helix motifs. These motifs can be combined in the same affinity ligand.

Antibodies are useful as the affinity ligands. Antibodies can be obtained commercially or produced using well established methods. For example, Johnstone and Thorpe, *Immunochemistry In Practice* (Blackwell Scientific Publications, Oxford, England, 1987) on pages 30-85, describe general methods useful for producing both polyclonal and monoclonal antibodies. The entire book describes many general techniques and principles for the use of antibodies in assay systems. Numerous antibodies and other affinity ligands are known that bind to particular proteins, carbohydrates, glycoproteins, molecules, cells, tissues, etc. Such antibodies can be used in the disclosed components and compositions.

Examples of cell penetrating peptides are described in, for example, U.S. Patent Application Publication Nos. 20100061942, 20100061932, 20100048487, 20100022466, 20100016215, 20090280058, 20090186802, 20080234183, 20060014712, 20050260756, and 20030077289, which are hereby incorporated by reference in their entirety and specifically for their description of cell penetrating peptides and motifs. Examples of endosomal escape molecules are described in, for example, U.S. Patent Application Publication Nos. 20090325866, 20090317802, 20080305119, 20070292920, 20060147997, 20050038239, 20040219169, 20030148263, 20030082143, 20020132990, and 20020068272, which are hereby incorporated by reference in their entirety and specifically for their description of endosomal escape molecules and motifs. Examples of subcellular targeting molecules are described in, for example, U.S. Patent Application Publication Nos. 2009031733, 20090258926, 20090176660, 20080311136, 20070287680, 20070157328, 20070111270, 20070111251, 20060257942, 20060154340, 20060014712, 20050281805, 20050233356, 20040005309, 20030082176, and 20010021500, which are hereby incorporated by reference in their entirety and specifically for their description of subcellular targeting molecules and motifs. Examples of nuclear targeting molecules are described in, for example, U.S. Patent Application Publication Nos. 10100143454, 20100099627, 20090305329, 20090176710, 20090087899, 20070231862, 20070212332, 20060242725, 20060233807, 20060147922, 20060070133, 20060051315, 20050147993, 20050071088, 20030166601, 20030125283, 20030083261, 20030003100, 20020068272, and 20020055174, which are hereby incorporated by reference in their entirety and specifically for their description of nuclear targeting molecules and motifs.

As disclosed herein, the term "cargo" refers to any composition of matter that can be used with the disclosed peptides. Similarly, the term "cargo composition" refers to any composition of matter that can be used with the disclosed peptides. Generally, for example, a cargo or cargo composition can be any composition to be targeted to cells and tissues having FN-EDB, TNC-C, or both. For example, a cargo or cargo composition can be a molecule, a conjugate, an association of molecules, a composition, and a mixture. Examples of cargos and cargo compositions include, but are not limited to, cancer chemotherapeutic agents, cytotoxic agents, pro-apoptotic agents, immunomodulatory agents, pro-inflammatory agents, immunostimulating agents, anti-inflammatory agents, anti-arthritic agents, polypeptides, nucleic acid molecules, small molecules, nanoparticles, microparticles, fluorophores, fluorescein, rhodamine, a radionuclide, Lutetium-177 ($^{177}$Lu), Rhenium-188 ($^{188}$Re), Gallium-68 ($^{68}$Ga), Yttrium-90 ($^{90}$Y), Technetium-99m ($^{99}$mTc), Holmium-166 ($^{166}$Ho), Iodine-131 ($^{131}$I), Indium-111 ($^{111}$In), Flourine-18 ($^{18}$F), Carbon-11 ($^{11}$C), Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), Iodine-123 ($^{123}$I), or a combination thereof.

The disclosed components can be used with any therapeutic agents since they represent a general mode and platform for aiding in delivery of therapeutic agents to cells and tissues. Thus, any therapeutic agent can be used in or with the disclosed compositions. Comprehensive lists of therapeutic agents and drugs can be found in a number of places, such as the Orange Book and other lists maintained by the U.S. Food and Drug Administration (information available at websites fda.gov/Drugs/InformationOnDrugs/ucm129662.htm and fda.gov/Drugs/InformationOnDrugs/ApprovedDrugs/default.htm) and similar lists maintained by other countries, and at clinicaltrials.gov/(for drugs and therapeutic agents undergoing clinical trials).

In some forms, the therapeutic agents can be one or more small molecule kinase inhibitors or phytochemicals or nucleic acid drugs such as deoxyribozymes, ribozymes, siRNA, shRNA, DNA, PNAs, RNA and DNA aptamers, or miRNAs, small molecules, antibodies, peptides, amino acids, lipids, polysaccharides, growth factors, cytokines, bioactive peptides, enzymes, and cytotoxic drugs.

Cargos and cargo compositions can be moieties. As used herein, the term "moiety" is used broadly to mean a physical, chemical, or biological material that generally imparts a biologically useful function to a linked cargo or a linked cargo composition. A moiety can be any natural or non-natural material including, without limitation, a biological material, such as a cell, phage or other virus; an organic chemical such as a small molecule; a nanoparticle, a radionuclide; a nucleic acid molecule or oligonucleotide; a polypeptide; or a peptide. For example, moieties that affect the target, such as moieties with therapeutic effect, or that facilitate detection, visualization or imaging of the target, such as fluorescent molecule or radionuclides.

Components of the disclosed cargos and cargo compositions can be combined, linked and/or coupled in any suitable manner. For example, moieties and other molecules can be associated covalently or non-covalently, directly or indirectly, with or without a linker moiety.

In some embodiments, a cargo or cargo composition can comprise a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab; paclitaxel such as Abraxane; Doxil.

A cargo or cargo composition can comprise a therapeutic agent. Useful therapeutic agents can be, for example, a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, Pseudomonas exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In some forms, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic peptides; immunomodulatory peptides, pro-inflammatory peptides, immunostimulating peptides; anti-inflammatory peptides; immunosuppressing peptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α. (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, Pseudomonas exotoxin A, cholera toxin, a ligand fusion toxin such as DAB389EGF or ricin; a pro-apoptotic polypeptide, such as $_D$(KLAKLAK)$_2$; an immunomodulatory peptide; a pro-inflammatory peptide, an immunostimulating peptide; an anti-inflammatory peptide; an immunosuppressing peptide; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

A therapeutic agent useful in the disclosed cargos and cargo compositions can be an anti-angiogenic agent. As used herein, the term "anti-angiogenic agent" means a molecule that reduces or prevents angiogenesis, which is the growth and development of blood vessels. The cargos and cargo compositions can be used to treat or diagnose any disease, condition, or disorder associated with angiogenesis. For example, macular degeneration and diabetic vascular complications can be diagnosed and/or treated. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Some other examples of useful therapeutic agents include nitrogen mustards, nitrosoureas, ethyleneimine, alkane sulfonates, tetrazine, platinum compounds, pyrimidine analogs, purine analogs, antimetabolites, folate analogs, anthracyclines, taxanes, *vinca* alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cholophosphamide, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel, Pamidronate, Pentostatin, Phenesterine, Plicamycin, Prednimustine, Procarbazine, Rapamycin, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE@, Rhone-Poulenc Rorer, Antony, France); Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above. Useful cargos and cargo compositions include, for example, doxorubicin, Herceptin, and liposomal doxorubicin.

The cargo or cargo composition can also comprise a boron containing compound. Boron containing compounds have received increasing attention as therapeutic agents over the past few years as technology in organic synthesis has expanded to include this atom (Boron Therapeutics on the horizon, Groziak, M. P.; American Journal of Therapeutics (2001) 8, 321-328). The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides (Organic boron compounds as herbicides. Barnsley, G. E.; Eaton, J. K.; Airs, R. S.; (1957), DE 1016978 19571003), boron neutron capture therapy (Molecular Design and Synthesis of B-10 Carriers for Neutron Capture Therapy. Yamamoto, Y.; Pure Appl. Chem., (1991) 63, 423-426), serine protease inhibition (Borinic acid inhibitors as probes of the factors involved in binding at the active sites of subtilisin Carlsberg and alpha-chymotrypsin. Simpelkamp, J.; Jones, J. B.; Bioorganic & Medicinal Chemistry Letters, (1992), 2(11), 1391-4; Design, Synthesis and Biological Evaluation of Selective Boron-containing Thrombin Inhibitors. Weinand, A.; Ehrhardt, C.; Metternich, R.; Tapparelli, C.; Bioorganic and Medicinal Chemistry, (1999), 7, 1295-1307), acetylcholinesterase inhibition (New, specific and reversible bifunctional alkylborinic acid inhibitor of acetylcholinesterase. Koehler, K. A.; Hess, G. P.; Biochemistry (1974), 13, 5345-50) and as antibacterial agents (Boron-Containing Antibacterial Agents: Effects on Growth and Morphology of Bacteria Under Various Culture Conditions. Bailey, P. J.; Cousins, G.; Snow, G. A.; and White, A. J.; Antimicrobial Agents and Chemotherapy, (1980), 17, 549-553). The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity (Preparation of diarylborinic acid esters as DNA methyl transferase inhibitors. Benkovic, S. J.; Shapiro, L.; Baker, S. J.; Wahnon, D. C.; Wall, M.; Shier, V. K.; Scott, C. P.; Baboval, J.; PCT Int. Appl. (2002), WO 2002044184).

The cargo or cargo composition can also have one or more isotopes. Such isotopes can be useful, for example, as a therapeutic agent, as a detectable agent, or both. Examples of useful isopes include Lutetium-177 ($^{177}$Lu), Rhenium-188 ($^{188}$Re), Gallium-68 ($^{68}$Ga), Yttrium-90 ($^{90}$Y), Technetium-99m ($^{99}$mTc), Holmium-166 ($^{166}$Ho), Iodine-131 ($^{131}$I), Indium-111 ($^{111}$In), Flourine-18 ($^{18}$F), Carbon-11 ($^{11}$C), Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), and Iodine-123 ($^{123}$I).

The cargo or cargo composition can also comprise a detectable agent. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed compositions and imaging methods include yet are not limited to radiolabels and fluorescent molecules. The detectable agent can be, for example, any moiety that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrast agent. The contrast agent can be, for example, Feridex. In some embodiments, for instance, the detectable agent comprises a tantalum compound. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, iron oxide and Gd can be used as a non-radioactive detectable agent in certain embodiments. Detectable agents can also include radioactive isotopes, enzymes, fluorophores, and quantum dots (Qdot®). For example, the detection moiety can be an enzyme, biotin, metal, or epitope tag. Other known or newly discovered detectable markers are contemplated for use with the provided compositions. In some embodiments, for instance, the detectable agent comprises a barium compound, e.g., barium sulfate.

The detectable agent can be (or the cargo or cargo composition can include) one or more imaging agents. Examples of imaging agents include radiologic contrast agent, such as diatrizoic acid sodium salt dihydrate, iodine, and barium sulfate, a fluorescing imaging agent, such as Lissamine Rhodamine PE, a fluorescent or non-fluorescent stain or dye, for example, that can impart a visible color or that reflects a characteristic spectrum of electromagnetic radiation at visible or other wavelengths, for example, infrared or ultraviolet, such as Rhodamine, a radioisotope, a positron-emitting isotope, such as $^{18}$F or $^{124}$I (although the short half-life of a positron-emitting isotope may impose some limitations), a metal, a ferromagnetic compound, a paramagnetic compound, such as gadolinium, a superparamagnetic compound, such as iron oxide, and a diamagnetic compound, such as barium sulfate. Imaging agents can be selected to optimize the usefulness of an image produced by a chosen imaging technology. For example, the imaging agent can be selected to enhance the contrast between a feature of interest, such as a gastrointestinal polyp, and normal gastrointestinal tissue. Imaging can be accomplished using any suitable imaging techniques such as X-Ray, computed tomography (CT), MRI, Positron Emission Tomography (PET) or SPECT. In some forms, the cargo or cargo composition can be coupled to a nuclear medicine imaging agent such as Indium-III or Technetium-99, to PET imaging agents, or to MRI imaging agents such as nanoparticles.

Examples of imaging techniques include magnetic resonance imaging (MRI), computerized tomography (CT), single photon emission computerized tomography (SPECT), and positron emission tomography (PET). Imaging agents generally can be classified as either being diagnostic or therapeutic in their application. Because of radiation's damaging effect on tissues, it is useful to target the biodistribution of radiopharmaceuticals as accurately as possible. PET can use imaging agents labeled with, for example, the positron-emitters such as $^{18}F$, $^{11}C$, $^{13}N$ and $^{15}O$, $^{75}Br$, $^{76}Br$ and $^{124}$. SPECT can use imaging agents labeled with, for example, the single-photon-emitters such as $^{201}Tl$, $^{99}Tc$, $^{123}I$, and $^{131}I$. Glucose-based and amino acid-based compounds can be used as imaging agents.

Amino acid-based compounds are more useful in analyzing tumor cells, due to their faster uptake and incorporation into protein synthesis. Of the amino acid-based compounds, $^{11}C$- and $^{18}F$-containing compounds have been used with success. $^{11}C$-containing radiolabeled amino acids suitable for imaging include, for example, L-[1-$^{11}C$]leucine (Keen et al. J. Cereb. Blood Flow Metab. 1989 (9):429-45), L-[1-$^{11}C$]tyrosine (Wiesel et al. J. Nucl. Med. 1991 (32):2041-49), L-[methyl-$^{11}C$]methionine (Comar et al. Eur. J. Nucl. Med. 1976 (1):11-14) and L-[1-$^{11}C$]methionine (Bolster et al. Appl. Radiat. Isot. 1986 (37):1069-70).

PET involves the detection of gamma rays in the form of annihilation photons from short-lived positron emitting radioactive isotopes including, but not limited to, $^{18}F$ with a half-life of approximately 110 minutes, $^{11}C$ with a half-life of approximately 20 minutes, $^{13}N$ with a half-life of approximately 10 minutes and $^{15}O$ with a half-life of approximately 2 minutes, using the coincidence method. For PET imaging studies, compounds such as [$^{11}C$]meta-hydroxyephedrine (HED) and 2-[$^{18}F$]fluoro-2-deoxy-D-glucose (FDG) can be used. SPECT can use longer-lived isotopes including, but not limited to, $^{99}mTc$ with a half-life of approximately 6 hours and $^{201}Tl$ with a half-life of approximately 74 hours. Radio-iodinated meta-iodobenzylguanidine (MIBG) is a radiotracing agent that can be used in nuclear medicine imaging studies.

The cargo or cargo composition can be a microparticle or a nanoparticle, such as a nanosphere, nanoshell, nanoworm, heat generating nanoshell, and the like. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with, for example, a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

Fatty acids (i.e., lipids) that can be conjugated to the disclosed compositions and cargos and cargo compositions include those that allow the efficient incorporation of the peptide into liposomes. Generally, the fatty acid is a polar lipid. Thus, the fatty acid can be a phospholipid. The provided compositions can comprise either natural or synthetic phospholipid. The phospholipids can be selected from phospholipids containing saturated or unsaturated mono or disubstituted fatty acids and combinations thereof. These phospholipids can be, for example, dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palmtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

The other molecules, elements, moieties, etc. can be covalently linked to or non-covalently associated with, for example, the disclosed cargos, cargo compositions, F/T/F&T composition, L/S/R composition, protein, peptide, or amino acid sequence. Such molecules, elements, moieties, etc. can be linked, for example, to the amino terminal end of the disclosed protein, peptide, amino acid sequence, L/S/R peptide, or F/T/F&T peptide; to an internal amino acid of the disclosed protein, peptide, amino acid sequence, L/S/R peptide, or F/T/F&T peptide; to the carboxy terminal end of the disclosed protein, peptide, or amino acid sequence; to the protein, peptide, amino acid sequence on the N terminal side of the disclosed peptide; via a linker to the disclosed protein, peptide, amino acid sequence, L/S/R peptide, or F/T/F&T peptide; or a combination. The disclosed compositions can further comprise a linker connecting such molecules, elements, moieties, etc. and disclosed composition, protein, peptide, amino acid sequence, L/S/R peptide, or F/T/F&T peptide. The disclosed composition, protein, peptide, amino acid sequence, L/S/R peptide, or F/T/F&T peptide can also be conjugated to a coating molecule such as bovine serum albumin (BSA; see Tkachenko et al., (2003) J Am Chem Soc, 125, 4700-4701) that can be used to coat nanoparticles, nanoworms, nanoshells, and the like with the protein, peptide, amino acid sequence, L/S/R peptide, or F/T/F&T peptide.

Protein crosslinkers that can be used to crosslink other molecules, elements, moieties, etc. to the disclosed cargos, cargo compositions, F/T/F&T compositions, L/S/R compositions, proteins, peptides, amino acid sequences, etc. are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSO-COES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-

(gamma-Maleimidobutryloxy) sulfosuccinimide ester), SMPH (Succinimidyl-6-(beta-maleimidopropionamido-hexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-$\beta$-hydroxybenzimidate hydrochloride, 98%), DMA (Dimethyladipimidate hydrochloride).

Components of cargos or cargo composition can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide](Avanti Polar Lipids) by making use of a free cysteine sulfhydryl group on the component. The reaction can be performed, for example, in aqueous solution at room temperature for 4 hours. This coupling chemistry can be used to couple components of cargos and cargo compositions.

The disclosed compounds, components, and compositions can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., 2001). The particles can have surface modifications, for example, for reticuloendothelial system avoidance (PEG) and homing peptides, endosome escape (pH-sensitive peptide; for example, Pirello et al., 2007), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery.

The disclosed peptides, amino acid sequences, proteins, molecules, conjugates, and compositions themselves can be coupled to other components as disclosed herein using any known technique or the techniques described herein (although generally not, as described elsewhere herein, to the disclosed cargos). A maleimide function can also be used as a coupling group. These chemistries can be used to couple the disclosed peptides, amino acid sequences, proteins, molecules, conjugates, and compositions to each other and to other components.

The disclosed peptides, amino acid sequences, and proteins can also be coupled to other components using, for example, maleimide coupling. By way of illustration, the disclosed peptides, amino acid sequences, and proteins can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the peptides, amino acid sequence, or protein. The reaction can be performed, for example, in aqueous solution at room temperature for 4 hours. This coupling chemistry can be used to couple the disclosed peptides, amino acid sequences, and proteins to many other components, molecules and compositions.

E. Methods and Uses

The disclosed peptides, compositions, and other materials can be used in a variety of methods to accomplish various purposes and can be put to various uses. Most significantly, the disclosed peptides and compositions can be used in methods and for uses that involve binding of the peptides to target molecules. Such binding can occur in vitro, ex vivo, and in vivo depending on the needs and purposes of the method or use.

Thus, disclosed are methods comprising exposing a tumor to any one or more of the disclosed compositions. In some forms, the composition selectively binds to the tumor. In some forms, the tumor is in a subject. In some forms, the tumor is exposed to the composition by administering the composition to the subject. In some forms, the tumor expresses FN-EDB, TNC-C, or both FN-EDB and TNC-C. In some forms, the composition selectively binds to the tumor expressing FN-EDB, TNC-C, or both FN-EDB and TNC-C.

Also disclosed are methods comprising exposing extracellular matrix to any one or more of the disclosed compositions. In some forms, the composition selectively binds to the extracellular matrix. In some forms, the extracellular matrix is in a subject. In some forms, the extracellular matrix is exposed to the composition by administering the composition to the subject. In some forms, the extracellular matrix has FN-EDB, TNC-C, or both FN-EDB and TNC-C. In some forms, the composition selectively binds to the extracellular matrix having FN-EDB, TNC-C, or both FN-EDB and TNC-C.

In some forms, the composition has a therapeutic effect. In some forms, the therapeutic effect can comprise increase in apoptosis. In some forms, the subject has a disease or condition. In some forms, the disease is cancer. In some forms, the composition selectively homes to tumors expressing FN-EDB, TNC-C, or both FN-EDB and TNC-C. In some forms, the composition selectively homes to extracellular matrix having FN-EDB, TNC-C, or both FN-EDB and TNC-C.

Also disclosed are any of the disclosed compositions for use as a medicament. Also disclosed are any of the disclosed compositions for use in the treatment of cancer in a subject. Also disclosed are any of the disclosed compositions for use in the detection of cancer in a subject. Also disclosed are any of the disclosed compositions for use in the visualization of cancer in a subject. Also disclosed are any of the disclosed compositions for use in the localization of cancer in a subject.

Also disclosed is use of any of the disclosed compositions for the manufacture of a medicament for cancer treatment. Also disclosed is use of any of the disclosed compositions for the manufacture of a medicament for cancer detection.

Also disclosed are cancer diagnosis methods comprising administering an effective amount of any one or more of the disclosed compositions to a subject in need thereof.

In some forms of the disclosed methods, the disclosed compositions, or the disclosed uses, the cancer can be a cancer in Table 10.

TABLE 10

| Example Cancers. |
| --- |
| Acute Lymphoblastic Leukemia (ALL), Acute Myeloid Leukemia (AML), Adrenocortical Carcinoma, AIDS-Related Cancers, Kaposi Sarcoma, AIDS-Related Lymphoma, Primary CNS Lymphoma, Anal Cancer, Appendix Cancer (Gastrointestinal Carcinoid Tumors), Astrocytomas, Atypical Teratoid/Rhabdoid Tumor, Brain Cancer, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Non-Hodgkin Lymphoma, Carcinoid Tumors, Carcinoma of Unknown Primary, Cardiac (Heart) Tumors, Embryonal Tumors, Germ Cell Tumor, Primary CNS Lymphoma, Cervical Cancer, Cholangio-carcinoma, Chordoma, Chronic Lymphocytic Leukemia (CLL), Chronic Myelogenous Leukemia (CML), Chronic Myeloproliferative Neoplasms, Colorectal Cancer, Cranio-pharyngioma, Cutaneous T-Cell Lymphoma (Mycosis Fungoides and Sézary Syndrome), Ductal Carcinoma In Situ (DCIS), Endometrial Cancer, Ependymoma, Esophageal Cancer, Esthesioneuro-blastoma, Ewing Sarcoma, Extracranial Germ Cell Tumor, Eye Cancer, Intraocular Melanoma, Fallopian Tube Cancer, Fibrous Histiocytoma of Bone, Osteosarcoma, Gallbladder Cancer, Gastric Cancer, Stomach Cancer, Gastrointestinal Carcinoid Tumor, Gastrointestinal Stromal Tumors (GIST), Central Nervous System Germ Cell Tumors, Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis (Langerhans Cell), Hodgkin Lymphoma, Hypopharyngeal Cancer, Intraocular Melanoma, Islet Cell Tumors, Pancreatic Neuroendocrine Tumors, Kidney Cancer, Renal Cell Cancer, Langerhans Cell Histiocytosis, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Intraocular (Eye) Melanoma, Merkel Cell Carcinoma (Skin Cancer), Malignant Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, and Oropharyngeal Cancer, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Recurrent Cancer, Retinoblastoma, Rhabdomyosarcoma, Salivary Gland Cancer, Sarcoma, Vascular Tumors, Uterine Sarcoma, Sézary Syndrome (Lymphoma), Small Cell Lung Cancer, Small Intestine |

TABLE 10-continued

| Example Cancers. |
|---|
| Cancer, Soft Tissue Sarcoma, Squamous Cell Carcinoma, Stomach (Gastric) Cancer, Throat Cancer, Thymoma, Thymic Carcinoma, Thyroid Cancer, Transitional Cell Cancer of the Renal Pelvis and Ureter, Carcinoma of Unknown Primary, Ureter and Renal Pelvis, Transitional Cell Cancer, Urethral Cancer, Uterine Cancer, Vaginal Cancer, Vulvar Cancer, Wilms Tumor |

In some forms of the disclosed methods, the disclosed compositions, or the disclosed uses, the cancer can be a solid tumor cancer such as those listed in Table 11.

TABLE 11

| Examples of Solid Tumr Cancers. |
|---|
| Adrenocortical Carcinoma, AIDS-Related Cancers, Kaposi Sarcoma, Anal Cancer, Appendix Cancer (Gastrointestinal Carcinoid Tumors), Astrocytomas, Atypical Teratoid/Rhabdoid Tumor, Brain Cancer, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Carcinoid Turnors, Carcinoma of Unknown Primary, Cardiac (Heart) Tumors, Embryonal Tumors, Germ Cell Tumor, Cervical Cancer, Cholangio-carcinoma, Chordoma, Colorectal Cancer, Cranio-pharyngioma, Ductal Carcinoma In Situ (DCIS), Endometrial Cancer, Ependymoma, Esophageal Cancer, Esthesioneuro-blastoma, Ewing Sarcoma, Extracranial Germ Cell Tumor, Eye Cancer, Intraocular Melanoma, Fallopian Tube Cancer, Fibrous Histiocytoma of Bone, Osteosarcoma, Gallbladder Cancer, Gastric Cancer, Stomach Cancer, Gastrointestinal Carcinoid Tumor, Gastrointestinal Stromal Tumors (GIST), Central Nervous System Germ Cell Tumors, Extracranial Germ Cell Tumors, Extragonadal Germ Cell Tumors, Ovarian Germ Cell Tumors, Testicular Cancer, Gestational Trophoblastic Disease, Head and Neck Cancer, Heart Tumors, Hepatocellular (Liver) Cancer, Histiocytosis (Langerhans Cell), Hypopharyngeal Cancer, Intraocular Melanoma, Islet Cell Tumors, Pancreatic Neuroendocrine Tumors, Kidney Cancer, Renal Cell Cancer, Langerhans Cell Histiocytosis, Laryngeal Cancer, Lip and Oral Cavity Cancer, Liver Cancer, Lung Cancer (Non-Small Cell and Small Cell), Male Breast Cancer, Malignant Fibrous Histiocytoma of Bone and Osteosarcoma, Melanoma, Intraocular (Eye) Melanoma, Merkel Cell Carcinoma (Skin Cancer), Malignant Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Nasal Cavity and Paranasal Sinus Cancer, Nasopharyngeal Cancer, Neuroblastoma, Non-Small Cell Lung Cancer, Oral Cancer, and Oropharyngeal Cancer, Ovarian Cancer, Pancreatic Cancer, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Peritoneal Cancer, Prostate Cancer, Rectal Cancer, Recurrent Cancer, Retinoblastoma, Rhabdomyosarcoma, Salivary Gland Cancer, Sarcoma, Vascular Tumors, Uterine Sarcoma, Small Cell Lung Cancer, Small Intestine Cancer, Soft Tissue Sarcoma, Squamous Cell Carcinoma, Stomach (Gastric) Cancer, Throat Cancer, Thymoma, Thymic Carcinoma, Thyroid Cancer, Transitional Cell Cancer of the Renal Pelvis and Ureter, Carcinoma of Unknown Primary, Ureter and Renal Pelvis, Transitional Cell Cancer, Urethral Cancer, Uterine Cancer, Vaginal Cancer, Vulvar Cancer, Wilms Tumor |

Also disclosed are methods of enhancing targeting, delivery, or both of a cargo to a cell, tissue, or both. In some forms, the method can comprising exposing the cell, tissue, or both to the cargo and an F/T/F&T composition, thereby enhancing targeting, delivery, or both of the cargo to the cell, tissue, or both. The F/T/F&T composition can comprise any of the disclosed F/T/F&T peptides or any of the disclosed compositions that comprise an F/T/F&T peptide. In some forms, the F/T/F&T composition and the cargo are not covalently coupled or directly non-covalently associated with each other prior to exposing the cell, tissue, or both.

Also disclosed are methods of enhancing targeting, delivery, or both of a cargo to a cell, tissue, or both. In some forms, the method can comprising exposing the cell, tissue, or both to the cargo and an L/S/R composition, thereby enhancing targeting, delivery, or both of the cargo to the cell, tissue, or both. The L/S/R composition can comprise any of the disclosed L/S/R peptides or any of the disclosed compositions that comprise an L/S/R peptide. In some forms, the L/S/R composition and the cargo are not covalently coupled or directly non-covalently associated with each other prior to exposing the cell, tissue, or both.

Also disclosed are methods of enhancing targeting, delivery, or both of a cargo composition to a cell, tissue, or both. In some forms, the method can comprise exposing the cell, tissue, or both to the cargo composition and an F/T/F&T composition, thereby enhancing targeting, delivery, or both of the cargo composition to the cell, tissue, or both. The F/T/F&T composition can comprise any of the disclosed F/T/F&T peptides or any of the disclosed compositions that comprise an F/T/F&T peptide. In some forms, the F/T/F&T composition and the cargo composition can be covalently coupled or non-covalently associated with each other.

Also disclosed are methods of enhancing targeting, delivery, or both of a cargo composition to a cell, tissue, or both. In some forms, the method can comprise exposing the cell, tissue, or both to the cargo composition and an L/S/R composition, thereby enhancing targeting, delivery, or both of the cargo composition to the cell, tissue, or both. The L/S/R composition can comprise any of the disclosed L/S/R peptides or any of the disclosed compositions that comprise an L/S/R peptide. In some forms, the L/S/R composition and the cargo composition can be covalently coupled or non-covalently associated with each other.

Also disclosed are methods of enhancing targeting, delivery, or both to a cell, tissue, or both. In some forms, the method can comprise exposing the cell, tissue, or both to an F/T/F&T composition, thereby enhancing targeting, delivery, or both to the cell, tissue, or both. The F/T/F&T composition can comprise any of the disclosed F/T/F&T peptides or any of the disclosed compositions that comprise an F/T/F&T peptide.

Also disclosed are methods of enhancing targeting, delivery, or both to a cell, tissue, or both. In some forms, the method can comprise exposing the cell, tissue, or both to an L/S/R composition, thereby enhancing targeting, delivery, or both to the cell, tissue, or both. The L/S/R composition can comprise any of the disclosed L/S/R peptides or any of the disclosed compositions that comprise an L/S/R peptide.

In some forms, the cell, tissue, or both can be in a subject. In some forms, the cell, tissue, or both can be exposed to the F/T/F&T composition and the cargo by administering the F/T/F&T composition and the cargo to the subject. In some forms, the cell, tissue, or both can be exposed to the F/T/F&T composition and the cargo composition by administering the F/T/F&T composition and the cargo composition to the subject. In some forms, the cell, tissue, or both can be exposed to the F/T/F&T composition by administering the F/T/F&T composition to the subject. In some forms, the cell, tissue, or both can be exposed to the L/S/R composition and the cargo by administering the L/S/R composition and the cargo to the subject. In some forms, the cell, tissue, or both can be exposed to the L/S/R composition and the cargo composition by administering the L/S/R composition and the cargo composition to the subject. In some forms, the cell, tissue, or both can be exposed to the L/S/R composition by administering the L/S/R composition to the subject.

In some forms, the F/T/F&T composition can selectively home to cells and tissues having FN-EDB, TNC-C, or both. In some forms, the F/T/F&T composition can selectively home to cells and tissues having FN-EDB, TNC-C, or both. In some forms, the F/T/F&T composition and the cargo can be administered to the subject simultaneously. In some forms, the F/T/F&T composition and the cargo can be administered to the subject in a single composition comprising the F/T/F&T composition and the cargo. In some forms, the F/T/F&T composition and the cargo can be administered to the subject in separate compositions. In some forms, the F/T/F&T composition and the cargo can be administered to the subject at different times. In some forms, the F/T/F&T composition and the cargo can be administered to the subject in separate compositions. In some forms, the F/T/F&T composition and the cargo can be administered to the subject by separate routes.

In some forms, the L/S/R composition can selectively home to cells and tissues having FN-EDB, TNC-C, or both. In some forms, the L/S/R composition can selectively home to cells and tissues having FN-EDB, TNC-C, or both. In some forms, the L/S/R composition and the cargo can be administered to the subject simultaneously. In some forms, the L/S/R composition and the cargo can be administered to the subject in a single composition comprising the L/S/R composition and the cargo. In some forms, the L/S/R composition and the cargo can be administered to the subject in separate compositions. In some forms, the L/S/R composition and the cargo can be administered to the subject in separate compositions. In some forms, the L/S/R composition tion and the cargo can be administered to the subject at different times. In some forms, the L/S/R composition and the cargo can be administered to the subject in separate compositions. In some forms, the L/S/R composition and the cargo can be administered to the subject by separate routes.

In some forms, the cell, tissue, or both can be exposed to a plurality of peptides. In some forms, the cell, tissue, or both can be exposed to a plurality of cargo compositions. In some forms, the cell, tissue, or both can be exposed to a plurality of L/S/R compositions. In some forms, the cell, tissue, or both can be exposed to a plurality of cargos.

In some forms, the F/T/F&T composition, cargo, and/or cargo composition can have a therapeutic effect. In some forms, the therapeutic effect can be a slowing in the increase of or a reduction of tumor burden. In some forms, the therapeutic effect can be a slowing of the increase of or reduction of tumor size. In some forms, the subject can have one or more sites to be targeted, where the F/T/F&T composition, cargo, and/or cargo composition homes to one or more of the sites to be targeted. In some forms, the subject can have cells and tissues having FN-EDB, TNC-C, or both, where the F/T/F&T composition, cargo, and/or cargo composition has a therapeutic effect on the tumor.

In some forms, the L/S/R composition, cargo, and/or cargo composition can have a therapeutic effect. In some forms, the therapeutic effect can be a slowing in the increase of or a reduction of tumor burden. In some forms, the therapeutic effect can be a slowing of the increase of or reduction of tumor size. In some forms, the subject can have one or more sites to be targeted, where the L/S/R composition, cargo, and/or cargo composition homes to one or more of the sites to be targeted. In some forms, the subject can have cells and tissues having FN-EDB, TNC-C, or both, where the L/S/R composition, cargo, and/or cargo composition has a therapeutic effect on the tumor.

In some forms, the cell, tissue, or both can be exposed to a plurality of peptides. In some forms, the cell, tissue, or both can be exposed to a plurality of cargo compositions. In some forms, the cell, tissue, or both can be exposed to a plurality of F/T/F&T compositions. In some forms, the cell, tissue, or both can be exposed to a plurality of L/S/R compositions. In some forms, the cell, tissue, or both can be exposed to a plurality of cargos.

Multiple different F/T/F&T peptides, F/T/F&T compounds, F/T/F&T conjugates, F/T/F&T compositions, or a combination can be used together. Similarly, multiple different cargos, multiple different cargo compositions, or a combination can be used together. Where such multiple different F/T/F&T peptides, F/T/F&T compounds, F/T/F&T conjugates, F/T/F&T compositions, or a combination are used together, they can be used with a single type of cargo, a single type of cargo composition, multiple different cargos, multiple different cargo compositions, or a combination. Similarly, when multiple different cargos, multiple different cargo compositions, or a combination can be used together, they can be used with a single type of F/T/F&T peptide, F/T/F&T compound, F/T/F&T conjugate, F/T/F&T composition, or with multiple different F/T/F&T peptides, F/T/F&T compounds, F/T/F&T conjugates, F/T/F&T compositions, or a combination.

For example, an PPRRGLIKLKTS (SEQ ID NO:1) can be used together with one or multiple different F/T/F&T peptides, F/T/F&T compounds, F/T/F&T conjugates, F/T/F&T compositions, or a combination, one or multiple different cargos, multiple different cargo compositions, or a combination, or any combination of these. In such combinations, the PPRRGLIKLKTS (SEQ ID NO:1) itself can be combined in the same conjugate or composition with one or more cargo compositions, one or more accessory molecules, etc.

Multiple different L/S/R peptides, L/S/R compounds, L/S/R conjugates, L/S/R compositions, or a combination can be used together. Similarly, multiple different cargos, multiple different cargo compositions, or a combination can be used together. Where such multiple different L/S/R peptides, L/S/R compounds, L/S/R conjugates, L/S/R compositions, or a combination are used together, they can be used with a single type of cargo, a single type of cargo composition, multiple different cargos, multiple different cargo compositions, or a combination. Similarly, when multiple different cargos, multiple different cargo compositions, or a combination can be used together, they can be used with a single type of L/S/R peptide, L/S/R compound, L/S/R conjugate, L/S/R composition, or with multiple different L/S/R peptides, L/S/R compounds, L/S/R conjugates, L/S/R compositions, or a combination.

For example, an PPRRGLIKLKTS (SEQ ID NO:1) can be used together with one or multiple different L/S/R peptides, L/S/R compounds, L/S/R conjugates, L/S/R compositions, or a combination, one or multiple different cargos, multiple different cargo compositions, or a combination, or any combination of these. In such combinations, the PPRR-GLIKLKTS (SEQ ID NO:1) itself can be combined in the same conjugate or composition with one or more cargo compositions, one or more accessory molecules, etc.

The cell, tissue, or both can be exposed to combinations of different F/T/F&T components and combinations of different cargos by administering the F/T/F&T components and the cargos to the subject. One or more of the F/T/F&T components and one or more of the cargos can be administered to the subject simultaneously. One or more of the F/T/F&T components and one or more of the cargos can be administered to the subject in one or more single compositions comprising the F/T/F&T component(s) and the cargo(s). One or more of the F/T/F&T components and one or more of the cargos can be administered to the subject in one or more separate compositions. One or more of the F/T/F&T components and one or more of the cargos can be administered to the subject at different times. The F/T/F&T composition and the cargo can be administered to the subject in one or more separate compositions. One or more of the F/T/F&T components and one or more of the cargos can be administered to the subject by one or more separate routes. In some forms, the F/T/F&T composition and the cargo are not bound to each other.

The cell, tissue, or both can be exposed to combinations of different L/S/R components and combinations of different cargos by administering the L/S/R components and the cargos to the subject. One or more of the L/S/R components and one or more of the cargos can be administered to the subject simultaneously. One or more of the L/S/R components and one or more of the cargos can be administered to the subject in one or more single compositions comprising the L/S/R component(s) and the cargo(s). One or more of the L/S/R components and one or more of the cargos can be administered to the subject in one or more separate compositions. One or more of the L/S/R components and one or more of the cargos can be administered to the subject at different times. The L/S/R composition and the cargo can be administered to the subject in one or more separate compositions. One or more of the L/S/R components and one or more of the cargos can be administered to the subject by one or more separate routes. In some forms, the L/S/R composition and the cargo are not bound to each other.

The cell, tissue, or both can be exposed to combinations of different F/T/F&T components and combinations of different cargo compositions by administering the F/T/F&T components and the cargo compositions to the subject. One or more of the F/T/F&T components and one or more of the cargo compositions can be administered to the subject simultaneously. One or more of the F/T/F&T components and one or more of the cargo compositions can be administered to the subject in one or more single compositions comprising the F/T/F&T component(s) and the cargo composition(s). One or more of the F/T/F&T components and one or more of the cargo compositions can be administered to the subject in one or more separate compositions. One or more of the F/T/F&T components and one or more of the cargo compositions can be administered to the subject at different times. The F/T/F&T composition and the cargo composition can be administered to the subject in one or more separate compositions. One or more of the F/T/F&T components and one or more of the cargo compositions can be administered to the subject by one or more separate routes.

The cell, tissue, or both can be exposed to combinations of different L/S/R components and combinations of different cargo compositions by administering the L/S/R components and the cargo compositions to the subject. One or more of the L/S/R components and one or more of the cargo compositions can be administered to the subject simultaneously. One or more of the L/S/R components and one or more of the cargo compositions can be administered to the subject in one or more single compositions comprising the L/S/R component(s) and the cargo composition(s). One or more of the L/S/R components and one or more of the cargo compositions can be administered to the subject in one or more separate compositions. One or more of the L/S/R components and one or more of the cargo compositions can be administered to the subject at different times. The L/S/R composition and the cargo composition can be administered to the subject in one or more separate compositions. One or more of the L/S/R components and one or more of the cargo compositions can be administered to the subject by one or more separate routes.

The F/T/F&T peptide or the L/S/R peptide can be comprised in an amino acid sequence in a protein or peptide. In some forms, the protein or peptide can be targeted, delivered, or both to cells and tissues having FN-EDB, TNC-C, or both when the amino acid sequence is present in the protein or peptide but not when the amino acid sequence is not present in the protein or peptide. In some forms, the protein or peptide can be targeted, delivered, or both to cells and tissues having FN-EDB, TNC-C, or both when the amino acid sequence is present in the protein or peptide but not when the amino acid sequence is not present in the protein or peptide. In some forms, the amino acid sequence is the only functional homing molecule in the protein or peptide.

The disclosed peptides home to specific cells (cells and tissues having FN-EDB, TNC-C, or both) and many homing molecules home to the vasculature of the target tissue. However, for the sake of convenience homing is referred to in some places herein as homing to the tissue associated with FN-EDB, TNC-C, or both, or with the vasculature, to which the peptide or homing peptide may actually home. Thus, for example, a homing peptide that homes to cells and tissues having FN-EDB, TNC-C, or both can be referred to herein as homing to tumor tissue or to tumor cells. By including or associating a peptide or homing peptide with, for example, a protein, peptide, amino acid sequence, cargo, or cargo composition, the protein, peptide, amino acid sequence, cargo, or cargo composition can be targeted or can home to the target of the peptide or homing peptide. In this way, the protein, peptide, amino acid sequence, cargo, or cargo composition, or can be said to home to the target of the peptide or homing peptide. For convenience and unless otherwise indicated, reference to homing of a protein, peptide, amino acid sequence, cargo, cargo composition, etc. is intended to indicate that the protein, peptide, amino acid sequence, cargo, cargo composition, etc. includes or is associated with an appropriate peptide or homing peptide.

The amino acid sequence can be selected for homing to cells and tissues having FN-EDB, TNC-C, or both. The protein or peptide can be selected for homing to cells and tissues having FN-EDB, TNC-C, or both. The conjugate can be selected for homing to cells and tissues having FN-EDB, TNC-C, or both. The composition can be selected for homing to cells and tissues having FN-EDB, TNC-C, or both.

The F/T/F&T peptide, F/T/F&T conjugate, F/T/F&T composition, amino acid sequence, protein or peptide, conjugate, composition, cargo, cargo composition, or a combination can selectively home to cells and tissues having FN-EDB, TNC-C, or both. The F/T/F&T peptide, F/T/F&T conjugate, F/T/F&T composition, amino acid sequence, protein or peptide, conjugate, composition, cargo, cargo composition, or a combination can selectively home to cells and tissues having FN-EDB, TNC-C, or both. The F/T/F&T peptide, F/T/F&T conjugate, F/T/F&T composition, amino acid sequence, protein or peptide, conjugate, composition, cargo, cargo composition, or a combination can selectively home to one or more particular types of tumor. The F/T/F&T peptide, F/T/F&T conjugate, F/T/F&T composition, amino acid sequence, protein or peptide, conjugate, composition, cargo, cargo composition, or a combination can selectively home to the vasculature of one or more particular types of tumor. The F/T/F&T peptide, F/T/F&T conjugate, F/T/F&T composition, amino acid sequence, protein or peptide, conjugate, composition, cargo, cargo composition, or a combination can selectively home to one or more particular stages of a tumor or cancer. The F/T/F&T peptide, F/T/F&T conjugate, F/T/F&T composition, amino acid sequence, protein or peptide, conjugate, composition, cargo, cargo composition, or a combination can selectively home to the vasculature of one or more particular stages of a tumor or cancer. The F/T/F&T peptide, F/T/F&T conjugate, F/T/F&T composition, amino acid sequence, protein or peptide, conjugate, composition, cargo, cargo composition, or a combination can selectively home to one or more particular stages of one or more particular types of tumor. The F/T/F&T peptide, F/T/F&T conjugate, F/T/F&T composition, amino acid sequence, protein or peptide, conjugate, composition, cargo, cargo composition, or a combination can selectively home to the vasculature of one or more different stages of one or more particular types of tumor.

The L/S/R peptide, L/S/R conjugate, L/S/R composition, amino acid sequence, protein or peptide, conjugate, composition, cargo, cargo composition, or a combination can selectively home to cells and tissues having FN-EDB, TNC-C, or both. The L/S/R peptide, L/S/R conjugate, L/S/R composition, amino acid sequence, protein or peptide, conjugate, composition, cargo, cargo composition, or a combination can selectively home to cells and tissues having FN-EDB, TNC-C, or both. The L/S/R peptide, L/S/R conjugate, L/S/R composition, amino acid sequence, protein or peptide, conjugate, composition, cargo, cargo composition, or a combination can selectively home to one or more particular types of tumor. The L/S/R peptide, L/S/R conjugate, L/S/R composition, amino acid sequence, protein or peptide, conjugate, composition, cargo, cargo composition, or a combination can selectively home to the vasculature of one or more particular types of tumor. The L/S/R peptide, L/S/R conjugate, L/S/R composition, amino acid sequence, protein or peptide, conjugate, composition, cargo, cargo composition, or a combination can selectively home to one or more particular stages of a tumor or cancer. The L/S/R peptide, L/S/R conjugate, L/S/R composition, amino acid sequence, protein or peptide, conjugate, composition, cargo, cargo composition, or a combination can selectively home to the vasculature of one or more particular stages of a tumor or cancer. The L/S/R peptide, L/S/R conjugate, L/S/R composition, amino acid sequence, protein or peptide, conjugate, composition, cargo, cargo composition, or a combination can selectively home to one or more particular stages of one or more particular types of tumor. The L/S/R peptide, L/S/R conjugate, L/S/R composition, amino acid sequence, protein or peptide, conjugate, composition, cargo, cargo composition, or a combination can selectively home to the vasculature of one or more different stages of one or more particular types of tumor.

The cell, tissue, or both can be exposed to a plurality of accessory molecules. The cell, tissue, or both can be exposed to a plurality of peptides. The cell, tissue, or both can be exposed to a plurality of cargo compositions. The cell, tissue, or both can be exposed to a plurality of F/T/F&T peptides. The cell, tissue, or both can be exposed to a plurality of L/S/R peptides. The cell, tissue, or both can be exposed to a plurality of cargos.

"Internalization" refers to passage through a plasma membrane or other biological barrier. "Penetration" refers to passage into and through a cell, tissue, or other biological barrier. Penetration generally involves and includes internalization. The disclosed F/T/F&T peptides generally promote and allow internalization (such as internalization into a cell).

By "internalization into a cell" is meant that that a component is capable of penetrating or passing through the plasma membrane, thereby being internalized into the cell. This internalization can occur with, for example, 10, 20, 30, 40, 50, 60, 70, 80, 90, or 100% efficiency for a given component and a given cell. By "permeable" is meant the ability and/or condition of cells and/or tissues to allow compositions, conjugates, molecules, etc. in proximity to the cells and/or tissues to enter and or pass through the cells and/or tissues.

As used herein, "tissue penetration" and "penetration of tissue" refer to passage to a tissue beyond or through the outer or a first layer of cells or through a tissue membrane. Such passage or penetration through tissue (which can also be referred to as extravasation and tissue penetration) can be a function of, for example, cell internalization and passage between cells in the tissue.

Subjects harboring cells and tissues having FN-EDB, TNC-C, or both, can be identified as a candidate for a disclosed therapy by, for example, (a) exposing tissue from the subject to an F/T/F&T peptide; and (b) determining if the F/T/F&T peptide bound to the tissue, wherein binding to the tissue identifies the subject as being a candidate for a disclosed therapy. Any form or type of F/T/F&T peptide, F/T/F&T peptide, F/T/F&T protein, F/T/F&T conjugate, or F/T/F&T composition can be used in these methods.

Subjects harboring cells and tissues having FN-EDB, TNC-C, or both, can be identified as a candidate for a disclosed therapy by, for example, (a) exposing tissue from the subject to an L/S/R peptide; and (b) determining if the L/S/R peptide bound to the tissue, wherein binding to the tissue identifies the subject as being a candidate for a disclosed therapy. Any form or type of L/S/R peptide, L/S/R peptide, L/S/R protein, L/S/R conjugate, or L/S/R composition can be used in these methods.

The disclosed peptides (and other disclosed forms) and cargos can be administered together or separately; in the same form and manner or in different forms and/or manners; at the same time or at different times; with the disclosed peptide (or other disclosed form) administered first or second. Administration can be, for example, co-administration (at the same time and by the same or different route/means/form), separate administration (parallel administration by the same or different route/means/form), sequential administration (at different times by the same or different route/means/form), etc. When the cargo and the peptide (or other form) are administered at different times, a variety of different delays can be used between the administrations. For example, the peptide (or other form) can be administered 1, 2, 3, 4, 5, 6, 7, 8, 9, 10, 11, 12, 13, 15, 20, 30, 40, 45, 50, 60, 70, 80, 90, 100, 110, or 120 minutes or more before administering a cargo. The peptide (or other form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more before administering a cargo. The peptide (or other form) can be administered 1, 2, 3, 4, 5, 6, or 7 days or more before administering a cargo. The peptide (or other form) can be administered 1, 2, 3, 4, 5, 6, 7, 8, 9, 10, 11, 12, 13, 15, 20, 30, 40, 45, 50, 60, 70, 80, 90, 100, 110, or 120 minutes or more after administering a cargo. The peptide (or other form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more after administering a cargo. The peptide (or other form) can be administered 1, 2, 3, 4, 5, 6, or 7 days or more after administering a cargo.

The disclosed peptides (or other disclosed forms) can be administered within 1, 2, 3, 4, 5, 6, 7, 8, 9, 10, 11, 12, 13, 15, 20, 30, 40, 45, 50, 60, 70, 80, 90, 100, 110, or 120 minutes before administering a cargo. The disclosed peptides (or other disclosed forms) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours before administering a cargo. The disclosed peptides (or other disclosed forms) can be administered within 1, 2, 3, 4, 5, 6, or 7 days before administering a cargo. The disclosed peptides (or other disclosed forms) can be administered within 1, 2, 3, 4, 5, 6, 7, 8, 9, 10, 11, 12, 13, 15, 20, 30, 40, 45, 50, 60, 70, 80, 90, 100, 110, or 120 minutes after administering a cargo. The disclosed peptides (or other disclosed forms) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours after administering a cargo. The disclosed peptides (or other disclosed forms) can be administered within 1, 2, 3, 4, 5, 6, or 7 days after administering a cargo. Administration within the same day or hour is particularly useful.

The F/T/F&T composition, F/T/F&T conjugate, F/T/F&T molecule, F/T/F&T protein, or F/T/F&T peptide and the cargo can be administered to the subject simultaneously. By simultaneously is meant during overlapping or contiguous time periods. The F/T/F&T composition, F/T/F&T conjugate, F/T/F&T molecule, F/T/F&T protein, or F/T/F&T peptide and the cargo can be administered to the subject in a single composition comprising the F/T/F&T composition, F/T/F&T conjugate, F/T/F&T molecule, F/T/F&T protein, or F/T/F&T peptide and the cargo. The F/T/F&T composition, F/T/F&T conjugate, F/T/F&T molecule, F/T/F&T protein, or F/T/F&T peptide and the cargo can be administered to the subject in separate compositions. The F/T/F&T peptide and the cargo can be administered to the subject at different times. The F/T/F&T peptide and the cargo can be administered to the subject in separate compositions. By separate compositions is meant compositions that are not mixed or in contact with each other (except as may occur following administration). The F/T/F&T peptide and the cargo can be administered to the subject by separate routes. By separate routes is meant in separate locations, by different means or mode, or both.

The L/S/R composition, L/S/R conjugate, L/S/R molecule, L/S/R protein, or L/S/R peptide and the cargo can be administered to the subject simultaneously. By simultaneously is meant during overlapping or contiguous time periods. The L/S/R composition, L/S/R conjugate, L/S/R molecule, L/S/R protein, or L/S/R peptide and the cargo can be administered to the subject in a single composition comprising the L/S/R composition, L/S/R conjugate, L/S/R molecule, L/S/R protein, or L/S/R peptide and the cargo. The L/S/R composition, L/S/R conjugate, L/S/R molecule, L/S/R protein, or L/S/R peptide and the cargo can be administered to the subject in separate compositions. The L/S/R peptide and the cargo can be administered to the subject at different times. The L/S/R peptide and the cargo can be administered to the subject in separate compositions. By separate compositions is meant compositions that are not mixed or in contact with each other (except as may occur following administration). The L/S/R peptide and the cargo can be administered to the subject by separate routes. By separate routes is meant in separate locations, by different means or mode, or both.

The peptide can selectively home to cells and tissues having FN-EDB, TNC-C, or both. The peptide can selectively home to cells and tissues having FN-EDB, TNC-C, or both. The peptide can selectively home to one or more particular types of tumor. The peptide can selectively home to the vasculature of one or more particular types of tumor. The peptide can selectively home to one or more particular stages of a tumor or cancer. The peptide can selectively home to the vasculature of one or more particular stages of a tumor or cancer. The peptide can selectively home to one or more particular stages of one or more particular types of tumor. The peptide can selectively home to the vasculature of one or more different stages of one or more particular types of tumor.

The composition can selectively home to cells and tissues having FN-EDB, TNC-C, or both. The composition can selectively home to cells and tissues having FN-EDB, TNC-C, or both. The composition can selectively home to one or more particular types of tumor. The composition can selectively home to the vasculature of one or more particular types of tumor. The composition can selectively home to one or more particular stages of a tumor or cancer. The composition can selectively home to the vasculature of one or more particular stages of a tumor or cancer. The composition can selectively home to one or more particular stages of one or more particular types of tumor. The composition can selectively home to the vasculature of one or more different stages of one or more particular types of tumor.

The cargo can selectively home to cells and tissues having FN-EDB, TNC-C, or both. The cargo can selectively home to cells and tissues having FN-EDB, TNC-C, or both. The cargo can selectively home to one or more particular types of tumor. The cargo can selectively home to the vasculature of one or more particular types of tumor. The cargo can selectively home to one or more particular stages of a tumor or cancer. The cargo can selectively home to the vasculature of one or more particular stages of a tumor or cancer. The cargo can selectively home to one or more particular stages of one or more particular types of tumor. The cargo can selectively home to the vasculature of one or more different stages of one or more particular types of tumor.

The F/T/F&T composition can selectively home to cells and tissues having FN-EDB, TNC-C, or both. The F/T/F&T composition can selectively home to cells and tissues having FN-EDB, TNC-C, or both. The F/T/F&T composition can selectively home to one or more particular types of tumor. The F/T/F&T composition can selectively home to the vasculature of one or more particular types of tumor. The F/T/F&T composition can selectively home to one or more particular stages of a tumor or cancer. The F/T/F&T composition can selectively home to the vasculature of one or more particular stages of a tumor or cancer. The F/T/F&T composition can selectively home to one or more particular stages of one or more particular types of tumor. The F/T/F&T composition can selectively home to the vasculature of one or more different stages of one or more particular types of tumor.

The L/S/R composition can selectively home to cells and tissues having FN-EDB, TNC-C, or both. The L/S/R composition can selectively home to cells and tissues having FN-EDB, TNC-C, or both. The L/S/R composition can selectively home to one or more particular types of tumor. The L/S/R composition can selectively home to the vasculature of one or more particular types of tumor. The L/S/R composition can selectively home to one or more particular stages of a tumor or cancer. The L/S/R composition can selectively home to the vasculature of one or more particular stages of a tumor or cancer. The L/S/R composition can selectively home to one or more particular stages of one or more particular types of tumor. The L/S/R composition can selectively home to the vasculature of one or more different stages of one or more particular types of tumor.

The F/T/F&T peptide can selectively home to cells and tissues having FN-EDB, TNC-C, or both. The F/T/F&T peptide can selectively home to cells and tissues having FN-EDB, TNC-C, or both. The F/T/F&T peptide can selectively home to one or more particular types of tumor. The F/T/F&T peptide can selectively home to the vasculature of one or more particular types of tumor. The F/T/F&T peptide can selectively home to one or more particular stages of a tumor or cancer. The F/T/F&T peptide can selectively home to the vasculature of one or more particular stages of a tumor or cancer. The F/T/F&T peptide can selectively home to one or more particular stages of one or more particular types of tumor. The F/T/F&T peptide can selectively home to the vasculature of one or more different stages of one or more particular types of tumor.

The L/S/R peptide can selectively home to cells and tissues having FN-EDB, TNC-C, or both. The L/S/R peptide can selectively home to cells and tissues having FN-EDB, TNC-C, or both. The L/S/R peptide can selectively home to one or more particular types of tumor. The L/S/R peptide can selectively home to the vasculature of one or more particular types of tumor. The L/S/R peptide can selectively home to one or more particular stages of a tumor or cancer. The L/S/R peptide can selectively home to the vasculature of one or more particular stages of a tumor or cancer. The L/S/R peptide can selectively home to one or more particular stages of one or more particular types of tumor. The L/S/R peptide can selectively home to the vasculature of one or more different stages of one or more particular types of tumor.

The cargo composition can selectively home to cells and tissues having FN-EDB, TNC-C, or both. The cargo composition can selectively home to cells and tissues having FN-EDB, TNC-C, or both. The cargo composition can selectively home to one or more particular types of tumor. The cargo composition can selectively home to the vasculature of one or more particular types of tumor. The cargo composition can selectively home to one or more particular stages of a tumor or cancer. The cargo composition can selectively home to the vasculature of one or more particular stages of a tumor or cancer. The cargo composition can selectively home to one or more particular stages of one or more particular types of tumor. The cargo composition can selectively home to the vasculature of one or more different stages of one or more particular types of tumor.

The cargo molecule can selectively home to cells and tissues having FN-EDB, TNC-C, or both. The cargo molecule can selectively home to cells and tissues having FN-EDB, TNC-C, or both. The cargo molecule can selectively home to one or more particular types of tumor. The cargo molecule can selectively home to the vasculature of one or more particular types of tumor. The cargo molecule can selectively home to one or more particular stages of a tumor or cancer. The cargo molecule can selectively home to the vasculature of one or more particular stages of a tumor or cancer. The cargo molecule can selectively home to one or more particular stages of one or more particular types of tumor. The cargo molecule can selectively home to the vasculature of one or more different stages of one or more particular types of tumor.

The surface molecule can selectively home to cells and tissues having FN-EDB, TNC-C, or both. The surface molecule can selectively home to cells and tissues having FN-EDB, TNC-C, or both. The surface molecule can selectively home to one or more particular types of tumor. The surface molecule can selectively home to the vasculature of one or more particular types of tumor. The surface molecule can selectively home to one or more particular stages of a tumor or cancer. The surface molecule can selectively home to the vasculature of one or more particular stages of a tumor or cancer. The surface molecule can selectively home to one or more particular stages of one or more particular types of tumor. The surface molecule can selectively home to the vasculature of one or more different stages of one or more particular types of tumor.

As used herein, "administered with, "administered together with," and like terms means that one component is administered in the same composition as another component. As used herein, "administered at the same time as" and like terms means that one component is administered at the same time as another component. By at the same time is meant simultaneously and/or overlapping in time. As used herein, "administered during the same treatment period," "administered during overlapping treatment periods," or like terms means that one component is administered during the period when the other component remains therapeutically effective. The period when a component remains therapeutically effective refers to the period before the component is turned over, cleared, broken down, altered, etc. to a subtherapeutic amount or concentration.

The disclosed compositions and cargos and cargo compositions can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

The disclosed compositions and cargos and cargo compositions can be used therapeutically in combination with a pharmaceutically acceptable carrier. Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

The preparation can be administered to a subject or organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to a subject or organism.

Herein the term "active ingredient" refers to the preparation accountable for the biological effect. For example F/T/F&T peptides, F/T/F&T compositions, F/T/F&T conjugates, F/T/F&T molecules, F/T/F&T proteins, L/S/R peptides, L/S/R compositions, L/S/R conjugates, L/S/R molecules, L/S/R proteins, compositions, cargos, and cargo compositions that have a biological effect can be considered active ingredients.

As used herein, the phrases "physiologically acceptable carrier" and "pharmaceutically acceptable carrier" which can be interchangeably used refer to a carrier or a diluent that does not cause significant irritation to a subject or organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in Remington's Pharmaceutical Sciences, Mack Publishing Co., Easton, Pa., latest edition, which is incorporated herein by reference.

Any suitable route of administration can be used for the disclosed compositions. Routes of administration can, for example, include topical, enteral, local, systemic, or parenteral. For example, administration can be intratumoral, peritumoral, epicutaneous, inhalational, enema, conjunctival, eye drops, ear drops, alveolar, nasal, intranasal, vaginal, intravaginal, transvaginal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

For homing to cells and tissue, particularly suitable routes of administration include parenteral, either local or systemic. For example, particularly suitable routes of administration for homing to cells and tissues include intravenous, injection, infusion, intraarterial, intramuscular, intratumoral, peritumoral, intracerebral, intraventricular, intracerebroventricular, intracardiac, subcutaneous, intraosseous, intradermal, intrathecal, intraperitoneal, intravesical, intramedullar, intraocular, intracranial, intracisternal, epidural, peridural, and intravitreal. The disclosed compositions can be used in and with any other procedure. For example, the disclosed compositions can be administered as part of HIPEC therapy. In HIPEC a heated sterile solution containing a composition of interest is continuously circulated throughout the peritoneal cavity.

Pharmaceutical compositions can be manufactured by processes well known in the art, e.g., by means of conventional mixing, dissolving, granulating, dragee-making, levigating, emulsifying, encapsulating, entrapping or lyophilizing processes.

Pharmaceutical compositions for use in the disclosed methods thus can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients can be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

The preparations described herein can be formulated for parenteral administration, e.g., by bolus injection or continuous infusion. Formulations for injection can be presented in unit dosage form, e.g., in ampoules or in multidose containers with optionally, an added preservative. The compositions can be suspensions, solutions or emulsions in oily or aqueous vehicles, and can contain formulatory agents such as suspending, stabilizing and/or dispersing agents.

Pharmaceutical compositions for parenteral administration include aqueous solutions of the active preparation in water-soluble form. Additionally, suspensions of the active ingredients can be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents which increase the solubility of the active ingredients to allow for the preparation of highly concentrated solutions.

Alternatively, the active ingredient can be in powder form for constitution with a suitable vehicle, e.g., sterile, pyrogen-free water based solution, before use.

The disclosed compositions can be provided in any suitable formulation. For example, solid, liquid, solution, gel, slow release, timed release, etc.

Pharmaceutical compositions for use in the disclosed methods include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the disclosed methods, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al in The Pharmacological Basis of Therapeutics, Ch. 1 p. 1. (1975)).

Dosage amount and interval can be adjusted individually to provide plasma of antibodies which are sufficient to prevent or reduce viral entry (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels, target site measurements, or other suitable measure above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected, diminution of the disease state is achieved, or other therapeutic effect is achieved.

The amount of a composition to be administered will, of course, be dependent on the subject being treated, the severity of the affliction, the manner of administration, the judgment of the prescribing physician, etc.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. In particular, pets and livestock can be a subject. The subject can be an invertebrate, such as a worm or an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

The disclosed peptides can be used to augment tumor imaging and tumor treatment with anti-cancer drugs. The effect of the disclosed peptides on imaging can be tested. For example, optical imaging with, for example, near infrared fluorophores using a Kodak IN VIVO Fx imager and Li-Cor Odyssey imager (e.g. Simberg et al., 2007; Sugahara et al., 2009), and MRI imaging can be used. For MRI imaging, the cargo or cargo composition can be an MRI contrast agent such as Feridex iron oxide nanoparticles and gadolinium compounds. These compounds can be injected into tumor-bearing mice, for example, with and without an L/S/R or F/T/F&T peptide or a combination of peptides, followed by imaging. The results can be used to determine effectiveness of treatments and to assess different treatment protocols for using L/S/R and F/T/F&T peptides with therapeutics as the cargo or cargo composition.

Combinations of different L/S/R or F/T/F&T peptides and different cargos and/or cargo compositions can be tested for optimal accumulation and distribution of the cargo or cargo composition in the target cells and tissue by, for example, varying the dose of the drug and using the dose of the peptide that gives the maximal effect. The disclosed results show that RVL-drug combinations can reduce the amount of drug needed and therefore, the side effects, while producing the same anti-tumor effect. The disclosed peptides can also produce effects not achievable by using the cargo or cargo composition alone. For example, use of the disclosed peptides can allow higher concentrations of the cargo or cargo composition in cells and tissues that is otherwise possible. In such cases, the effectiveness of the cargo or cargo composition can be beyond that obtainable with conventional therapy.

The disclosed compositions and methods can be further understood through the following numbered paragraphs.

1. An isolated peptide comprising an amino acid sequence comprising the sequence PPRRGLIKLKTS (SEQ ID NO:1) or a variant of the sequence PPRRGLIKLKTS (SEQ ID NO:1) with one, two, three, four, five, six, seven, eight, nine, or ten amino acid substitutions, wherein position 6 remains leucine and position 11 remains threonine.

2. The peptide of paragraph 1, wherein the amino acid sequence comprises the sequence PPRRGLIKLKTS (SEQ ID NO:1) or a variant of the sequence PPRRGLIKLKTS (SEQ ID NO:1) with one, two, three, four, five, six, seven, or eight amino acid substitutions.

3. The peptide of paragraph 1, wherein the amino acid sequence comprises the sequence PPRRGLIKLKTS (SEQ ID NO:1) or a variant of the sequence PPRRGLIKLKTS (SEQ ID NO:1) with one, two, three, four, five, or six amino acid substitutions.

4. The peptide of paragraph 1, wherein the amino acid sequence comprises the sequence PPRRGLIKLKTS (SEQ ID NO:1) or a variant of the sequence PPRRGLIKLKTS (SEQ ID NO:1) with one, two, three, or four amino acid substitutions.

5. The peptide of any one of paragraphs 1-4, wherein the amino acid sequence comprises the sequence PPRRG-LIKLKTS (SEQ ID NO:1) or a variant of the sequence PPRRGLIKLKTS (SEQ ID NO:1) having at least 50% sequence identity with the sequence PPRRGLIKLKTS (SEQ ID NO:1).

6. The peptide of any one of paragraphs 1-4, wherein the amino acid sequence comprises the sequence PPRRG-LIKLKTS (SEQ ID NO:1) or a variant of the sequence PPRRGLIKLKTS (SEQ ID NO:1) having at least 58% sequence identity with the sequence PPRRGLIKLKTS (SEQ ID NO:1).

7. The peptide of any one of paragraphs 1-4, wherein the amino acid sequence comprises the sequence PPRRG-LIKLKTS (SEQ ID NO:1) or a variant of the sequence PPRRGLIKLKTS (SEQ ID NO:1) having at least 66% sequence identity with the sequence PPRRGLIKLKTS (SEQ ID NO:1).

8. The peptide of any one of paragraphs 1-4, wherein the amino acid sequence comprises the sequence PPRRG-LIKLKTS (SEQ ID NO:1) or a variant of the sequence PPRRGLIKLKTS (SEQ ID NO:1) having at least 75% sequence identity with the sequence PPRRGLIKLKTS (SEQ ID NO:1).

9. The peptide of any one of paragraphs 1-4, wherein the amino acid sequence comprises the sequence PPRRG-LIKLKTS (SEQ ID NO:1) or a variant of the sequence PPRRGLIKLKTS (SEQ ID NO:1) having at least 83% sequence identity with the sequence PPRRGLIKLKTS (SEQ ID NO:1).

10. The peptide of any one of paragraphs 1-4, wherein the amino acid sequence comprises the sequence PPRRG-LIKLKTS (SEQ ID NO:1) or a variant of the sequence PPRRGLIKLKTS (SEQ ID NO:1) having at least 91% sequence identity with the sequence PPRRGLIKLKTS (SEQ ID NO:1).

11. The peptide of any one of paragraphs 1-10, wherein the amino acid sequence comprises the formula $X_1$-$X_2$-$X_3$-$X_4$-$X_5$-$X_6$-$X_7$-$X_8$-$X_9$-$X_{10}$-$X_{11}$-$X_{12}$, wherein $X_6$ is leucine, wherein $X_7$ is isoleucine, leucine, or valine, wherein $X_9$ is leucine, isoleucine, or valine, wherein $X_{11}$ is threonine, and wherein $X_1$, $X_2$, $X_3$, $X_4$, $X_5$, $X_8$, $X_{10}$, and $X_{12}$ are each, independently, any amino acid.

12. The peptide of paragraph 11, wherein $X_1$ is proline, glycine, alanine, serine, or asparagine, wherein $X_2$ is proline, glycine, alanine, serine, or asparagine, and wherein $X_5$ is glycine, alanine, valine, leucine, or isoleucine.

13. The peptide of paragraphs 11 or 12, wherein $X_7$ is isoleucine and wherein $X_9$ is leucine.

14. The peptide of any one of paragraphs 11-13, wherein $X_2$ is proline.

15. The peptide of any one of paragraphs 11-14, wherein $X_3$ is arginine, lysine, histidine, glutamate, glutamine, aspartate, asparagine, or alanine, wherein $X_4$ is arginine, lysine, histidine, glutamate, glutamine, aspartate, asparagine, or alanine, wherein $X_8$ is alanine, lysine, histidine, arginine, glutamate, glutamine, tyrosine, or tryptophan, wherein $X_{10}$ is alanine, lysine, histidine, arginine, glutamate, glutamine, tyrosine, or tryptophan, and wherein $X_{12}$ is serine, alanine, glycine, asparagine, threonine, glutamine, aspartate, or proline.

16. The peptide of any one of paragraphs 11-15, wherein $X_1$ is proline, glycine, or alanine, wherein $X_3$ is arginine, lysine, or histidine, wherein $X_4$ is arginine, lysine, or histidine, wherein $X_5$ is glycine, alanine, or valine, wherein $X_8$ is alanine, lysine, histidine, or arginine, wherein $X_{10}$ is alanine, lysine, histidine, or arginine, and wherein $X_{12}$ is serine, alanine, glycine, asparagine, or threonine.

17. The peptide of any one of paragraphs 11-16, wherein any amino acid substitution at $X_7$ and $X_9$ are conservative amino acid substitutions.

18. The peptide of any one of paragraphs 1-17, wherein any amino acid substitutions are conservative amino acid substitutions.

19. The peptide of any one of paragraphs 1-16, wherein the amino acid sequence comprises the sequence PPRRG-LIKLKTS (SEQ ID NO:1).

20. An isolated peptide comprising an amino acid sequence comprising the sequence TSKQNSR (SEQ ID NO:3) or a variant of the sequence TSKQNSR (SEQ ID NO:3) with one, two, three, four, five, or six amino acid substitutions, wherein position 7 remains arginine and/or position 6 remains serine.

21. The peptide of paragraph 20, wherein the amino acid sequence comprises the sequence TSKQNSR (SEQ ID NO:3) or a variant of the sequence TSKQNSR (SEQ ID NO:3) with one, two, three, four, or five amino acid substitutions.

22. The peptide of paragraph 20, wherein the amino acid sequence comprises the sequence TSKQNSR (SEQ ID NO:3) or a variant of the sequence TSKQNSR (SEQ ID NO:3) with one, two, three, or four amino acid substitutions.

23. The peptide of paragraph 20, wherein the amino acid sequence comprises the sequence TSKQNSR (SEQ ID NO:3) or a variant of the sequence TSKQNSR (SEQ ID NO:3) with one, two, or three amino acid substitutions.

24. The peptide of paragraph 20, wherein the amino acid sequence comprises the sequence TSKQNSR (SEQ ID NO:3) or a variant of the sequence TSKQNSR (SEQ ID NO:3) with one or two amino acid substitutions.

25. The peptide of any one of paragraphs 20-24, wherein the amino acid sequence comprises the sequence TSKQNSR (SEQ ID NO:3) or a variant of the sequence TSKQNSR (SEQ ID NO:3) having at least 14% sequence identity with the sequence TSKQNSR (SEQ ID NO:3).

26. The peptide of any one of paragraphs 20-24, wherein the amino acid sequence comprises the sequence TSKQNSR (SEQ ID NO:3) or a variant of the sequence TSKQNSR (SEQ ID NO:3) having at least 28% sequence identity with the sequence TSKQNSR (SEQ ID NO:3).

27. The peptide of any one of paragraphs 20-24, wherein the amino acid sequence comprises the sequence TSKQNSR (SEQ ID NO:3) or a variant of the sequence TSKQNSR (SEQ ID NO:3) having at least 42% sequence identity with the sequence TSKQNSR (SEQ ID NO:3).

28. The peptide of any one of paragraphs 20-24, wherein the amino acid sequence comprises the sequence TSKQNSR (SEQ ID NO:3) or a variant of the sequence TSKQNSR (SEQ ID NO:3) having at least 57% sequence identity with the sequence TSKQNSR (SEQ ID NO:3).

29. The peptide of any one of paragraphs 20-24, wherein the amino acid sequence comprises the sequence TSKQNSR (SEQ ID NO:3) or a variant of the sequence TSKQNSR (SEQ ID NO:3) having at least 71% sequence identity with the sequence TSKQNSR (SEQ ID NO:3).

30. The peptide of any one of paragraphs 20-24, wherein the amino acid sequence comprises the sequence TSKQNSR (SEQ ID NO:3) or a variant of the sequence TSKQNSR (SEQ ID NO:3) having at least 85% sequence identity with the sequence TSKQNSR (SEQ ID NO:3).

31. The peptide of any one of paragraphs 20-30, wherein the amino acid sequence comprises the formula $X_{13}$-$X_{14}$-$X_{15}$-$X_{16}$-$X_{17}$-$X_{18}$-$X_{19}$, wherein $X_{19}$ is arginine, lysine, histidine, glutamate, glutamine, aspartate, asparagine, or alanine, wherein $X_{18}$ is serine, alanine, glycine, asparagine, or threonine, and wherein $X_{13}$, $X_{14}$, $X_{15}$, $X_{16}$, and $X_{17}$ are each, independently, any amino acid.

32. The peptide of paragraph 31, wherein $X_{16}$ is glutamine, asparagine, glutamate, serine, threonine, aspartate, arginine, lysine, histidine, alanine, or glycine, wherein $X_{14}$ is serine, asparagine, alanine, glycine, glutamine, threonine, aspartate, glutamate, arginine, lysine, or histidine, and wherein $X_{15}$ is lysine, arginine, histidine, glutamate, glutamine, aspartate, asparagine, or alanine.

33. The peptide of paragraphs 31 or 32, wherein $X_{17}$ is asparagine, serine, threonine, glutamine, aspartate, alanine, glycine, arginine, valine, glutamate, tyrosine, tryptophan, or lysine, and wherein $X_{13}$ is threonine, asparagine, serine, valine, alanine, glycine, tyrosine, tryptophan, glutamine, isoleucine, leucine, phenylalanine, lysine, or aspartate.

34. The peptide of any one of paragraphs 31-33, wherein $X_{19}$ is arginine, lysine, or histidine, wherein $X_{18}$ is serine or asparagine.

35. The peptide of any one of paragraphs 31-34, wherein $X_{16}$ is glutamine, asparagine, glutamate, serine, threonine, aspartate, or arginine, wherein $X_{14}$ is serine, asparagine, alanine, glycine, glutamine, threonine, or aspartate, and wherein $X_{15}$ is lysine, arginine, histidine, glutamate, glutamine, aspartate, asparagine, or alanine.

36. The peptide of any one of paragraphs 31-35, wherein $X_{19}$ is arginine, wherein $X_{18}$ is serine.

37. The peptide of any one of paragraphs 31-36, wherein $X_{16}$ is glutamine or asparagine, wherein $X_{14}$ is serine or asparagine, and wherein $X_{15}$ is lysine, arginine, or histidine.

38. The peptide of any one of paragraphs 31-37, wherein any amino acid substitution at $X_{19}$ and $X_{18}$ are conservative amino acid substitutions.

39. The peptide of any one of paragraphs 20-38, wherein any amino acid substitutions are conservative amino acid substitutions.

40. The peptide of any one of paragraphs 20-37, wherein the amino acid sequence comprises the sequence TSKQNSR (SEQ ID NO:3).

41. An isolated peptide comprising an amino acid sequence comprising the sequence AGRGRLVR (SEQ ID NO:4) or a variant of the sequence AGRGRLVR (SEQ ID NO:4) with one, two, three, four, five, six, or seven amino acid substitutions, wherein position 3 remains arginine.

42. The peptide of paragraph 41, wherein the amino acid sequence comprises the sequence AGRGRLVR (SEQ ID NO:4) or a variant of the sequence AGRGRLVR (SEQ ID NO:4) with one, two, three, four, five, or six amino acid substitutions, wherein position 6 remains leucine and/or position eight remains arginine.

43. The peptide of paragraph 41, wherein the amino acid sequence comprises the sequence AGRGRLVR (SEQ ID NO:4) or a variant of the sequence AGRGRLVR (SEQ ID NO:4) with one, two, three, four, or five amino acid substitutions, wherein position 6 remains leucine, position eight remains arginine, and position 5 remains arginine.

44. The peptide of paragraph 41, wherein the amino acid sequence comprises the sequence AGRGRLVR (SEQ ID NO:4) or a variant of the sequence AGRGRLVR (SEQ ID NO:4) with one, two, three, or four amino acid substitutions.

45. The peptide of paragraph 41, wherein the amino acid sequence comprises the sequence AGRGRLVR (SEQ ID NO:4) or a variant of the sequence AGRGRLVR (SEQ ID NO:4) with one, two, or three amino acid substitutions.

46. The peptide of paragraph 41, wherein the amino acid sequence comprises the sequence AGRGRLVR (SEQ ID NO:4) or a variant of the sequence AGRGRLVR (SEQ ID NO:4) with one or two amino acid substitutions.

47. The peptide of any one of paragraphs 41-46, wherein the amino acid sequence comprises the sequence AGR-GRLVR (SEQ ID NO:4) or a variant of the sequence AGRGRLVR (SEQ ID NO:4) having at least 25% sequence identity with the sequence AGRGRLVR (SEQ ID NO:4).

48. The peptide of any one of paragraphs 41-46, wherein the amino acid sequence comprises the sequence AGR-GRLVR (SEQ ID NO:4) or a variant of the sequence AGRGRLVR (SEQ ID NO:4) having at least 37% sequence identity with the sequence AGRGRLVR (SEQ ID NO:4).

49. The peptide of any one of paragraphs 41-46, wherein the amino acid sequence comprises the sequence AGR-GRLVR (SEQ ID NO:4) or a variant of the sequence AGRGRLVR (SEQ ID NO:4) having at least 50% sequence identity with the sequence AGRGRLVR (SEQ ID NO:4).

50. The peptide of any one of paragraphs 41-46, wherein the amino acid sequence comprises the sequence AGR-GRLVR (SEQ ID NO:4) or a variant of the sequence AGRGRLVR (SEQ ID NO:4) having at least 62% sequence identity with the sequence AGRGRLVR (SEQ ID NO:4).

51. The peptide of any one of paragraphs 41-46, wherein the amino acid sequence comprises the sequence AGR-GRLVR (SEQ ID NO:4) or a variant of the sequence AGRGRLVR (SEQ ID NO:4) having at least 75% sequence identity with the sequence AGRGRLVR (SEQ ID NO:4).

52. The peptide of any one of paragraphs 41-46, wherein the amino acid sequence comprises the sequence AGR-GRLVR (SEQ ID NO:4) or a variant of the sequence AGRGRLVR (SEQ ID NO:4) having at least 87% sequence identity with the sequence AGRGRLVR (SEQ ID NO:4).

53. The peptide of any one of paragraphs 41-52, wherein the amino acid sequence comprises the formula $X_{20}$-$X_{21}$-$X_{22}$-$X_{23}$-$X_{24}$-$X_{25}$-$X_{26}$-$X_{27}$, wherein $X_{22}$ is arginine, lysine, or histidine, wherein $X_{25}$ is leucine, isoleucine, valine, or alanine, wherein $X_{27}$ is arginine, lysine, histidine, glutamate, glutamine, aspartate, asparagine, or alanine, and wherein $X_{20}$, $X_{21}$, $X_{23}$, $X_{24}$, and $X_{26}$ are each, independently, any amino acid.

54. The peptide of paragraph 53, wherein $X_{24}$ is arginine, lysine, histidine, glutamate, glutamine, aspartate, asparagine, or alanine.

55. The peptide of paragraphs 53 or 54, wherein $X_{21}$ is glycine, alanine, valine, leucine, or isoleucine, $X_{23}$ is glycine, alanine, valine, leucine, or isoleucine and wherein $X_{26}$ is valine, leucine, isoleucine, glycine, or alanine.

56. The peptide of any one of paragraphs 53-55, wherein $X_{20}$ is alanine, glycine, valine, leucine, or isoleucine.

57. The peptide of any one of paragraphs 53-56, wherein $X_{22}$ is arginine or lysine, wherein $X_{25}$ is leucine, isoleucine, or valine, wherein $X_{27}$ is arginine, lysine, or histidine.

58. The peptide of any one of paragraphs 53-57, wherein $X_{24}$ is arginine, lysine, or histidine.

59. The peptide of any one of paragraphs 53-58, wherein $X_{24}$ is arginine or lysine.

60. The peptide of any one of paragraphs 53-59, wherein $X_{22}$ is arginine, wherein $X_{25}$ is leucine, wherein $X_{27}$ is arginine.

61. The peptide of any one of paragraphs 53-60, wherein $X_{24}$ is arginine.

62. The peptide of any one of paragraphs 53-61, wherein any amino acid substitution at $X_{22}$, $X_{25}$, and $X_{27}$ are conservative amino acid substitutions.

63. The peptide of any one of paragraphs 41-62, wherein any amino acid substitutions are conservative amino acid substitutions.

64. The peptide of any one of paragraphs 41-61, wherein the amino acid sequence comprises the sequence AGR-GRLVR (SEQ ID NO:4).

65. The peptide of any one of paragraphs 41-61, wherein the amino acid sequence comprises the sequence AGR-GRLVRAKLAAALE (SEQ ID NO:14).

66. An isolated peptide comprising a first amino acid sequence comprising the sequence TSKQNSR (SEQ ID NO:3) or a variant of the sequence TSKQNSR (SEQ ID NO:3) with one, two, three, four, five, or six amino acid substitutions, wherein position 7 remains arginine and/or position 6 remains serine, and a second amino acid sequence comprising the sequence AGRGRLVR (SEQ ID NO:4) or a variant of the sequence AGRGRLVR (SEQ ID NO:4) with one, two, three, four, five, six, or seven amino acid substitutions, wherein position 3 remains arginine.

67. The peptide of any one of paragraphs 1-66, wherein the peptide can selectively bind to fibronectin extra domain B (FN-EDB) via the amino acid sequence.

68. The peptide of paragraph 67, wherein the peptide comprises an amino acid sequence having the sequence TSKQNSR (SEQ ID NO:3).

69. The peptide of any one of paragraphs 1-66, wherein the peptide can selectively bind to tenascin-C C domain (TNC-C) via the amino acid sequence.

70. The peptide of paragraph 69, wherein the peptide comprises an amino acid sequence having the sequence AGRGRLVR (SEQ ID NO:4).

71. The peptide of any one of paragraphs 1-70, wherein the peptide can selectively bind to both fibronectin extra domain B (FN-EDB) and tenascin-C C domain (TNC-C) via the amino acid sequence.

72. The peptide of any one of paragraphs 1-71, wherein the peptide is less than 20 amino acids in length.

73. The peptide of any one of paragraphs 1-72, wherein the peptide is less than 15 amino acids in length.

74. The peptide of any one of paragraphs 1-73, wherein the peptide is 12 amino acids in length.

75. The peptide of any one of paragraphs 1-19, wherein the peptide comprises the sequence PPRRG-LIKLKTSSNTKENSVVASLRP (SEQ ID NO:2).

76. The peptide of any one of paragraphs 1-75, wherein the peptide is linear.

77. The peptide of any one of paragraphs 1-75, wherein the peptide is cyclic.

78. The peptide of any one of paragraphs 1-77, wherein the peptide is a modified peptide.

79. The peptide of one of paragraphs 1-78, wherein the peptide is a methylated peptide.

80. The peptide of paragraph 79, wherein the methylated peptide comprises a methylated amino acid segment.

81. The peptide of any one of paragraphs 1-80, wherein the peptide is N- or C-methylated in at least one position.

82. A composition comprising the peptide of any one of paragraphs 1-81.

83. The composition of paragraph 82 further comprising a cargo composition, wherein the peptide and the cargo composition are covalently coupled or non-covalently associated with each other.

84. The composition of paragraph 82 or 83, wherein the peptide selectively homes to tumors expressing FN-EDB, TNC-C, or both FN-EDB and TNC-C.

85. The composition of paragraph 82 or 83, wherein the composition selectively homes to extracellular matrix having FN-EDB, TNC-C, or both FN-EDB and TNC-C.

86. The composition of any one of paragraphs 83-85, wherein the cargo composition comprises a therapeutic agent, a detectable agent, a carrier, vehicle, surface molecule, or combinations thereof.

87. The composition of any one of paragraphs 83-86, wherein the cargo composition comprises a therapeutic agent.

88. The composition of paragraph 86 or 87, wherein the therapeutic agent is an anti-angiogenic agent, an anti-bacterial agent, an anti-cancer agent, an anti-inflammatory agent, a chemotherapeutic agent (such as a cancer chemotherapeutic agent), a cytotoxic agent, an immunostimulating agent, an immunosuppressing agent, a nucleic acid molecule, a polypeptide, a pro-angiogenic agent, a pro-apoptotic agent, a pro-inflammatory agent, a small molecule, or a toxin.

89. The composition of any one of paragraphs 86-88, wherein the therapeutic agent is $_D$(KLAKLAK)$_2$.

90. The composition of any one of paragraphs 83-89, wherein the cargo composition comprises a detectable agent.

91. The composition of any one of paragraphs 86-90, wherein the detectable agent is a label, a labeling agent, a contrast agent, an imaging agent, a microbubble (such as a fluorocarbon microbubble), a fluorophore (such as FAM, fluorescein, or rhodamine), or a radionuclide (such as carbon-11, carbon-13, indium-111, or technetium-99).

92. The composition of any one of paragraphs 86-91, wherein the detectable agent is FAM.

93. The composition of any one of paragraphs 83-92, wherein the cargo composition comprises a carrier, a vehicle, a surface molecule, or combinations thereof.

94. The composition of any one of paragraphs 86-93, wherein the carrier, vehicle and/or surface molecule independently comprise a bead, a liposome, a micelle, a microparticle, a nanoparticle (such as an albumin nanoparticle, an iron oxide nanoparticle, or a silver nanoparticle), a nanoworm (such as an iron oxide nanoworm), a phospholipid, a polymer, a phage, a phage capsid, a phage particle, a viral capsid, a viral particle, a virus, a virus-like particle, or a microbubble (such as a fluorocarbon microbubble).

95. The composition of any one of paragraphs 83-94, wherein the composition comprises a plurality of cargo compositions.

96. The composition of any one of paragraphs 83-95, wherein the cargo composition comprises a surface molecule.

97. The composition of paragraph 96, wherein the peptide is conjugated with the surface molecule.

98. The composition of paragraph 96 or 97, wherein one or more of the conjugated peptides is indirectly conjugated to the surface molecule via a linker.

99. The composition of any one of paragraphs 96-98, wherein the composition further comprises a plurality of linkers.

100. The composition of paragraph 98 or 99, wherein at least one of the linkers comprises polyethylene glycol.

101. The composition of any one of paragraphs 96-100, wherein the surface molecule comprises a nanoparticle, a nanoworm, an iron oxide nanoworm, an iron oxide nanoparticle, an albumin nanoparticle, a silver nanoparticle, a liposome, a micelle, a phospholipid, a polymer, a microparticle, or a fluorocarbon microbubble.

102. The composition of any one of paragraphs 96-101, wherein the surface molecule comprises a liposome.

103. The composition of any one of paragraphs 82-102, wherein the composition binds tumors expressing FN-EDB, TNC-C, or both FN-EDB and TNC-C.

104. The composition of any one of paragraphs 82-102, wherein the composition binds extracellular matrix having FN-EDB, TNC-C, or both FN-EDB and TNC-C.

105. The composition of any one of paragraphs 82-104, wherein the composition is internalized in cells.

106. The composition of any one of paragraphs 82-105, wherein the composition reduces tumor growth.

107. The composition of any one of paragraphs 82-106, further comprising one or more copies of the peptide.

108. The composition of paragraph 107, wherein the composition comprises at least 100 copies of the peptide.

109. The composition of paragraph 108, wherein the composition comprises at least 1000 copies of the peptide.

110. A method comprising exposing a tumor to the composition of any one of paragraphs 82-109.

111. The method of paragraph 110, wherein the composition selectively binds to the tumor.

112. The method of paragraph 110 or 111, wherein the tumor is in a subject.

113. The method of paragraph 112, wherein the tumor is exposed to the composition by administering the composition to the subject.

114. The method of any one of paragraphs 110-113, wherein the tumor expresses FN-EDB, TNC-C, or both FN-EDB and TNC-C.

115. The method of paragraph 114, wherein the composition selectively binds to the tumor expressing FN-EDB, TNC-C, or both FN-EDB and TNC-C.

116. A method comprising exposing extracellular matrix to the composition of any one of paragraphs 82-109.

117. The method of paragraph 116, wherein the composition selectively binds to the extracellular matrix.

118. The method of paragraph 116, wherein the extracellular matrix is in a subject.

119. The method of paragraph 118, wherein the extracellular matrix is exposed to the composition by administering the composition to the subject.

120. The method of any one of paragraphs 116-119, wherein the extracellular matrix has FN-EDB, TNC-C, or both FN-EDB and TNC-C.

121. The method of paragraph 120, wherein the composition selectively binds to the extracellular matrix having FN-EDB, TNC-C, or both FN-EDB and TNC-C.

122. The method of any one of paragraphs 110-121, wherein the composition has a therapeutic effect.

123. The method of paragraph 122, wherein the therapeutic effect comprises increase in apoptosis.

124. The method of any one of paragraphs 112-115 or 118-123, wherein the subject has a disease or condition.

125. The method of paragraph 124, wherein the disease is cancer.

126. The method of any one of paragraphs 110-125, wherein the composition selectively homes to tumors expressing FN-EDB, TNC-C, or both FN-EDB and TNC-C.

127. The method of paragraph 126, wherein the composition selectively homes to extracellular matrix having FN-EDB, TNC-C, or both FN-EDB and TNC-C.

128. The composition of any one of paragraphs 82-109 for use as a medicament.

129. The composition of any one of paragraphs 82-109 for use in the treatment of cancer in a subject.

130. The composition of any one of paragraphs 82-109 for use in the detection of cancer in a subject.

131. The composition of any one of paragraphs 82-109 for use in the visualization of cancer in a subject.

132. The composition of any one of paragraphs 82-109 for use in the localization of cancer in a subject.

133. Use of the composition of any one of paragraphs 82-109 for the manufacture of a medicament for cancer treatment.

134. Use of the composition of any one of paragraphs 82-109 for the manufacture of a medicament for cancer detection.

135. A cancer diagnosis method comprising administering an effective amount of the composition of any one of paragraphs 90-109 to a subject in need thereof.

136. The method of any one of paragraphs 125-127, the composition for use of any one of paragraphs 129-132, the use of paragraph 133 or 134, or the method of paragraph 135, wherein the cancer is a cancer in Table 10.

137. In some forms of the disclosed methods, the disclosed compositions, or the disclosed uses, the cancer can be a solid tumor cancer such as a solid tumor cancer in Table 11.

138. The composition of any one of paragraphs 82-102, wherein the composition binds tumors expressing NRP-1, TNC-C, or both NRP-1 and TNC-C.

139. The composition of any one of paragraphs 82-102, wherein the composition binds extracellular matrix having NRP-1, TNC-C, or both NRP-1 and TNC-C.

140. The composition of any one of paragraphs 82-102, wherein the composition binds cells expressing NRP-1, TNC-C, or both NRP-1 and TNC-C.

141. The composition of any one of paragraphs 138-140, wherein the composition is internalized in cells.

142. The peptide of any one of paragraphs 41-66, wherein the peptide can selectively bind to NRP-1 via the amino acid sequence.

143. The peptide of paragraph 142, wherein the peptide can selectively bind to the NRP-1 b1b2 domain via the amino acid sequence.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Selection and Properties of PL1 Peptide and Related Peptides

A. Materials and Methods

1. Materials

Phosphate-buffered saline (PBS) was purchased from Lonza (Verviers, Belgium), $K_3[Fe (CN)_6]$, HCl, Nuclear Fast Red, Xylene substitute, isopropanol, Triton-X, Tween-20, $CHCl_3$, MeOH, and dimethylformamide (DMF) were purchased from Sigma-Aldrich (Munich, Germany). Cloning, expression, purification of proteins (FN-EDB, TNC-C, NRP1, NCL and single chain antibodies FN-EDB-L19 and TNC-C-G11), and generation of polyclonal rabbit antibodies are described below and in Table 1.

TABLE 1

List of antibodies used

| Antibody | Vendor | Catalogue number | Dilution |
|---|---|---|---|
| anti-His-tag | Abcam, Icosagen | ab5000, A2-501-100 | 1:5000 |
| anti-fluorescein | Thermo Fisher Scientific | A889 | 1:200 |
| CD31 | BD Biosciences | 557355, 553370 | 1:200 |
| nestin | Thermo Fisher Scientific | MA1-110 | 1:100 |
| CD11b | BD Biosciences | 557395 | 1:100 |
| LYVE-1 | eBioscience | 14044382 | 1:200 |
| CD68 | Bio-Rad | MCA1957A488 | 1:100 |
| Ki67 | Novusbio | NB500-170 | |
| cleaved caspase-3 | Cell Signaling Technology | 966 | 1:200 |
| FN-EDB | Absoluteantibody | Ab00634 | 10 µg |
| ScFV L19 FN-EDB | In house | | 10 µg |
| ScFV G11 TNC-C | In house | | 10 µg |
| Rabbit poly TNC-C | In house | | 1:250 |
| Rabbit poly FN-EDB | In house | | 1:250 |
| Donkey Anti-Mouse IgG (H + L) HRP | Jackson Immuno Research | 715-035-1510 | 1:5000 1:10000 |
| Donkey Anti-Rabbit IgG (H + L) HRP | Jackson Immuno Research | 711-035-1520 | 1:5000 1:10000 |
| Alexa 546 goat anti mouse IgG (H + L) | Invitrogen/Molecular Probes | A11003 | 1:400 |
| Alexa 546 goat anti rat IgG (H + L) | Invitrogen/Molecular Probes | A11081 | 1:400 |
| Alexa 546 donkey anti goat IgG (H + L) | Invitrogen/Molecular Probes | A11056 | 1:400 |
| Alexa 546 anti-hamster IgG (H + L) | Invitrogen/Molecular Probes | A21111 | 1:400 |
| Alexa 546 goat anti-rabbit IgG (H + L) | Invitrogen/Molecular Probes | A11010 | 1:400 |
| Alexa 488 goat anti-rabbit IgG (H + L) | Invitrogen/Molecular Probes | A11008 | 1:400 |
| Alexa 488 goat anti-mouse IgG (H + L) | Invitrogen/Molecular Probes | A11001 | 1:400 |
| Alexa 647 goat anti-rabbit IgG (H + L) | Invitrogen/Molecular Probes | A21245 | 1:400 |

TABLE 1-continued

List of antibodies used

| Antibody | Vendor | Catalogue number | Dilution |
|---|---|---|---|
| Alexa 647 goat anti-rat IgG (H + L) | Invitrogen/Molecular Probes | A21247 | 1:400 |
| IRDye 800CW Goat anti-Mouse IgG (H + L) | LI-COR Biosciences | 926-32210 | 1:20000 |
| IRDye 680RD Goat anti-Rabbit IgG (H + L) | LI-COR Biosciences | 926-68071 | 1:20000 |

2. Cell Lines

U87MG GBM and PC3 prostate carcinoma cells were obtained from ATCC, and NCH421K cells from CLS Cell Lines Service GmbH (Eppelheim, Germany). WT-GBM and VEGF-KO GBM cells were a gift from Gabriele Bergers (Leuven, Belgium).

3. Clinical Samples

Fresh surgical samples of GBMs were obtained from Tartu University Clinics, Tartu, Estonia under protocols approved by the Ethics Committee of the University of Tartu, Estonia (permit #243/T27).

4. Animal Experiments

Animal experimentation procedures were approved by the Estonian Ministry of Agriculture, Committee of Animal Experimentation, project #42 and #48. Athymic nude mice (HD) were housed in a pathogen-free environment at the Animal Facility of the Institute of Biomedicine and Translational Medicine, University of Tartu (Tartu, Estonia). For tumor modelling, nude mice bearing orthotopic GBM (NCH421K, U87MG and, WT-GBM) and s.c. prostate carcinoma (PC3) were used. For orthotopic GBM induction, the mice were placed into the ear bars of a stereotactic frame, a midline incision was made using a scalpel exposing the sagittal and coronal sutures, and a burr hole was scraped through the skull 0.5 mm anterior to the bregma and 2.5 mm lateral to the midline using a syringe. GBM cells in 3 µL PBS were injected at a depth of 3 mm with a Hamilton syringe over 4 min, and the needle was removed 5 min after the injection. Bone wax was used to close the burr hole, the surface was cleaned with a sterile cotton swab, and the skin was closed by sutures.

5. Phage Biopanning

The NNK-encoded cyclic CX7C and linear $X_7$ peptide libraries (diversity ~5×10$^8$) displayed on T7 415-1b phage scaffold were used for biopanning (Novagen, EMD Biosciences, MA, USA). To identify bispecific peptides that interact with both TNC-C and FN-EDB, cross screens were performed on both targets. During the first round of selection, microtiter plates coated with 20 µg/ml recombinant purified TNC-C were blocked with PBS containing 1% bovine serum albumin (BSA), followed by incubation with 5×10$^8$ pfu of phages in PBS at 4° C. overnight, by washes to remove background, and by phage rescue and amplification in BLT5403 strain of *E. coli* (Novagen, EMD Biosciences, MA, USA) (Teesalu et al., Methods Enzymol. 503: 35-56 (2012)). The following rounds of biopanning were carried on Ni-NTA Magnetic Agarose Beads (QIAGEN, Hilden, Germany) coated with hexahistidine-tagged FN-EDB (3 µg/µl beads) at room temperature. After 5 rounds of selection, a set of random clones was sequenced, and individual peptide-phage clones and control (G7 peptide-displaying or insertless) phages were incubated with FN- EDB and TNC-C-coated magnetic beads. RPARPAR phage (SEQ ID NO:5) and His-tagged NRP-1 b1b2 domain were used as positive control (Teesalu et al., Proc. Natl. Acad. Sci. U.S.A 106:16157-62 (2009)). To address the specificity of the peptide phage binding to the FN-EDB and TNC-C, the protein-coated beads were pre-incubated with 20 µg/ml blocking rabbit polyclonal antibodies.

6. Synthesis of Peptides and Nanoparticles

The peptides were synthesized in-house or ordered from TAG Copenhagen (Frederiksberg, Denmark). Peptides were synthesized using Fmoc/t-Bu chemistry on the microwave-assisted automated peptide synthesizer (Liberty, CEM Corporation, NC, USA), purified by HPLC using 0.1% TFA in acetonitrile-water to 90%-95% purity, and validated by Q-TOF mass spectral analysis. All peptides were synthesized with free carboxyl termini; 5 (6)-carboxyfluorescein (FAM) or biotin was attached via the 6-aminohexanoic acid spacer to the N-terminus of the peptide. The iron oxide nanoworms (NWs) were prepared according to a published protocol by (Park et al., Adv. Mater. 20:1630-1635 (2008)) with minor modifications. The aminated NWs were PEGylated using maleimide-5K-PEG-NHS. Peptides were coupled to NWs through a thioether bond between the thiol group of a cysteine residue added to the N-terminus of the peptide and the maleimide on the functionalized particles. Isotopically pure silver nanoparticles (AgNPs) were synthesized and functionalized as previously described (Willmore et al., Nanoscale. 8:9096-9101 (2016)).

7. Cell-Free Peptide Binding Assay

The FAM-labeled peptides were coated on ELISA plates (Nunc Maxisorp, Thermo Fisher Scientific Inc., MA, USA), blocked with PBS containing 1% BSA, and incubated with recombinant proteins at 2 µg/well in PBS for 6 h. The protein was detected using an anti-His-tag antibody, followed by horseradish peroxidase-conjugated secondary antibody, chromogenic reaction, and measurement of absorbance at 450 nm with a microplate reader (Tecan Austria GmbH, Gradig, Austria).

8. Laser Ablation ICP-MS-Based AgNP Biodistribution Studies

Isotopically pure $Ag^{107}NPs$ and $Ag^{109}NPs$ were prepared as described (Willmore et al., Nanoscale. 8:9096-9101 (2016)) and functionalized with biotinylated PL1 peptide (PL1-$Ag^{109}$NPs) or biotin (biotin-$Ag^{107}$NPs) particles. PL1-functionalized and control AgNPs were mixed at 1:1 ratio and injected i.v. in nude mice bearing U87MG orthotropic GBM. 5 h later, the mice were perfused via the left ventricle of the heart with 20 mL PBS. Organs were snap-frozen for cryosectioning and ICP-MS analysis. Snap-frozen organs were cryosectioned (30 µm) and stored at −20° C. Before the LA-ICP-MS analysis, the samples were thawed and dried in a desiccator.

Mapping of $^{109}$Ag and $^{107}$Ag isotopes on tissue sections (2-D mapping and line scans) was performed using a Cetac LSX-213 G2+ laser ablation (LA) system using a HelEx 2-volume ablation cell, coupled to Agilent 8800 QQQ ICP-MS. The LA-ICP-MS setup was optimized using NIST 612 glass. Main parameters for LA-ICP-MS are shown in Table 2. $^{13}$C, $^{107}$Ag, and $^{109}$Ag isotopes were detected with dwell times of 9.5 and 14 ms respectively, corresponding to a duty cycle of 0.05 s. $^{13}$C was used as an internal standard to account for differences in the volume of ablated tissue. Data reduction and elemental and isotope ratio maps were constructed using Chromium 2.2 and Iolite v3.62 software. Multiple parallel line raster scans were performed to generate distribution maps. The raster lines were directly adjacent to each other (with 65 µm offset) and the whole mapping area was ablated. A typical sample area was ~14×8 mm, and run time for a single sample was ~4 h.

TABLE 2

| Operating parameters used for LA ICP MS. | |
| --- | --- |
| Laser power density | 0.9 J/cm$^2$ (line) or 3.6 J/cm$^2$ (map) |
| Laser beam diameter | 40 µm circle (line) or 65 µm square (map) |
| Raster rate | 40 µm/s (line) or 130 µm square (map) |
| Laser repetition rate | 20 Hz |
| He carrier gas | 0.80 L/min |
| Ar carrier gas | 0.95 L/min |
| RF power | 1450 W |
| Acquisition mode | Peak hopping |
| Integration time/mass | $^{13}$C - 9.5 ms |
| | $^{107}$Ag- 14 ms |
| | $^{109}$Ag - 14 ms |
| Runtime Line raster | 7 min |
| Runtime Mapping | 460 min |

9. In Vivo Biodistribution Studies of NWs

For NW biodistribution studies, NWs (7.5 mg/kg) in PBS were injected into the tail vein of the tumor-bearing mice, followed by cardiac perfusion with 20 ml PBS/DMEM before collection tumor and control organs for imaging. In control experiments, NW injection was preceded by systemic pre-injection of blocking FN-EDB and/or TNC-C antibodies (30 µg/mouse) 15 min prior to injection of the NWs.

10. Confocal Microscopy

Snap-frozen 10 µm tumor cryosections were mounted on Superfrost™⁺ slides. The sections were equilibrated at RT and fixed with 4% paraformaldehyde/methanol and permeabilized with PBST (PBS+0.05% Tween 20), blocked with PBST, 5% BSA, 5% goat serum (GE Healthcare, Little Chalfont, UK) at RT for 30 min, followed by primary antibody incubation at RT for 1 h. The primary antibodies were rabbit anti-fluorescein IgG (cat. no. A889, Thermo Fisher Scientific, MA, USA), rat anti-mouse CD31 (BD Biosciences, CA, USA), mouse anti-human nestin (#MA1-110,Thermo Fisher Scientific Inc.), rat anti-mouse CD31, rat anti-mouse CD11b (cat. no. 553370; 557395, BD Biosciences, CA, USA), rat anti-mouse LYVE-1 (cat. no. 14044382, eBioscience, CA, USA), rat anti-mouse CD68 (#MCA1957A488, Bio-Rad, CA, USA), rabbit polyclonal anti-Ki67 (cat. no. NB500-170, Novusbio, UK), and rabbit anti-cleaved caspase-3 (cat. no. 966, Cell Signaling Technology, MA, USA), and in-house prepared CF647 (or CF546)-labeled single chain antibodies ScFV L19 (against FN-EDB) and ScFV GI1 (against TNC-C). The secondary antibodies, Alexa 488 goat anti-rabbit IgG, Alexa 647 goat anti-rat IgG, and Alexa 546 goat anti-mouse IgG, were from Invitrogen (USA). Nuclei were counterstained with DAPI (Molecular Probes) at 1 µg/ml. The coverslips were mounted on glass slides with Fluoromount-G (Electron Microscopy Sciences, PA, USA), imaged using confocal microscopy (Olympus FV1200MPE, Tokyo, Japan) and analyzed using the FV10-ASW4.2 viewer, Imaris software and ImageJ freeware.

11. NW Overlay Assay

Fresh surgical GBMs (obtained during autopsy) were snap-frozen in liquid nitrogen, cryosectioned at 8 µm, fixed with methanol, and permeabilized with TBS followed by blocking buffer containing 5% BSA, 5% goat serum and 5% FBS in TBS. For overlay, the sections were incubated with 20 g/slide of PL1-NW or NW at 4° C. overnight. The sections were washed and blocked with blocking buffer, followed by immunostaining using rabbit anti-fluorescein primary antibodies and detection with the Alexa-488 anti-rabbit secondary antibody. FN-EDB and TNC-C were detected by fluorescently labeled single-chain antibodies ScFV L19 FN-EDB-CF647 and ScFV G11 TNC-C-CF555.

12. In Vivo Angiogenesis Model and Multiphoton Intravital Imaging

Angiogenesis was induced by injecting $2.5 \times 10^8$ PFU of an adenoviral vector driving expression of mouse VEGF[164] (Ad-VEGF[164]) intradermally into the left ear of 7-8 week-old female nude mice (Nagy et al., Methods Enzymol. 444:43-64 (2008)). The right ear served as a control. PL1-NW or NW (at 7.5 mg/kg) were i.v. injected 4 days after induction of angiogenesis and 24 h before intravital imaging. Texas Red/Evans Blue was i.v. injected at 30 mg/kg to allow visualization of blood vessels. The ear was fixed on the coverslip for imaging using a veterinary-grade glue tape, and a mold was prepared around the ear from agarose for imaging. The body temperature was maintained throughout the experiment with a heat mat. Images and videos were acquired at an excitation wavelength of 920 nm, optical sections were taken under identical conditions, and experiments were repeated in triplicates. Intravital imaging was performed with multi-photon laser scanning fluorescence microscope (Olympus FV1200MPE-BX61WI) equipped with MaiTai DeepSee IR laser (Spectra-Physics) and with XLPLN25x/1.05 NA water-immersion objective (Olympus).

13. Magnetic Resonance Imaging

For MRI, nude mice bearing orthotopic NCH421k GBM were i.v. injected with iron oxide nanoworms at 5 mg/kg. Five hours after NW injection, the mice were anesthetized with isoflurane and subjected to MRI using a 9.4 Tesla BioSpec 94/21 (Bruker BioSpin MRI GmbH, Ettlingen, Germany) equipped with ParaVision Acquisition 6.0.1 software (Bruker, Ettlingen, Germany). Following intravital MRI, the animals were perfused with PBS to remove blood and background circulating NWs and subjected to postmortem MRI. After imaging, tumors and control tissues were harvested and sectioned for immunofluorescence staining. Mice received isoflurane in oxygen mix (1.5%, flow rate of 200 ml/min) for anesthesia; the body temperature and breathing rate were monitored throughout the experiments. T2* map MGE (Multiple Gradient Echo) sequences were acquired in sagittal and coronal orientations. The following parameters were used during the data acquisition: slice thickness −0.375 mm (3 slices averaged offline for improved signal/noise ratio); inter-slice gap −0.375 mm; repetition time −800; Echo time ~3.5-38.5 ms; flip angle ~50°; axial slices ~128, pixel bandwidth ~292.9; imaging frequency ~400.3; matrix ~256×256, and magnetic field strength ~9.4. To calculate T2 relaxation times, regions of interest (ROIs) were drawn manually on the images by using image sequence analysis (ISA) tool package (Paravision 5, Bruker) using T2vtr fit function $y = A + C^* \exp(-t/T2)$ (A=Absolute bias, C=signal intensity, T2=spin-spin relaxation time) for T2 evaluation. To calculate mean signal intensity in the tumor to a reference region, ROIs were drawn manually on the images at given echo time (TE). Experiments were repeated in triplicate.

14. Experimental Tumor Therapy

U87MG cells ($4 \times 10^6$) in 100 μl PBS were implanted subcutaneously into the right flank of 11-15 week old male nude mice. The weight of animals and tumor volume [length×(width×width)/2] was recorded on every other day until tumor volume reached −100 mm³. Animals were randomized into 4 groups (PBS, FAM-$_D$[KLAKLAK]$_2$-NWs, FAM-PL1-NWs, and FAM-PL1-$_D$[KLAKLAK]$_2$-NWs; 8 mice/group). 100 μl of NWs (at 5 mg/kg body weight of iron) or PBS was intravenously injected into the tail vein every other day for ten injections. Tumor size, body weight, survival, and behavior were recorded during treatment and post-therapy. When the tumor volume reached 2000 mm³ (or >10% body weight), the mice were sacrificed, and organs and tumors were excised, macroscopically observed and snap frozen. Tumor volume, Kaplan-Meier survival and body weight curves were calculated using the GraphPad Prism 6 software with p-values <0.05 considered significant. For experimental therapy on intracranially-implanted NCH421k GBM, 32 tumor mice were randomized into 4 groups 3 days after the tumor implantation. 100 μl of the PBS or PBS containing FAM-D[KLAKLAK]$_2$-NWs, FAM-PL1-NWs and FAM-PL1-D[KLAKLAK]$_2$-NWs (5 mg/kg body weight of iron; SEQ ID NO:6) were injected i.v. every other day for 10 total injections. Tumor size, body weight, survival, and behavior were recorded during and post-treatment. Kaplan-Meier survival and body weight curves were calculated using GraphPad Prism 6 and P values <0.05 were considered significant.

15. Statistical Analysis

Prism 6 software was used to perform statistical analyses. The results are presented as mean with error bars indicating ±SEM. For comparison of 2 groups, unpaired t-test or ANOVA test was used (p<0.05 was considered significant). P-values were considered as follows: $*p \leq 0.05$, $p \leq 0.01$, $*p \leq 0.001$ and $****p \leq 0.0001$. Details of analysis are shown in Table 3.

TABLE 3

| | | | ANOVA | | t-test | |
|---|---|---|---|---|---|---|
| Details of statistical analysis | | | | | | |
| Test | N | P value | Degrees of freedom | F value | Degrees of freedom | t-value |
| Two-tailed Student unpaired t-test | 3 independent experiment | <0.0001 | NA | NA | 2 | 1644 |
| | | 0.0019 | NA | NA | 1 | 331.4 |
| | | 0.0677 | NA | NA | 1 | 9.374 |
| Two-tailed Student unpaired t-test | 3 independent experiment with 3 triplicate each | 0.0002 | NA | NA | 2 | 80.07 |
| | | 0.0160 | NA | NA | 2 | 7.798 |
| Two-tailed Student unpaired t-test | 6 | <0.0001 | NA | NA | 10 | 6.348 |
| | 3 | <0.0001 | NA | NA | 9 | 10.42 |
| | 3 | 0.0079 | NA | NA | 8 | 3.519 |
| | 4 | 0.0015 | NA | NA | 4 | 7.732 |
| | 11 | 0.0015 | NA | NA | 16 | 3.820 |

TABLE 3-continued

Details of statistical analysis

| | | | ANOVA | | t-test | |
|---|---|---|---|---|---|---|
| Test | N | P value | Degrees of freedom | F value | Degrees of freedom | t-value |
| | 8 | 0.0128 | NA | NA | 13 | 2.884 |
| | 8 | 0.0214 | NA | NA | 14 | 2.590 |
| one-way ANOVA with | 11 | <0.0001 | 29 | 22.64 | NA | NA |
| Dunnett's multiple comparisons test | 11 | <0.0001 | 29 | 22.64 | NA | NA |
| Two-tailed Student unpaired t-test | 4 | 0.0005 | NA | NA | 9 | 5.245 |
| one-way ANOVA with | 5 | <0.0001 | 14 | 364.8 | NA | NA |
| Bonferroni's multiple comparisons test | | 0.0010 | 14 | 364.8 | NA | NA |
| Two-way ANOVA with Bonferroni's multiple comparisons test | 6 | 0.0001 | 243 | 7.317 | NA | NA |
| Kaplan-Meier analysis with Log-rank (Mantel-Cox) test | 8 | 0.0125 | 1 | NA | NA | NA |
| Two-tailed Student unpaired t-test | 4 | 0.0222 | NA | NA | 5 | 3.269 |
| Two-tailed Student unpaired t-test | 3 | 0.0043 | NA | NA | 6 | 4.454 |
| | | 0.0291 | NA | NA | 6 | 2.851 |
| | | 0.0364 | NA | NA | 6 | 2.681 |

For animal study, the sample size was estimated on the basis of previous experiments yielding effect size 1.2 and 2.3 respectively (Sugahara et al., Cancer Cell. 16:510-520 (2009)) and unpublished data. Therefore, an effect size of 1.5 was conservatively assumed for sample calculation. To have at least >80% probability of detecting a difference in means between the control and peptide-conjugated nanoparticle group of 2.2 standard deviations, a sample size of 8 mice was assigned in each treatment group. Sample size calculations were performed in PASS (NCSS 2008) or G Power (Faul et al., Behavior Research Methods 39:175-191 (2007)) power analysis software using the Inequality Tests for Two Means procedure. NCH421k animals were blindly assigned to experimental or control groups. U87 animals were randomly assigned to experimental or control groups once tumor reached 100 $mm^3$. None of the animals were excluded from the analysis. No blinding was used during the experiment. Our experimental design ensures that minimal bias (or noise) is introduced, that could be mistaken as being treatment effects (by ensuring same sex, similar animal weight at start of experiment, same animal age, same type of stabling, several animals caged together).

16. Cloning, Expression and Purification of FN-EDB and TNC-C

Vector Construction. A pF1K (Promega, #FXC00319)-derivative plasmid containing full length cDNA of TNC and pASK75-Fn7B8/pASK75-Fn789 plasmids were kindly provided by Dr. Arne Skerra. cDNA regions encoding TNC-C and FN-EDB were amplified by PCR using Phusion Hot Start II High-Fidelity DNA Polymerase (Thermo Fisher Scientific Inc #F-537L; primer pairs: 5'-CTCCTCT-CATATGGAGGCCCTGCCCCTTC-3' (SEQ ID NO:7) and 5'-CAGACACTCGAGTTATCATGTAACAATCTC-3' (SEQ ID NO:8) for domain TNC-C and 5'-CTCCTCT-CATATGGAGGTGCCCCAACTCA-3' (SEQ ID NO:9) and 5'-CAGACACTCGAGTTATCACGTTTGTTGTGT-3' (SEQ ID NO:10) for FN-EDB; NdeI and XhoI restriction sites italicized). The fragments were cloned in pET28a+ plasmid for expression as an N-terminally His-tagged protein.

Expression and purification of TNC-C and FN-EDB. The pET28a+TNC-C and pET28a+FN-EDB plasmids were transformed into E. coli BL21 Rosetta 2 (DE3) pLysS strain (Novagen, #70956). The protein expression was induced by addition of isopropyl (β-D-1-thiogalactopyranoside (IPTG) (Sigma, #16758) at 0.5 mM final concentration and the bacteria were cultured at 18° C. for 16 hours. Bacterial cells were collected by centrifugation, resuspended in ice-cold IMAC buffer (25 mM Tris-HCL, 400 mM NaCl, 25 mM imidazole pH 8, containing EDTA-free protease inhibitor cocktail and DNase I and lysed by sonification (Bandelin Sonopuls HD 2070, Germany). The cleared bacterial lysate was purified using HiTrap IMAC HP columns (GE Health-care #17-0920-05) on AKTA purification system (GE Healthcare) and the eluate was dialyzed against PBS using 3.5 kDa cut-off 3 mL Slide-A-Lyzer Dialysis Cassettes (Thermo Scientific #66330). FN-EDB and TNC-C concentration was determined by bicinchoninic acid assay (Thermo Scientific #23227) and the purity of the proteins was assessed by SDS-PAGE. Mass spectrometry and de novo peptide sequencing were used to confirm the size and sequence of the purified proteins.

17. Antibody Production

Single-chain antibodies: The cDNA sequences encoding FN-EDB-L19-ScFv and TNC-C-G11-scFV were retrieved from US patent applications (U.S. Pat. No. 8,455,625 B2 and EP2157102 A1, respectively), and used to generate pET28a+-based protein expression constructs. The E. coli BL21 Rosetta™ 2 (DE3) pLysS (Novagen, #70956) cells were transformed with recombinant plasmids driving the expression single-chain antibodies. Antibodies were purified using Protein A GraviTrap Sepharose (GE Healthcare #28-9852-54), followed by affinity purification on immobilized FN-EDB and TNC-C. Purified single chain antibodies were analyzed by SDS-PAGE. Pull-down assay was used to verify the interaction of the purified single chain antibodies with the target FN-EDB and TNC-C domains.

Polyclonal rabbit antibodies: Rabbits were immunized with recombinant TNC-C and FN-EDB at LabAs LLC (Tartu, Estonia). Polyclonal antibodies (PAbs) were purified from immune sera using protein G columns followed by affinity purification on immobilized FN-EDB and TNC-C. Specificity of PAbs was confirmed by ELISA and Western blot on FN-EDB, TNC-C and control proteins.

18. Preparation and Characterization of Iron Oxide Nanoworms (NWs)

The NWs were prepared according to a published protocol with minor modifications. 0.63 g of FeCl3·6H2O (Sigma-Aldrich #44944) and 0.25 g of FeCl2·4H2O (Sigma-Aldrich #44939) were mixed with 4.5 g of Dextran T20 (Pharmacosmos) in 30 ml deionized (DI) water. The reaction mixture was cooled to 0° C. on ice and under a steady flow of nitrogen and vigorous stirring, 1 ml of 28% aqueous ammonium hydroxide (Sigma-Aldrich #338818) was added over 45 min. Next, the reaction mixture was heated at 80° C. for 1 hour and cooled to room temperature (RT). After diluting with 90 ml of DI water, the colloidal suspension was centrifuged in 50 ml Falcon tubes at 335 G at RT for 20 min to remove aggregates. The supernatant was transferred to 100,000 MWCO centrifugal filters (Millipore), centrifuged at 760 G at 4° C. for 30 min, topped off with DI water, and resuspended. The dextran was crosslinked with epichlorohydrin, and the NWs were aminated using 28% aqueous ammonium hydroxide (24 h), and dialyzed against 1×PBS for 48 hours. Peptides with extra cysteine residue were coupled to the NWs through a maleimide-PEG (5000)-NHS linker (Jenkem). NWs were filtered through a 0.22 µm filter and used within 1 week.

The concentration of the NWs was determined by constructing a calibration curve with iron oxide and measuring the absorbance of NWs at 400 nm with a NanoDrop 2000c spectrophotometer (Thermo Scientific). The concentration measurements were confirmed by ICP-MS. Transmission electron microscopy (TEM, Tecnai 10, Philips, Netherlands) was used to image the nanoparticles. Dynamic Light Scattering (DLS; Zetasizer Nano ZS, Malvern Instruments, UK) was used to assess the zeta potential, polydispersity and size of NWs.

19. AgNP Synthesis and Characterization

Synthesis of wild type (wt) and isotopic ($Ag^{107}$ and $Ag^{109}$) AgNPs was carried out as described earlier. The CF555-N-hydroxysuccinimide-dye (NHS-dye) was conjugated to terminal amine group of PEG, and biotinylated peptides were coated on the NeutrAvidin (NA) on the surface of the AgNPs. Transmission electron microscopy (TEM, Tecnai 10, Philips, Netherlands) was used to image and DLS (Zetasizer Nano ZS, Malvern Instruments, UK) was used to assess the zeta potential, polydispersity and size of AgNPs.

B. Results

1. Identification of a Bispecific TNC-C and FN-EDB Binding Peptide

Figure 1A:
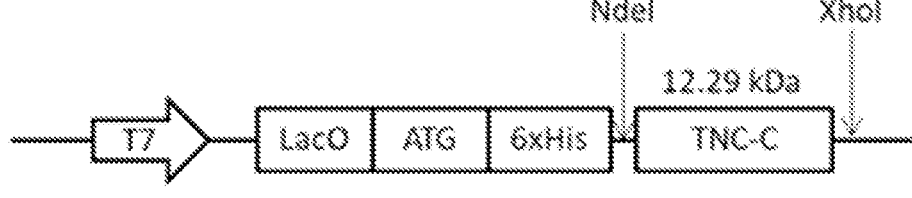
Figure 1B:
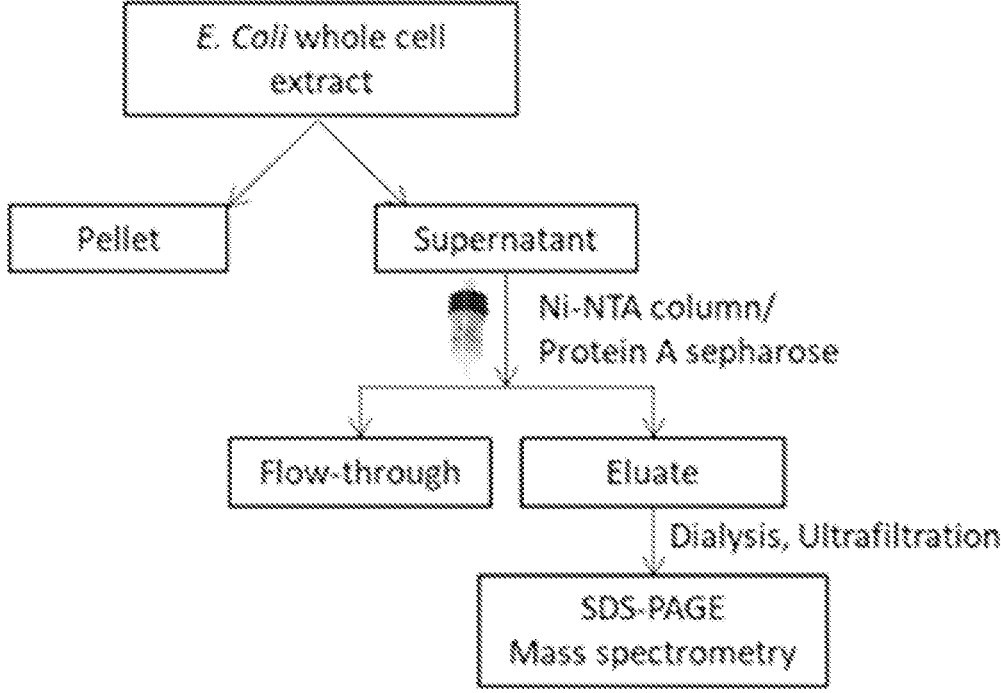

For selection of bispecific peptides capable of binding both FN-EDB and TNC-C, cross-screening of random heptapeptide libraries displayed on T7 phage on recombinant FN-EDB and TNC-C fragments was employed (FIG. 1). The proteins were analyzed by Western blot of FN-EDB and TNC-C using rabbit polyclonal antibodies (data not shown). The FN-EDB and TNC-C were blotted along control proteins: Neuropilin-1 b1b2 domain (NRP1) and nucleolin (NCL). Blots were probed with the primary polyclonal antibodies reactive with FN-EDB and TNC-C and secondary IRDye-680RD-labeled goat anti-rabbit antibody. The proteins were also analyzed by SDS-PAGE of ScFV-L19-FN-EDB (26.02 kDa) and ScFV-G11-TNC-C (28.33 kDa) (data not shown).

First round of biopanning was performed on TNC-C immobilized on polystyrene plates, followed by several rounds of selection on hexahistidine-tagged FN-EDB coated onto magnetic Ni-NTA beads. By round 5 of selection, >1000 fold enrichment in phage binding was seen. Specifically, ~3000-fold enrichment in binding to Fn-EDB was observed in round 5 of selection. Whereas most of the of the 48 peptide phages individually tested from round 5 pool conferred phage binding to either target alone, a 26-amino acid (aa) peptide PPRRGLIKLKTSSNTKENSVVASLRP (PL5; SEQ ID NO:2) possessed the desired dual binding ability (data not shown). The amino acid sequences of recombinant proteins are shown in plaintext (starting at amino acid position 22) and 6× His-tag sequence and vector-derived sequences are in italic.

```
TNC-C (112 amino acids; molecular weight
12299.19 Da)
                              (SEQ ID NO: 15)
MGSSHHHHHHSSGLVPRGSHMEALPLLENLTISDINPYGFTVSWMASENA

FDSFLVTVVDSGKLLDPQEFTLSGTQRKLELRGLITGIGYEVMVSGFTQG

HQTKPLRAEIVT

FN-EDB (112 amino acids; molecular weight
12008.62 Da)
                              (SEQ ID NO: 16)
MGSSHHHHHHSSGLVPRGSHMEVPQLTDLSFVDITDSSIGLRWTPLNSST

IIGYRITVVAAGEGIPIFEDFVDSSVGYYTVTGLEPGIDYDISVITLING

GESAPTTLTQQT
```

The genome of the PL5 phage harbored a single nucleotide deletion in the peptide-encoding segment resulting in frameshift and conversion of 7-aa peptide displayed at the C-terminus of the phage major capsid protein to a 26-aa peptide (Table 4). Genomic DNA (SEQ ID NO:11) and amino acid sequence (SEQ ID NO:12) of the C-terminal portion of the T7 major coat protein 10 (plain text) and the adjacent exogenous PL5 peptide (bold italic). The single nucleotide deletion in the peptide-encoding DNA is at nucleotide position 32. PL5 and its shorter derivative PL1 peptide retain the ability to bind both target proteins.

```
         10        20        30        40        50        60
ATGCTCGGGGATCCGAATTCTCCGCCGAGAC-GTGGTCTAATTAAGCTTAAAACCTCGTC
 M   L   G   D   P   N   S   P P R R G L I K L T S S 70        80        90       100
CAATACAAAAGAGAATTCTGTTGTGGCTTCGCTGAGGCCTTAA
 N T K E N S V V A S L R P   *
```

TABLE 4

| PL5 is SEQ ID NO: 2; PL1 is SEQ ID NO: 1; PL6 is SEQ ID NO: 13. | | |
| --- | --- | --- |
| ID | Peptide Sequence | Binding Specificity |
| PL5 | PPRRGLIKLKTSSNTK ENSVVASLRP | TNC-C + FN-EDB |
| PL1 | PPRRGLIKLKTS | TNC-C + FN-EDB |
| PL6 | IKLKTS | |

It is significant to note that this result was more difficult to achieve than is typical for phage display screens. It took ten attempts (with each attempt taking about two to three weeks of work) to identify the bispecific PL5 peptide. Usually, only three cycles of selection are needed to obtain a specific peptide. Here, five cycles were needed. Indeed, after three cycles, the phage binding was only a bit over 10 fold greater than background, which is still quite flat. After five cycles (about three weeks of work, versus two weeks for three cycles), a 1000 fold increase in phage binding was achieved. Before this result was obtained, it was possible that no bispecific peptide could be identified by phage display screening. The result here was the first demonstration that this was possible. Finally, the discovery was also based on an unexpected and unplanned mutation in one of the phages. A library of random peptides of 7 amino acids was used. With such a library, it was expected and almost universal that hit peptides would have 7 amino acids (the same as the length of the library peptides). Surprisingly, the discovery peptide (PL5) had 26 amino acids, which occurred due to a random frameshift mutation in the phage sequence.

A panel of shorter derivatives of the PL5 peptide was created and a 12-aa peptide that was found, which was designated PL1 (PPRRGLIKLKTS; SEQ ID NO:1), retained the ability to bind to both FN-EDB and TNC-C, both when displayed on phage particles, and as a synthetic FAM-labeled peptide. The binding was specific: PL1 phage did not interact with a recombinant control protein NRP-1, and the phage binding was inhibited by function-blocking polyclonal antibodies against FN-EDB and TNC-C. Immobilized FAM-PL1 was probed with recombinant His-tagged EDB and TNC-C (or control BSA), followed by sequential incubation with rabbit anti-His-tag primary antibody, secondary goat anti-rabbit HRP antibody and a chromogenic peroxidase reaction. Alanine scanning mutagenesis suggested that the PL1 peptide interacts with FN-EDB and TNC-C using an overlapping binding site, with L6 and T11 playing a critical role in both interactions (FIG. 2).

2. PL1-Functionalized Iron Oxide Nanoparticles Home to Tumor Lesions

To explore the utility of PL1 peptide as a systemic tumor-targeting probe, the effect of PL1 coating on biodistribution of dextran-coated PEGylated paramagnetic iron oxide nanoworms (NW) was studied. The NWs are a nanoscale agent designed for systemic affinity targeting as a drug carrier and an MRI contrast agent (Park et al., Adv. Mater. 20:1630-1635 (2008)). Properties of PL1-nanoworms (PL1-NWs) are summarized below, including physicochemical properties, zeta potential, and size distribution of different NWs as measured by DLS.

| Zeta Potential | |
| --- | --- |
| NW: | $-7.8 \pm 0.4$ mV |
| PL1-NW: | $-10.3 \pm 0.7$ mV |
| $_D$(KLAKLAK)$_2$-NW: | $-9.5 \pm 0.4$ mV |
| PL1-$_D$(KLAKLAK)$_2$-NW: (n = 3) | $-10.4 \pm 0.2$ mV |
| Size by DLS | |
| $84 \pm 40$ nm (n = 3) | |

PL1-NWs were audited for homing upon systemic administration in mice bearing orthotopic GBM (NCH421K, WT-GBM), and s.c. GBM (U87MG), and prostate carcinoma (PC3) xenografts. Compared to non-targeted control NWs, PL1 functionalization increased tumor accumulation of the NWs in all models tested (data not shown).

NWs coated with FAM-labeled PL1 peptide or control FAM-NWs were i.v. injected at 7.5 mg/kg into mice bearing s.c. U87MG, orthotopic NCH421K, and orthotopic WT GBM glioblastoma xenografts. After 5 hours of circulation, the mice were perfused through the heart with PBS/DMEM and organs were collected. Cryosections were immunostained with antibodies against fluorescein to visualize NWs, endothelial cells (CD31), and stem cell-like cells (nestin in NCH421K) and examined using confocal microscopy (data not shown). The stained nanoworms could be seen along the tumor blood vessels and extravasated. FAM signal was quantitated by Fiji ImageJ. In vivo homing of PL1 nanoparticles probed with antibody blockade was shown to be specific. PL1-NWs (7.5 mg iron/kg body weight) alone, or in combination with individual anti-EDB, or anti-TNC-C antibodies, or a cocktail of both antibodies, were i.v. injected into mice bearing U87 xenograft tumors. Five hours after the injection, the mice were perfused through the heart with PBS/DMEM and organs were collected for cryosectioning and examination by confocal microscopy. The FAM signal was quantified from representative images using Fiji ImageJ.

NWs coated with FAM-labeled PL1 peptide or FAM were i.v. injected at 7.5 mg/kg body weight into mice bearing PC3 human prostate cancer xenografts. Five hours after the injection, the mice were perfused through the heart with PBS/DMEM, and organs were collected. Cryosections were immunostained with antibodies against endothelial cells (CD31), the nuclei were stained with DAPI, and the sections were imaged by confocal microscopy (data not shown). PL1-NW could be seen along the blood vessels and extravasated. Quantification of FAM signal in representative tissue sections of tumors and control organs (mean pixel intensity). Error bars, mean±SEM (N=4 mice per group); Statistical analysis: P-value determined using Student unpaired t-test, two-tailed; ns P >0.05; **P<0.01. Iron oxide NWs coated with FAM-labeled PL1 peptide (or non-peptide NWs) were i.v. injected at 7.5 mg/kg into mice bearing PC3, U87, NCH421k and WT GBM tumors. Five h after the injection, the mice were perfused through the heart with PBS/DMEM and the tumors and control organs were collected. Sections of control organs were immunostained with antibodies to FAM, CD31, and nuclei were counterstained with DAPI (data not shown).

Confocal fluorescence microscopy showed that PL1-NWs accumulate in the perivascular matrix in peripheral, intermediate and core regions of the tumors. Compared to non-targeted NWs, the increase in PL1-NW accumulation was 8.8-fold in NCH421K, 5-fold in U87MG, 3.3-fold in WT, and 4.7 fold in PC3 tumors, whereas in the control organs (the liver, kidney, spleen, and lung) the signal for PL1-functionalized and non-targeted NWs was similar.

The tumor tropism of PL1-NWs was confirmed by Prussian blue histochemical staining for iron and light microscopy. Mice bearing U87MG tumors were i.v. injected with PL1-NWs or control NWs (at 7.5 mg/kg). Five h after the injection, the mice were perfused through the heart with PBS/DMEM and the organs were collected. Sections of tumor, spleen, lung, liver, and kidney were subjected to Pearls Prussian blue histochemistry to visualize iron deposits in tissue sections as dark blue Prussian blue pigment. In PL1-NW-injected mice, blue signal was evident in the tumor, spleen and liver and some extent in the lung and kidney. Whereas the tumors from control NW-injected mice showed no Prussian blue staining, the signal in normal organs appeared similar to than seen in mice injected with PL1-NWs.

Next the relationship between the homing pattern of the PL1-IONWs and the distribution of the FN-EDB and TNC-C immunoreactivities in tumors was studied. Cryosections of U87MG and NCH421K tumors from PL1-NW-injected mice were stained with FN-EDB-specific (ScFV L19) and TNC-C-specific (ScFV G11) single-chain antibodies. PL1-NW signal in tumor tissue showed extensive overlap with FN-EDB and TNC-C immunoreactivities. PL1-NWs colocalize with FN-EDB and TNC-C in subcutaneous U87MG and orthotopic NCH421K GMB tumors. Tumor tissues were stained with anti-FAM antibody to detect PL1-NWs and with either ScFvG11 recognizing TNC-C or ScFvL19 recognizing FN-EDB.

Coadministration of PL1-NWs with blocking rabbit polyclonal antibodies against either FN-EDB or TNC-C resulted in a significant decrease in tumor homing. Furthermore, cocktail of both FN-EDB and TNC-C antibodies almost completely inhibited the homing. These results show that PL1 functionalization increases tumor accumulation of NWs in an FN-EDB and TNC-C-dependent manner and that dual targeting enhances the NW accumulation.

The elongated shape of NWs contributes to their ability to attach to target cells and enhances magnetic relaxivity by MRI (Park et al., Adv. Mater. 20:1630-1635 (2008)). Next the potential application for PL1-functionalized NWs as a precision MRI contrast agent was investigated. Orthotopic NCH421K GBM mice were subjected to MRI scans before injection of NWs. MRI was performed 5 h after systemic NW, and after terminal imaging. NCH421K glioblastoma mice were i.v. injected with PL1-NWs or control NWs (5 mg/kg iron). Axial slice views were taken of T2-weighted images prior to NW injection (pre-scan), at 5 hours after NW circulation (post-scan), and terminal images after perfusion with PBS to remove blood and circulating NWs (perfused; T, tumor) (data not shown). An increased dark signal was seen in tumor of a mouse injected with PL1-NWs, but not with control NWs. Confocal imaging of cryosections from mice used for MRI studies. NWs, anti-human nestin, and nuclei were stained with different color labels.

T2-weighted and T2* images of NCH421k PL1-NWs tumors from mice injected with PL1-NWs displayed a hypointense signal mediated by the iron oxide nanoparticles. In contrast, in animals injected with nontargeted NWs, no changes in signal intensity within the tumors were seen under the same imaging conditions. In PL1-NW-injected mice, T2* relaxation time within the tumor significantly decreased by 27-36% (from about $23\pm2$ ms to $17\pm1$ ms and $14\pm4$ ms; $p\leq0.0001$, 3 mice per group, for each time point 10-11 data points per mice). In mice injected with nontargeted NWs, relaxation time did not change (from $21\pm5$ ms to $22\pm3$ and $20\pm6$). Following MRI, the tissues were collected for post-MRI confocal fluorescent imaging to confirm the selective accumulation of PL1-NW in the GBMs. These results emphasize the potential application of PL1-NWs as a tumor-detecting and imaging agent.

FN-EDB and TNC-C are upregulated in angiogenic blood vessels during development and disease. To study the contribution of angiogenesis-associated component to the homing of PL1, the biodistribution of PL1-NWs in mice having a locally-induced angiogenic response was studied. An adenoviral vector driving the expression of VEGF-A164 was injected into ears of nude mice intradermally. Four days after the injection of the adenovirus, the animals were injected with Texas Red/Evans Blue to visualize patent blood vessels, followed by injection of PL1-NWs. PL1-NWs accumulated in the angiogenic blood vessels. Non-targeted NWs show no homing to the Ad-VEGF-A164 induced angiogenic site. PL1-NWs and nontargeted NWs showed no signal in the normal ear vessels. In vivo multiphoton analysis showed a significant ~3-fold increase in accumulation of PL1-NWs (relative to nontargeted NWs) in the angiogenic vessels of adenovirus-injected ear but not in the contralateral normal ear (n=3 mice per group, $p\leq0.001$ using two-tailed unpaired t-test). Background labeling was seen in the blood vessels in the normal ear for both PL1 and control NWs. These results show that PL1 acts as an affinity ligand for angiogenic neovessels.

3. PL1-Silver Nanoparticles Home to Tumors

The structural and physicochemical properties of NPs can have dramatic effect on their biodistribution and targetability with affinity ligands. To determine whether PL1 affinity targeting is compatible with precision delivery of nanocarriers other than NWs, silver nanoparticles (AgNP; a model nanoscale platform developed for biodistribution studies in vitro and in vivo) were used. AgNPs plasmonically enhance the emission from surface fluorophores for ultrasensitive detection and extracellular AgNPs can be dissolved by exposure to a mild and biocompatible etching solution—a feature particularly useful for cellular uptake studies (Braun et al., Nat. Mater. 13:904-11 (2014)).

To quantify in vivo biodistribution of systemic PL1-AgNPs in tumor bearing mice, laser-ablation inductively-coupled plasma mass spectrometry (LA-ICP-MS) was used to measure Ag. To overcome issues related to interanimal differences in dosing, tumor properties, and physiological status, tumor-bearing mice were injected with a cocktail of isotopically-barcoded PL1-targeted and nontargeted AgNPs. Mice bearing orthotopic U87MG GBM were i.v. injected with an equimolar mix of PL1-$Ag^{109}$NP and $Ag^{107}$NP. After 5 h circulation, 30 μm cryosections of tumor and control tissues were subjected to line- and rasterized laser ablation mapping of the isotopic content by ICP-MS. The mapped tumor brain tissue area showing the intensity and distribution of control $Ag^{107}$NPs and targeted PL1 $Ag^{109}$NPs in tumor brain tissue were mapped. Laser ablation line scans for $Ag^{109}/Ag^{107}$ profile using 40-μm spot were performed on the tissue sections. The analysis of $Ag^{109}/Ag^{107}$ ratio showed that PL1 functionalization significantly increased $Ag^{109}$NP homing to the GBM: average ~2.7 fold over the $Ag^{109}/Ag^{107}$ ratio in the input mixture (data not shown). Intratumoral $Ag^{109}/Ag^{107}$ ratio showed significant heterogeneity, with some areas showing a $Ag^{109}/Ag^{107}$ ratio ~30 and above. The homing of the PL1-$Ag^{109}$NPs was tumor-specific, as the $Ag^{109}/Ag^{107}$ ratio in control organs was close to the input ratio (liver) or lower (in the lung and normal brain). PL1-NW concentration in glioma is 2.6 to 30-fold higher than that in the control tissues. These data show that PL1 can be used for tumor delivery using different nanoscale platforms.

4. PL1-Targeted Proapoptotic Nanoparticles have Anti-GBM Activity

To determine the effect of the PL1 peptide functionalization on therapeutic efficacy of anticancer nanoparticles, NWs coated with $_D$[KLAKLAK]$_2$ peptide were used as a model nanodrug. The pro-apoptotic $_D$[KLAKLAK]$_2$ peptide exerts its cell-killing activity by destabilizing the mitochondrial membranes (Agemy et al., Proc. Natl. Acad. Sci. 108:17450-17455 (2011); Ellerby et al., Nat. Med. 5:1032-1038 (1999)). Chimeric $_D$[KLAKLAK]$_2$-PL1 was covalently linked to the NWs through a 5K-polyethylene glycol (PEG) linker. In the first treatment study s.c. U87MG tumors that display an angiogenic well-perfused vasculature were used (Candolfi et al., J. Neurooncol. 85:133-148 (2007)). This allowed monitoring of tumor size, rather than using survival, as the endpoint. Mice bearing s.c. U87MG tumors were treated with systemic injections every other day for 20 days. All mice from the PBS-treated group reached 2 cm$^3$ tumor volume within 37 days after initial tumor injection and were sacrificed. Tumor growth was significantly inhibited in the FAM-PL1-$_D$[KLAKLAK]$_2$-NW-treated group, whereas only a slight reduction in tumor growth was seen in animals treated with PL1-NWs or FAM- $_D$[KLAKLAK]$_2$-NWs.

Next, the anti-GBM efficacy of PL-1- $_D$[KLAKLAK]$_2$-NWs was evaluated in human NCH421k orthotopic xenografts, which displays both angiogenic and infiltrative features. The treatment was initiated three days after tumor implantation. Frozen sections of individual patient tumors were incubated with PL1-NWs or nontargeted NWs, immunostained, and examined by confocal microscopy. PL1-NWs showed binding to the tumor sections, and co-localize with EDB and TNC-C of all of the tested glioblastomas (data not shown). Control non-targeted NWs exhibit no binding to the tumor sections. Tissues were stained for FAM (anti-FITC), EDB (ScFv L19), TNC-C(ScFv G11) and nuclei (DAPI) (not shown). The median survival of NCH421k mice treated with PL1-D[KLAKLAK]2-NWs was significantly longer than of control mice treated with PBS, FAM-D[KLAKLAK] 2-NWs, or PL1-NWs. Moreover, one mouse in the NCH421k group that received FAM-PL1- $_D$[KLAKLAK]$_2$-NWs survived 150 days without any signs of recurrence, suggesting a cure. The treatments showed no overt systemic toxicities as evidenced by maintenance of normal body weight and normal histology of organs from the treated animals (Tables 5 and 6). For the dynamics of body weight of the U87MG and NCH421K tumor mice during the treatment, the endpoint was set at either ≥20% of starting body weight or 2000 mm$^3$ tumor volume. Every other day the tumor mice were weighed and tumor volume was calculated. Kaplan-Meier analysis of median survival of the different treatment groups and percent of the surviving mice at different time points for U87MG (Table 5) and NCH421K (Table 6) tumor models.

TABLE 5

| Days | PBS | $_D$[KLAKLAK]$_2$-NW | PL1-NW | PL1-$_D$[KLAKLAK]$_2$-NW |
|---|---|---|---|---|
| 0 | 100% | 100% | 100% | 100% |
| 29 | 88% | 100% | 88% | 100% |
| 31 | 73% | 88% | 75% | 100% |
| 33 | 44% | 88% | 75% | 100% |
| 35 | 29% | 75% | 63% | 75% |
| 37 | 0% | 50% | 63% | 75% |

TABLE 5-continued

| Days | PBS | $_D$[KLAKLAK]$_2$-NW | PL1-NW | PL1-$_D$[KLAKLAK]$_2$-NW |
|---|---|---|---|---|
| 39 | | 50% | 38% | 75% |
| 41 | | 25% | 25% | 63% |
| 43 | | 13% | 25% | 63% |
| 45 | | 13% | 13% | 38% |
| 49 | | 13% | 13% | 25% |
| 57 | | 13% | 0% | 13% |
| 61 | | 0% | | 13% |
| 150 | | | | 13% |
| Median survival | 33 days | 39 days | 39 days | 45 days |

TABLE 6

| Days | PBS | $_D$[KLAKLAK]$_2$-NW | PL1-NW | PL1-$_D$[KLAKLAK]$_2$-NW |
|---|---|---|---|---|
| 0 | 100% | 100% | 100% | 100% |
| 32 | 75% | 100% | 100% | 100% |
| 35 | 60% | 100% | 875% | 100% |
| 37 | 60% | 87% | 75% | 100% |
| 38 | 60% | 62% | 62.5% | 100% |
| 39 | 50% | 62% | 62.5% | 100% |
| 40 | 50% | 62% | 62.5% | 75% |
| 41 | 25% | 62% | 62.5% | 62.5% |
| 42 | 25% | 37.5% | 37.5% | 62.5% |
| 43 | 0% | 37.5% | 25% | 62.5% |
| 44 | | 25% | 0% | 62.5% |
| 45 | | 12.5% | | 50% |
| 46 | | 0% | | 37.5% |
| 52 | | | | 12.5% |
| 150 | | | | 12.5% |
| Median survival | 40 days | 42 days | 42 days | 45.5 days |

Staining of tumor sections at the end of the treatment showed a significant decrease in the number of CD31-positive blood vessels in the FAM-PL1- $_D$[KLAKLAK]$_2$-NW group compared with the control groups, whereas there was no difference in Ki67-positive cells, caspase-3-positive cells, CD11b and CD68 macrophages or LYVE-1-positive lymphatic vessels. The tumor tissues were sectioned and stained with an anti-CD31 antibody to highlight blood vessels, anti-LYVE-1 to visualize lymphatic endothelial cells, antibodies against CD11b and CD68 to detect macrophages, anti-Ki67 to detect proliferating cells, and anti-caspase-3 to detect apoptotic cells.

To explore the translational relevance of the PL-1 targeting system, binding of PL1-NWs to clinical GBM samples was studied. Cryosections of GBM were overlaid with FAM-PL1-NWs or FAM-labeled control NWs, washed and subjected to confocal imaging. PL1-NWs showed binding to all human GBM samples tested, with binding at perivascular structures as well as in the tumor parenchyma. Frozen sections of tumors were incubated with PL1-NWs or control non-targeted NWs, stained FAM-reactive antibody to detect NWs and examined by confocal microscopy. Multiple parallel sections were used for quantification. PL1-NWs colocalized with tumor FN-EDB and TNC-C that are highly overexpressed in clinical GBM samples (Pedretti et al., Br. J. Cancer. 103:827-836 (2010); Carnemolla et al., Am. J. Pathol. 154:1345-1352 (1999)). In contrast, control NWs showed only a background fluorescence signal. These data suggest that PL1-functionalized probes are translationally relevant for human GBM targeting.

C. Discussion

Alternatively spliced isoforms of ECM proteins fibronectin and tenascin-C are abundant and readily accessible targets that are overexpressed in many solid tumors. A bispecific dodecapeptide, PL1, that targets both fibronectin FN-EDB and TNC-C for precision targeting of the tumor ECM, was evaluated and preclincally validated. It was shown that PL1 specifically homes to solid tumors and angiogenic vessels to effectively deliver nanoparticle payloads. PL1-functionalized NWs showed preclinical utility as a precision MRI contrast agent, and when loaded with a proapoptotic peptide, -suppressed the progression of GBM. These observations suggest applications for the PL1 peptide in the management of solid tumors positive for FN-EDB and TNC-C expression.

Dual targeting with affinity ligands is an increasingly popular strategy to increase the number of available binding sites in order to address inter- and intratumoral heterogeneity in the expression and accessibility of tumor-associated markers (Wang et al., Neurotherapeutics (2017), doi: 10.1007/s13311-016-0510-y; Ehlerding et al., J. Nucl. Med., doi:10.2967/jnumed.117.199877). Using two different tumor homing peptides in tandem can improve biodistribution of payloads within malignant tissues, but may result in long peptides that may be immunogenic, and the two components may also interfere with one another's binding to the receptor. PL1 is a short peptide from an agnostic screen for phage-displayed peptides that bind both to Fn-EBD and TNC-C. It was shown that dual targeting by PL1 results in potentiation of tumor delivery of nanoparticles through participation of both receptor proteins. That this is the case, is evidenced by the fact that in vivo blockade of either receptor by a neutralizing antibody resulted in robust decrease in FAM-PL1-NW accumulation in terms of both fluorescence intensity and area positive for the presence of the nanoparticles. Overexpression of FN-EDB and TNC in the tumor angiomatrix and tumor parenchyma may result in domains with high-density and availability of both receptors resulting in an increased probability of PL1-receptor interaction and enthalpic gain for selective NP adsorption (Wang and Dormidontova, Phys. Rev. Lett. 109:238102 (2012)).

The tumor ECM is increasingly recognized as a translationally relevant target for affinity delivery of drugs and imaging agents. Compared to targeting membrane-bound receptors on specific (sub)populations of tumor cells, the therapy with ECM-targeted compounds may result in higher treatment efficacy due to a broader effect on different cell populations in the tumor tissue and to absence of lysosomal drug sequestration and inactivation. FN-EDB and TNC have emerged as clinically relevant receptors for affinity targeting of malignant disease. Over the years, researchers have identified several monospecific targeting ligands for FN-EDB, such as FN-EDB-ScFV L19 (Nilsson et al., Cancer Res. 61:711-716 (2001)), and for TNC, such as TNC-C-ScFV GI1 (Silacci et al., Protein Eng. Des. Sel. 19:471-478 (2006)), TNC aptamer (Daniels et al., Proc. Natl. Acad. Sci. U.S.A 100:15416-15421 (2003)), and TNC-binding FHK peptide (Kim et al., Mol. Cells. 33:71-77 (2012)). To study PL1 as a nanoparticle-guiding ligand, PEGylated iron oxide NWs—a nanoscale payload optimized for in vivo targeting (Simberg et al., Proc. Natl. Acad. Sci. U.S.A 104:932-6 (2007); Park et al., Adv. Mater. 20:1630-1635 (2008)) was used. Fluorescence imaging demonstrated that PL1-functionalized NWs home specifically to the FN-EDB- and TNC-C-positive areas in a panel of solid tumors and intradermal angiogenic sites induced by injection with an adenovirus driving VEGF expression. The GBMs commonly overexpress VEGF—a known direct inducer of FN-EDB expression (Khan et al., Angiogenesis. 8, 183-196 (2005); Trachsel et al., J. Invest. Dermatol. 127:881-886 (2007)).

Multiphoton imaging of live mice showed that angiogenic blood vessels are targeted by systemically administered PL1-NWs. Moreover, PL1-functionalized NWs can serve as a tumor-specific contrast agent; T2 MRI demonstrated intravital accumulation of the NWs in orthotopic NCH421K GBM lesions. PL1-functionalization also increased tumor selectivity in another nanosystem (metallic AgNPs). Ratiometric LA-ICP-MS on tissues from tumor mice dosed with an equimolar cocktail of isotopically-barcoded PL1 and control AgNPs, demonstrated in tumor tissue an up to 30-fold over-representation of PL1-AgNPs, whereas the PL1-AgNP/AgNP ratio in control organs was ~1.

As a proof-of-concept experimental therapy, an anticancer payload consisting of a mitochondrial membrane-destabilizing D(KLAKLAK)2 peptide was used. This peptide was originally designed and developed as an antibacterial agent (Ellerby et al., Nat. Med. 5:1032-1038 (1999)). Nanoparticles coated with the D[KLAKLAK]2 peptide have been reported to be internalized into cells after having been brought to the cell surface by a non-internalizing peptide (Agemy et al., Proc. Natl. Acad. Sci. 108:17450-17455 (2011)). The PL1-$_D$[KLAKLAK]$_2$-NW system significantly reduced tumor volume and increased the lifespan of mice. Non-internalizing ECM-targeting ADC drugs can be engineered to efficiently release their cytotoxic payloads in the extracellular environment to mediate a potent therapeutic activity (Dal Corso et al., J. Control. Release. 264:211-218 (2017); Casi and Neri, Mol. Pharm. 12:1880-1884 (2015)). Similar strategies will be employed to develop PL1-functionalized chemotherapeutics in future studies. The results reported here are translationally relevant: FN-EDB and TNC-C are conserved between mice and humans, and the studies on clinical samples show colocalization of PL1-NWs with these target molecules.

In summary, the dual targeting PL1 peptide allows specific delivery of nanoscale payloads to solid tumors that express FN-EDB and TNC-C, resulting in a high tumor selectivity and efficacy of anticancer and imaging agents. PL1-based imaging agents can be developed into companion diagnostic tests to stratify patients for therapeutic targeting FN-EDB and TNC-C-positive tumors and to assess the efficacy of anticancer interventions.

Example 2: Selection and Properties of PL2 Peptide and Related Peptides

Peptides were selected and tested for binding to FN-EDB generally using techniques and protocols as described in Example 1. The data and results are shown in FIGS. 3-5 and 22.

A. Materials and Methods

1. Materials

Phosphate-buffered saline (PBS) was purchased from Lonza (Verviers, Belgium). K$_3$[Fe(CN)$_6$], HCl, isopropanol, Triton-X, Tween-20, CHCl3, MeOH, Isopropyl R-D-1-thiogalactopyranoside (IPTG) and dimethylformamide (DMF) were purchased from Sigma-Aldrich (Munich, Germany).

2. Peptides and Proteins

Cys-5(6)-carboxyfluorescein (FAM)-PL2 and Cys-FAM peptides with 6-aminohexanoic acid spacer were purchased from TAG Copenhagen (Denmark). The pASK75-Fn7B8 and pASK75-Fn789 plasmids kindly provided by Prof. Dr. Arne Skerra (Schiefner et al., 2012). Gene fragments for Fn-EDB domains were amplified from the plasmids and cloned into pET28a+ plasmid containing His6-tag at N-terminal for expression in *E. coli* BL21 Rosetta™ 2 (DE3) pLysS (Novagen, #70956) strain. Recombinant Fn-EDB were produced as a soluble protein and purified using HiTrap IMAC HP column (GE Healthcare, #17-0920-05). Protein purity, size and sequence were determined with SDS-PAGE, Mass spectrometry (MS) intact protein and shotgun analysis. NRP-1 b1b2 protein was purified at the Protein Production and Analysis Facility at the Sanford Burnham Prebys Medical Discovery Institute (La Jolla, CA, US).

3. Cell Lines and Experimental Animals

The human glioblastoma (U87MG, HTB-14) cells and prostate carcinoma (PC3, CRL1435) cells were purchased from ATCC (VA, USA). Murine WT-GBM glioblastoma cells were a kind gift from Gabriele Bergers (UCSF, USA) and P3, P13 stem cell-like were a kind gift from Rolf Bjerkvig, (University of Bergen, Norway). Cells and tumors were prepared as previously described (Bougnaud et al., 2016; Keunen et al., 2011; Talasila et al., 2013). Athymic nude mice (Hsd/Athymic Fox1 nu Harlan) were purchased from Harlan Sprague Dawley (HSD, Indianapolis, IN, USA) and maintained under standard housing conditions of the Animal Facility of the Institute of Biomedicine and Translational Medicine, University of Tartu (Tartu, Estonia). Orthotopic GBM tumor models, NCH421K, P13, and P3 stem cell-like, WT-GBM cells around $2\text{-}3\times10^5$ in 3 μL PBS were intracranially implanted into mice brain 2 mm right and 1 mm anterior to the bregma suture. Subcutaneous model, U87 GBM and Prostate carcinoma (PC3) cells injected $2\text{-}9\times10^6$ cells in 100 μl PBS were implanted subcutaneously into the right flank of 11-15 week old male and female nude mice. Animal experimentation procedures were approved by the Estonian Ministry of Agriculture, Committee of Animal Experimentation, project #42 and #48.

4. T7 Phage Peptide Library Biopanning

NNK-encoded $X_7$ peptide phage libraries with diversity $\sim5\times10^8$ displayed on T7 415-1b phage display system (Novagen, EMD Biosciences, MA, USA) were used for biopanning on recombinant Fn-EDB. The first panning round were performed on Fn-EDB immobilized on Costar 96-Well enzyme-linked immunosorbent assay (ELISA) plate (#3590, Corning Life Sciences, Tewksbury, MA, USA). The plate was coated with 20 μg/ml recombinant Fn-EDB in 100 μl of PBS overnight at 4° C., followed by blocking with 1% bovine serum albumin (BSA) in PBS overnight at 4° C. The phage library solution ($5\times10^8$ pfu in 100 μl of PBS-BSA) were incubated overnight at 4° C., followed by 6 wash with PBS+BSA+0.1% Tween 20 to remove non-specifically bound background phages, and by phage rescue and amplification in *E. coli* strain BLT5403 (Novagen, EMD Biosciences, MA, USA) (Teesalu et al., 2012). The consequent rounds of selection were performed on Ni-NTA Magnetic Agarose Beads (QIAGEN, Hilden, Germany) coated with His-6X tagged Fn-EDB (30 μg/10 μl beads) at room temperature for 1 hour in 400 μl of PBS. The Fn-EDB immobilized beads were washed three times with PBS+BSA+0.1% NP40, followed by incubation of previous round phage ($5\times10^8$ pfu in 100 μl of PBS+BSA+0.1% NP40) for 1 hour at room temperature. The unbound/weakly bound phage removed by rinsing six times with PBS+BSA+0.1% NP40, binding phage were eluted with 1 ml of PBS+500 mM Imidazole+0.1% NP40. The recovered phage was titered and amplified for a subsequent round of selection. After 6 rounds of selection, a peptide-encoding phage DNA from a randomly picked set of 48 clones from round 5 were subjected to Sanger sequencing to obtain information on the displayed peptides (Ikemoto et al., 2017; Teesalu et al., 2012)

For cell-free binding studies using individually amplified phage clones; phage was incubated with Fn-EDB coated magnetic beads as described above. RPARPAR phage on NRP-1-coated beads was used as a positive control (Teesalu et al., 2009), Nucleolin (NCL) and Tenascin C-C domain (TNC-C) were used as negative control. Phage clones displaying heptaglycine peptide (GGGGGGG, G7 (SEQ ID NO:20)) or insert less phage clones were used as negative controls.

5. In Vivo Play-Off Phage Auditioning

In vivo play-off was used to evaluate systemic homing of peptide phage to xenograft tumor models. The in vitro selected candidate Fn-EDB binding peptides, phages displaying published tumor homing peptides, and control peptides were amplified and purified by precipitation with PEG-8000 (Sigma-Aldrich, St. Louis, MO, USA), followed by $CsCl_2$ gradient ultracentrifugation and dialysis. The amplified phage peptides were pooled in equimolar, and injected intravenously (final $1\times10^{10}$ pfu in 200 μl PBS) in tumor-bearing mice for two hours' circulation, after which mice were anesthetized and 2.5% avertin and perfused with DMEM intracardially. The tumors and organs were collected in lysogeny broth (LB)+1% NP40, the tissues were homogenized for phage peptide rescue. The tissue lysates were amplified in *E. coli*, purified by precipitation with PEG-8000 and DNA was extracted using a DNA extraction kit (High Pure PCR Template Preparation Kit; Roche, Basel, Switzerland). Next-generation sequencing of phage genomic DNA evaluated the representation of each phage in input mixture, in tumor and control organs with Ion Torrent next generation sequencing system (Thermo Fisher Scientific, Waltham, MA, USA). The next generation deep sequencing of phage library was done using Ion Torrent according to the manufacturer's protocol with slight modification. The FASTQ data from Ion Torrent was processed by a custom python script that identified the barcodes, constant flanking residues, extracted the reads of the correct length.

6. Peptide Binding Assay

The FAM-labeled peptides 20 μg/100 μl in PBS were coated on ELISA plates (Nunc Maxisorp, Thermo Fisher Scientific Inc., MA, USA) at 37° C. overnight, blocked with PBS containing 1% BSA for 1 hour at 37° C. The wells were washed with blocking solution (PBS containing 1% BSA and 0.1% Tween-20), incubated with recombinant proteins at 2 μg/well in PBS for 6 h, and washed three times with blocking solution. The bound protein was detected using an anti-His-tag antibody (Abcam/Icosagen, Estonia) for 1 hour at 37° C., washed three times with blocking solution, followed by horseradish peroxidase-conjugated secondary antibody (Jackson Immuno Research, Cambridgeshire, UK). The wells were washed three times with blocking solution and the peroxidase reaction was done by adding 100 μL/well of freshly prepared solution from TMB Peroxidase EIA Substrate Kit (Bio-Rad, Hercules, CA, USA), followed by incubation at 37° C. for 5 min. The reaction was stopped by 1 N $H_2SO_4$, and absorbance was measured at 450 nm with a microplate reader (Tecan Austria GmbH, Salzburg, Austria).

7. Nanoparticle Synthesis and Functionalization

The iron oxide nanoworms (NWs) were prepared as described in (Park et al., 2008) with minor modifications. The aminated NWs were PEGylated using maleimide-5K-PEG-NH. Peptides were coupled to NWs through a thioether bond between the thiol group of a cysteine residue added to the N-terminus of the peptide. The concentration of the NWs was determined by constructing a calibration curve with iron oxide and measuring the absorbance of NWs at 400 nm with a NanoDrop 2000c spectrophotometer (Thermo Scientific). Isotopically pure silver nanoparticles (AgNPs) were synthesized and functionalized as described (Willmore et al., 2016), CF647-N-hydroxysuccinimide-dye (NHS-dye) was conjugated to terminal amine group of PEG, and biotinylated peptides were coated on the NeutrAvidin (NA) on the surface of the AgNPs. Transmission electron microscopy (TEM, Tecnai 10, Philips, Netherlands) was used to image and DLS (Zetasizer Nano ZS, Malvern Instruments, UK) was used to assess the zeta potential, polydispersity and size of nanopartiles.

8. Tumor-Targeted Delivery and Biodistribution Studies

FAM-labeled PL2 peptide coupled NW or control FAM-NW (7.5 mg/kg) in PBS were injected into the tail vein of the subcutaneous U87, PC3, and orthotropic WT-GBM tumor mice. Five h after circulation, the tumor and organs were collected by cardiac perfusion of mice with 20 ml PBS/DMEM under deep anesthesia. Tissues were imaged under an Illuminatool Bright Light System LT-9900 (Lightools Research, Encinitas, CA, USA) before Snap-frozen. The frozen tissues were cryosectioned 8-10 μm and mounted on a superfrost+ slides. The sections were equilibrated at RT and fixed with 4% paraformaldehyde/methanol. The immunostaining performed with following primary antibodies; rabbit anti-fluorescein IgG fragment (cat. no. A889, Thermo Fisher Scientific, MA, USA), rat anti-mouse CD31 (BD Biosciences, CA, USA), and in-house prepared CF647 or CF546-labeled single chain antibodies ScFV G11, for secondary antibodies; Alexa 488 goat anti-rabbit IgG, Alexa 647 goat anti-rat IgG, and Alexa 546 goat anti-mouse IgG, were from Invitrogen, CA, USA. Nuclei were counterstained with 4',6-diamidino-2-phenylindole (DAPI, Molecular Probes) at one 1 μg/ml. The coverslips were mounted onto glass slides with Fluoromount-G (Electron Microscopy Sciences, PA, USA) imaged using confocal microscopy (Olympus FV1200MPE, Hamburg, Germany), and analyzed using the FV10-ASW4.2 viewer/Imaris software/Fiji ImageJ.

9. Ex Vivo Dipping Assay on Clinical Tumor Samples

Fresh surgical ovarian carcinoma samples obtained during autopsy under protocols approved by the Ethics Committee of the University of Tartu, Estonia (permit #243/T27). The dipping assay, fresh ovarian carcinoma tissues were immediately washed with DMEM and explants about 1 cm³ were incubated at 37° C. with PL2-NW/NWs (40 g/mL Fe diluted in DMEM supplemented with 1% of BSA) for four h. Next, the explants were washed with PBS, snap-frozen, cryosectioned at 10 μm, and immunostained using rabbit anti-fluorescein primary antibodies, followed by detection with the Alexa-488 anti-rabbit secondary antibody (Invitrogen, Thermo Fisher Scientific, MA, USA).

10. Clinical Samples

Fresh surgical samples of ovarian carcinoma were obtained from Tartu University Clinics, Tartu, Estonia under protocols approved by the Ethics Committee of the University of Tartu, Estonia (permit #243/T27).

11. Statistical Analysis

Prism 6 software was used to perform statistical analysis. The results are presented as mean with error bars indicating ±SEM. For comparison of two groups, a comparison using an unpaired t-test and multiple groups ANOVA test was used. P<0.05 was considered significant, P-values depicted as follows: *P less than or equal to 0.05, P less than or equal to 0.01, *P less than or equal to 0.001 and ****P less than or equal to 0.0001.

B. Results

1. Identification of a FN-EDB Binding Peptide

For selection of peptides capable of specifically binding to FN-EDB domain, biopanning was performed using X7 T7 phage library. The first round of biopanning was carried out on FN-EDB immobilized polystyrene well plates, followed by several rounds of selection on hexahistidine-tagged FN-EDB coated onto magnetic Ni-NTA beads. By round 6 of selection, >3000-fold enrichment in phage binding was observed. From 48 clones selected for sequencing, 7 peptide sequences identified with Fn-EDB binding ability were chosen as lead candidates for further evaluation (Table 7).

TABLE 7

| Clone No | Peptide Phage | Fold over G7 |
|---|---|---|
| 2 | TKRKGKG (SEQ ID NO: 21) | 58 |
| 3 | GLGGRRIKLKTS (SEQ ID NO: 22) | 2064 |
| 4 | GRRGRVIKLKTSEPPQ (SEQ ID NO: 23) | 1185 |
| 10 | GTRRRSRINLAAALE (SEQ ID NO: 24) | 1563 |
| 17 | KVKKRGA (SEQ ID NO: 25) | 44 |
| 24 | VHERTRI (SEQ ID NO: 26) | 1 |
| 33 | RESRRGRVKLAAALE (SEQ ID NO: 27) | 209 |
| 46 | TSKQNSR (SEQ ID NO: 3) | 89 |

To identify the best tumor-targeting and efficiency among the candidate phage peptides in vivo, homing was audited upon systemic administration in mice bearing xenografts tumor models. The tumor and control organs peptide-encoding portion of the phage genome was subjected to High throughput sequencing (HTS) and analyzed using custom bioinformatics tools (Phage Display Parser internet site canbio.ut.ee). The results showed a Fn-EDB binding peptide, designated PL2 (TSKQNSR; SEQ ID NO:3), had better targeting, and homing effect in different tumor models compared to other peptides. The PL2 peptide had an R ending amino acid which fulfills CendR rule and has been previously shown to bind to Neuropilin 1 b1b2 domain (NRP1)(Teesalu et al., 2009). Testing was done to confirm this binding ability with purified NRP1 protein together with Fn-EDB. The results confirmed that PL2 retained the ability to bind specifically to both Fn-EDB and NRP1 when displayed on phage particles. Alanine scanning mutagenesis performed for evaluating structure-functional relationship showed key amino acid residues Serine (S) and Arginine (R) near the C-terminus were important for Fn-EDB binding (FIG. 4C). In addition, synthetic FAM-labeled PL2 peptide showed similar binding ability as a phage PL2 peptide in a plate coated with Fn-EDB in ELISA experiment.

2. PL2-Functionalized Iron Oxide Nanoparticles Home to Tumor Lesions

To evaluate the utility of PL2 peptide as a systemic tumor-targeting probe, the effect of PL2 coating on dextran-coated PEGylated paramagnetic iron oxide nanoworms (NW) was studied. The NWs are a nanoscale agent designed for systemic affinity targeting as a drug carrier and an MRI contrast agent (Park et al., Adv. Mater. 20:1630-1635 (2008)). PL2-nanoworms (PL2-NWs) did not alter the physicochemical properties, zeta potential, and size distribution of different NWs as measured by DLS. PL2-NWs were audited for homing upon systemic administration in mice bearing orthotopic GBM WT-GBM and s.c. GBM (U87MG), and prostate carcinoma (PC3) xenografts. PL2 functionalization increased tumor accumulation of the NWs in all models tested compared to non-targeted control NWs.

The observed PL2 homing pattern was mainly localized to tumor blood vessels including stromal regions, intermediate and core regions of the tumors, as seen by localized CD31 marker. There were some regions where signal was detected away from the blood vessels. In contrast, control NW showed only background signals in tumor tissue. The PL2-NW accumulation was 7.5-fold in U87MG, 2-fold in WT, and 6.9 fold in PC3 tumors, whereas in the control organs (the liver, kidney, spleen, and lung) the signal for PL1-functionalized and non-targeted NWs was similar (data not shown).

Next the immunostaining analysis was studied by ex-vivo Illumatool imaging of organs from PL2-NW injected U87 mice. Macroscopic images of tumor organs again illustrated the specific targeting of the efficiency of the PL2 peptide. Next the relationship between the homing pattern of the PL2-IONWs and the distribution of the FN-EDB immunoreactivities in U87 tumor was studied. The cryosections of U87MG tumors from PL2-NW-injected mice were stained with FN-EDB-specific (ScFV L19) single-chain antibodies. PL2-NW signal in U87MG tumor tissue showed extensive overlap with FN-EDB and colocalization with FN-EDB. Tumor tissues were stained with anti-FAM antibody to detect PL2-NWs and with ScFvL19 recognizing FN-EDB.

3. PL2-NW Binding to Surgical Explants of Human Clinical Cancers

Figure 9:
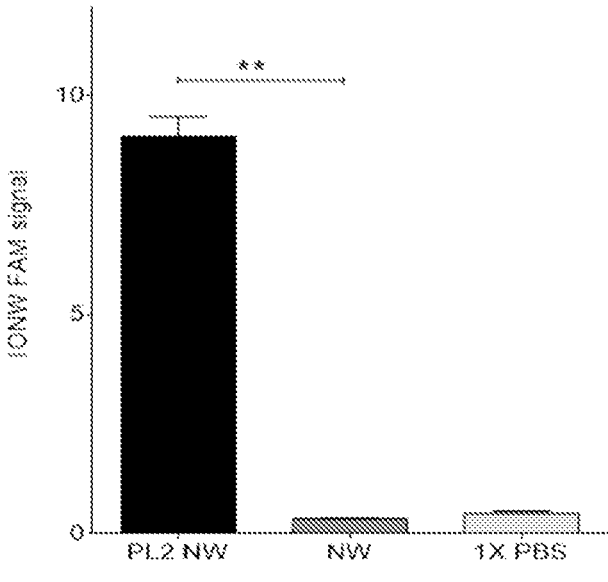
FIG. 9 is a graph showing binding and penetration of PL2 NWs to the tumor tissue compared to control NWs or PBS.

The translational relevance and tissue penetration effect of PL2-NW based targeting system on freshly extracted human ovarian carcinoma cancer tissue was explored. In a tumor dipping assay, PL2 NWs showed binding, and penetration to the tumor tissue 9 fold higher compared to control NWs or PBS (FIG. 9). The penetration effect was observed to a few micrometers inside explants in some areas, whereas binding associated mainly with the tumor tissue surface. These data show that PL2 guided probes are translationally relevant for solid tumor targeting.

C. Discussion

The extracellular matrix protein glycoprotein Fibronectin Extra Domain-B (Fn-EDB) is specially expressed in the stroma of various cancers and in angiogenic blood vessels. The Fn-EDB is an excellent marker of angiogenesis and is essentially undetectable in healthy adult individuals. A novel Fn-EDB specific PL2 peptide (TSKQNSR; SEQ ID NO:3) was developed for selectively targeting gliomas and prostate cancer vasculature. T7 phage display was used to identify EDB targeting peptides. The selected phage peptides targeting properties were first assessed by in vitro and in mice bearing various orthotopic xenografts of glioblastoma (GBM) and prostate tumors using high throughput sequencing (HTS). The PL2 peptide showed highly specific tumor homing while sparing normal organs and also bound to Neuropilin-1. A synthetic FAM-PL2 peptide functionalized with iron oxide nanoworms (NWs) demonstrated active homing in GBMs and prostate carcinoma xenografts. Ex-vivo imaging and tumor tissue showed enhanced nanoparticle delivery and retention, mainly distributed inside the tumor. Further PL2 NWs show the ability to home to human ovarian carcinoma cancer tissue, showing its translational relevance for targeted delivery of nanoscale payloads to the aggressive solid tumors.

In most solid tumors, angiogenesis is a common feature that expresses distinct markers plays a critical role in tumor initiation, progression, and metastasis (Jain, 1999; Matejuk et al., 2011). The tumor blood vessels are dilated, leaky and tortuous. For the tumor cells to survive and proliferate, they must be in a certain distance to blood vessels to receive sufficient oxygen and nutrients (Forster et al., 2017). Tumor growth is critically dependent on angiogenesis and the formation of new blood vessels requires interactions between vascular endothelial cells and the extracellular matrix (ECM) (Ruiz-Cabello et al., 2002; Schliemann and Neri, 2007; Teesalu et al., 2012). Many different strategies are currently used for vascular targeting including antiangiogenic agents, vascular targeting agents, stereotactic body radiation therapy (SBRT) and tumor antivascular alpha therapy (TAVAT) (Forster et al., 2017). Many other targeted therapies and chemotherapy generally rely on tumor vasculature to deliver the drugs to the tumor cells.

The high levels of receptor expression and its accessibility from the bloodstream are ideal target for targeted therapy (Ruoslahti et al., 2010). ECM components are usually present in large amounts, and are located in the perivascular space of tumor vessels. Among them, Fibronectin extra-domain B (Fn-EDB) is selectively expressed in tumor blood vessels that are typically absent in quiescent healthy adult and mature blood vessels (Khan et al., 2005; Zardi et al., 1987). The Fn-EDB is specifically expressed during embryogenesis and neoangiogenesis, and is highly overexpressed in tumor blood vessels in many aggressive solid tumors (Park et al., 2012; Schiefner et al., 2012). The EDB domain is specific for neovascularizing tumors and therefore offers advantages of a good molecular target.

To date, several EDB targeting legends including antibodies and peptides have been developed to mediate delivery of cytokines, cytotoxic agents, chemotherapeutic drugs, and radioisotopes to treat EDB-expressing tumors. EDB-FN-specific antibodies and peptides that mediate delivery of cytokines, cytotoxic agents, chemotherapeutic drugs, and radioisotopes have been developed. Some are being examined in clinical trials and exert therapeutic effects in EDB-FN-positive cancer patients. One of these, the L19 antibody, has exhibited potential in preclinical and clinical studies, demonstrating that high-affinity molecules specific for EDB may enable effective, specific tumor targeting.

Peptide phage display was used on the recombinant FN-EDB domain to identify small peptides. Among seven peptides, PL2 interacts specifically with FN-EDB and in an in vivo playoff experiment showed better accumulation compared to other peptides on different tumor models. To study PL2 as a nanoparticle-guiding ligand, PEGylated iron oxide NWs were used. Systemic PL2-guided iron oxide nanoparticles accumulated in a panel of tumor xenografts implanted in mice and homed specifically to the FN-EDB positive areas in a panel of solid tumors. The FN-EDB targeted nanoparticles were useful for solid tumor detection, imaging and anticancer payload. This study indicates that PL2 guided agents can be used for improved detection and therapy of solid tumors.

Example 3: Selection and Properties of PL3
Peptide and Related Peptides

Figure 7:
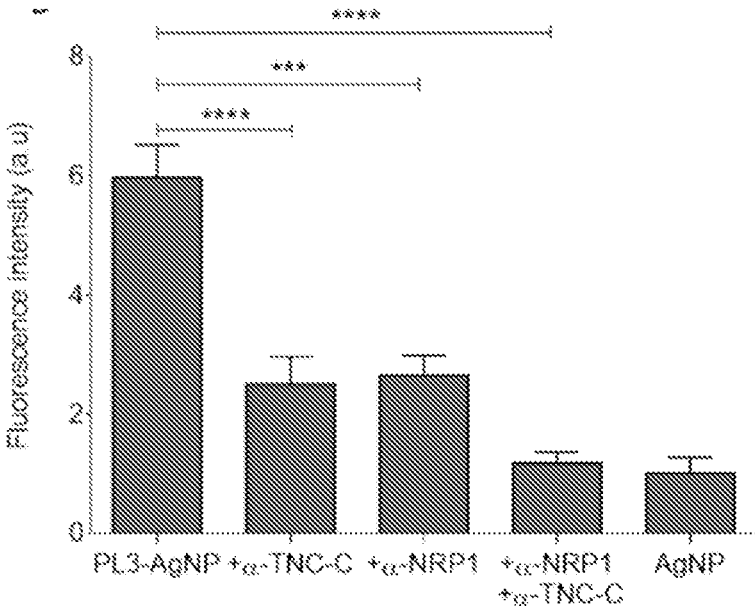
FIG. 7 is a graph showing quantification of the effect of TNC-C and NRP-1 antibodies on tumor accumulation of PL3-AgNPs assayed by confocal microscopy. PL3-AgNPs alone, or in combination with anti-TNC-C and/or anti-NRP1 antibodies were i.v injected into mice bearing U87-MG xenograft tumors. Mice were perfused through the heart with PBS/DMEM 5 h after injection and organs were collected for cryosectioning and confocal microscopy.
Figure 8:
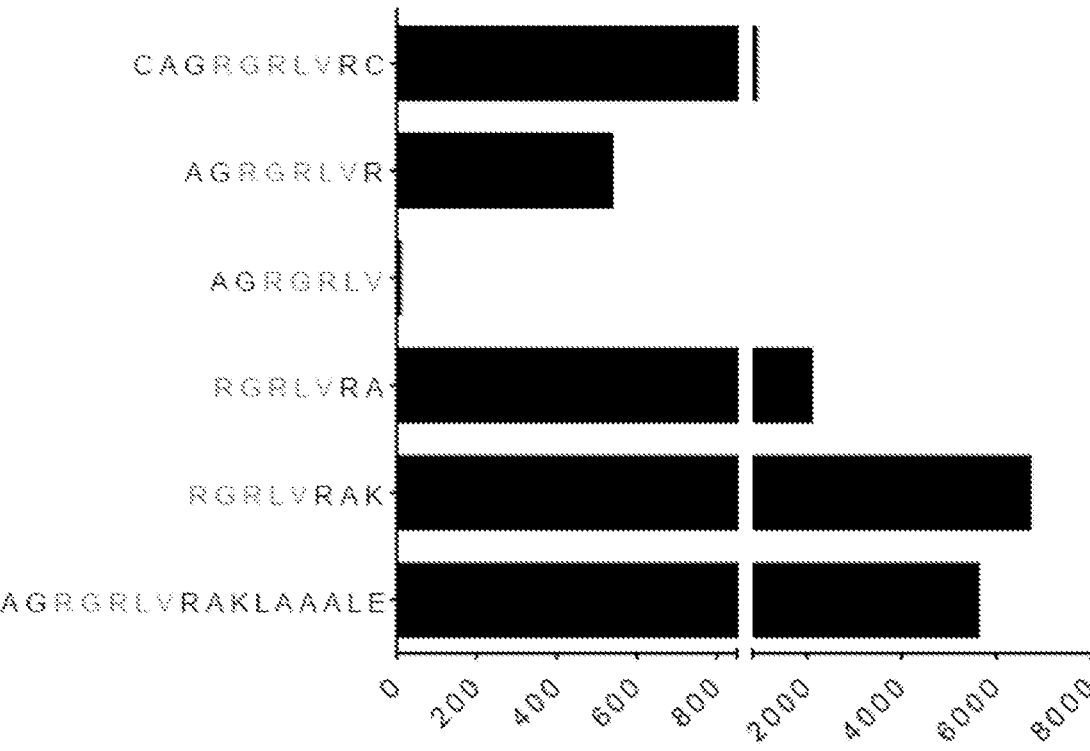
FIG. 8 is a graph of binding of peptide variants of PL3 to TNC-C. Amino acid sequences in FIG. 8, from top to bottom, are SEQ ID NOs:46, 4, 85, 38, 47, and 14.

Peptides were selected and tested for binding to TNC-C generally using techniques and protocols as described in Example 1. Some of the data and results are shown in FIGS. 6-8.

A. Materials and Methods

1. Materials

Phosphate-buffered saline (PBS) was purchased from Lonza (Verviers, Belgium). $K_3[Fe(CN)_6]$, HCl, isopropanol, Triton-X, Tween-20, CHCl3, MeOH, Isopropyl β-D-1-thio-galactopyranoside (IPTG) and dimethylformamide (DMF) were purchased from Sigma-Aldrich (Munich, Germany). Cys-fluorescein (FAM)-PL3 and Cys-FAM peptides with 6-aminohexanoic acid spacer were purchased from TAG Copenhagen (Denmark). $[_D(KLAKLAK)_2]$ and $[_D(KLAK-LAK)_2]$-PL3 peptides were synthesized using Fmoc/t-Bu chemistry on a microwave-assisted automated peptide synthesizer (Liberty; CEM Corporation, Matthews, NC, USA). Peptides were purified by high-performance liquid chromatography (HPLC) using 0.1% trifluoroacetic acid (TFA) in acetonitrile-water mixtures to 90%-95% purity and validated by quadrupole time-of-flight (Q-TOF) mass spectral analysis. CF647 amine dye was purchased from Biotium, Hayward, CA, USA.

2. Cell Lines and Experimental Animals

The U87 (human glioblastoma, HTB-14) cells and PC3 (prostate carcinoma, CRL1435) cells and PPC1 (primary prostate carcinoma-1) cells were purchased from ATCC. Murine WT-GBM glioblastoma cells were a kind gift from Gabriele Bergers (UCSF, USA) and P3, P8, P13 stem cell-like, P22, NCH421K cells were a kind gift from Rolf Bjerkvig, (University of Bergen, Norway). M21 melanoma cells were the gift of David Cheresh (USA). Cells and tumors were prepared as previously described (Bougnaud et al., 2016; Keunen et al., 2011; Talasila et al., 2013).

Athymic nude mice (Hsd/Athymic Fox1 nu Harlan) were purchased from Envigo (Netherlands) and maintained under standard housing conditions of the Animal Facility of the Institute of Biomedicine and Translational Medicine, University of Tartu (Tartu, Estonia). For orthotropic GBM tumor models, NCH421K, P13, and P3 stem cell-like, WT-GBM cells were used. The respective GBM cells around $2-3 \times 10^5$ in 3 µL PBS were intracranially implanted into mice brain 2 mm right and 1 mm anterior to the bregma suture. U87-MG and Prostate carcinoma (PC3) cells were used as subcutaneous models. $2-9 \times 10^6$ cells in 100 µl PBS were injected subcutaneously into the right flank of 11-15 week old male and female nude mice. Animal experimentation procedures were approved by the Estonian Ministry of Agriculture, Committee of Animal Experimentation, project #42 and #48.

3. Clinical Samples

Fresh surgical samples of glioma and ovarian carcinoma were obtained from Tartu University Clinics, Tartu, Estonia under protocols approved by the Ethics Committee of the University of Tartu, Estonia (permit #243/T27).

4. Peptide Phage Biopanning

For biopanning on recombinant TNC-C, NNK-encoded CX7C and $X_7$ peptide phage libraries with diversity $\sim 5 \times 10^8$ displayed on T7 415-1b phage (Novagen, EMD Biosciences, MA, USA) were used. Throughout our screens, the phage recovered during a round of selection was amplified using plate amplification protocol (Teesalu et al., 2012). The 1st and 4th round of biopanning were performed on TNC-C immobilized on Costar 96-Well ELISA plate (#3590, Corning Life Sciences, Tewksbury, MA, USA). Briefly, the multiwell plate was coated with 20 µg/ml recombinant TNC-C in 100 µl of PBS overnight at 4° C., followed by blocking with 1% bovine serum albumin (BSA) in PBS overnight at 4° C. The phage library solution ($5 \times 10^8$ pfu in 100 µl of PBS-BSA) were incubated overnight at 4° C., followed by 6 washes with PBS+1% BSA+0.1% Tween 20 to remove non-specifically bound background phages, and by phage rescue and amplification in *E. coli* strain BLT5403 (Novagen, EMD Biosciences, MA, USA) (Lingasamy, P. et al., Biomaterials 119373. 2019). The subsequent rounds of selection were performed on Ni-NTA Magnetic Agarose Beads (QIAGEN, Hilden, Germany) coated with His-6X tagged TNC-C (30 µg/10 µl beads) at room temperature for 1 hour in 400 µl of PBS. The TNC-C immobilized beads were washed three times with PBS+1% BSA+0.1% NP40, followed by incubation of previous round phage ($5 \times 10^8$ pfu in 100 µl of PBS+1% BSA+0.1% NP40) to TNC-C coated beads for 1 hour at room temperature. The unbound/weakly bound (background) phages were removed by rinsing six times with PBS+1% BSA+0.1% NP40, and the bound phages were eluted with 1 ml of PBS+500 mM Imidazole+0.1% NP40.

The recovered phage was tittered and amplified for a subsequent round of selection. After 5 rounds of selection, a peptide-encoding phage DNA from a randomly picked set of 48 clones were subjected to Sanger sequencing to obtain information on the displayed peptides (Ikemoto et al., 2017; Teesalu et al., 2012) For cell-free binding studies using individually amplified phage clones; phage was incubated with TNC-C coated magnetic beads as described above. RPARPAR phage on NRP-1-coated beads was used as a positive control (Teesalu et al., 2009). Phage clones displaying heptaglycine peptide (GGGGGGG, G7 (SEQ ID NO:20)) or insert less phage clones were used as negative controls.

5. Nanoparticle Synthesis and Functionalization

The iron oxide nanoworms (NWs) were prepared according to a published protocol by (Park et al., 2008) with minor modifications. The aminated NWs were PEGylated using maleimide-5K-PEG-NH. Peptides were coupled to NWs through a thioether bond between the thiol group of a cysteine residue added to the N-terminus of the peptide. The concentration of the NWs was determined by constructing a calibration curve with iron oxide and measuring the absorbance of NWs at 400 nm with a NanoDrop 2000c spectrophotometer (Thermo Scientific). Isotopically pure silver nanoparticles (AgNPs) were synthesized and functionalized as described (Willmore et al., 2016), CF647-N-hydroxysuccinimide-dye (NHS-dye) was conjugated to terminal amine group of PEG, and biotinylated peptides were coated on the NeutrAvidin (NA) on the surface of the AgNPs. Transmission electron microscopy (TEM, Tecnai 10, Philips, Netherlands) was used to image the NPs and DLS (Zetasizer Nano ZS, Malvern Instruments, UK) was used to assess the zeta potential, polydispersity and size of nanopartiles.

6. In Vivo Play-Off Phage Auditioning

In vivo play-off was used to evaluate systemic homing of peptide phage to xenograft tumor models. The in vitro selected candidate TNC-C binding peptides, phages displaying published tumor homing peptides, and control peptides were amplified and purified by precipitation with PEG-8000 (Sigma-Aldrich, St. Louis, MO, USA), followed by CsCl2 gradient ultracentrifugation and dialysis. The amplified phage peptides were pooled in equimolar quantities, and injected intravenously (final $1 \times 10^{10}$ pfu in 200 µl PBS) in tumor-bearing mice for two hour circulation, after which mice were anesthetized with 2.5% avertin and intracardially perfused with DMEM intracardially. The tumors and organs were collected in lysogeny broth (LB)+1% NP40, and the tissues were homogenized using a hand-held homogenizer for phage peptide rescue. Phages in the tissue lysates were amplified in *E. coli*, purified by precipitation with PEG-8000 and DNA was extracted using a DNA extraction kit (High Pure PCR Template Preparation Kit; Roche, Basel, Switzerland). Next-generation sequencing of phage genomic DNA evaluated the representation of each phage in input mixture, in tumor and control organs with Ion Torrent system (Thermo Fisher Scientific, Waltham, MA, USA). The next generation deep sequencing of phage library was done using Ion Torrent according to the manufacturer's protocol with slight modification. The FASTQ data from Ion Torrent was processed by a custom python script that identified the barcodes, constant flanking residues, and extracted the reads of the correct length.

7. In Vivo Fluorescence Imaging with the IVIS Spectrum System

Live imaging of PL3 peptide tumor homing was assessed by in vivo fluorescence imaging with the IVIS Spectrum imaging system (PerkinElmer, Waltham, MA) in U87-MG xenograft mice model (Male, 18-20 weeks of age). AgNPs with CF647 dye-labeled neutravidin coating was functionalized with biotinylated PL3 peptide (AgNP-PL3) or control biotin (AgNP). AgNP PL3 and AgNP particles were injected intravenously into the mice. For assessment of tumor PL3 targeted delivery and homing by IVIS, mice were placed in a dark imaging chamber under isoflurane anesthesia, and imaged with the following parameters. Specific excitation filter, 650 nm; emission filter, 665 nm; auto exposure time; binning, medium; field of view, 12; f/stop, 2; open filter. The images were captured at pre-injection (0 hours) and five-hour post-injection. The signal was expressed in total Radiant Efficiency $[\text{p/s}]/[\mu\text{W/cm}^2]$. The regions of interest (ROIs) were drawn covering the whole tumor in each mouse after tissue background correction, and radiant efficiency signal was quantitated. An automated spectral unmixing algorithm was used, images were analyzed by using Living Image 4.4 software (Caliper Life Sciences, Hopkinton, MA). Three animals per experimental group were analyzed. For the receptor blocking studies, PL3-AgNP injection was preceded by systemic pre-injection of blocking TNC-C and/or NRP1 antibodies (30 µg/mouse) 15 minutes prior to injection of the AgNPs.

8. Tumor-Targeted Delivery and Biodistribution Studies

FAM-labeled PL3 peptide coupled NWs or control FAM-NWs (7.5 mg/kg) in PBS were injected into the tail vein of the mice bearing subcutaneous U87-MG, PC3, and orthotropic WT-GBM tumors. Five hours after circulation, the tumor and organs were collected by cardiac perfusion of mice with 20 ml PBS/DMEM under deep anesthesia. Tissues were ex vivo imaged using an Illuminatool Bright Light System LT-9900 (Lightools Research, Encinitas, CA, USA) and snap-frozen. The frozen tissues were cryosectioned at 8-10 µm and mounted on a superfrost+ slides. The sections were equilibrated at RT and fixed with 4% paraformaldehyde at RT for 20 minutes, or with methanol at −20C for 1 minute. The immunostaining was performed with following primary antibodies; rabbit anti-fluorescein IgG fragment (cat. no. A889, Thermo Fisher Scientific, MA, USA), rat anti-mouse CD31 (BD Biosciences, CA, USA), and in-house prepared CF647 or CF546-labeled single chain antibodies ScFV G11. Secondary antibodies were Alexa 488 goat anti-rabbit IgG, Alexa 647 goat anti-rat IgG, and Alexa 546 goat anti-mouse IgG (all Invitrogen, CA, USA). Nuclei were counterstained with 4',6-diamidino-2-phenylindole (DAPI, Molecular Probes) at one 1 µg/ml. The coverslips were mounted onto glass slides with Fluoromount-G (Electron Microscopy Sciences, PA, USA), imaged using confocal microscopy (Olympus FV1200MPE, Hamburg, Germany), and analyzed using the FV10-ASW4.2 viewer/Imaris software/Fiji ImageJ.

9. Experimental Therapy

U87 xenograft GBM model was established by subcutaneously injecting U87-MG cells ($8 \times 10^6$) into the right dorsal flank of 18-20 week male nude mice with 38±5 g. The mice were randomly assigned into four groups (N=6/group) when the initial tumor volume reached 100±20 mm$^3$. The respective groups were treated with 100 µl of PBS, FAM-D [KLAKLAK]$_2$-NWs, FAM-PL3-NWs and FAM-PL3- $_D$[KLAKLAK]$_2$-NWs intravenously (IV) injected via tail vein every other day for ten injections. The body weight, survival, animal well-being (behavior, appearance, grooming), and tumor volume was monitored once in two days with a vernier digital caliper until the end of the treatment. The tumor volume was calculated with this formula: Volume (V) (mm$^3$)=[length×(width)$^2$]/2. The endpoint of the study was fixed, when tumor volume reached 2000 mm$^3$ (or >20% body weight), the mice were sacrificed by perfusion, and organs and tumors were excised and snap frozen for histological studies. Tumor volume, Kaplan-Meier survival and body weight curves were calculated for each group using the GraphPad Prism 6 software with p values <0.05 being considered significant.

10. Overlay and Ex Vivo Dipping Assay on Clinical Tumor Samples

Human samples including fresh surgical glioblastoma brain and ovarian carcinoma samples were obtained during autopsy under protocols approved by the Ethics Committee of the University of Tartu, Estonia (permit #243/T27). Freshly excised human samples were obtained during surgeries from Department of Neurosurgery, Tartu University Hospital, Estonia. The informed consent was obtained from all patients. The glioma tissues were snap-frozen in liquid nitrogen, cryosectioned at 10 µm, fixed with methanol, and permeabilized with PBST buffer (1× Phosphate-Buffered Saline, 0.1% Tween 20) followed by incubation with blocking buffer containing 5% BSA, 5% goat serum, 5% FBS in PBST. For overlay, the sections were incubated with 20% g/slide PL3-NW and NW overnight at 4° C. The sections were washed and blocked with blocking buffer, followed by immunostaining using rabbit anti-fluorescein primary antibodies and detection with the Alexa-488 anti-rabbit and mouse anti-TNC-C antibody and detection with the 647 goat anti-mouse IgG. For the dipping assay, fresh ovarian carcinoma tissues were immediately washed with DMEM and explants about 1 cm$^3$ were incubated at 37° C. with PL3-NW/NWs (40 g/mL Fe diluted in DMEM supplemented with 1% of BSA) for four hours. Next, the explants were washed with PBS, snap-frozen, cryosectioned at 10 µm, and immunostained using rabbit anti-fluorescein primary antibodies, followed by detection with the Alexa-488 anti-rabbit secondary antibody (Invitrogen, Thermo Fisher Scientific, MA, USA).

11. Statistical Analysis

Prism 6 software was used to perform statistical analysis. The results are presented as mean with error bars indicating ±SEM. For comparison of two groups, a comparison using an unpaired t-test and multiple groups ANOVA test was used. P<0.05 was considered significant. P-values are depicted as follows: *P less than or equal to 0.05, P less than or equal to 0.01, *P less than or equal to 0.001 and ****P less than or equal to 0.0001.

12. Cell Binding and Internalization Experiments

U87-MG, PPC1, and M21 cells cultured on glass coverslips were incubated with CF555-labeled AgNPs at 37° C. for 1 hour, followed by washing with medium to remove background AgNPs. Etching solution freshly diluted from 0.2 M stock solutions of $Na_2S_2O_3$ and $K_3Fe(CN)_6$ to 10 mM working concentration in PBS was applied to cells for 3 minutes, followed by PBS washes. The cells on coverslips were fixed with −20° C. methanol for 1 minute. The cell membrane was visualized by staining with Alexa Fluor 488-labeled wheat germ agglutinin (WGA) at 1:1000 at RT for 1 h. Nuclei were stained with 4',6-diamidino-2-phenylindole (DAPI, Molecular Probes) at 11 µg/mL. Fluoromount-G (Electron Microscopy Sciences) medium was used to mount the coverslips on microscope slides for confocal imaging.

B. Results

1. Identification of a TNC-C Binding Peptide

To identify the peptides that target specifically to TNC-C domain, the first 91 amino acid TNC-C domain was expressed in *E. coli* and purified using affinity chromatography on Ni-NTA matrix. Five rounds of CX7C T7 phage peptide biopanning was performed, the first and fourth-round selection carried on his-tagged TNC-C immobilized polystyrene 96 well plates to avoid selection of histidine-containing peptides on the Ni-NTA matrix. Subsequent rounds were performed on TNC-C immobilized on magnetic Ni-NTA beads. In round five, >1000-fold enrichment in the binding of the selected phage pool to TNC-C was seen. Sanger sequencing of a peptide-encoding portion of the phage genome of 38 randomly selected phage clones from round 4 library demonstrated a dramatic shift away from original CX7C library configuration due to frameshifts in the peptide-encoding region and overrepresentation of the peptides containing the following motifs: RGRLXR (SEQ ID NO:28; 7 repeats), RGRLR (SEQ ID NO:86; 18 repeats), and RLXR (SEQ ID NO:45; 12 repeats). See Table 8. A panel of T7 phage clones displaying peptides derived from the phage clone 5 that contains the longest enriched motif, RGRLXR, was created and their binding to TNC-C was characterized (FIG. 8). 15 peptide sequences identified with TNC-C binding ability were selected as a lead candidate for further evaluation. Among them, AGRGRLVRAKLAAALE peptide (SEQ ID NO:14) showed the highest binding ability and several shorter permutations of this TNC-C binding peptides were created and validated with TNC-C. Binding of various TNC-C binding peptides are shown in Table 8.

TABLE 8

Properties of TNC-C binding peptides. The table shows peptide sequences of the 38 sequenced clones, and quantitation of binding of individual peptide phages to TNC-C (fold binding over control heptaglycine phage). RGRLXR motif is shown in italic, RGRLR motif is underlined, and RLXR motif is indicated in bold.

| Clone No. | Peptide sequence | Seq ID No. | Repeats | TNC-C binding (fold G7 control phage) |
|---|---|---|---|---|
| 1 | AGVGRLRRAKLAAALE | 29 | 1 | 3259 |
| 2 | CRGVLRRAKLAAALE | 30 | 4 | 5955 |
| 3 | AV*RGRLR*VAKLAAALE | 31 | 7 | 5333 |
| 4 | CSRRGILRAKPAAALE | 33 | 5 | 4889 |
| 5 | AGRG*RLVR*AKLAAALE | 14 | 1 | 5785 |
| 7 | AV*RGRLR*VAKLAAALE | 31 | 7 | 7111 |
| 35 | RRLVRVA | 34 | 2 | 1223 |
| 30 | VGRVRFSRKLAAALE | 35 | 1 | 3702 |
| 36 | CQRMGVVGAKLAAALE | 36 | 2 | 3928 |
| 44 | *RGRLRR*VE | 37 | 4 | 886 |
| 45 | RG*RLVR*A | 38 | 2 | 737 |
| 46 | GRLTRVR | 39 | 2 | 115 |

To identify the best tumor-targeting and efficiency among the candidate TNC-C-targeting peptides, in vivo phage play-off auditioning was carried out with different xenografts tumor models in mice. Homing was audited upon systemic administration in mice bearing orthotopic glioblastoma xenografts tumor models WT-GBM, P3 stem cell-like, P1, NCH421K and subcutaneous glioma (U87MG) and prostate carcinoma (PC3) xenografts tumor models (Table 9). The tumor and control organs peptide-encoding portion of the phage genome was subjected to High throughput sequencing (HTS), and sequencing data were analyzed using custom bioinformatics tools (Phage Display Parser internet site canbio.ut.ee). It was observed that a T7 clone displaying an AGRGRLVR (SEQ ID NO:4) octapeptide was overrepresented in tumor tissue across models tested. Next generation sequencing (NGS) results showed TNC-C peptide designated PL3 (AGRGRLVR; SEQ ID NO:4) had better targeting, and homing effect in different tumor models compared to other peptides.

2. PL3 Peptide Interacts with Recombinant TNC-C and NRP-1 and is Taken Up by Cultured Tumor Cells Next, the binding of alanine-substituted PL3-derivative peptide-phages was studied to determine the amino acids important for peptide binding. The substitution of arginine or leucine residues in PL3 peptide resulted in decreased binding to recombinant TNC-C (FIG. 6). In contrast, alanine substitutions of glycine and valine had a minimal effect. In contrast to robust interaction with TNC-C, the PL3 phage did not bind to fibronectin EDB-domain, a protein with similar size and negative surface charge as TNC-C. These results showed that key amino acids residues arginine (R) and leucine (L) are important for TNC-C binding. Alanine substitutions of amino acids at other positions of the PL3 peptide did not alter its binding.

The PL3 peptide includes a C-terminal RXXR motif which fulfills CendR rule and has been previously shown to bind to Neuropilin 1 b1b2 domain (NRP1) (Teesalu et al., 2009). Testing was done to confirm this binding ability with purified NRP1 protein together with TNC. PL-3 phage bound to recombinant b1b2 domain of NRP-1-200 fold more than heptaglycine control phage. Interaction with NRP-1 was dependent on the presence of C-terminal arginine, as the phage with a PL3-derivative peptide having terminal R to A substitution showed dramatically reduced binding (FIG. 6). The results confirmed that PL3 retained the ability to bind specifically to both TNC-C and NRP1 when displayed on phage particles.

Many cultured tumor cell lines overexpress NRP-1 and internalize peptides with active CendR motif. The uptake of CF555-labeled PL3-AgNPs in NRP-1-positive U87-MG glioma and PPC1 prostate carcinoma cells, and in NRP-1-negative M21 melanoma cells was investigated. The dye-labeled AgNP cores are well suited for fluorescence imaging as the AgNP increases the brightness of the surface-bound dye by about an order of magnitude by plasmonic enhance-ment. The AgNPs labeled with CF647 dye were coated with neutravidin (NA) and PEGylated, creating a stable colloid ready for coating with biotinylated peptides. The transmission electron microscopy (TEM) and dynamic light scattering (DLS) showed that particles had an average size of 66.9±27.6 nm, and zeta potential of −5.09±0.19 mV in PBS. After 1 h incubation with U87-MG and PPC1 cells, PL3-AgNPs were robustly endocytosed with perinuclear accumulation, whereas control nanoparticles showed only a background binding. In contrast, NRP-1-negative M21 cells showed a low background-like uptake with both PL3 and control AgNPs. Extracellular AgNPs can be removed by treatment with a mild biocompatible hexacyanoferrate/thiosulfate redox-based destain solution so that only internalized AgNP signal remains (Braun et al., 2014). In U87-MG and PPC1 cells, etching resulted in a modest decrease of the cellular PL3-AgNP signal, suggesting that most of the cell-associated particles were internalized and protected from etching by the cellular membrane. These experiments showed that PL3 peptide interacts with TNC-C and NRP-1 and that PL3-functionalized nanoparticles are taken up by NRP-1-positive cultured cells.

TABLE 9

Representation of phage clones after in vivo play off homing experiments. An equimolar mix of TNC-C-selected phages was i.v. injected in mice bearing WT-GBM, P3 stem cell-like, P13, U87-MG glioblastoma, or PC3 prostate carcinoma xenografts at 1 × 1010 pfu/mouse. After 2 h circulation, background phages were removed by perfusion. Representation of each phage in tumor tissue or in normal brain was assessed by Ion-Torrent high-throughput sequencing. The peptides are, from top to bottom, SEQ ID NOs: 20, 29-31, 33, 14, 35, 34, 38-39, 4, and 46-47.

| | Phage-displayed peptides in the "play-off" cocktail | | Representation of phage in tumors or in control brain tissue (fold G7 control phage) | | | | | |
| --- | --- | --- | --- | --- | --- | --- | --- | --- |
| | | | WT-GBM | P3 SCL | P13 | U87-MG | PC3 | Norm. brain |
| Control | GGGGGGG | Control | 1.0 | 1.0 | 1.0 | 1.0 | 1.0 | 1 |
| TNC-C-selected (round 5) | AGVGRLRRAKLAAALE | Clone-1 | 2.3 | 0.9 | 0.9 | 1.0 | 1.4 | 0.2 |
| | CRGVLRRAKLAAALE | Clone-2 | 1.6 | 0.4 | 0.4 | 0.7 | 0.9 | 0.1 |
| | AVRGRLRVAKLAAALE | Clone-3 | 1.3 | 0.6 | 0.6 | 0.8 | 1.0 | 0.1 |
| | CSRRGILRAKPAAALE | Clone-4 | 1.5 | 0.9 | 0.8 | 1.1 | 1.2 | 0.1 |
| | AGRGRLVRAKLAAALE | Clone-5 | 23.9 | 0.4 | 0.1 | 0.2 | 0.3 | 0.0 |
| | VGRVRFSRKLAAALE | Clone-30 | 2.5 | 0.4 | 0.5 | 0.7 | 1.2 | 0.1 |
| | RRLVRVA | Clone-35 | 1.4 | 0.3 | 0.4 | 0.6 | 0.9 | 0.1 |
| | RGRLVRA | Clone-45 | 3 | 0.3 | 0.4 | 0.8 | 1.8 | 0.1 |
| | GRLTRVR | Clone-46 | 1.9 | 0.5 | 0.5 | 0.9 | 0.9 | 0.1 |

TABLE 9-continued

Representation of phage clones after in vivo play off homing experiments.
An equimolar mix of TNC-C-selected phages was i.v. injected in mice
bearing WT-GBM, P3 stem cell-like, P13, U87-MG glioblastoma, or PC3
prostate carcinoma xenografts at 1 x 1010 pfu/mouse. After 2 h circulation,
background phages were removed by perfusion. Representation of each phage
in tumor tissue or in normal brain was assessed by Ion-Torrent high-
throughput sequencing. The peptides are, from top to bottom, SEQ ID NOs:
20, 29-31, 33, 14, 35, 34, 38-39, 4, and 46-47.

| | Phage-displayed peptides in the "play-off" cocktail | | Representation of phage in tumors or in control brain tissue (fold G7 control phage) | | | | | |
|---|---|---|---|---|---|---|---|---|
| | | | WT-GBM | P3 SCL | P13 | U87-MG | PC3 | Norm. brain |
| Clone 5-derivative peptides | AGRGRLVR | Modified clone-5 (PL3) | 24.1 | 2.1 | 4.7 | 2.1 | 3.9 | 0.4 |
| | CAGRGRLVRC | Modified clone-5 | 0.9 | 0.2 | 0.4 | 0.1 | 0.4 | 0.0 |
| | RGRLVRAK | Modified clone-5 | 23.8 | 0.3 | 0.1 | 0.5 | 3.0 | 0.2 |

3. Systemic PL3-Functionalized Nanoparticles Accumulate in Tumor Lesions

Next, the effect of functionalization with synthetic PL3 peptide on in vivo tumor tropism of two classes of synthetic nanoparticles, iron oxide NWs and AgNPs was evaluated.

The effect of PL3 functionalization on tumor homing of dextran-coated PEGylated paramagnetic NWs—a dual-use model nanoplatform that can be used as a carrier for drugs and for MR imaging due to intrinsic T2 contrast properties (Lingasamy, et al., 2019; Park et al., 2008) was evaluated. To evaluate the efficiency of PL3 specific targeting, delivery of nanoparticles into tumors, and penetration into tumor tissue, FAM PL3 peptide was conjugated to dextran-coated PEGylated paramagnetic iron oxide nanoworms (NW). NWs conjugated to FAM dye-labeled PL3 peptide and FAM-Cys control did not affect their structure, size and surface charge. The transmission electron microscopy (TEM) and dynamic light scattering (DLS) of NW showed that particles had an average size of 88.8±5 nm, and zeta potential of −7.8±2 mV in PBS.

Initially, systemic IV administration of PL3-NW specific homing pattern was studied in U87 and PC3 subcutaneous and orthotropic WT GBM tumor xenograft models. NWs were i.v. administered at 7.5 mg/kg NWs in mice bearing prostate cancer xenografts (PC3 s.c. tumors), or gliomas (s.c. U87-MG and orthotopic WT-GBM), both known to overexpress TNC-C and NRP-1. Five h after IV injection of PL3-NW, examination of tumor tissue showed significantly higher accumulation and very specific homing of PL3-NWs, but not control NWs, to all the tumor models tested. The PL3 homing pattern mainly observed localized to tumor blood vessels all over the tissues including stromal regions, as seen by localized to CD31 marker. Confocal analysis demonstrated that whereas the PL3-NW homing was mainly overlapping or associated with CD31-positive vascular structures, in some regions, the PL3-NWs extravasated and accumulated in the tumor parenchyma. In control organs, PL3-NWs and control NWs showed similar background. There are some regions where signal was detected away from the blood vessels. In contrast, control NW showed only background signals in tumor tissue. The quantitative biodistribution analysis of PL3-NW and NW showed nonspecific accumulation in liver, lung and some extension to the kidney in all the three different models tested. Results were comparable to previous reports on NW.

The immunostaining analysis was reconfirmed by ex-vivo Illumatool imaging of organs from PL3-NW/NW injected U87 mice. The macroscopic images of tumor organs again illustrate the specific targeting of the efficiency of the PL3 peptide. PL3 colocalization to TNC-C and NRP1 in U87 subcutaneous tumor models was further examined by immunostaining with the clinical stage single chain antibody (scFV) G11 and rabbit NRP1 antibody. Macroscopic imaging confirmed preferential tumor accumulation of the PL3-NWs in U87-MG tumor mice. The TNC-C expression in U87 tumor model is diffused and more prominent in tumor blood vessels. In tumor tissue, PL3-NWs showed colocalization with areas positive for TNC-C and NRP1 immunoreactivities, whereas control NW showed no signal.

The binding of PL3 and control NWs to the clinical glioma was also examined. The NWs were overlaid on cryosections of GBM, washed, and subjected to confocal imaging. PL3-NWs showed co-localization with TNC-C-positive structures in tumor perivascular space and parenchyma. For TNC-C detection, an in-house monoclonal antibody was used, and as a specificity control, it was confirmed that preincubation of the antibody with recombinant TNC-C resulted in reduced staining.

4. In Vivo Imaging of Glioma-Bearing Nude Mice Using PL3-Functionalized Nanoparticles The effect on tumor homing of PL3 coating of near-infrared dye-labeled AgNPs was also examined. AgNP with CF647 dye-labeled with neutravidin coated particle were conjugated biotin PL3 and biotin, did not alter particle size or surface charge. The transmission electron microscopy (TEM) and dynamic light scattering (DLS) of AgNP showed that particles had an average size of 66.9±27.6 nm, and zeta potential of −5.09±0.19 mV in PBS. To determine in vivo targeting specificity and nanoparticle accumulation, AgNP PL3, and AgNP control particles were administered intravenously in nude mice bearing U87 subcutaneous GBM tumor. As judged by intravital fluorescence imaging with IVIS Spectrum system, the PL3-CF647-AgNPs accumulated in glioma lesions ~10 fold (5 hours) more than control non-peptide CF647-AgNP (5 hours). Tumor homing of PL3-AgNPs was confirmed by confocal imaging. Coadministration of PL3-AgNPs with blocking rabbit polyclonal antibodies against either TNC-C or NRP-1 resulted in a decrease in tumor homing, and a cocktail of both antibodies almost completely inhibited the tumor accumulation (FIG. 7). The targeting efficiency of NWs in U87 glioma mice was also investigated and in vivo optical signals showed similar results. Some tumor-bearing mice showed background signal from GI tract at the pre-injection time point. Noninvasive intravital imaging results were corroborated using terminal the ex-vivo Illumatool imaging of excised organs from perfused mice at 5 h time point. These data show that PL3 functionalization results in specific tumor homing of different classes of nanoparticles.

5. PL3 Targeted Proapoptotic NWs Show Anti-Glioma Activity

The effect of PL3-functionalization on anticancer efficacy was examined. To confirm the targeted therapeutic effect and delivery of PL3-NWs, proapoptotic $_D$(KLAKLAK)$_2$ peptide was used as a model drug for U87-MG subcutaneous xenograft GBM model. The U87-MG tumor model was used in order to monitor tumor size, rather than survival, as the endpoint.

Starting on day 36 after tumor induction (when the tumors had reached 100 mm$^3$), the tumor mice were treated with i.v. PL3- $_D$(KLAKLAK)$_2$-NWs, $_D$(KLAKLAK)$_2$-NWs, PL3-NWs, or PBS for 10 injections every other day, and tumor volume and survival of the mice were recorded. The tumor volume of PBS, PL3-NW, and $_D$(KLAKLAK)2-NW-treated mice rapidly increased during the treatment compared to $_D$(KLAKLAK)2-PL3 group. The tumor growth of mice treated with $_D$(KLAKLAK)$_2$-PL3 NW was significantly suppressed. The median survival of PBS, $_D$(KLAKLAK)$_2$-NW, PL3-NW, and PL3- $_D$(KLAKLAK)$_2$-NW groups was 55, 58, 54 and 70 days, respectively. 50% of mice in the $_D$(KLAKLAK)$_2$-PL3 group showed prolonged survival compared to mice in the other groups. The anti-tumor effect was due to specific targeting and delivery effect of PL3. Immunostaining of post-treatment tumor tissue with anti-CD31 antibody to visualize tumor vasculature showed that compared to controls, PL3- $_D$(KLAKLAK)$_2$-NW-treated tumors had a significant reduction in CD31-positive area. The body weight was measured during the treatment to evaluate the systemic toxicity of the PL3-NW formulations. There was no loss of body weight observed during the treatment in the entire group, suggesting that no significant systemic toxicity was induced by PL3-NW derivatives. Further immunofluorescence studies indicated no significant changes in tissue-macrophage CD68 staining, cellular proliferation Ki67 staining, and apoptotic cells as assayed by cleaved Caspase-3 staining.

To explore the translational relevance and tissue penetration effect of PL3 based targeting system, overlay assay and tumor dipping assay were performed on the clinical glioma brain samples and freshly extracted human ovarian carcinoma cancer tissue. The binding of PL3 and control NWs to the clinical glioma was examined. The PL3 NW and control NW particles were overlaid with GBM cryosections, washed and subjected to confocal imaging. PL3 NWs showed binding extensively to human GBM samples at TNC-C-positive structures in perivascular space and in tumor parenchyma. For TNC-C detection, an in-house monoclonal antibody was used, and as a specificity control, it was confirmed that preincubation of the antibody with recombinant TNC-C resulted in reduced staining. PL3-NWs colocalized with tumor TNC-C that is highly overexpressed in the clinical glioma samples (Giblin and Midwood, 2015). In different types of GBM tissues, TNC-C showed heterogeneous expression pattern with very high abundance in gliosarcoma, glioblastoma, Anaplastic oligodendroglioma, Oligodendroglioma, and diffuse astrocytoma. In contrast, control NW showed only a background fluorescence signal. In the tumor dipping assay, PL3 NWs showed binding, and penetration to the tumor tissue two-fold higher compared to control NWs or PBS. The penetration effect was observed to few micrometers inside explants in some areas, whereas binding associated mainly with tumor tissue surface. These data show that PL3 guided probes are translationally relevant for solid tumor targeting.

C. Discussion

Most affinity-based precision delivery strategies target receptors on the surface of tumor cells. This approach, while useful, has limitations, as it relies on targeting a limiting number of systemically accessible receptors on genetically unstable malignant cells. Compared to surface antigens on tumor cells, tumor-associated ECM represents an abundant and stable target with low shedding (Raavé, R., et al., J. Control. Release 274:1-8. (2018)). ECM directed affinity targeting strategies may allow simultaneous targeting of both malignant tumor cells and tumor support cells (e.g., fibroblasts, immune and vascular cells) and can be beneficial for improving treatment efficacies.

TNC, an ECM component expressed at the invasive tumor front and in the angiomatrix provides specific targeting opportunities due to precisely controlled expression of its multiple structurally and functionally different isoforms (Spenlé et al., 2015). TNC-C is expressed abundantly in most solid tumors and shows very high expression especially in GBMs. Further, TNC expression is highly associated with angiogenesis in a wide range of disease states, including cancer (Orend et al., 2012; Rupp et al., 2016).

The data disclosed herein shows development of a novel PL3 peptide that is capable of targeting solid tumor ECM component tenascin C FnIII C domain. The affinity ligand, octameric PL3 peptide that targets C-domain of TNC also interacts with NRP-1, a pleiotropic hub receptor upregulated in angiogenic sites and in malignant tissues involved in regulation of vascular permeability. Its ability to target both in vitro and in vivo in various preclinical tumor models has been demonstrated. The nanoparticle conjugated PL3 peptide have shown targeted delivery and homing in various tumor models and real-time in vivo intravital imaging. Systemic PL3 phage nanoparticles and two types of synthetic PL3-guided nanocarriers home to solid tumors implanted in mice and bind to receptor-positive regions in clinical tumor samples. For therapeutic nanoparticles, PL3 functionalization improves their anticancer activity. The PL3 targeted delivery of proapoptotic NW showed tumor suppression and increased survival in the mice. This data indicates that the PL3 peptide offers a powerful tool for TNC-C specific targeting for imaging and further therapeutic applications in various solid tumors.

Various promising approach have been developed to target tenascin C, legends coupling to cytotoxicity agents including bispecific CD95/anti-tenascin-C antibody (Herrmann et al., 2008), anti-tenascin-C antibody (G11) with IL2 (Marlind et al., 2008), B8C6 anti-tenascin-C antibody coupling cytotoxic radioactivity (Reardon et al., 2008), DNA based aptamers (Hicke et al., 2006), FHK peptide (Kim et al., 2012), a bispecific PL1 peptide that in addition to TNC-C also targets fibronectin extra domain B (Lingasamy, et al., 2019), TNC-C/D targeting monoclonal antibody 81C6 (Lee, et al., Cancer Res. 48:584-588 (1988)) and F3 peptide conjugated to tLyp-1 (Hu et al., 2013). These and other ECM-reactive affinity ligands have proven useful for tumor delivery of extracellularly-acting anticancer payloads such as cytokines/growth factors, or payloads with intrinsic internalizing ability, such as proapoptotic $_D$(KLKLAK)$_2$ peptide nanoparticles, or cell-permeable cytotoxic compounds. However, a challenge for these and other ECM-directed systemic compounds is that they can only reach extravascular tumor tissue passively, through the increased leakiness of aberrant tumor microvasculature, a phenomenon known as enhanced permeability and retention (EPR) effect. However, considering its restricted expression, accessibility, and its therapeutic potential, TNC-C specific affinity peptide has not been found to date. The disclosed PL3 peptide is eight amino acids short and is highly specific to TNC-C domain, which has restricted expression pattern, and NRP1.

The vitro biopanning experiment yielded 15 fold high TNC-C binding peptides that could be used for drug delivery applications. It has been shown that in vivo phage display technology together with phage genome HTS sequencing allow for validation of TNC-C binding peptides and demonstration of their homing preference in vivo models. Interestingly, in vivo playoff experiments showed that among the tested peptide phages in different tumor models, PL3 revealed superior accumulation in tumors. However, in vitro PL3 showed moderate binding performance compare to other peptides. Hence, it has been shown that high affinity may impair efficient tumor penetration and diminish effective in vivo targeting (Adams et al., 2001). The C-terminal RLVR of PL3 corresponds to RXXR CendR consensus motif that, when exposed at the C-terminus, interacts with b1 domain of NRP-1 to trigger a trans-tissue pathway that mediates exit from the blood vessels and extravascular transport through tumor tissue (Ruoslahti, 2012; Teesalu et al., 2009; Teesalu et al., Front. Oncol. 3, 216 (2013)). It has been demonstrated that PL3 peptide also binds to NRP1 protein in vitro. Specific binding of PL3 nanoparticles to recombinant NRP-1 b1b2 domain and not to b1b2 with mutated CendR binding pocket, and binding and internalization of the PL3 nanoparticles in NRP-1-positive PPC1 cells and no interaction with NRP-1-negative M21 melanoma cells were observed. PL3 peptide binding to NRP1 facilitate the not only binding to tumor ECM but also penetration in tumor parenchyma and cells.

In the present study, PL3 NW data clearly demonstrate that the efficient targeting of GBMs and pancreatic cancer models. In the biodistribution analysis, PL3 NWs exhibited superior accumulation and tumor targeting performance 4-8 fold higher then control NWs in all the models tested. Keeping the physical and chemical parameters nanoparticles in mind, real-time imaging of PL3 AgNP accumulation in U87 tumor mice suggests similar targeting behavior among the nanoparticles. In both nanoparticle formulations, the strongest fluorescence was observed in the tumor of the mice treated with PL3 compared with control. In addition, PL3 co-localized with the tenascin C and abundantly penetrated in the neovascular and perivascular area. PL3's clinical potential was shown with human cancer GBMs and ovarian carcinoma tissues. In addition, the localized expression of TNC-C can be a highly valuable target for tumor specific delivery of therapeutics and digenesis as proved in clinical trials of TNC specific monoclonal antibodies (Spenlé et al., 2015).

In vivo, NPs, including biological bacteriophage nanoparticles, because of their size are particularly prone to be excluded from difficult-to-access parts of tumors, and PL3 functionalization may mitigate this problem. Studies document the ability of CendR peptides to specifically increase the accumulation of a variety of anticancer therapeutics, such as chemotherapeutic agents, antibodies and NPs, in tumors (Sugahara et al., 2009). For PL3 peptide, combination of CendR activity with the tumor ECM homing function may increase accessibility of TNC-C deeper in tumor parenchyma than would be possible under the conditions of physiological EPR with simple docking-based affinity targeting. A chimeric 19-mer chimeric peptide composed of TNC-A-D domain binding peptide and tLyP-1 tumor penetrating peptide that targets NRP-1 on tumor cells was reported to allow anti-glioma drug delivery via NRP-1- and TNC-mediated specific penetration of nanoparticles into glioma parenchyma (Roth, L. et al., Oncogene 31:3754-3763 (2012); Kang, T. et al., Biomaterials 101: 60-75 (2016)). Compared to that peptide, the 8-amino acid PL3 peptide we have identified has the advantage of being smaller, and hence is less likely to be immunogenic and simpler to produce and develop for clinical applications. In both these peptides, the CendR motif is C-terminally exposed and does not need on-site proteolytic activation, as seen for several other tumor penetrating peptides.

In summary, this study describes the identification of an 8-amino acid homing peptide, PL3, which interacts with TNC-C and with the cell- and tissue penetration receptor NRP-1. Systemic PL3-guided nanoparticles accumulated in tumor xenografts implanted in mice. The PL3-guided nanoparticles were useful for tumor detection, imaging and served as a tumor-seeking carrier for a proapoptotic peptide anticancer payload.

Throughout this application, various publications are referenced. The disclosures of these publications in their entireties are hereby incorporated by reference into this application in order to more fully describe the state of the art to which this invention pertains.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

---

The invention claimed is:

1. An isolated peptide comprising PPRRGLIKLKTS (SEQ ID NO:1) or PPRRGLIKLKTSSNTKENSVVASLRP (SEQ ID NO:2).

2. The isolated peptide of claim 1, wherein the isolated peptide is less than 20 amino acids in length, is less than 15 amino acids in length, or is 12 amino acids in length, optionally wherein the isolated peptide is linear or cyclic, and optionally wherein the isolated peptide is a modified peptide.

3. The isolated peptide of claim 1, wherein the isolated peptide is a methylated peptide.

4. An isolated peptide comprising an amino acid sequence, wherein the amino acid sequence consists of PPRRGLIKLKTS (SEQ ID NO:1) or of a variant of SEQ ID NO:1 with one, two, three, four, five, six, seven, or eight amino acid substitutions, wherein position 6 of SEQ ID NO:1 remains leucine and position 11 of SEQ ID NO:1 remains threonine, and wherein all of the amino acid substitutions are conservative amino acid substitutions.

5. An isolated peptide comprising any one of SEQ ID NOs:1, 2, 54, 56-59, or 61-65, wherein the isolated peptide selectively binds to fibronectin extra domain B (FN-EDB), tenascin-C C domain (TNC-C), or both FN-EDB and TNC-C.

6. A composition comprising the isolated peptide claim 1.

7. The composition of claim 6, wherein the composition further comprises a cargo molecule, and wherein the isolated peptide and the cargo molecule are covalently coupled or non-covalently associated with each other.

8. The composition of claim 7, wherein the cargo molecule is a therapeutic agent, a detectable agent, a carrier, a vehicle, a surface molecule, or combinations thereof.

9. The composition of claim 8, wherein the therapeutic agent is an anti-angiogenic agent, an anti-bacterial agent, an anti-cancer agent, an anti-inflammatory agent, a chemotherapeutic agent, a cytotoxic agent, an immunostimulating agent, an immunosuppressing agent, a nucleic acid molecule, a polypeptide, a pro-angiogenic agent, a pro-apoptotic agent, a pro-inflammatory agent, a small molecule, or a toxin.

10. The composition of claim 8, wherein the therapeutic agent is the peptide klaklakklaklak.

11. The composition of claim 8, wherein the carrier or vehicle is a bead, a liposome, a micelle, a microparticle, a nanoparticle, a nanoworm, a phospholipid, a polymer, a phage, a phage capsid, a phage particle, a viral capsid, a viral particle, a virus, a virus-like particle, or a microbubble.

12. The composition of claim 8, wherein the isolated peptide is conjugated to the carrier or vehicle.

13. The composition of claim 12, wherein the isolated peptide is indirectly conjugated to the carrier or vehicle via a linker.

14. The composition of claim 8, wherein the carrier or vehicle is a liposome.

15. The composition of claim 7, wherein the cargo molecule is a detectable agent.

16. The composition of claim 15, wherein the detectable agent is a labeling agent, a contrast agent, an imaging agent, a fluorophore, or a radionuclide.

17. The composition of claim 15, wherein the detectable agent is fluorescein amidite (FAM).

18. The composition of claim 7, wherein the composition further comprises a plurality of linkers that connect the isolated peptide and the cargo molecule.

19. The composition of claim 18, wherein at least one of the linkers comprises polyethylene glycol.

20. The composition of claim 6, wherein the composition selectively homes to tumors expressing FN-EDB, TNC-C, or both FN-EDB and TNC-C, selectively homes to extracellular matrix having FN-EDB, TNC-C, or both FN-EDB and TNC-C, selectively binds tumors expressing FN-EDB, TNC-C, or both FN-EDB and TNC-C, or selectively binds extracellular matrix having FN-EDB, TNC-C, or both FN-EDB and TNC-C.

21. The composition of claim 6, wherein the composition comprises more than one copy of the isolated peptide.

22. The composition of claim 21, wherein the composition comprises at least 100 or at least 1000 copies of the isolated peptide.

23. A method of targeting a tumor expressing FN-EDB, TNC-C, or both FN-EDB and TNC-C, wherein the method comprises administering the composition of claim 6 to a subject having the tumor expressing FN-EDB, TNC-C, or both FN-EDB and TNC-C, and wherein the composition selectively binds to the tumor expressing FN-EDB, TNC-C, or both FN-EDB and TNC-C.

24. A method of detecting extracellular matrix having FN-EDB, TNC-C, or both FN-EDB and TNC-C, the method comprising administering the composition of claim 10 to a subject having the extracellular matrix having FN-EDB, TNC-C, or both FN-EDB and TNC-C, and wherein the composition selectively binds to the extracellular matrix having FN-EDB, TNC-C, or both FN-EDB and TNC-C.

* * * * *

SEQUENCE LISTING

```
<160> NUMBER OF SEQ ID NOS: 86

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 1

Pro Pro Arg Arg Gly Leu Ile Lys Leu Lys Thr Ser
1               5                   10

<210> SEQ ID NO 2
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 2

Pro Pro Arg Arg Gly Leu Ile Lys Leu Lys Thr Ser Ser Asn Thr Lys
1               5                   10                  15

Glu Asn Ser Val Val Ala Ser Leu Arg Pro
            20                  25

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 3

Thr Ser Lys Gln Asn Ser Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Ala Gly Arg Gly Arg Leu Val Arg
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Arg Pro Ala Arg Pro Ala Arg
1               5

<210> SEQ ID NO 6
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 6

Lys Leu Ala Lys Leu Ala Lys Lys Leu Ala Lys Leu Ala Lys
1               5                   10

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
ctcctctcat atggaggccc tgcccttc                                        29

<210> SEQ ID NO 8
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 8
cagacactcg agttatcatg taacaatctc                                      30

<210> SEQ ID NO 9
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 9
ctcctctcat atggaggtgc cccaactca                                       29

<210> SEQ ID NO 10
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 10
cagacactcg agttatcacg tttgttgtgt                                      30

<210> SEQ ID NO 11
<211> LENGTH: 102
<212> TYPE: DNA
```

-continued

```
<213> ORGANISM: Artificial Sequence
<220> FEATURE:
<223> OTHER INFORMATION: Synthetic Oligonucleotide

<400> SEQUENCE: 11
atgctcgggg atccgaattc tccgccgaga cgtggtctaa ttaagcttaa aacctcgtcc      60
aatacaaaag agaattctgt tgtggcttcg ctgaggcctt aa                        102

<210> SEQ ID NO 12
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 12

Met Leu Gly Asp Pro Asn Ser Pro Pro Arg Arg Gly Leu Ile Lys Leu
1               5                   10                  15

Lys Thr Ser Ser Asn Thr Lys Glu Asn Ser Val Val Ala Ser Leu Arg
            20                  25                  30

Pro

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 13

Ile Lys Leu Lys Thr Ser
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 14

Ala Gly Arg Gly Arg Leu Val Arg Ala Lys Leu Ala Ala Ala Leu Glu
1               5                   10                  15

<210> SEQ ID NO 15
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 15

Met Gly Ser Ser His His His His His His Ser Ser Gly Leu Val Pro
1               5                   10                  15

Arg Gly Ser His Met Glu Ala Leu Pro Leu Leu Glu Asn Leu Thr Ile
            20                  25                  30

Ser Asp Ile Asn Pro Tyr Gly Phe Thr Val Ser Trp Met Ala Ser Glu
        35                  40                  45

Asn Ala Phe Asp Ser Phe Leu Val Thr Val Val Asp Ser Gly Lys Leu
    50                  55                  60

Leu Asp Pro Gln Glu Phe Thr Leu Ser Gly Thr Gln Arg Lys Leu Glu
65                  70                  75                  80
```

-continued

```
Leu Arg Gly Leu Ile Thr Gly Ile Gly Tyr Glu Val Met Val Ser Gly
                85                  90                  95

Phe Thr Gln Gly His Gln Thr Lys Pro Leu Arg Ala Glu Ile Val Thr
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 16

Met Gly Ser Ser His His His His His His Ser Ser Gly Leu Val Pro
1               5                   10                  15

Arg Gly Ser His Met Glu Val Pro Gln Leu Thr Asp Leu Ser Phe Val
            20                  25                  30

Asp Ile Thr Asp Ser Ser Ile Gly Leu Arg Trp Thr Pro Leu Asn Ser
        35                  40                  45

Ser Thr Ile Ile Gly Tyr Arg Ile Thr Val Val Ala Ala Gly Glu Gly
    50                  55                  60

Ile Pro Ile Phe Glu Asp Phe Val Asp Ser Ser Val Gly Tyr Tyr Thr
65                  70                  75                  80

Val Thr Gly Leu Glu Pro Gly Ile Asp Tyr Asp Ile Ser Val Ile Thr
                85                  90                  95

Leu Ile Asn Gly Gly Glu Ser Ala Pro Thr Thr Leu Thr Gln Gln Thr
            100                 105                 110

<210> SEQ ID NO 17
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 17

Lys Leu Ala Lys Lys Leu Ala Lys Leu Ala Lys Lys Leu Ala
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 18

Lys Ala Ala Lys Lys Ala Ala Lys Ala Ala Lys Lys Ala Ala
1               5                   10

<210> SEQ ID NO 19
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 19

Lys Leu Gly Lys Lys Leu Gly Lys Leu Gly Lys Lys Leu Gly Lys Leu
1               5                   10                  15

Gly Lys Lys Leu Gly
            20
```

-continued

```
<210> SEQ ID NO 20
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 20

Gly Gly Gly Gly Gly Gly Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 21

Thr Lys Arg Lys Gly Lys Gly
1               5

<210> SEQ ID NO 22
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 22

Gly Leu Gly Gly Arg Arg Ile Lys Leu Lys Thr Ser
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 23

Gly Arg Arg Gly Arg Val Ile Lys Leu Lys Thr Ser Glu Pro Pro Gln
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 24

Gly Thr Arg Arg Arg Ser Arg Ile Asn Leu Ala Ala Ala Leu Glu
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 25

Lys Val Lys Lys Arg Gly Ala
1               5
```

<210> SEQ ID NO 26
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 26

Val His Glu Arg Thr Arg Ile
1               5

<210> SEQ ID NO 27
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 27

Arg Glu Ser Arg Arg Gly Arg Val Lys Leu Ala Ala Ala Leu Glu
1               5                   10                  15

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 28

Arg Gly Arg Leu Xaa Arg
1               5

<210> SEQ ID NO 29
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 29

Ala Gly Val Gly Arg Leu Arg Arg Ala Lys Leu Ala Ala Ala Leu Glu
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 30

Cys Arg Gly Val Leu Arg Arg Ala Lys Leu Ala Ala Ala Leu Glu
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 31

Ala Val Arg Gly Arg Leu Arg Val Ala Lys Leu Ala Ala Ala Leu Glu

```
1               5                   10                  15
```

```
<210> SEQ ID NO 32
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 32

Cys Ser Arg Arg Gly Ile Leu Arg Ala Lys Leu Ala Ala Ala Leu Glu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 33

Cys Ser Arg Arg Gly Ile Leu Arg Ala Lys Pro Ala Ala Ala Leu Glu
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 34

Arg Arg Leu Val Arg Val Ala
1               5

<210> SEQ ID NO 35
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 35

Val Gly Arg Val Arg Phe Ser Arg Lys Leu Ala Ala Ala Leu Glu
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 36

Cys Gln Arg Met Gly Val Val Gly Ala Lys Leu Ala Ala Ala Leu Glu
1               5                   10                  15

<210> SEQ ID NO 37
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 37

Arg Gly Arg Leu Arg Arg Val Glu
1               5
```

```
<210> SEQ ID NO 38
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 38

Arg Gly Arg Leu Val Arg Ala
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 39

Gly Arg Leu Thr Arg Val Arg
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 40

Cys Gly Gly Gly Gly Gly Gly Gly Cys
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 41

Ser Ser Val Asp Lys Leu
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 42

Cys Ala Gly Ala Leu Cys Tyr
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 43

Gly Arg Pro Ala Arg Pro Ala Arg
1               5
```

```
<210> SEQ ID NO 44
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 44

Cys Arg Gly Asp Lys Gly Pro Asp Cys
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 45

Arg Leu Xaa Arg
1

<210> SEQ ID NO 46
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 46

Cys Ala Gly Arg Gly Arg Leu Val Arg Cys
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 47

Arg Gly Arg Leu Val Arg Ala Lys
1               5

<210> SEQ ID NO 48
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 48

Ala Gly Val Gly Arg Leu Arg Arg Ala Lys Leu
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 49
```

```
Cys Arg Gly Val Leu Arg Arg Ala Lys Leu
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 50

Ala Val Arg Gly Arg Leu Arg Val Ala Lys Leu
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 51

Cys Ser Arg Arg Gly Ile Leu Arg Ala Lys Pro
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 52

Ala Gly Arg Gly Arg Leu Val Arg Ala Lys Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 53

Val Gly Arg Val Arg Phe Ser Arg Lys Leu
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 54

Pro Pro Arg Arg Gly Leu Ile Lys Leu Lys Thr Ala
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 55

Pro Pro Arg Arg Gly Leu Ile Lys Leu Lys Ala Ser
```

-continued

```
1               5                  10

<210> SEQ ID NO 56
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 56

Pro Pro Arg Arg Gly Leu Ile Lys Leu Ala Thr Ser
1               5                  10

<210> SEQ ID NO 57
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 57

Pro Pro Arg Arg Gly Leu Ile Lys Ala Lys Thr Ser
1               5                  10

<210> SEQ ID NO 58
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 58

Pro Pro Arg Arg Gly Leu Ile Ala Leu Lys Thr Ser
1               5                  10

<210> SEQ ID NO 59
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 59

Pro Pro Arg Arg Gly Leu Ala Lys Leu Lys Thr Ser
1               5                  10

<210> SEQ ID NO 60
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 60

Pro Pro Arg Arg Gly Ala Ile Lys Leu Lys Thr Ser
1               5                  10

<210> SEQ ID NO 61
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 61

Pro Pro Arg Arg Ala Leu Ile Lys Leu Lys Thr Ser
1               5                  10
```

<210> SEQ ID NO 62
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 62

Pro Pro Arg Ala Gly Leu Ile Lys Leu Lys Thr Ser
1               5               10

<210> SEQ ID NO 63
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 63

Pro Pro Ala Arg Gly Leu Ile Lys Leu Lys Thr Ser
1               5               10

<210> SEQ ID NO 64
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 64

Pro Ala Arg Arg Gly Leu Ile Lys Leu Lys Thr Ser
1               5               10

<210> SEQ ID NO 65
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 65

Ala Pro Arg Arg Gly Leu Ile Lys Leu Lys Thr Ser
1               5               10

<210> SEQ ID NO 66
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 66

Cys Gly Arg Arg Ile Lys Leu Lys Thr Ser Cys
1               5               10

<210> SEQ ID NO 67
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 67

Gly Arg Arg Ile Lys Leu Lys Thr Ser
1               5

-continued

```
<210> SEQ ID NO 68
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 68

Gly Gly Arg Arg Ile Lys
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 69

Arg Glu Ser Arg Arg Gly Arg Val Lys Leu
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 70

Thr Ser Lys Gln Asn Ser Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 71

Thr Ser Lys Gln Asn Ala Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 72

Thr Ser Lys Gln Ala Ser Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 73

Thr Ser Lys Ala Asn Ser Arg
1               5
```

```
<210> SEQ ID NO 74
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 74

Thr Ser Ala Gln Asn Ser Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 75

Thr Ala Lys Gln Asn Ser Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 76

Ala Ser Lys Gln Asn Ser Arg
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 77

Cys Thr Val Arg Thr Ser Ala Asp Cys
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 78

Ala Gly Arg Gly Arg Leu Val Ala
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 79

Ala Gly Arg Gly Arg Leu Ala Arg
1               5

<210> SEQ ID NO 80
```

-continued

```
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 80

Ala Gly Arg Gly Arg Ala Val Arg
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 81

Ala Gly Arg Gly Ala Leu Val Arg
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 82

Ala Gly Arg Ala Arg Leu Val Arg
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 83

Ala Gly Ala Gly Arg Leu Val Arg
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 84

Ala Ala Arg Gly Arg Leu Val Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 85

Ala Gly Arg Gly Arg Leu Val
1               5

<210> SEQ ID NO 86
<211> LENGTH: 5
```

-continued

```
<212> TYPE: PRT
<213> ORGANISM: Artificial Sequence
<220> FEATURE:
<223> OTHER INFORMATION: Synthetic Peptide

<400> SEQUENCE: 86

Arg Gly Arg Leu Arg
1               5
```